(12) United States Patent
Chang et al.

(10) Patent No.: US 7,919,506 B2
(45) Date of Patent: Apr. 5, 2011

(54) DIBENZYL AMINE COMPOUNDS AND DERIVATIVES

(75) Inventors: George Chang, Old Saybrook, CT (US); Ravi S. Garigipati, South Glastonbury, CT (US); Bruce Lefker, Gales Ferry, CT (US); David A. Perry, Mystic, CT (US); Dongxiang Zeng, Rocky Hill, CT (US)

(73) Assignee: Pfizer Inc., New York, NY (US)

( * ) Notice: Subject to any disclaimer, the term of this patent is extended or adjusted under 35 U.S.C. 154(b) by 378 days.

(21) Appl. No.: 11/619,277

(22) Filed: Jan. 3, 2007

(65) Prior Publication Data

US 2007/0213371 A1 Sep. 13, 2007

Related U.S. Application Data

(60) Provisional application No. 60/780,993, filed on Mar. 10, 2006.

(51) Int. Cl.
*A61K 31/445* (2006.01)
*A61K 31/41* (2006.01)
*C07D 405/00* (2006.01)
*C07D 257/00* (2006.01)

(52) U.S. Cl. ......... 514/318; 546/210; 548/252; 514/381

(58) Field of Classification Search .................. 548/242; 514/359, 318; 546/210
See application file for complete search history.

(56) References Cited

U.S. PATENT DOCUMENTS

| | | | |
|---|---|---|---|
| 6,426,365 B1 | 7/2002 | Shinkai et al. | 514/513 |
| 6,653,334 B1 | 11/2003 | Yamazaki et al. | 514/375 |
| 7,332,514 B2 | 2/2008 | Maeda et al. | 514/374 |
| 7,652,049 B2 | 1/2010 | Ali et al. | 514/376 |
| 7,737,295 B2 | 6/2010 | Ali et al. | 560/115 |

FOREIGN PATENT DOCUMENTS

| | | |
|---|---|---|
| JP | 2003221376 | 8/2003 |
| WO | 2004020393 | 3/2004 |
| WO | 2005100298 | 10/2005 |
| WO | 2006014357 | 2/2006 |
| WO | 2006014413 | 2/2006 |
| WO | 2006056854 | 6/2006 |
| WO | WO 2006/056854 A1 * | 6/2006 |

OTHER PUBLICATIONS

Gordon, et al., *Circulation*, vol. 79, pp. 8-15 (1989).
United States Published Patent Application No. 2006/0063803, published Mar. 23, 2006.
United States Published Patent Application No. 2006/0247272, published Nov. 2, 2006.
United States Published Patent Application No. 2007/0213314, published Sep. 13, 2007.
United States Published Patent Application No. 2007/0149567, published Jun. 28, 2007.
United States Published Patent Application No. 2004/0204450, published Oct. 14, 2004.
United States Published Patent Application No. 2006/0122224, published Jun. 8, 2006.
United States Published Patent Application No. 2009/239865, published Sep. 24, 2009.
Derwent Abstract XP002436736.

* cited by examiner

*Primary Examiner* — Janet L Andres
*Assistant Examiner* — Binta M Robinson
(74) *Attorney, Agent, or Firm* — Jennifer A. Kispert; Lisa A. Samuels

(57) ABSTRACT

Dibenzyl amine compounds and derivatives, pharmaceutical compositions containing such compounds and the use of such compounds to elevate certain plasma lipid levels, including high density lipoprotein-cholesterol and to lower certain other plasma lipid levels, such as LDL-cholesterol and triglycerides and accordingly to treat diseases which are exacerbated by low levels of HDL cholesterol and/or high levels of LDL-cholesterol and triglycerides, such as atherosclerosis and cardiovascular diseases in some mammals, including humans.

5 Claims, No Drawings

DIBENZYL AMINE COMPOUNDS AND DERIVATIVES

BACKGROUND OF INVENTION

This invention relates to dibenzyl amine compounds and derivatives, pharmaceutical compositions containing such compounds and their use to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of this condition has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon, D. J., et al., "High-density Lipoprotein Cholesterol and Cardiovascular Disease", Circulation, (1989), 79: 8-15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies are on the market today. Niacin can significantly increase HDL, but has serious toleration issues which reduce compliance. Fibrates and the HMG CoA reductase inhibitors raise HDL-C, but in some patients, the result is an increase of modest porportions (~10-12%). As a result, there is an unmet medical need for an approved therapeutic agent that elevates plasma HDL levels, thereby reversing or slowing the progression of atherosclerosis.

Thus, although there are a variety of anti-atherosclerosis therapies, there is a continuing need and a continuing search in this field of art for alternative therapies.

SUMMARY OF THE INVENTION

This invention is directed to compounds according to Formula I

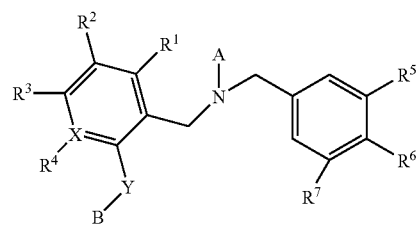

Formula I or a pharmaceutically acceptable salt of said compound; wherein

A is —COO($C_1$-$C_4$)alkyl, cyano, —CHO, —CONH$_2$, —CO($C_1$-$C_4$)alkyl or Q wherein Q is a five or six membered fully saturated, partially unsaturated or fully unsaturated ring wherein each ring atom, except for the atom connected to N of Formula I, may be replaced by a nitrogen, oxygen or sulfur atom, and wherein each ring atom may optionally be mono- or di-substituted by oxo, cyano, a fully saturated, partially unsaturated or fully unsaturated straight or branched chain having 1 to 6 carbon atoms, or a fully saturated, partially unsaturated or fully unsaturated ring having 3 to 8 carbon atoms, wherein each carbon atom of said chain or ring is optionally replaced by a heteroatom selected from nitrogen, oxygen or sulfur, and said carbon atom of said chain or ring is optionally mono-, di- or tri-substituted with amino, halo, cyano, hydroxy, oxo, carboxyl, ($C_1$-$C_6$)alkoxycarbonyl, (($C_1$-$C_6$)alkyl optionally substituted with one to nine halo or one or two hydroxyl), (($C_1$-$C_6$)alkoxy optionally substituted with one to nine halo or one or two hydroxyl), or (($C_1$-$C_6$)alkylthio optionally substituted with one to nine halo or one or two hydroxyl), and said nitrogen atom of said chain or ring is optionally mono- or disubstituted with cyano, oxo, ($C_1$-$C_6$)alkoxycarbonyl or (($C_1$-$C_6$)alkyl optionally substituted with one to nine halo or one or two hydroxyl), said sulfur atom of said chain or ring is substituted with one or two oxo, one to five fluorines or amino, and said chain or ring is optionally mono-, di- or trisubstituted with a group V wherein V is a three to six membered fully saturated, partially saturated or fully unsaturated ring containing zero to four heteroatoms selected from nitrogen, oxygen or sulfur and optionally substituted by one to five groups selected from hydrogen, halo, cyano, hydroxy, oxo, carboxyl, ($C_1$-$C_6$)alkoxycarbonyl, (($C_1$-$C_6$)alkyl optionally substituted with one to nine halo or one or two hydroxyl), (($C_1$-$C_6$)alkoxy optionally substituted with one to nine halo or one or two hydroxyl), or (($C_1$-$C_6$)alkylthio optionally substituted with one to nine halo or one or two hydroxyl);

B is —OR$^{17}$ or —S(O)$_n$R$^{18}$

X is C or N, wherein if X is N, R$^4$ is absent;

Y is —CR$^{11}$R$^{12}$;

R$^1$, R$^2$, R$^3$, R$^4$, R$^5$, R$^6$, and R$^7$ are each independently hydrogen, halo, cyano, hydroxy, nitro, (($C_1$-$C_6$)alkyl optionally substituted with one to nine halo, one or two hydroxyl, one or two ($C_1$-$C_6$)alkoxy, one or two amino, cyano, oxo, or carboxy), (($C_1$-$C_6$)alkoxy optionally substituted with one to nine halo, one or two hydroxyl, or cyano), or (($C_1$-$C_6$)alkylthio optionally substituted with one to nine halo, one or two hydroxyl, or cyano), or $R^1$ and $R^2$ or $R^2$ and $R^3$ are taken together to form a 5 to 7-membered partially unsaturated or fully unsaturated ring wherein each carbon atom of said ring is optionally replaced with an oxygen atom, wherein the oxygen atoms are not connected to each other, wherein said ring is optionally mono-, di-, tri- or tetra-substituted with halo, and optionally mono- or di-substituted with hydroxy, amino, nitro, cyano, oxo, carboxy, (($C_1$-$C_6$)alkyl optionally substituted with one to nine halo, one or two hydroxyl, one or two ($C_1$-$C_6$)alkoxy, one or two amino, one or two nitro, cyano, oxo, or carboxy), or (($C_1$-$C_6$)alkoxy optionally substituted with one to nine halo, one or two hydroxyl, or cyano);

each $R^8$, $R^9$, $R^{10}$, $R^{13}$, and $R^{14}$ are each independently hydrogen, aryl or (($C_1$-$C_6$)alkyl optionally substituted with one to nine halo);

$R^{11}$ and $R^{12}$ are each independently hydrogen, a fully saturated, partially unsaturated or fully unsaturated chain having 1 to 2 carbon atoms, or a fully saturated, partially unsaturated or fully unsaturated mono- or bi-cyclic ring having 3 to 10 carbon atoms, wherein said ring is optionally bicyclic, and wherein each carbon atom of said ring is optionally replaced by a heteroatom selected from nitrogen, oxygen or sulfur, and said carbon atom of said chain or ring is optionally mono-, di- or tri-substituted with $R^{19}$, and wherein $R^{11}$ and $R^{12}$ are not attached to the carbon of Y at a heteroatom, and wherein $R^{11}$ and $R^{12}$ are not both hydrogen, or $R^{11}$ and $R^{12}$ are taken together to form a 3 to 8-membered fully saturated or partially unsaturated mono- or bicyclic ring having optionally one to four heteroatoms selected from oxygen, nitrogen and sulfur, wherein the ring is optionally mono- di- or tri-substituted with $R^{19}$;

$R^{17}$ and $R^{18}$ are each independently —($C_1$-$C_6$)alkyl-$NR^8R^9$, —($C_0$-$C_6$)alkyl-CO—$NR^8R^9$, —($C_0$-$C_6$)alkyl-CO—$OR^{10}$, —($C_1$-$C_6$)alkyl-$NR^{13}$—($C_0$-$C_6$)alkyl-CO—O—$R^{10}$, —($C_1$-$C_6$)alkyl-$NR^{13}$—($C_0$-$C_6$)alkyl-CO—$R^{14}$, —($C_1$-$C_6$)alkyl-$NR^{13}$—($C_0$-$C_6$)alkyl-$SO_2$—$R^{10}$, —($C_1$-$C_6$)alkyl-O—CO—$NR^8R^9$, —($C_2$-$C_6$)alkenyl-CO—O—$R^{10}$, —($C_0$-$C_6$)alkyl-aryl, —($C_0$-$C_6$)alkyl-heteroaryl, —($C_1$-$C_6$)alkyl-O-aryl, —($C_1$-$C_6$)alkyl-O-heteroaryl, —($C_0$-$C_6$)alkyl-heterocycle, —($C_0$-$C_6$)alkyl-($C_3$-$C_6$)cycloalkyl, —($C_0$-$C_6$)alkyl-($C_3$-$C_6$)cycloalkenyl, ($C_2$-$C_6$)alkynyl, ($C_2$-$C_6$)alkenyl, ($C_1$-$C_6$)alkyl, or —CO—($C_1$-$C_6$)alkyl, wherein said $R^{17}$ and $R^{18}$ aryl, heteroaryl, heterocycle, cycloalkenyl, cycloalkyl, alkynyl, alkenyl, and alkyl groups are each optionally substituted independently with one to nine halo, one or two hydroxy, one to three ($C_1$-$C_6$)alkyl, one to three ($C_1$-$C_6$)haloalkyl, one to three ($C_1$-$C_6$)alkoxy, one to three ($C_1$-$C_6$)haloalkoxy, one or two amino, one or two nitro, cyano, oxo, or carboxy, except $R^{17}$ is not aryl or heteroaryl;

each $R^{19}$ is independently —($C_0$-$C_6$)alkyl-$NR^8R^9$, —($C_0$-$C_6$)alkyl-CO—$NR^8R^9$, —($C_0$-$C_6$)alkyl-CO—$OR^{10}$, —($C_0$-$C_6$)alkyl-$NR^{13}$—($C_0$-$C_6$)alkyl-CO—O—$R^{10}$, —($C_0$-$C_6$)alkyl-$NR^{13}$—($C_0$-$C_6$)alkyl-CO—$R^{14}$, —($C_0$-$C_6$)alkyl-$NR^{13}$—($C_0$-$C_6$)alkyl-$SO_2$—$R^{10}$, —($C_0$-$C_6$)alkyl-O—CO—$NR^8R^9$, —O—($C_1$-$C_6$)alkyl-CO—O—$R^{10}$, —($C_2$-$C_6$)alkenyl-CO—O—$R^{10}$, —($C_0$-$C_6$)alkyl-aryl, —($C_0$-$C_6$)alkyl-heteroaryl, —O—($C_0$-$C_6$)alkyl-aryl, —O—($C_0$-$C_6$)alkyl-heteroaryl, —($C_0$-$C_6$)alkyl-O-aryl, —($C_0$-$C_6$)alkyl-O-heteroaryl, —($C_0$-$C_6$)alkyl-heterocycle, —O—($C_0$-$C_6$)alkyl-heterocycle, —($C_0$-$C_6$)alkyl-($C_3$-$C_6$)cycloalkyl, —O—($C_0$-$C_6$)alkyl-($C_3$-$C_6$)cycloalkyl, —($C_0$-$C_6$)alkyl-($C_3$-$C_6$)cycloalkenyl, halo, ($C_2$-$C_6$)alkynyl, ($C_2$-$C_6$)alkenyl, ($C_1$-$C_6$)alkyl, ($C_3$-$C_6$)cycloalkyl, hydroxy, ($C_1$-$C_6$)alkoxy, ($C_1$-$C_4$)alkylthio, nitro, cyano, oxo, or —CO—($C_1$-$C_6$)alkyl, wherein said aryl, heteroaryl, heterocycle, cycloalkenyl, cycloalkyl, alkynyl, alkenyl, alkyl and alkoxy groups are each optionally substituted independently with one to nine halo, one or two hydroxy, one to three ($C_1$-$C_6$)alkyl, one to three ($C_1$-$C_6$)haloalkyl, one to three ($C_1$-$C_6$)alkoxy, one to three ($C_1$-$C_6$)haloalkoxy, one or two amino, one or two nitro, cyano, oxo, or carboxy; and n is 0, 1 or 2.

In addition, the present invention provides pharmaceutical compositions which comprise a therapeutically effective amount of a compound of the present invention, or a pharmaceutically acceptable form of said compound and a pharmaceutically acceptable vehicle, diluent or carrier.

In addition, the present invention provides pharmaceutical compositions for the treatment of atherosclerosis, coronary artery disease, coronary heart disease, coronary vascular disease, peripheral vascular disease, dyslipidemia, hyperbetalipoproteinemia, hypoalphalipoproteinemia, hypercholesterolemia, hypertriglyceridemia, familial-hypercholesterolemia or myocardial infarction in a mammal which comprise a therapeutically effective amount of a compound of the present invention, or a pharmaceutically acceptable form of said compound and a pharmaceutically acceptable vehicle, diluent or carrier.

Moreover, the present invention provides pharmaceutical combination compositions comprising: a therapeutically effective amount of a composition comprising a first compound, said first compound being a compound of the present invention, or a pharmaceutically acceptable form of said compound;

a second compound, said second compound being an HMG CoA reductase inhibitor, an MTP/Apo B secretion inhibitor, a PPAR modulator, a bile acid reuptake inhibitor, a cholesterol absorption inhibitor, a cholesterol synthesis inhibitor, a fibrate, niacin, an antihypertensive, a combination of niacin and lovastatin, an ion-exchange resin, an antioxidant, an ACAT inhibitor or a bile acid sequestrant (preferably an HMG-CoA reductase inhibitor, a PPAR modulator, fenofibrate, gemfibrozil, lovastatin, simvastatin, pravastatin, fluvastatin, atorvastatin, rivastatin, rosuvastatin or pitavastatin); and a pharmaceutical vehicle, diluent or carrier. This composition may be used to treat the aforementioned diseases, including atherosclerosis.

Also, the present invention provides a kit for achieving a therapeutic effect in a mammal comprising packaged in association a first therapeutic agent comprising a therapeutically effective amount of a compound of the present invention, a prodrug thereof, or a pharmaceutically acceptable salt of said compound or of said prodrug and a pharmaceutically acceptable carrier, a second therapeutic agent comprising a therapeutically effective amount of an HMG CoA reductase inhibitor, a PPAR modulator, a cholesterol absorption inhibitor, a cholesterol synthesis inhibitor, a fibrate, niacin, a combination of niacin and lovastatin, an ion-exchange resin, an antioxidant, an ACAT inhibitor or a bile acid sequestrant and a pharmaceutically acceptable carrier and directions for administration of said first and second agents to achieve the therapeutic effect.

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of exemplary embodiments of the invention and the examples included therein.

Before the present compounds, compositions and methods are disclosed and described, it is to be understood that this invention is not limited to specific synthetic methods of making that may of course vary. It is also to be understood that the terminology used herein is for the purpose of describing particular embodiments only and is not intended to be limiting.

The present invention also relates to the pharmaceutically acceptable acid addition salts of compounds of the present invention. The acids which are used to prepare the pharmaceutically acceptable acid addition salts of the aforementioned base compounds of this invention are those which form non-toxic acid addition salts, (i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The invention also relates to base addition salts of the compounds of the present invention. The chemical bases that may be used as reagents to prepare pharmaceutically acceptable base salts of those compounds of the present invention that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention are also included.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

This invention also includes isotopically-labeled compounds, which are identical to those described by formula I, except for the fact that one or more atoms are replaced by one or more atoms having specific atomic mass or mass numbers. Examples of isotopes that can be incorporated into compounds of the invention include isotopes of hydrogen, carbon, nitrogen, oxygen, sulfur, fluorine, and chlorine such as $^2$H, $^3$H, $^{13}$C, $^{14}$C, $^{15}$N, $^{18}$O, $^{17}$O, $^{18}$F, and $^{36}$Cl respectively. Compounds of the present invention, prodrugs thereof, and pharmaceutically acceptable salts of the compounds or of the prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated (i.e., $^3$H), and carbon-14 (i.e., $^{14}$C), isotopes are particularly preferred for their ease of preparation and delectability. Further, substitution with heavier isotopes such as deuterium (i.e., $^2$H), can afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out the procedures disclosed in the schemes and/or in the Examples below, by substituting a readily available isotopically labeled reagent for a non-isotopically labeled reagent.

In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated require a tighter range.

As used herein, the term mammals is meant to refer to all mammals which contain CETP in their plasma, for example, rabbits and primates such as monkeys and humans, including males and females. Certain other mammals e.g., dogs, cats, cattle, goats, sheep and horses do not contain CETP in their plasma and so are not included herein.

The term "treating", "treat" or "treatment" as used herein includes preventative (e.g., prophylactic) and palliative treatment.

By "pharmaceutically acceptable" is meant the carrier, diluent, excipients, and/or salt must be compatible with the other ingredients of the formulation, and not deleterious to the recipient thereof.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. By "tautomers" is meant chemical compounds that may exist in two or more forms of different structure (isomers) in equilibrium, the forms differing, usually, in the position of a hydrogen atom. Various types of tautomerism can occur, including keto-enol, ring-chain and ring-ring tautomerism. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the present invention include but are not limited to those having a carboxyl moiety wherein the free hydrogen is replaced by ($C_1$-$C_4$)alkyl, ($C_2$-$C_7$)alkanoyloxymethyl, 1-(alkanoyloxy)ethyl having from 4 to 9 carbon atoms, 1-methyl-1-(alkanoyloxy) ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

The following paragraphs describe exemplary ring(s) for the generic ring descriptions contained herein.

By "halo" or "halogen" is meant chloro, bromo, iodo, or fluoro.

By "alkyl" is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, isobutyl, pentyl, isopentyl, neopentyl, tertiary pentyl, 1-methylbutyl, 2-methylbutyl, 3-methylbutyl, hexyl, isohexyl, heptyl and octyl.

"Alkenyl" referred to herein may be linear or branched, and they may also be cyclic (e.g. cyclobutenyl, cyclopentenyl, cyclohexenyl) or bicyclic or contain cyclic groups. They contain 1-3 carbon-carbon double bonds, which can be cis or trans.

By "alkoxy" is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "heteroaryl" means a carbocyclic aromatic system containing one, two, three or four heteroatoms selected independently from oxygen, nitrogen and sulfur and having one, two or three rings wherein such rings may be fused. The term "fused" means that a second ring is present (ie, attached or formed) by having two adjacent atoms in common (ie, shared) with the first ring. The term "fused" is equivalent to the term "condensed". The term "heteroaryl" embraces aromatic radicals such as quinolinyl, benzofuranyl, benzodioxanyl, piprazinyl, pyridinyl, isoxazolyl, imidazolyl, triazolyl, tetrazolyl, oxazolyl, oxadiazolyl, isoxazolyl, pyrazolyl, thiazolyl and thiadiazolyl.

The term "heterocycle" means a nonaromatic carbocyclic system containing one, two, three or four heteroatoms selected independently from oxygen, nitrogen and sulfur and having one, two or three rings wherein such rings may be fused, wherein fused is defined above. The term "heterocycle" includes but is not limited to lactones, lactams, cyclic ethers and cyclic amines, including the following exemplary ring systems: epoxide, tetrahydrofuran, tetrahydropyran, dioxane, aziridines, pyrrolidine, piperidine, and morpholine.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

As used herein, the expressions "reaction-inert solvent" and "inert solvent" refer to a solvent or a mixture thereof which does not interact with starting materials, reagents, intermediates or products in a manner which adversely affects the yield of the desired product.

In one embodiment of the compounds of the present invention, X is C.

In another embodiment, A is —COO($C_1$-$C_4$)alkyl, —CO($C_1$-$C_4$)alkyl or Q wherein Q is a five or six membered fully unsaturated ring wherein each ring atom, except for the atom connected to N of Formula I, may be replaced by a nitrogen, oxygen or sulfur atom, and wherein each ring atom may optionally be substituted by cyano, a fully saturated, partially unsaturated or fully unsaturated straight or branched chain having 1 to 6 carbon atoms, or a fully saturated, partially unsaturated or fully unsaturated ring having 3 to 8 carbon atoms, wherein each carbon atom of said chain or ring is optionally replaced by a heteroatom selected from nitrogen, oxygen or sulfur, and said carbon atom of said chain or ring is optionally mono-, di- or tri-substituted with hydrogen, amino, halo, cyano, hydroxy, oxo, carboxyl, ($C_1$-$C_6$)alkoxycarbonyl, or (($C_1$-$C_6$)alkoxy optionally substituted with one to nine halo or one or two hydroxyl), and said nitrogen atom of said chain or ring is optionally mono- or disubstituted with hydrogen, ($C_1$-$C_6$)alkoxycarbonyl or (($C_1$-$C_6$)alkyl optionally substituted with one to nine halo or one or two hydroxyl), said sulfur atom of said chain or ring is substituted with one or two oxo.

In another embodiment, Q is

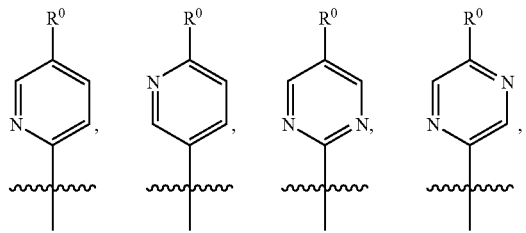

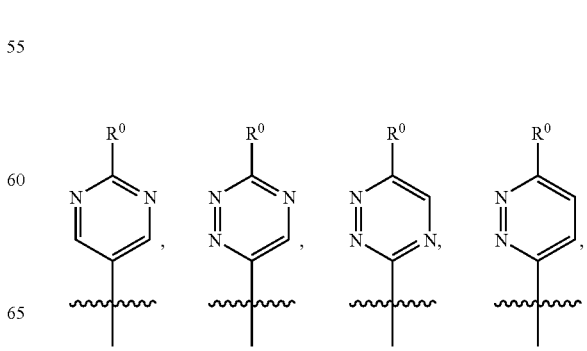

-continued
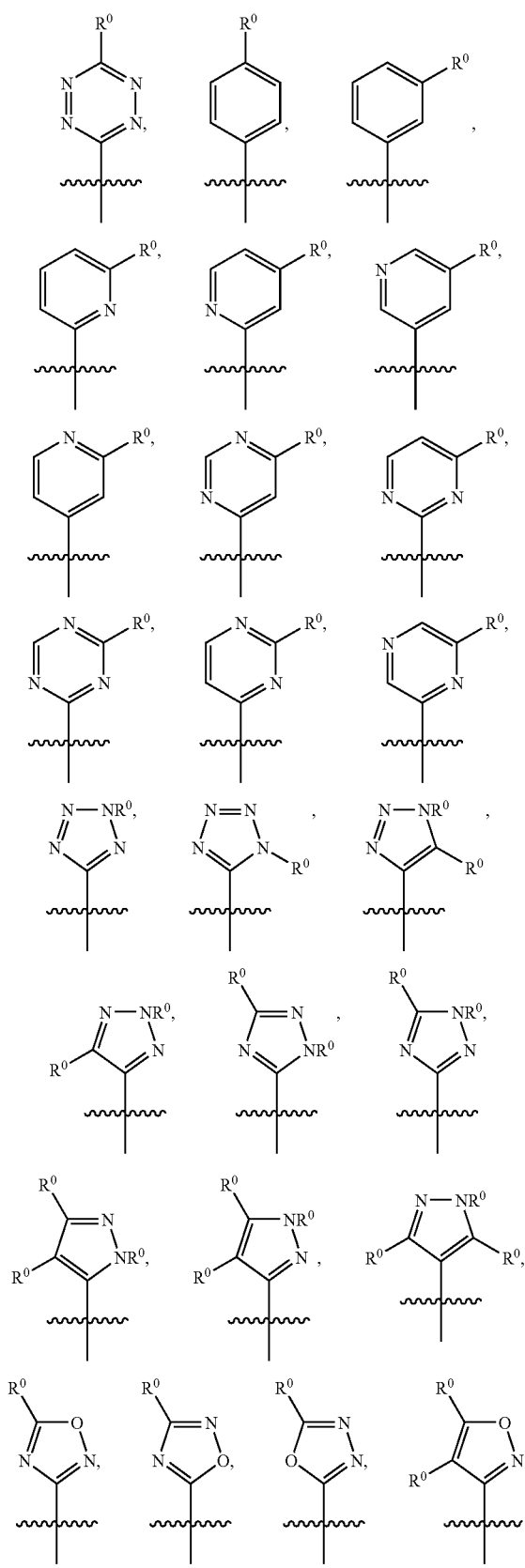
-continued
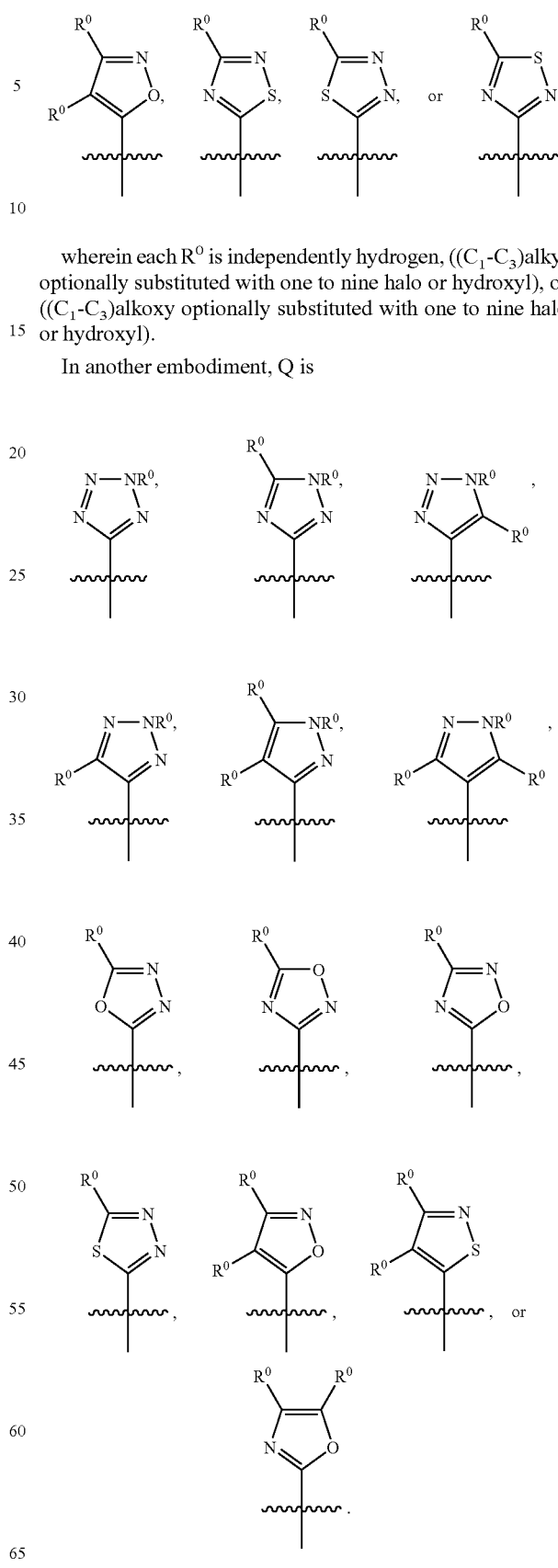
wherein each $R^0$ is independently hydrogen, $((C_1\text{-}C_3)$alkyl optionally substituted with one to nine halo or hydroxyl), or $((C_1\text{-}C_3)$alkoxy optionally substituted with one to nine halo or hydroxyl).
In another embodiment, Q is In another embodiment, Q is

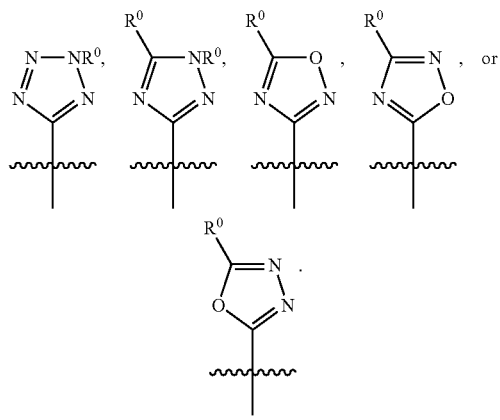

In another embodiment, Q is

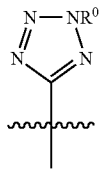

and $R^0$ is hydrogen, $(C_1-C_3)$alkyl optionally substituted with one to five halo or one or two hydroxyl, or $(C_1-C_3)$alkoxy optionally substituted with one to five halo or one or two hydroxyl.

In another embodiment, A is —COO$(C_1-C_4)$alkyl, —CO$(C_1-C_4)$alkyl or Q wherein Q is a five or six membered fully unsaturated ring wherein each ring atom, except for the atom connected to N of Formula I, may be replaced by a nitrogen, oxygen or sulfur atom, and wherein each ring atom may optionally be substituted by cyano, a fully saturated, partially unsaturated or fully unsaturated straight or branched chain having 1 to 6 carbon atoms, or a fully saturated, partially unsaturated or fully unsaturated ring having 3 to 8 carbon atoms, wherein each carbon atom of said chain or ring is optionally replaced by a heteroatom selected from nitrogen, oxygen or sulfur, and said carbon atom of said chain or ring is optionally mono-, di- or tri-substituted with hydrogen, amino, halo, cyano, hydroxy, oxo, carboxyl, $(C_1-C_6)$alkoxycarbonyl, or $((C_1-C_6)$alkoxy optionally substituted with one to nine halo or one or two hydroxyl), and said nitrogen atom of said chain or ring is optionally mono- or disubstituted with hydrogen, $(C_1-C_6)$alkoxycarbonyl or $((C_1-C_6)$alkyl optionally substituted with one to nine halo or one or two hydroxyl), said sulfur atom of said chain or ring is substituted with one or two oxo; $R^1$ and $R^6$ are each hydrogen; $R^4$ is absent or is hydrogen; $R^{11}$ is not hydrogen; $R^{12}$ is hydrogen; and $R^2$, $R^3$, $R^5$, and $R^7$ are each independently hydrogen, cyano, $((C_1-C_6)$alkyl optionally substituted with one to nine fluorines) or $((C_1-C_6)$alkoxy optionally substituted with one to nine fluorines).

In another embodiment, X is C; and $R^2$, $R^3$, $R^5$, and $R^7$ are each hydrogen, methyl, cyano, or $CF_3$.

In another embodiment, X is C; $R^1$, $R^4$ and $R^6$ are each hydrogen; $R^2$, $R^3$, $R^5$, and $R^7$ are each hydrogen, methyl, cyano, or $CF_3$ and A is —COOCH$_2$CH$_3$, —COOCH$_3$, —COCH$_2$CH$_3$, —COCH$_3$, or Q wherein Q is triazolyl, tetrazolyl, oxadiazolyl, isoxazolyl, or pyrazolyl, and wherein Q is optionally substituted with halo, $((C_1-C_6)$alkyl optionally substituted with one or two oxo, one or two hydroxyl or one to nine halo), hydroxy, $((C_1-C_6)$alkoxy optionally substituted with one or two oxo, one or two hydroxyl or one to nine halo), cyano, oxo, carboxy, or $(C_1-C_6)$alkyloxycarbonyl.

In another embodiment, Q is

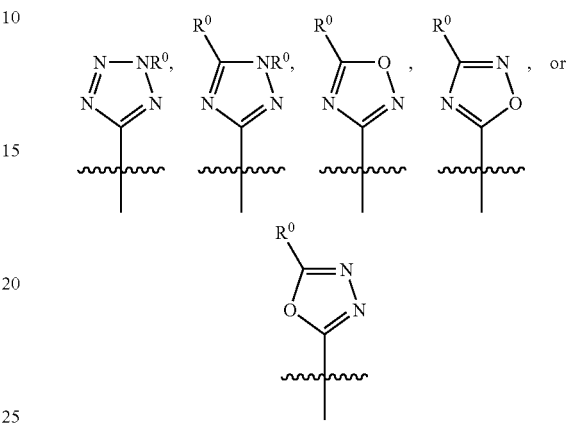

wherein each $R^0$ is independently hydrogen, halo, $((C_1-C_{10})$alkyl optionally substituted with one or two oxo, one or two hydroxyl and one to nine halo), hydroxy, $((C_1-C_6)$alkoxy optionally substituted with one or two oxo, one or two hydroxyl and one to nine halo), amino, amido, cyano, carboxy, or $((C_1-C_6)$alkyloxycarbonyl optionally substituted with one or two oxo, one or two hydroxyl and one to nine halo).

In another embodiment, Q is

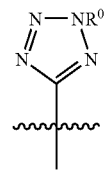

and $R^0$ is hydrogen, $(C_1-C_3)$alkyl optionally substituted with one to five halo or one or two hydroxyl, or $(C_1-C_3)$alkoxy optionally substituted with one to five halo or one or two hydroxyl.

In another embodiment, B is —OR$^{17}$ or —SR$^{18}$ wherein $R^{17}$ and $R^{18}$ are each independently —$(C_1-C_6)$alkyl-NR$^8$R$^9$, —$(C_0-C_6)$alkyl-CO—NR$^8$R$^9$, —$(C_0-C_6)$alkyl-CO—OR$^{10}$, —$(C_1-C_6)$alkyl-NR$^{13}$—$(C_0-C_6)$alkyl-CO—O—R$^{10}$, —$(C_1-C_6)$alkyl-NR$^{13}$—$(C_0-C_6)$alkyl-NR$^{13}$—$(C_0-C_6)$alkyl-SO$_2$—R$^{10}$, —$(C_1-C_6)$alkyl-O—CO—NR$^8$R$^9$, —$(C_2-C_6)$alkenyl-CO—O—R$^{10}$, —$(C_0-C_6)$alkyl-aryl, —$(C_0-C_6)$alkyl-heteroaryl, —$(C_1-C_6)$alkyl-O-aryl, —$(C_1-C_6)$alkyl-O-heteroaryl, —$(C_0-C_6)$alkyl-heterocycle, —$(C_0-C_6)$alkyl-$(C_3-C_6)$cycloalkyl, —$(C_0-C_6)$alkyl-$(C_3-C_6)$alkenyl, $(C_2-C_6)$alkynyl, $(C_2-C_6)$alkenyl, $(C_1-C_6)$alkyl, cyano, or —CO—$(C_1-C_6)$alkyl, wherein said aryl, heteroaryl, heterocycle, cycloalkenyl, cycloalkyl, alkynyl, alkenyl, and alkyl substituents are each optionally substituted independently with one to nine halo, one or two hydroxy, one or two $(C_1-C_6)$alkoxy, one or two $(C_1-C_6)$alkyl, one or two amino, one or two nitro, cyano, oxo, or carboxy, except $R^{17}$ is not aryl or heteroaryl.

In another embodiment, B is —OR$^{17}$ and R$^{17}$ is —(C$_1$-C$_6$)alkyl-aryl, —(C$_1$-C$_6$)alkyl-heteroaryl, —(C$_0$-C$_6$)alkyl-heterocycle, —(C$_0$-C$_6$)alkyl-(C$_3$-C$_6$)cycloalkyl, (C$_1$-C$_6$)alkyl, wherein said aryl, heteroaryl, heterocycle, cycloalkyl, and alkyl substituents are each optionally substituted independently with one to nine halo, one or two hydroxy, one to three (C$_1$-C$_6$)alkyl, one to three (C$_1$-C$_6$)haloalkyl, one to three (C$_1$-C$_6$)alkoxy, one to three (C$_1$-C$_6$)haloalkoxy, one or two amino, one or two nitro, cyano, oxo, or carboxy.

In another embodiment, R$^{11}$ is optionally mono- or di-substituted with R$^{19}$ and R$^{19}$ is —(C$_0$-C$_6$)alkyl-aryl, —(C$_0$-C$_6$)alkyl-heteroaryl, —(C$_0$-C$_6$)alkyl-heterocycle, —(C$_0$-C$_6$)alkyl-(C$_3$-C$_6$)cycloalkyl, halo, (C$_2$-C$_6$)alkynyl, (C$_2$-C$_6$)alkenyl, (C$_1$-C$_6$)alkyl, hydroxy, (C$_1$-C$_6$)alkoxy, nitro, cyano, oxo, or —CO—(C$_1$-C$_6$)alkyl, wherein said aryl, heteroaryl, heterocycle, cycloalkenyl, cycloalkyl, alkynyl, alkenyl, alkyl and alkoxy groups are each optionally substituted independently with one to nine halo, one or two hydroxy, one to three (C$_1$-C$_6$alkyl, one to three (C$_1$-C$_6$)haloalkyl, one to three (C$_1$-C$_6$)alkoxy, one to three (C$_1$-C$_6$)haloalkoxy, one or two amino, one or two nitro, cyano, oxo, or carboxy.

In another embodiment R$^{11}$ and R$^{12}$ are taken together to form a 3 to 8-membered fully saturated or partially unsaturated mono- or bi-cyclic ring having optionally one to four heteroatoms selected from oxygen, nitrogen and sulfur, wherein the ring is optionally mono- di- or tri-substituted with R$^{19}$.

In one embodiment of the method of the present invention, atherosclerosis is treated.

In another embodiment of the method of the present invention, peripheral vascular disease is treated.

In another embodiment of the method of the present invention, dyslipidemia is treated.

In another embodiment of the method of the present invention, hyperbetalipoproteinemia is treated.

In another embodiment of the method of the present invention, hypoalphalipoproteinemia is treated.

In another embodiment of the method of the present invention, familial-hypercholesterolemia is treated.

In another embodiment of the method of the present invention, coronary artery disease is treated.

In another embodiment of the method of the present invention, myocardial infarction is treated.

In one embodiment of the combination or kit of the present invention, the second compound is an HMG-CoA reductase inhibitor or a PPAR modulator.

In another embodiment of the combination or kit of the present invention, the second compound is fenofibrate, gemfibrozil, lovastatin, simvastatin, pravastatin, fluvastatin, atorvastatin, rivastatin, rosuvastatin or pitavastatin.

In another embodiment of the combination or kit of the present invention, the combination further comprising a cholesterol absorption inhibitor, wherein the cholesterol absorption inhibitor may be ezetimibe.

In general, the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section.

Analogous processes are disclosed in the following U.S. patents, which are hereby incorporated by reference herein in their entirety for all purposes: U.S. Pat. No. 6,140,342; U.S. Pat. No. 6,362,198; U.S. Pat. No. 6,147,090; U.S. Pat. No. 6,395,751; U.S. Pat. No. 6,147,089; U.S. Pat. No. 6,310,075; U.S. Pat. No. 6,197,786; U.S. Pat. No. 6,140,343; U.S. Pat. No. 6,489,478; and International Publication No. WO 00/17164 and International Patent Application No. PCT/IB2005/003500.

The Reaction Schemes herein described are intended to provide a general description of the methodology employed in the preparation of many of the Examples given. However, it will be evident from the detailed descriptions given in the Experimental section that the modes of preparation employed extend further than the general procedures described herein. In particular, it is noted that the compounds prepared according to these Schemes may be modified further to provide new Examples within the scope of this invention. For example, an ester functionality may be reacted further using procedures well known to those skilled in the art to give another ester, an amide, a carbinol or a ketone.

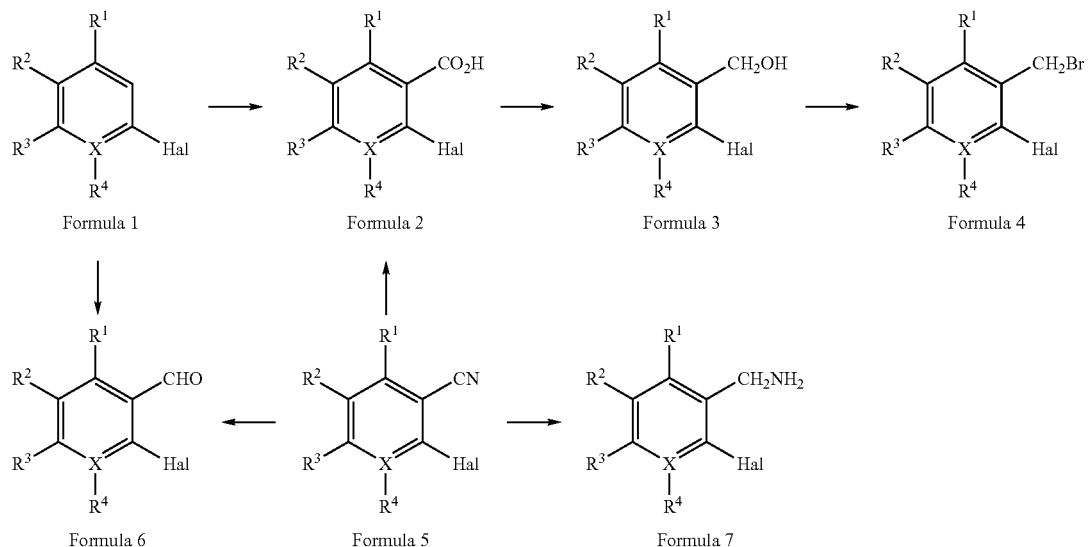

Scheme 1

According to reaction Scheme 1, Hal is a halogen, and X, $R^1$, $R^2$, $R^3$, and $R^4$ are as described above. The desired intermediate compounds of Formulas 4, 6 and 7 may be prepared from compounds of Formulas 1, 2 and 5. Compounds of Formulas 2 and 6 may be prepared from compounds of Formula 1 by methods known to those skilled in the art such as by directed metallation chemistry and trapping with a suitable electrophile such as carbon dioxide, dimethyl formamide (DMF), or N-formylmorpholine.

More specifically, treatment of compounds of Formula 1 with 1-lithium-2,2,6,6-tetramethylpiperidine and quenching with carbon dioxide (F. Mongin, O. Desponds, M. Schlosser *Tetrahedron Letters*, 1996, 37, 2767-2770) or dimethylformamide at low temperature, preferably between −100° C. and −78° C., in a reaction inert solvent such as ether or tetrahydrofuran (THF), preferably THF at −100° C., yields compounds of Formulas 2 and 6 respectively. Alternatively, the compound of Formula 2 may be prepared by acidic or basic hydrolysis of a compound of Formula 5, for example with a suitable acid such as sulphuric acid. The compound of Formula 6 may also be prepared from the Formula 5 compounds by partial reduction, for example with an aluminum hydride reagent such as diisobutylaluminum hydride (DIBAL) in a suitable reaction inert solvent such as THF at a temperature between −78° C. and 25° C.

As shown in Scheme 1, compounds of Formula 3 may be prepared by reduction of the compounds of Formula 2 with a suitable reducing agent such as lithium aluminium hydride (LAH), or borane-tetrahydrofuran complex in a reaction inert solvent such as dioxan, diethyl ether or THF. A preferred reducing agent for reduction of compounds of Formula 2 is borane-tetrahydrofuran complex, and the preferred solvent THF at a temperature between −78 and 100° C. preferably at 0-50° C. Alternatively, compounds of Formula 6 may be reduced to compounds of Formula 3 using sodium borohydride for which the preferred solvent is ethanol at a temperature between 0 and 100° C., preferably 0-50° C.

As shown in Scheme 1, compounds of Formula 4 may be prepared by reacting compounds of Formula 3 using a suitable reagent such as phosphorus tribromide or a combination of carbon tetrabromide and triphenylphosphine in a reaction inert solvent such as methylene chloride, THF, or dioxan. The preferred reagent is a combination of carbon tetrabromide and triphenylphosphine, and the preferred solvent is methylene chloride at a temperature between −78° C. and 100° C., preferably −10° C.-20° C.

As shown in Scheme 1, compounds of Formula 7 may be prepared by reduction of compounds of Formula 5 using a suitable reducing agent such as LAH, or in the specific case when Hal is F or Cl, by hydrogenation in the presence of a suitable hydrogenation catalyst such as palladium on carbon or palladium hydroxide in a reaction inert solvent such as methanol, ethanol or acetic acid. One reducing agent of choice is LAH in a suitable solvent such as THF, methylene chloride, or dioxan. One solvent of choice is THF at a temperature between −78° C. and 68° C., preferably −78° C.-40° C.

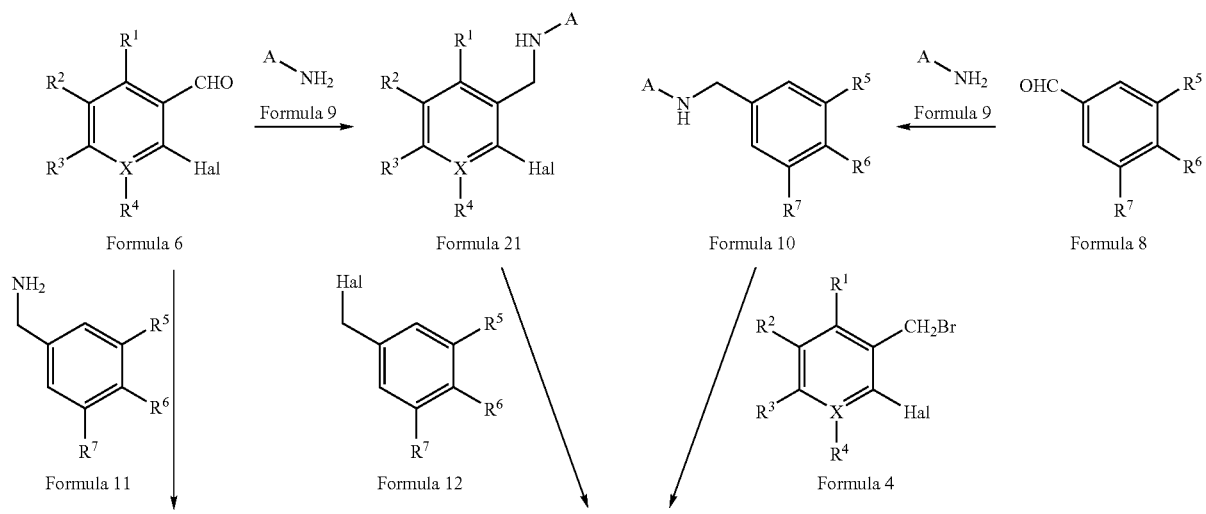

Scheme 2

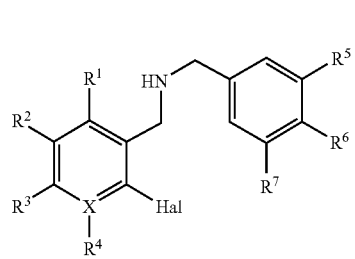

Formula 13

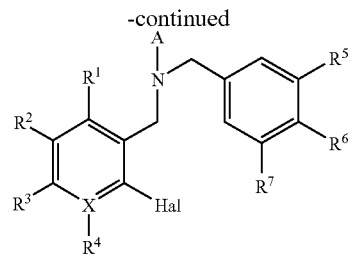

-continued

Formula 15

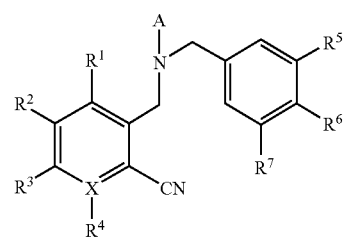

Formula 16

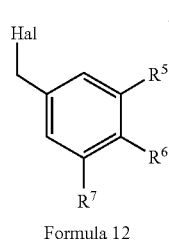

Formula 12

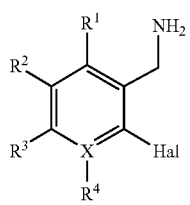

Formula 7

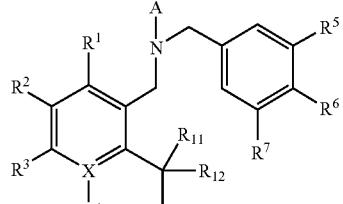

Formula 17

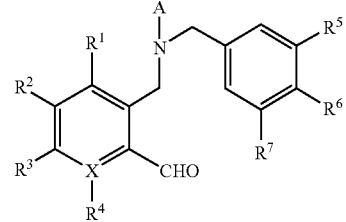

Formula 18

According to reaction Scheme 2, Hal is a halogen and A, X, $R^1, R^2, R^3, R^4, R^5, R^6, R^7 R^{11}$, and $R^{12}$ are as described above. The desired compounds depicted as Formula 15 in Scheme 2, may be prepared by alkylation of compounds of Formula 10 and compounds of Formula 4 with a suitable base such as sodium hydride, potassium-tert-butoxide or potassium hexamethyldisilazine in a suitable polar solvent such as THF, dimethylformamide, or N-methylpyrrolidinone. The base of choice is potassium-tert-butoxide, and the preferred solvent is THF at a temperature between 0° C. and 67° C., preferably 20° C.-67° C.

Compounds of Formula 10 may be prepared by reductive amination of compounds of aldehydes of Formula 8 with amines of Formula 9 and a suitable reducing agent such as sodium borohydride, sodium triacetoxyborohydride, or sodium cyanoborohydride, in a suitable solvent such as THF, methylene chloride, dioxan, or toluene. The method of choice is imine formation in the presence of 4 Å molecular sieves in toluene at a temperature between 20° C. and 111° C., preferably 100° C.-111° C., followed by removal of the solvent, dissolution of the residue in a polar solvent, preferably ethanol, then reduction of the imine with a suitable hydride reducing agent, preferably sodium borohydride, at a temperature between 0° C. and 78° C., preferably 20° C.-50° C.

Alternatively, compounds of Formula 15 may be prepared from compounds of Formula 13 by a variety of methods well known to those skilled in the arts. For example in the case where A is an optionally substituted aromatic ring it is often possible to use the appropriate halogen derivative of A and displace the halogen with the secondary amine of the Formula 13 compound generally in the presence of a base. Frequently these reactions are facilitated by the use of a palladium catalyst as described in U.S. Pat. No. 5,576,460; International Publication No. WO 98/15515; International Publication No. WO00/02887; International Publication No. WO04/052939; European Publication No. EP3009560.8; and European Publication No. EP99933785.0; all of which are incorporated herein in their entireties for all purposes. In another example when A is an optionally substituted 2-pyridyl, 2- or 4-pyrimidinyl or 2-pyrazinyl group, this reaction can be achieved without the use of a catalyst by use of the corresponding 2-halopyridine, 2- or 4-halopyrimidine or 2-pyrazine respectively in a suitable reaction inert solvent such as dimethylformamide (DMF), N-methylpyrrolidinone or N,N,N',N'-tetramethylurea using a suitable base such as triethylamine, diisopropylethylamine, potassium carbonate, or sodium carbonate. A preferred base is diisopropylethylamine in a suitable inert solvent such as THF, methylene chloride, or dioxan. A preferred solvent is dioxane at a temperature between –40° C. and 160° C., preferably 20° C.-140° C.

In another aspect of this invention the compounds of Formula 15 may be prepared from compounds of Formula 13 by a series of reactions, which are well known to those skilled in the art, during which the A ring is constructed de novo. Preferred examples of such processes include, but are not limited to, the reaction of the Formula 13 compounds with a cyanating agent such as cyanogen bromide or N-cyanoimidazole to produce a cyanamide intermediate. This may be further reacted with an azide source such as sodium azide, tri-n-butyltin azide or trimethylsilylazide to produce a tetrazole. Said tetrazole may be further reacted if desired, for example by alkylation. In another aspect, the said cyanamide intermediate may be reacted with hydroxylamine followed by an alkanoylating agent such as an acyl chloride to produce an oxadiazole compound (Ried, W and Eichhorn, T. A., *Archiv der Pharmazie* 1998, 321(9), 527). In yet another aspect, the said cyanamide intermediate may be reacted with an acylhydrazide to produce a triazole ring-containing compound (Ried, W and Eichhorn, T. A., *Archiv der Pharmazie* 1998, 321(9), 527).

In yet another alternative compounds of Formula 15 may be prepared by alkylation of compounds of Formula 21 with an alkyl halide of Formula 12 using a suitable base such as triethylamine, diisopropylethylamine, potassium carbonate, sodium hydride or potassium tert-butoxide, preferably potassium tert-butoxide in a suitable reaction inert solvent such as THF, methylene chloride or dioxane, preferably THF, at a temperature between −40° C. and 40° C., preferably 0-30° C.

Compounds of Formula 21 may be prepared by reductive amination of aldehydes of Formula 6 with amines of Formula 9 and a suitable reducing agent such as sodium borohydride, sodium triacetoxyborohydride, or sodium cyanoborohydride, in a suitable solvent such as THF, methylene chloride, dioxane or toluene. The reaction proceeds via formation of an imine which may be facilitated by a dehydrating agent such as 4 Å molecular sieves in toluene at a temperature between 20° C. and 111° C., preferably 100° C.-111° C., followed by removal of the solvent. Alternatively a titanium compound, preferably titanium tetraisopropoxide may be employed, preferably in the absence of a solvent at room temperature. The imine is then reduced in a suitable polar solvent, preferably ethanol, with a suitable hydride reducing agent, preferably sodium borohydride, at a temperature between 0° C. and 80° C., preferably 20° C.-50° C.

Compounds of Formula 13 may be prepared by reductive amination of compounds of Formula 6 and compounds of Formula 11 with a suitable reducing agent such as sodium borohydride, sodium triacetoxyborohydride, or sodium cyanoborohydride. The preferable reducing agent is sodium borohydride in a suitable solvent such as ethanol, THF, methylene chloride, dioxan, or toluene. The preferred solvent is ethanol at a temperature of −78° C. and 67° C. preferably 0-50° C.

Alternatively, compounds of Formula 13 may be prepared by alkylation of compounds of Formula 7 and compounds of Formula 12 using a suitable base such as triethylamine, diisopropylethylamine, potassium carbonate, or sodium carbonate. The preferred base is diisopropylethylamine in a suitable inert solvent such as THF, methylene chloride, or dioxan. The preferred solvent is methylene chloride at a temperature between −40° C. and 40° C., preferably 0-20° C.

Compounds of Formula 18 may be prepared by reduction of the nitriles of Formula 16 with DIBAL-H in a suitable solvent such as dichloromethane at a temperature between −40° C. and 40° C., preferably −20° C.

Compounds of Formula 17 wherein $R^{12}$ is H and $R^{11}$ is as described above may be prepared from compounds of Formula 16 by addition of a suitable organometallic reagent of the formula $R^{11}M$ where M is typically Li, MgCl, MgBr or MgI in a suitable reaction inert solvent such as THF, diethyl ether or toluene at a temperature between −78° C. and 100° C., preferably −10° C. to 30° C. After hydrolytic workup the intermediate ketone is treated with a suitable reducing agent such as sodium borohydride, sodium triacetoxyborohydride or lithium aluminum hydride in a suitable reaction inert solvent to give the desired alcohol of Formula 17. Preferred conditions utilize sodium borohydride in ethanol between 0° C. and 40° C., preferably 20° C.

Alternatively compounds of Formula 17 may be prepared from compounds of Formula 15 by first converting the aryl halide into an aryl metal derivative where the metal may be lithium, magnesium, boron or zinc followed by reaction with the appropriate carbonyl compound of formula $R^{11}R^{12}CO$, including such carbonyl compounds in which $R^{11}$ and $R^{12}$ are connected in the form of a ring. Methods for accomplishing these reactions are well known to those skilled in the art and include metal exchange with a Grignard reagent such as isopropylmagnesium chloride in a suitable reaction inert solvent such as THF, diethyl ether or toluene, preferably THF, at a temperature between −78° C. and 40° C., preferably −10° C. to 30° C. followed by reaction with the carbonyl compound $R^{11}R^{12}CO$ at a temperature between −78° C. and 100° C., preferably −10° C. to 30° C. Another example of suitable reaction conditions involving activation with a diborane such as 4,4,5,5-tetramethyl-2-(4,4,5,5-tetramethyl-1,3,2-dioxaborolan-2-yl)-1,3,2-dioxaborolane in the presence of a palladium catalyst as described above for the preparation of Formula 15 compounds from Formula 13 compounds. The resultant arylboronic ester or acid may be activated toward addition to the appropriate carbonyl compound in the presence of a rhodium catalyst as described by A. Fürstner and H. Krause, *Adv. Synth. Catal.* 2001 (4), 343.

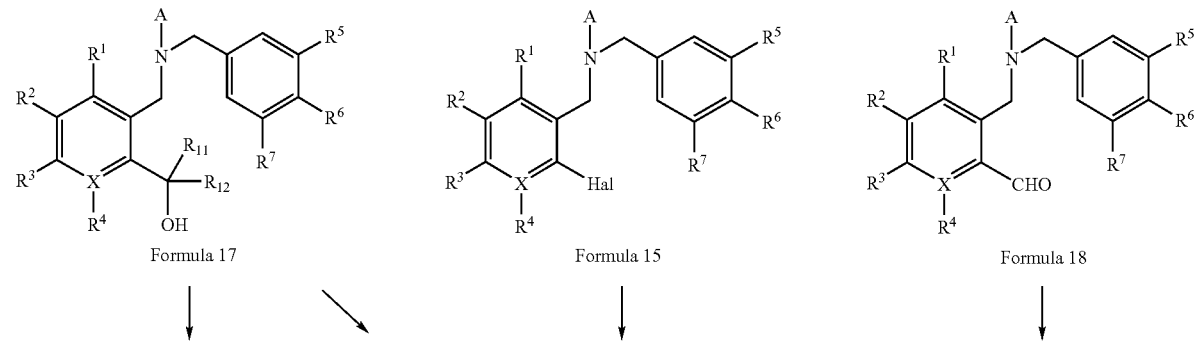

Scheme 3

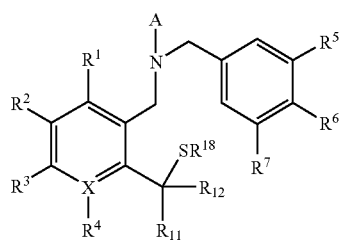

Formula 21

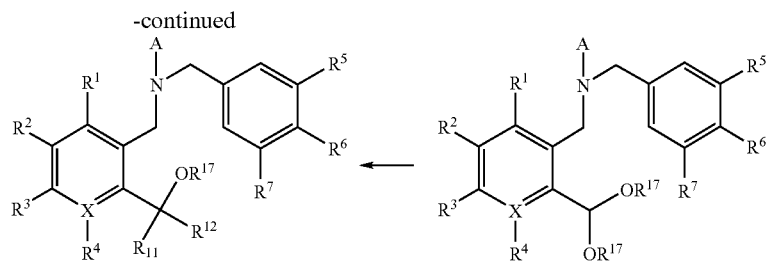

Formula 20    Formula 19

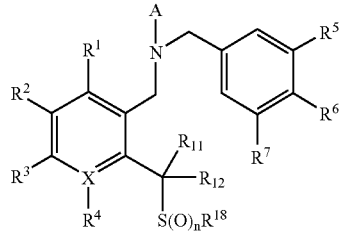

Formula 21A

According to reaction Scheme 3, A, n, X, $R^1$, $R^2$, $R^3$, $R^4$, $R^5$, $R^6$, $R^7$, $R^{11}$, $R^{12}$, $R^{17}$ and $R^{18}$ are as described above. The desired Formula 20 compounds may be prepared from compound 15 by reaction with metallic zinc in the presence of a cobalt salt as described by H. Fillon, C. Gosmini and J. Périchon (J. Amer. Chem. Soc., 2003, 125, 3867). The aryl zinc intermediate may then be reacted with the appropriate acetal or ketal of formula $R^{11}R^{12}C(OR^{17})_2$ as described by E. Le Gall, C. Gosmini and M. Troupel (Tet. Lett., 2006, 47, 455) to give the ether of Formula 20.

The desired ether Formula 20 compounds may also be prepared from the corresponding alcohol of Formula 17 by an alkylation reaction well known to those skilled in the art for example as described in L. A. Paquette (Ed), Encyclopedia of Reagents for Organic Synthesis, John Wiley and Sons, Chichester, England, 1995. In a preferred aspect of this invention the alcohol may be treated with a base such as sodium hexamethyldisilazide, potassium hydride or sodium hydride, preferably sodium hydride, in a reaction inert solvent such as THF and reacted with the appropriate alkylating agent $R^{17}L$ where L is a leaving group such as bromide, iodide, tosylate, triflate or tosylate to give the desired compound of Formula 20.

Alternatively the desired ether Formula 20 compounds may be prepared from the corresponding acetal of Formula 19 by reaction with an appropriate organometallic compound represented by $R^{11}M$ where M is preferably ZnHal, in a reaction inert solvent such as THF at a temperature between −10° C. and 60° C. The preparation of the $R^{11}$ ZnHal reagents from the $R^{11}$Hal compound by treatment with metallic zinc is well known to those skilled in the art for example as described in G. Wilkinson (Ed), Comprehensive Organometallic Chemistry, Pergamon, Oxford, 1982.

The desired acetals of Formula 19 may be prepared from the corresponding aldehyde of Formula 18 by reaction with the alcohol $R^{17}$OH in the presence of a dehydrating agent such as molecular sieves or titanium tetrachloride. Preferred conditions for this reaction are described by A. Clerici, N. Pastori and O. Porta (Tetrahedron Letters, 1998, 54, 15679).

The desired Formula 21 compounds wherein A, X, $R^1$, $R^2$, $R^3$, $R^4$, $R^5$, $R^6$, $R^7$, $R^{11}$, $R^{12}$ and $R^{18}$ are described above, may also be prepared from the corresponding alcohol of Formula 17 by conversion of the alcohol to a leaving group such as a mesylate, tosylate, triflate, chloride or bromide by standard procedures known to those skilled in the art. For example a bromide may be prepared by reacting compounds of Formula 17 using a suitable reagent such as phosphorus tribromide or a combination of carbon tetrabromide and triphenylphosphine in a reaction inert solvent such as methylene chloride, THF, or dioxan. The preferred reagent is a combination of carbon tetrabromide and triphenylphosphine, and the preferred solvent is methylene chloride at a temperature between −78° C. and 100° C., preferably −10° C. to 30° C. This intermediate is then reacted with the appropriate thiolate $R^{18}$SM where M is preferably sodium or potassium to give the desired compound of Formula 21. Alternatively the intermediate may be converted to a thiol ether by reaction with sodium hydrosulfide or by reaction with sodium, potassium or ammonium thiolacetate followed by hydrolysis of the thiolacetate with sodium hydroxide in a suitable solvent, typically in an alcohol such as ethanol at ambient temperature. This thiol is then alkylated with the appropriate alkylating agent $R^{18}L$ where L is a leaving group such as bromide, iodide, tosylate, triflate or tosylate to give the desired compound of Formula 21

The desired Formula 21A compounds wherein n is 1 or 2, may be prepared from the corresponding sulfide of Formula 21 by treatment with an oxidizing agent such as hydrogen peroxide or m-chloroperbenzoic acid in a reaction inert solvent such as dichloromethane. The desired degree of oxidation may be controlled by those skilled in the art and is usually achieved by appropriate choice of reaction temperature.

Scheme 4

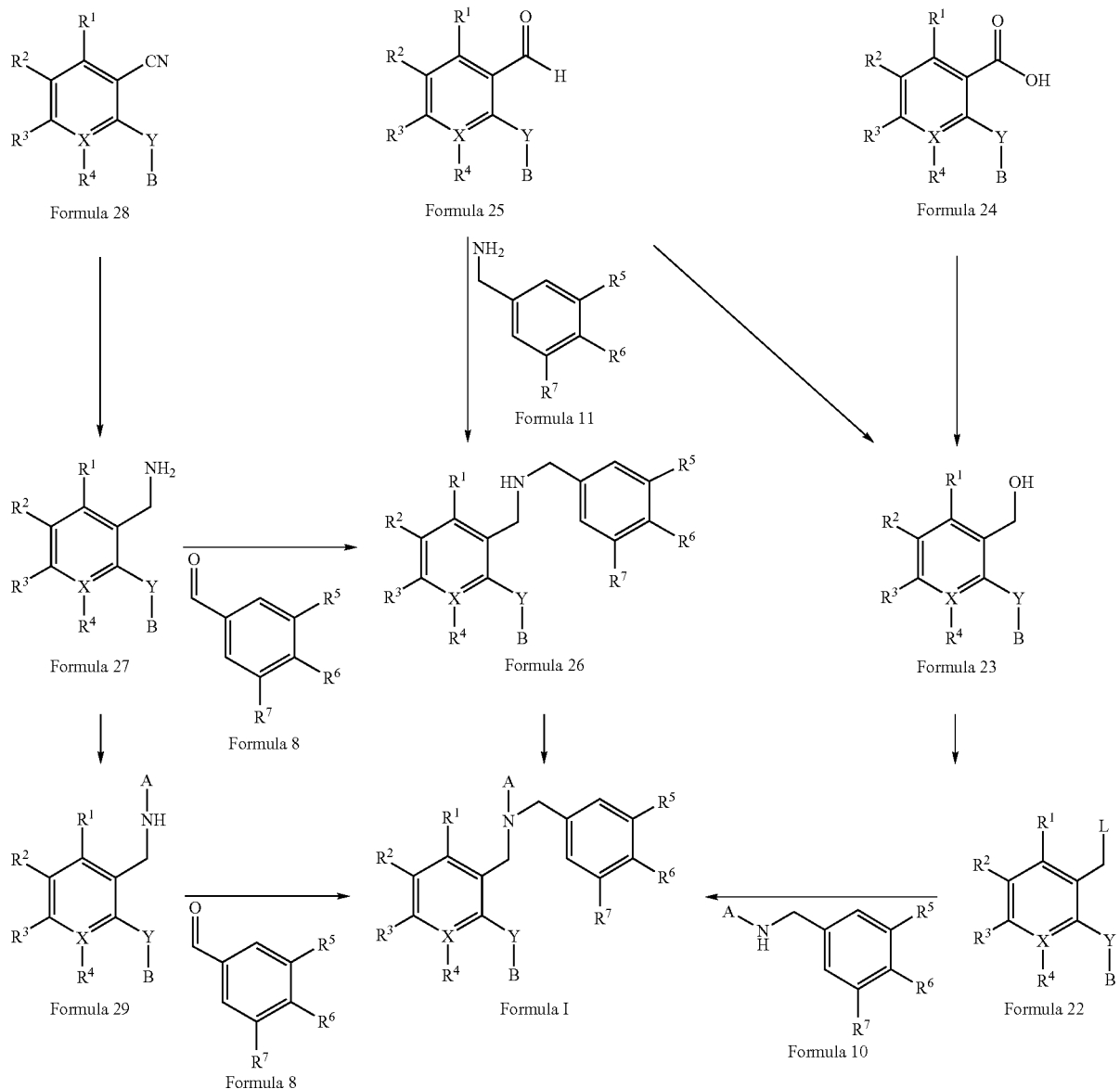

According to Scheme 4 the desired compounds of Formula I in which A, B, X, Y, $R^1$, $R^2$, $R^3$, $R^4$, $R^5$, $R^6$ and $R^7$ are as described above may be obtained by alkylation of a secondary amine of Formula 10 by a compound of Formula 22 in the presence of a suitable base such as triethylamine, diisopropylethylamine, potassium carbonate, sodium hydride or potassium tert-butoxide, preferably potassium tert-butoxide in a suitable reaction inert solvent such as THF, methylene chloride or dioxane, preferably THF, at a temperature between −40° C. and 40° C., preferably 0-30° C.

The compounds of Formula 22 may be prepared from the corresponding compound of Formula 23 by conversion of the alcohol to a leaving group L such as a mesylate, tosylate, triflate, chloride or bromide by standard procedures known to those skilled in the art. For example a bromide may be prepared by reacting compounds of Formula 17 using a suitable reagent such as phosphorus tribromide or a combination of carbon tetrabromide and triphenylphosphine in a reaction inert solvent such as methylene chloride, THF, or dioxan. The preferred reagent is a combination of carbon tetrabromide and triphenylphosphine, and the preferred solvent is methylene chloride at a temperature between −78° C. and 100° C., preferably −10° C. to 30° C.

The compounds of Formula 23 may be prepared from the corresponding compounds of either Formula 24 or Formula 25 with an appropriate reducing agent well known to those skilled in the art, such as lithium aluminum hydride, sodium borohydride or borane-THF complex as can be found in L. A. Paquette (Ed), *Encyclopedia of Reagents for Organic Synthesis*, John Wiley and Sons, Chichester, England, 1995.

In another aspect of this invention the compounds of Formula I may be prepared from compounds of Formula 26 by a variety of methods well known to those skilled in the arts. For example in the case where A is an optionally substituted aromatic ring it is often possible to use the appropriate halogen derivative of A and displace the halogen with the secondary amine of the Formula 13 compound generally in the presence of a base. Frequently these reactions are facilitated by the use of a palladium catalyst as described in U.S. Pat. No. 5,576,460; International Publication No. WO 98/15515; International Publication No. WO00/02887; International Publication No. WO04/052939; European Publication No. EP3009560.8; and European Publication No. EP99933785.0; all of which are incorporated herein in their entireties for all purposes. In another example when A is an optionally substituted 2-pyridyl, 2- or 4-pyrimidinyl or 2-pyrazinyl group this reaction can be achieved without the use of a catalyst by use of the corresponding 2-halopyridine, 2- or 4-halopyrimidine or 2-pyrazine respectively in a suitable reaction inert solvent such as dimethylformamide (DMF), N-methylpyrrolidinone or N,N,N',N'-tetramethylurea using a suitable base such as triethylamine, diisopropylethylamine, potassium carbonate, or sodium carbonate. The preferred base is diisopropylethylamine in a suitable inert solvent such as THF, methylene chloride, DMF or dioxan. The preferred solvent is DMF at a temperature between −40° C. and 160° C., preferably 20° C.-140° C.

In another aspect of this invention the compounds of Formula I may be prepared from compounds of Formula 26 by a series of reactions, which are well known to those skilled in the art, during which the A ring is constructed de novo. Preferred examples of such processes include, but are not limited to, the reaction of the Formula 26 compounds with a cyanating agent, such as cyanogen bromide or N-cyanoimidazole to produce a cyanamide intermediate. This may be further reacted with an azide source such as sodium azide, tri-n-butyltin azide or trimethylsilylazide to produce a tetrazole. Said tetrazole may be further reacted if desired, for example by alkylation. In another aspect, the said cyanamide intermediate may be reacted with hydroxylamine followed by an alkanoylating agent such as an acyl chloride to produce an oxadiazole compound (Ried, W and Eichhorn, T. A., Archiv der Pharmazie 1998, 321(9), 527). In yet another aspect, the said cyanamide intermediate may be reacted with an acylhydrazide to produce a triazole ring-containing compound (Ried, W and Eichhorn, T. A., Archiv der Pharmazie 1998, 321(9), 527).

The compounds of Formula 26 may be prepared from the corresponding compound of Formula 27 by reductive alkyation with a compound of Formula 8 with a suitable reducing agent such as sodium borohydride, sodium triacetoxyborohydride, or sodium cyanoborohydride. The preferable reducing agent is sodium borohydride in a suitable solvent such as ethanol, THF, methylene chloride, dioxan, or toluene. The preferred solvent is ethanol at a temperature of −78° C. and 67° C. preferably 0-50° C.

In another aspect of this invention the compounds of Formula 26 may be prepared from the corresponding compound of Formula 25 by reductive alkyation with an amine of Formula 11 with a suitable reducing agent such as sodium borohydride, sodium triacetoxyborohydride, or sodium cyanoborohydride. The preferable reducing agent is sodium borohydride in a suitable solvent such as ethanol, THF, methylene chloride, dioxan, or toluene. The preferred solvent is ethanol at a temperature of −78° C. and 67° C. preferably 0-50° C.

The compounds of Formula 27 may be prepared from the corresponding compound of Formula 28 by reduction with a suitable reducing agent such as lithium aluminum hydride as can be found in L. A. Paquette (Ed), *Encyclopedia of Reagents for Organic Synthesis*, John Wiley and Sons, Chichester, England, 1995.

In another aspect of this invention the compounds of Formula I may be prepared from compounds of Formula 29 and Formula 12 using a suitable base such as triethylamine, diisopropylethylamine, potassium carbonate, sodium hydride or potassium tert-butoxide, preferably potassium tert-butoxide in a suitable reaction inert solvent such as THF, methylene chloride or dioxane, preferably THF, at a temperature between −40° C. and 40° C., preferably 0-30° C.

Compounds of Formula 29 may be prepared from compounds of Formula 27 by a variety of methods well known to those skilled in the arts. For example in the case where A is an optionally substituted aromatic ring it is often possible to use the appropriate halogen derivative of A and displace the halogen with the primary amine of Formula 27 compound generally in the presence of a base. Frequently these reactions are facilitated by the use of a palladium catalyst as described in U.S. Pat. No. 5,576,460; International Publication No. WO 98/15515; International Publication No. WO00/02887; International Publication No. WO04/052939; European Publication No. EP3009560.8; and European Publication No. EP99933785.0; all of which are incorporated herein in their entireties for all purposes. In another example when A is an optionally substituted 2-pyridyl, 2- or 4-pyrimidinyl or 2-pyrazinyl group this reaction can be achieved without the use of a catalyst by use of the corresponding 2-halopyridine, 2- or 4-halopyrimidine or 2-pyrazine respectively in a suitable reaction inert solvent such as dimethylformamide (DMF), N-methylpyrrolidinone or N,N,N',N'-tetramethylurea using a suitable base such as triethylamine, diisopropylethylamine, potassium carbonate, or sodium carbonate. The preferred base is diisopropylethylamine in a suitable inert solvent such as THF, methylene chloride, DMF or dioxan. The preferred solvent is DMF at a temperature between −40° C. and 160° C., preferably 20° C.-140° C.

Scheme 5

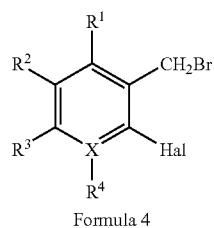

Formula 4

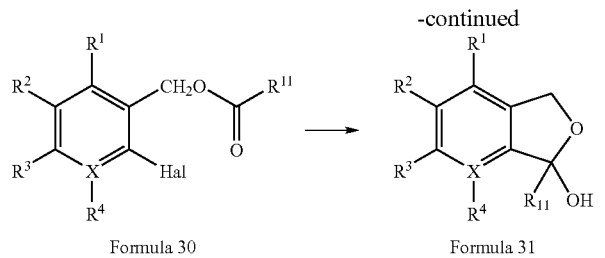

Formula 30 → Formula 31 → Formula 32

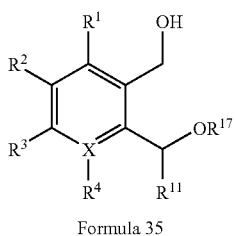

Formula 35 ← Formula 34 ← Formula 33

According to Scheme 5 the compound of Formula 30 in which X, $R^1$, $R^2$, $R^3$, $R^4$, and $R^{11}$ are as described above and Hal is chloro, bromo or iodo can be prepared from the compound of Formula 4 by reaction with the appropriate carboxylic acid in the presence of a suitable base such as triethylamine, diisopropylethylamine, potassium carbonate, cesium carbonate, sodium hydride or potassium tert-butoxide, preferably cesium carbonate in a suitable reaction inert solvent such as THF or DMF, preferably DMF, at a temperature between −40° C. and 40° C., preferably 0-30° C.

The compound of Formula 31 may be obtained from a compound of Formula 30 by treatment with a suitable organometallic reagent such as n-butyllithium, s-butyllithium or t-butyllithium, preferably s-butyllithium in a suitable reaction inert solvent such as THF at a temperature between −98° C. and 20° C., preferably −98° C. and 0° C. Depending on the nature of the substituents and the solvent in which it is dissolved this lactol may exist partially or completely in the ring-opened, or hydroxyketone form.

The compound of Formula 32 may be prepared from the corresponding compound of Formula 31 by treatment with a suitable reducing agent such as sodium borohydride, sodium triacetoxyborohydride or lithium aluminum hydride in a suitable reaction inert solvent to give the desired alcohol of Formula 32. Preferred conditions utilize sodium borohydride in ethanol between 0° C. and 40° C., preferably 20° C.

The compound of Formula 33, where P is an appropriate protecting group such as trityl, allyl, tertbutyldimethylsilyl or triisopropylsilyl may be prepared from the compound of Formula 32 by selective reaction at the less hindered alcohol group by procedures well known to those skilled in the art such as those described in T. W. Greene and P. G. M. Wuts, *Protective Groups in Organic Synthesis*, John Wiley and Sons, New York, USA, 1991. Particularly preferred is the triisopropylsilyl derivative which is prepared by treatment of the alcohol with triisopropylsilyl chloride in the presence of a suitable base such as imidazole in a suitable reaction inert solvent such as THF or DMF, preferably DMF, at a temperature between −40° C. and 40° C., preferably 0-30° C.

The compound of Formula 34 may be prepared from the corresponding alcohol of Formula 33 by an alkylation reaction well known to those skilled in the art for example as described in L. A. Paquette (Ed), Encyclopedia of Reagents for Organic Synthesis. John Wiley and Sons, Chichester, England, 1995. In a preferred aspect of this invention the alcohol may be treated with a base such as sodium hexamethyldisilazide, potassium hydride or sodium hydride, preferably sodium hydride, in a reaction inert solvent such as THF and reacted with the appropriate alkylating agent R17L where L is a leaving group such as bromide, iodide, tosylate, triflate or tosylate to give the desired compound of Formula 34.

The compound of Formula 23 wherein X, $R^1$, $R^2$, $R^3$, $R^4$ are as described above, Y is $CHR^{11}$ and B is $OR^{17}$, herein designated Formula 35, may be prepared from the compound of Formula 34 by deprotection by procedures well known to those skilled in the art such as those described in T. W. Greene and P. G. M. Wuts, *Protective Groups in Organic Synthesis*, John Wiley and Sons, New York, USA, 1991. In the preferred case where P is the triisopropylsilyl group the protecting group may be removed by treatment with a fluoride source, preferably tetrabutylammonium fluoride, in a suitable reaction inert solvent such as THF or DCM, preferably THF, at a temperature between −40° C. and 40° C., preferably 0-30° C.

Scheme 6

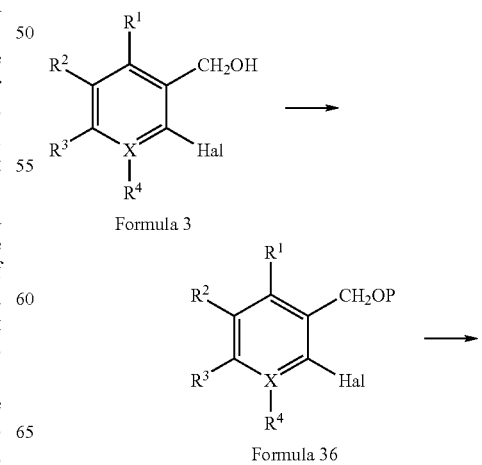

Formula 3

Formula 36

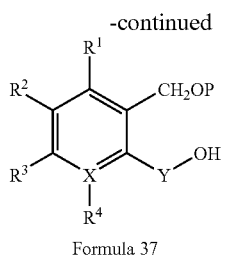

Formula 37

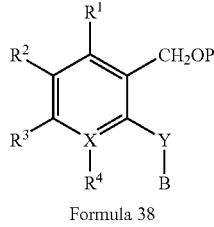

Formula 38

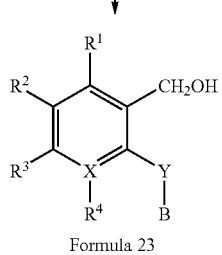

Formula 23

According to Scheme 6, the compound of Formula 36 wherein X, $R^1$, $R^2$, $R^3$, and $R^4$ are as described above and Hal is chloro, bromo or iodo, preferably bromo or iodo and P is an appropriate protecting group such as trityl, allyl, tertbutyldimethylsilyl or triisopropylsilyl may be prepared from the compound of Formula 3 by procedures well known to those skilled in the art such as those described in T. W. Greene and P. G. M. Wuts, *Protective Groups in Organic Synthesis*, John Wiley and Sons, New York, USA, 1991. Particularly preferred is the case where P is triisopropylsilyl which may be prepared by treatment of the alcohol with triisopropylsilyl chloride in the presence of a suitable base such as imidazole in a suitable reaction inert solvent such as THF or DMF, preferably DMF, at a temperature between −40° C. and 40° C., preferably 0-30° C.

The compound of Formula 37 wherein Y is $CR^{11}R^{12}$ may be prepared from the compound of Formula 36 by treatment with a suitable organometallic reagent such as n-butyllithium, s-butyllithium, t-butyllithium or isopropylmagnesium chloride, preferably n-butyllithium or isopropylmagnesium chloride in a suitable reaction inert solvent such as THF or diethyl ether at a temperature between −98° C. and 20° C., preferably −78° C. to 0° C., followed after a suitable interval by treatment with the carbonyl compound YO.

The compound of Formula 38, wherein B is $OR^{17}$ or $SR^{18}$ may be prepared from the alcohol of Formula 37 by the procedures described along with Scheme 3.

In an alternative preparation of the compound of Formula 23, wherein X, Y, B, $R^1$, $R^2$, $R^3$, $R^4$ are as described above, the compound of Formula 34 may be deprotected by procedures well known to those skilled in the art such as those described in T. W. Greene and P. G. M. Wuts, *Protective Groups in Organic Synthesis*, John Wiley and Sons, New York, USA, 1991. In the case where P is the triisopropylsilyl or tertbutyldimethylsilyl group the protecting group may be removed by treatment with a fluoride source, preferably tetrabutylammonium fluoride, in a suitable reaction inert solvent such as THF or DCM, preferably THF, at a temperature between −40° C. and 40° C., preferably 0-30° C.

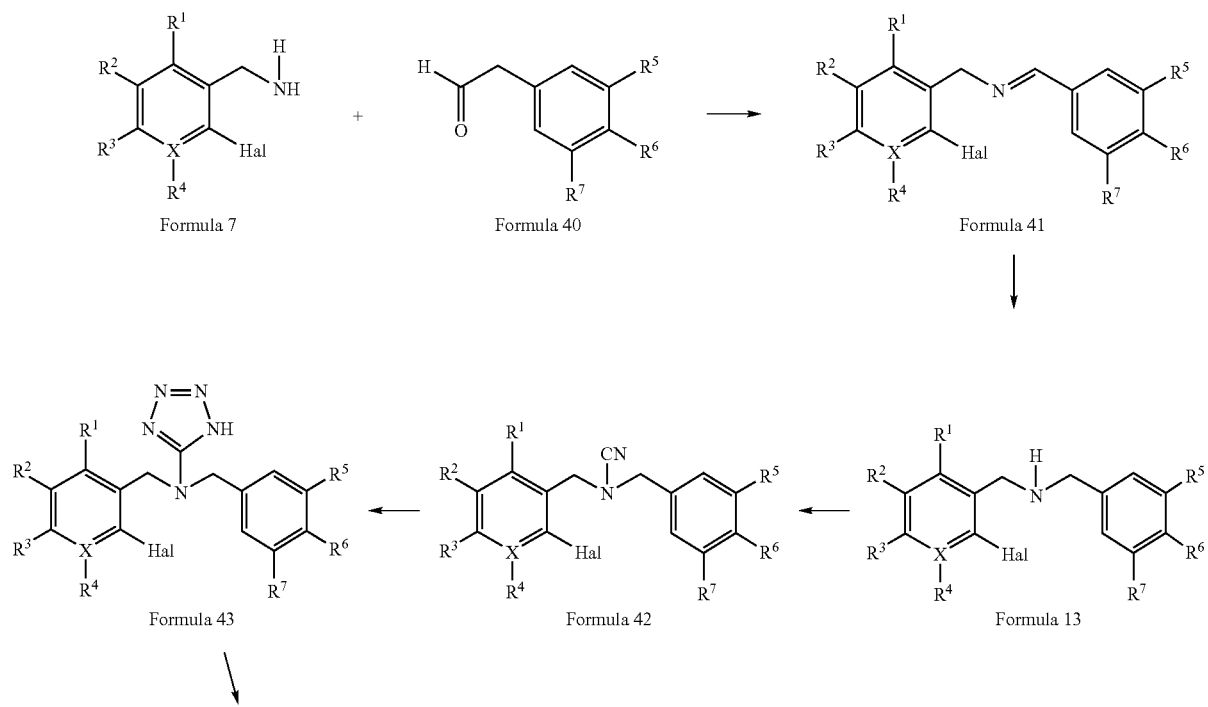

-continued

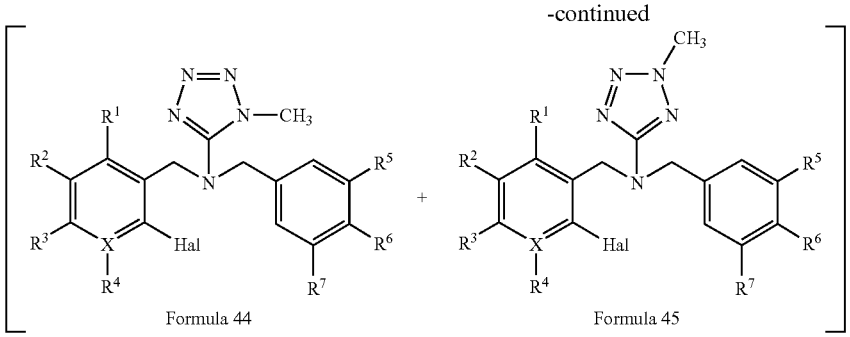 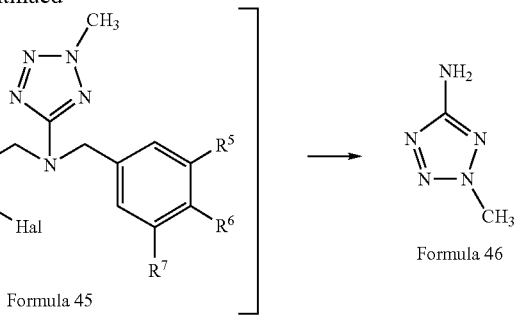

Formula 44　　　　　Formula 45　　　　　Formula 46

According to reaction Scheme 7, Hal is a halogen, X is C, and $R^1$, $R^2$, $R^3$, $R^4$, $R^5$, $R^6$ and $R^7$ are as described above. The desired compounds depicted as Formula 41 in Scheme 5, may be prepared from compounds of Formulas 7 and 40 by acid hydrolysis, for example in the presence of toluene sulfonic acid in a suitable solvent such as acetone, toluene, THF, or methylene chloride, preferably toluene, at a temperature between 0° C. and reflux, preferably room temperature.

Compounds of Formula 13 may be prepared by hydrating the double bond of Formula 41 by reaction with a reducing agent such as sodium borohydride, sodium triacetoxyborohydride, or sodium cyanoborohydride in a suitable solvent such as ethanol. The reaction proceeds at a temperature between 0° C. and 78° C., preferably between 20° C. and 50° C.

Compounds of Formula 42 may be prepared by reacting the amine of Formula 13 in a suitable base such as sodium acetate and a suitable solvent such as dichloromethane, and/or ethanol with a cyanating agent, such as cyanogen bromide or N-cyanoimidazole at ambient temperature. When the reaction is judged complete, it is purified into an oil.

Compounds of Formula 43 may be prepared by reacting the cyano-amine compound of Formula 42 with an azide source such as sodium azide, tri-n-butyltin azide or trimethylsilylazide in a solvent such as toluene, THF, or methylene chloride, preferably toluene at a temperature of 20° C. to 80° C.

A mixture of the methylated tetrazole-amine compounds having Formulas 44 and 45 are produced by alkylating the compound of Formula 43 with an alkylating agent such as dimethyl sulfate in a solvent such as 2-methyl THF, DMF and DMAc at a temperature of about 20° C. to 80° C.

Methyl 5-aminotetrazole may be produced by hydrogenating the mixture of the compounds of Formulas 44 and 45 using a hydrogenation catalyst such as palladium on carbon or palladium hydroxide under a hydrogen atmosphere of 35 to 70 psi, preferably 40 psi in a reaction inert solvent such as methanol, ethanol or acetic acid at a temperature of −78° to 70° C., preferably −78° C. to 40° C. Further methods for producing this compound are published in PCT patent application Nos. WO2006/056854 and WO2006/03302, which are incorporated herein.

As an initial note, in the preparation of compounds, it is noted that some of the preparation methods useful for the preparation of the compounds described herein may require protection of remote functionality (e.g., primary amine, secondary amine, carboxyl in intermediates). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, in the reaction schemes, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the compound.

Prodrugs of the compounds of the present invention may be prepared according to methods known to those skilled in the art. Exemplary processes are described below.

Prodrugs of this invention where a carboxyl group in a carboxylic acid of the compounds is replaced by an ester may be prepared by combining the carboxylic acid with the appropriate alkyl halide in the presence of a base such as potassium carbonate in an inert solvent such as dimethylformamide at a temperature of about 0 to 100° C. for about 1 to about 24 hours. Alternatively the acid is combined with an appropriate alcohol as solvent in the presence of a catalytic amount of acid such as concentrated sulfuric acid at a temperature of about 20 to 100° C., preferably at a reflux, for about 1 hour to about 24 hours. Another method is the reaction of the acid with a stoichiometric amount of the alcohol in the presence of a catalytic amount of acid in an inert solvent such as toluene or tetrahydrofuran, with concomitant removal of the water being produced by physical (e.g., Dean-Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as dimethylformamide at a temperature of about 0 to 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl) amides, N-(1-hydroxy-1-(alkoxycarbonyl)methyl) amides may be prepared by the reaction of the parent amide with the appropriate aldehyde under neutral or basic conditions (e.g., sodium ethoxide in ethanol) at temperatures between 25 and 70° C. N-alkoxymethyl or N-1-(alkoxy)alkyl derivatives can be obtained by reaction of the N-unsubstituted compound with the necessary alkyl halide in the presence of a base in an inert solvent.

The compounds of this invention may also be used in conjunction with other pharmaceutical agents (e.g., LDL-cholesterol lowering agents, triglyceride lowering agents) for the treatment of the disease/conditions described herein. For example, they may be used in combination with a HMG-CoA reductase inhibitor, a cholesterol synthesis inhibitor, a cholesterol absorption inhibitor, another CETP inhibitor, a MTP/Apo B secretion inhibitor, a PPAR modulator and other cholesterol lowering agents such as a fibrate, niacin, an ion-exchange resin, an antioxidant, an ACAT inhibitor, and a bile acid sequestrant. Other pharmaceutical agents would also include the following: a bile acid reuptake inhibitor, an ileal bile acid transporter inhibitor, an ACC inhibitor, an antihypertensive (such as NORVASC®), a selective estrogen receptor modulator, a selective androgen receptor modulator, an antibiotic, an antidiabetic (such as metformin, a PPARγ activator, a sulfonylurea, insulin, an aldose reductase inhibitor (ARI) and a sorbitol dehydrogenase inhibitor (SDI)), and aspirin (acetylsalicylic acid or a nitric oxide releasing asprin). As used herein, "niacin" includes all available forms such as immediate release, slow release, extended release and low-flushing niacin. Niacin may also be combined with other therapeutic agents such as prostaglandins and/or statins, i.e. lovastatin or simvastatin, which are an HMG-CoA reductase inhibitor and described further below. This combination therapy is known as ADVICOR® (Kos Pharmaceuticals Inc.) In combination therapy treatment, both the compounds of this invention and the other drug therapies are administered to mammals (e.g., humans, male or female) by conventional methods.

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. Exemplary statins include lovastatin, simvastatin, pravastatin, fluvastatin, atorvastatin, rivastatin, rosuvastatin, pitavastatin, (3R,5R)-7-(4-(benzylcarbamoyl)-2-(4-fluorophenyl)-5-isopropyl-1H-imidazol-1-yl)-3,5-dihydroxyheptanoic acid; (3R,5R)-7-(4((4-methylbenzyl)carbamoyl)-2-(4-fluorophenyl)-5-isopropyl-1H-pyrazol-1-yl)-3,5-dihydroxyheptanoic acid; and (3R,5R)-7-(4-((3-fluorobenzyl)carbamoyl)-5-cyclopropyl-2-(4-fluorophenyl)-1H-imidazol-1-yl)-3,5-dihydroxyheptanoic acid, and pharmaceutically acceptable salts thereof.

Atorvastatin calcium (i.e., atorvastatin hemicalcium), disclosed in U.S. Pat. No. 5,273,995, which is incorporated herein by reference, is currently sold as Lipitor® and has the formula

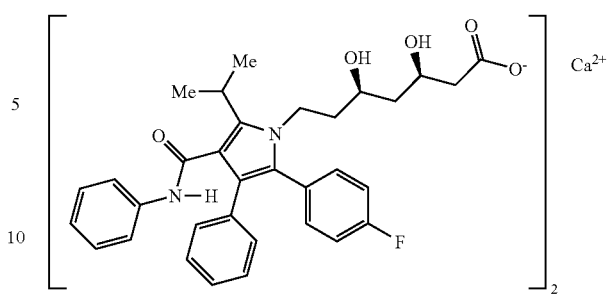

Atorvastatin calcium is a selective, competitive inhibitor of HMG-CoA. As such, atorvastatin calcium is a potent lipid lowering compound. The free carboxylic acid form of atorvastatin exists predominantly as the lactone of the formula

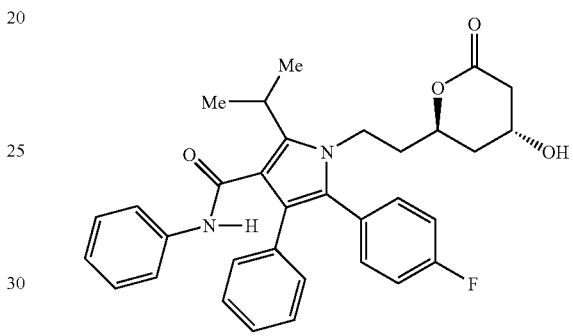

and is disclosed in U.S. Pat. No. 4,681,893, which is incorporated herein by reference.

Statins include such compounds as rosuvastatin disclosed in U.S. RE37,314 E, pitivastatin disclosed in EP 304063 B1 and U.S. Pat. No. 5,011,930, simvastatin, disclosed in U.S. Pat. No. 4,444,784, which is incorporated herein by reference; pravastatin, disclosed in U.S. Pat. No. 4,346,227 which is incorporated herein by reference; cerivastatin, disclosed in U.S. Pat. No. 5,502,199, which is incorporated herein by reference; mevastatin, disclosed in U.S. Pat. No. 3,983,140, which is incorporated herein by reference; velostatin, disclosed in U.S. Pat. No. 4,448,784 and U.S. Pat. No. 4,450,171, both of which are incorporated herein by reference; fluvastatin, disclosed in U.S. Pat. No. 4,739,073, which is incorporated herein by reference; compactin, disclosed in U.S. Pat. No. 4,804,770, which is incorporated herein by reference; lovastatin, disclosed in U.S. Pat. No. 4,231,938, which is incorporated herein by reference; dalvastatin, disclosed in European Patent Application Publication No 738510 A2; fluindostatin, disclosed in European Patent Application Publication No. 363934 A1; atorvastatin, disclosed in U.S. Pat. No. 4,681,893, which is incorporated herein by reference; atorvastatin calcium (which is the hemi-calcium salt of atorvastatin), disclosed in U.S. Pat. No. 5,273,995, which is incorporated herein by reference; and dihydrocompactin, disclosed in U.S. Pat. No. 4,450,171, which is incorporated herein by reference.

Further HMG CoA reductase inhibitors are disclosed in International Publication Nos. WO 2005/105079; and PCT/IB2005/003461 filed Nov. 14, 2005 (the disclosures of which are hereby incorporated by reference) including (3R,5R)-7-(4-(benzylcarbamoyl) 2-(4-fluorophenyl)-5-isopropyl-1H-imidazol-1-yl)-3,5-dihydroxyheptanoic acid; (3R,5R)-7-(4-((3-fluorobenzyl)carbamoyl)-5-cyclopropyl-2-(4- fluorophenyl) 1H-imidazol-1-yl)-3,5-dihydroxyheptanoic acid; and (3R,5R)-7-(4-((4-methylbenzyl)carbamoyl)-2-(4-fluorophenyl)-5-isopropyl-1H-pyrazol-1-yl)-3,5-dihydroxy-heptanoic acid and pharmaceutically acceptable salts of said compounds.

Any PPAR modulator may be used in the combination aspect of this invention. The term PPAR modulator refers to compounds which modulate peroxisome proliferator activator receptor (PPAR) activity in mammals, particularly humans. Such modulation is readily determined by those skilled in the art according to standard assays known in the literature. It is believed that such compounds, by modulating the PPAR receptor, regulate transcription of key genes involved in lipid and glucose metabolism such as those in fatty acid oxidation and also those involved in high density lipoprotein (HDL) assembly (for example, apolipoprotein Al gene transcription), accordingly reducing whole body fat and increasing HDL cholesterol. By virtue of their activity, these compounds also reduce plasma levels of triglycerides, VLDL cholesterol, LDL cholesterol and their associated components such as apolipoprotein B in mammals, particularly humans, as well as increasing HDL cholesterol and apolipoprotein Al. Hence, these compounds are useful for the treatment and correction of the various dyslipidemias observed to be associated with the development and incidence of atherosclerosis and cardiovascular disease, including hypoalphalipoproteinemia and hypertriglyceridemia. A variety of these compounds are described and referenced below, however, others will be known to those skilled in the art. International Publication Nos. WO 2004/048334; WO 2005/092845; and WO 2006/003495 (the disclosures of which are hereby incorporated by reference) disclose certain compounds which are PPARα activators including 3-[3-(1-Carboxy-1-methyl-ethoxy)-phenyl]-piperidine-1-carboxylic acid 3-trifluoromethyl-benzyl ester; 3-[3-(1-Carboxy-1-methyl-ethoxy)-phenyl]-piperidine-1-carboxylic acid 4-trifluoromethyl-benzyl ester; 5-[4-(4-Ethyl-benzylsulfanyl)-phenylsulfamoyl]-2-methyl-benzoic acid; and 5-{2-[4-(3,4-Difluoro-phenoxy)-phenyl]-ethylsulfamoyl}-2-methyl-benzoic acid; and pharmaceutically acceptable salts of said compounds.

Any other PPAR modulator may be used in the combination aspect of this invention. In particular, modulators of PPARβ and/or PPARγ may be useful in combination with compounds of the present invention. Exemplary PPAR inhibitors are described in International Publication No. WO 2003/084916 as {5-Methoxy-2-methyl-4-[4-(4-trifluoromethyl-benzyloxy)-benzylsulfany]-phenoxy}-acetic acid and {5-Methoxy-2-methyl-4-[4-(5-trifluoromethyl-pyridin-2-yl)-benzylsulfanyl]-phenoxy}-acetic acid; and pharmaceutically acceptable salts of said compounds.

Any MTP/Apo B (microsomal triglyceride transfer protein and or apolipoprotein B) secretion inhibitor may be used in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R. 1992; Science 258:999). A variety of these compounds are described and referenced below however other MTP/Apo B secretion inhibitors will be known to those skilled in the art, including implitapide (Bayer) and additional compounds such as those disclosed in WO 96/40640 and WO 98/23593, (two exemplary publications).

For example, the following MTP/Apo B secretion inhibitors are particularly useful:
4'-trifluoromethyl-biphenyl-2-carboxylic acid [2-(1H-[1,2,4,]triazol-3-ylmethyl)-1,2,3,4-tetrahydro-isoquinolin-6-yl]-amide;
4'-trifluoromethyl-biphenyl-2-carboxylic acid [2-(2-acetylamino-ethyl)-1,2,3,4-tetrahydro-isoquinolin-6-yl]-amide;
(2-{6-[(4'-trifluoromethyl-biphenyl-2-carbonyl)-amino]-3,4-dihydro-1H-isoquinolin-2-yl}-ethyl)carbamic acid methyl ester;
4'-trifluoromethyl-biphenyl-2-carboxylic acid [2-(1H-imidazol-2-ylmethyl)-1,2,3,4-tetrahydro-isoquinolin-6-yl]-amide;
4'-trifluoromethyl-biphenyl-2-carboxylic acid [2-(2,2-diphenyl-ethyl)-1,2,3,4-tetrahydro-isoquinolin-6-yl]-amide;
4'-trifluoromethyl-biphenyl-2-carboxylic acid [2-(2-ethoxy-ethyl)-1,2,3,4-tetrahydro-isoquinolin-6-yl]-amide;
(S)—N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide;
(S)-2-[(4'-Trifluoromethyl-biphenyl-2-carbonyl)-amino]-quinoline-6-carboxylic acid (pentylcarbamoyl-phenyl-methyl)-amide;
1H-indole-2-carboxamide, 1-methyl-N-[(1S)-2-[methyl(phenylmethyl)amino]-2-oxo-1-phenylethyl]-5-[[[4'-(trifluoromethyl)[1,1'-biphenyl]-2-yl]carbonyl]amino]; and
N-[(1S)-2-(benzylmethylamino)-2-oxo-1-phenylethyl]-1-methyl-5-[[[4'-(trifluoromethyl)biphenyl-2-yl]carbonyl]amino]-1H-indole-2-carboxamide.

Any HMG-CoA synthase inhibitor may be used in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155-160: Meth. Enzymol. 1985; 110:19-26 and references cited therein). A variety of these compounds are described and referenced below, however other HMG-CoA synthase inhibitors will be known to those skilled in the art. U.S. Pat. No. 5,120,729 (the disclosure of which is hereby incorporated by reference) discloses certain beta-lactam derivatives. U.S. Pat. No. 5,064,856 (the disclosure of which is hereby incorporated by reference) discloses certain spiro-lactone derivatives prepared by culturing a microorganism (MF5253). U.S. Pat. No. 4,847,271 (the disclosure of which is hereby incorporated by reference) discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such compounds may cause this effect by decreasing levels of SREBP (sterol receptor binding protein) by inhibiting the activity of site-1 protease (S1P) or agonizing the oxzgenal receptor or SCAP. Such regulation is readily determined by those skilled in the art according to standard assays (Meth. Enzymol. 1985; 110:9-19). Several compounds are described and referenced below, however other inhibitors of HMG-CoA reductase gene expression will be known to those skilled in the art. U.S. Pat. No. 5,041,432 (the disclosure of which is incorporated by reference) discloses certain 15-substituted lanosterol derivatives. Other oxygenated sterols that suppress synthesis of HMG-CoA reductase are discussed by E. I. Mercer (Prog. Lip. Res. 1993; 32:357-416).

Any additional compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in commonly assigned U.S. Pat. No. 6,140,343 and commonly assigned U.S. Pat. No. 6,197,786. CETP inhibitors disclosed in these patents include compounds, such as [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, which is also known as torcetrapib. CETP inhibitors are also described in U.S. Pat. No. 6,723,752, which includes a number of CETP inhibitors including (2R)-3-{[3-(4-Chloro-3-ethyl-phenoxy)-phenyl]-[[3-(1,1,2,2-tetrafluoro-ethoxy)phenyl]-methyl]-amino}-1,1,1-trifluoro-2-propanol. Moreover, CETP inhibitors included herein are also described in U.S. patent application Ser. No. 10/807,838 filed Mar. 23, 2004. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815-816 (1996), and *Bioorg. Med. Chem. Lett.*; 6:1951-1954 (1996), respectively.

Exemplary CETP inhibitors include [2R,4S]-4-[(3,5-Bis-trifluoromethyl-benzyl)-methoxycarbonyl-amino]-2-ethyl-6-trifluoromethyl-3,4-dihydro-2H-quinoline-1-carboxylic acid ethyl ester; cis-(2R,4S)-2-(4-{4-[(3,5-Bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide; (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol; and (2R, 4R, 4aS)-4-[Amino-(3,5-bis-trifluoromethyl-phenyl)methyl]-2-ethyl-6-trifluoromethyl-3,4-dihydro-2H-quinoline-1-carboxylic acid isopropyl ester or a pharmaceutically acceptable salt of said compounds.

Any squalene synthetase inhibitor may be used in the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (Meth. Enzymol. 1969; 15: 393-454 and Meth. Enzymol. 1985; 110:359-373 and references contained therein). A variety of these compounds are described in and referenced below however other squalene synthetase inhibitors will be known to those skilled in the art. U.S. Pat. No. 5,026,554 (the disclosure of which is incorporated by reference) discloses fermentation products of the microorganism MF5465 (ATCC 74011) including zaragozic acid. A summary of other patented squalene synthetase inhibitors has been compiled (Curr. Op. Ther. Patents (1993) 861-4).

Any squalene epoxidase inhibitor may be used in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466-471). A variety of these compounds are described and referenced below, however other squalene epoxidase inhibitors will be known to those skilled in the art. U.S. Pat. Nos. 5,011,859 and 5,064,864 (the disclosures of which are incorporated by reference) disclose certain fluoro analogs of squalene. EP publication 395,768 A (the disclosure of which is incorporated by reference) discloses certain substituted allylamine derivatives. PCT publication WO 9312069 A (the disclosure of which is hereby incorporated by reference) discloses certain amino alcohol derivatives. U.S. Pat. No. 5,051,534 (the disclosure of which is hereby incorporated by reference) discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (FEBS Lett. 1989; 244:347-350.). In addition, the compounds described and referenced below are squalene cyclase inhibitors, however other squalene cyclase inhibitors will also be known to those skilled in the art. PCT publication WO9410150 (the disclosure of which is hereby incorporated by reference) discloses certain 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine. French patent publication 2697250 (the disclosure of which is hereby incorporated by reference) discloses certain beta, beta-dimethyl-4-piperidine ethanol derivatives such as 1-(1,5,9-trimethyldecyl)-beta, beta-dimethyl-4-piperidineethanol Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 (the disclosures of which are incorporated by reference) disclose certain azadecalin derivatives. EP publication 468,434 (the disclosure of which is incorporated by reference) discloses certain piperidyl ether and thio-ether derivatives such as 2-(1-piperidyl)pentyl isopentyl sulfoxide and 2-(1-piperidyl)ethyl ethyl sulfide. PCT publication WO 9401404 (the disclosure of which is hereby incorporated by reference) discloses certain acyl-piperidines such as 1-(1-oxopentyl-5-phenylthio)-4-(2-hydroxy-1-methyl)-ethyl)piperidine. U.S. Pat. No. 5,102,915 (the disclosure of which is hereby incorporated by reference) discloses certain cyclopropyloxy-squalene derivatives.

The compounds of the present invention may also be administered in combination with naturally occurring compounds that act to lower plasma cholesterol levels. These naturally occurring compounds are commonly called nutraceuticals and include, for example, garlic extract and niacin. A slow-release form of niacin is available and is known as Niaspan. Niacin may also be combined with other therapeutic agents such as lovastatin, or another is an HMG-CoA reductase inhibitor. This combination therapy with lovastatin is known as ADVICOR™ (Kos Pharmaceuticals Inc.).

Any cholesterol absorption inhibitor can be used as an additional in the combination aspect of the present invention. The term cholesterol absorption inhibition refers to the ability of a compound to prevent cholesterol contained within the lumen of the intestine from entering into the intestinal cells and/or passing from within the intestinal cells into the lymph system and/or into the blood stream. Such cholesterol absorption inhibition activity is readily determined by those skilled in the art according to standard assays (e.g., J. Lipid Res. (1993) 34: 377-395). Cholesterol absorption inhibitors are known to those skilled in the art and are described, for example, in PCT WO 94/00480. An example of a recently approved cholesterol absorption inhibitor is ZETIA™ (ezetimibe) (Schering-Plough/Merck).

Any ACAT inhibitor may be used in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Eli Lilly and Pierre Fabre).

A lipase inhibitor may be used in the combination therapy aspect of the present invention. A lipase inhibitor is a compound that inhibits the metabolic cleavage of dietary triglycerides or plasma phospholipids into free fatty acids and the corresponding glycerides (e.g. EL, HL, etc.). Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a glyceride and fatty acid. In the intestine, the resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Methods Enzymol. 286: 190-231).

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Methods Enzymol. 286: 190-231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92,125 (1987). Such gastric lipase inhibition activity is readily determined by those skilled in the art according to standard assays (e.g., Methods Enzymol. 286: 190-231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis (iminocarbonyl)dioximes related thereto may be prepared as described in Petersen et al., *Liebig's Annalen,* 562, 205-229 (1949).

A variety of pancreatic lipase inhibitors are described herein below. The pancreatic lipase inhibitors lipstatin, (2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), (2S, 3S, 5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of *Actinomycetes* strain MG147-CF2, are disclosed in Kitahara, et al., *J. Antibiotics,* 40 (11), 1647-1650 (1987). The pancreatic lipase inhibitors, ebelactone A and ebelactone B, and a process for the preparation thereof by the microbial cultivation of *Actinomycetes* strain MG7-G1, are disclosed in Umezawa, et al., *J. Antibiotics,* 33, 1594-1596 (1980). The use of ebelactones A and B in the suppression of monoglyceride formation is disclosed in Japanese Kokai 108-143457, published Jun. 4, 1996.

Other compounds that are marketed for hyperlipidemia, including hypercholesterolemia and which are intended to help prevent or treat atherosclerosis include bile acid sequestrants, such as Welchol® Colestid®, LoCholest® and Questran®; and fibric acid derivatives, such as Atromid®, Lopid® and Tricor®.

Diabetes can be treated by administering to a patient having diabetes (especially Type II), insulin resistance, impaired glucose tolerance, metabolic syndrome, or the like, or any of the diabetic complications such as neuropathy, nephropathy, retinopathy or cataracts, a therapeutically effective amount of a compound of the present invention in combination with other agents (e.g., insulin) that can be used to treat diabetes. This includes the classes of anti-diabetic agents (and specific agents) described herein.

Any glycogen phosphorylase inhibitor can be used as the second agent in combination with a compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41 (1998) 2934-2938). A variety of glycogen phosphorylase inhibitors are known to those skilled in the art including those described in WO 96/39384 and WO 96/39385.

Any aldose reductase inhibitor can be used in combination with a compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, *Diabetes*, 29:861-864 (1980). "Red Cell Sorbitol, an Indicator of Diabetic Control"). A variety of aldose reductase inhibitors are known to those skilled in the art, such as those described in U.S. Pat. No. 6,579,879, which includes 6-(5-chloro-3-methyl-benzo-furan-2-sulfonyl)-2H-pyridazin-3-one.

Any sorbitol dehydrogenase inhibitor can be used in combination with a compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem (2000) 280: 329-331). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214).

A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Methods Enzymol. (1955) 1: 149). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R,3R,4R,5S)-3,4,5-trihydroxy-2-(hydroxymethyl)piperidino]-α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed in U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Additional anti-diabetic compounds, which can be used as the second agent in combination with a compound of the present invention, include, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1, 6-BPase(Metabasis/Sankyo), GLP-1/analogs (AC 2993, also known as exendin-4), insulin and insulin mimetics (Merck natural products). Other examples would include PKC-β inhibitors and AGE breakers. The compounds of the present invention can be used in combination with anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, $β_3$ adrenergic receptor agonists, apolipoprotein-B secretion/microsomal triglyceride transfer protein (apo-B/MTP) inhibitors, MCR-4 agonists, cholecystokinin-A (CCK-A) agonists, monoamine reuptake inhibitors (e.g., sibutramine), sympathomimetic agents, serotoninergic agents, cannabinoid receptor (CB-1) antagonists (e.g., rimonabant described in U.S. Pat. No. 5,624,941 (SR-141,716A), purine compounds, such as those described in US Patent Publication No. 2004/0092520; pyrazolo[1,5-a][1,3,5]triazine compounds, such as those described in U.S. Non-Provisional patent application Ser. No. 10/763,105 filed on Jan. 21, 2004; and bicyclic pyrazolyl and imidazolyl compounds, such as those described in U.S. Provisional Application No. 60/518,280 filed on Nov. 7, 2003), dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like.

Rimonabant (SR141716A also known under the tradename Accomplia™ available from Sanofi-Synthelabo) can be prepared as described in U.S. Pat. No. 5,624,941. Other suitable CB-1 antagonists include those described in U.S. Pat. Nos. 5,747,524, 6,432,984 and 6,518,264; U.S. Patent Publication Nos. US2004/0092520, US2004/0157839, US200410214855, and US2004/0214838; U.S. patent application Ser. No. 10/971,599 filed on Oct. 22, 2004; and PCT Patent Publication Nos. WO 02/076949, WO 03/075660, WO04/048317, WO04/013120, and WO 04/012671.

Preferred apolipoprotein-B secretion/microsomal triglyceride transfer protein (apo-B/MTP) inhibitors for use as anti-obesity agents are gut-selective MTP inhibitors, such as dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl)piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431. As used herein, the term "gut-selective" means that the MTP inhibitor has a higher exposure to the gastrointestinal tissues versus systemic exposure.

Any thyromimetic can be used as the second agent in combination with a compound of the present invention. Such thyromimetic activity is readily determined by those skilled in the art according to standard assays (e.g., Atherosclerosis (1996) 126: 53-63). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other antiobesity agents include sibutramine which can be prepared as described in U.S. Pat. No. 4,929,629. and bromocriptine which can be prepared as described in U.S. Pat. Nos. 3,752,814 and 3,752,888.

The compounds of the present invention can also be used in combination with other antihypertensive agents. Any antihypertensive agent can be used as the second agent in such combinations and examples are provided herein. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®.

Amlodipine and related dihydropyridine compounds are disclosed in U.S. Pat. No. 4,572,909, which is incorporated herein by reference, as potent anti-ischemic and antihypertensive agents. U.S. Pat. No. 4,879,303, which is incorporated herein by reference, discloses amlodipine benzenesulfonate salt (also termed amlodipine besylate). Amlodipine and amlodipine besylate are potent and long lasting calcium channel blockers. As such, amlodipine, amlodipine besylate, amlodipine maleate and other pharmaceutically acceptable acid addition salts of amlodipine have utility as antihypertensive agents and as antiischemic agents. Amlodipine besylate is currently sold as Norvasc®. Amlodipine has the formula

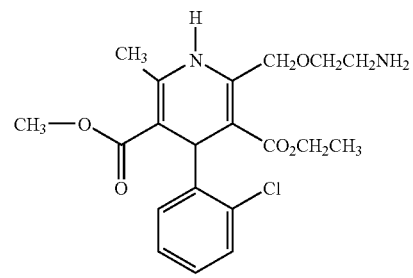

Calcium channel blockers which are within the scope of this invention include, but are not limited to: bepridil, which may be prepared as disclosed in U.S. Pat. No. 3,962,238 or U.S. Reissue No. 30,577; clentiazem, which may be prepared as disclosed in U.S. Pat. No. 4,567,175; diltiazem, which may be prepared as disclosed in U.S. Pat. No. 3,562, fendiline, which may be prepared as disclosed in U.S. Pat. No. 3,262,977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572, 909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485,847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267,104; lomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265,758; and perhexiline, which may be prepared as disclosed in British Patent No. 1,025,578. The disclosures of all such U.S. Patents are incorporated herein by reference.

Angiotensin Converting Enzyme Inhibitors (ACE-Inhibitors) which are within the scope of this invention include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046,889 and 4,105,776; ceronapril, which may be prepared as disclosed in U.S. Pat. No. 4,452,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361. The disclosures of all such U.S. patents are incorporated herein by reference.

Angiotensin-II receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578. The disclosures of all such U.S. patents are incorporated herein by reference.

Beta-adrenergic receptor blockers (beta- or β-blockers) which are within the scope of this invention include, but are not limited to: acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., Journal of Medicinal Chemistry, 1982, 25, 670; epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Helv. Chim. Acta, 1971, 54, 241; metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,769I; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., Journal of Medicinal Chemistry, 1966, 9, 88; sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824. The disclosures of all such U.S. patents are incorporated herein by reference.

Alpha-adrenergic receptor blockers (alpha- or α-blockers) which are within the scope of this invention include, but are not limited to: amosuialol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art. The disclosures of all such U.S. patents are incorporated herein by reference.

The term "vasodilator," where used herein, is meant to include cerebral vasodilators, coronary vasodilators and peripheral vasodilators. Cerebral vasodilators within the scope of this invention include, but are not limited to: bencyclane; cinnarizine; citicoline, which may be isolated from natural sources as disclosed in Kennedy et al., Journal of the American Chemical Society, 1955, 77, 250 or synthesized as disclosed in Kennedy, Journal of Biological Chemistry, 1956, 222, 185; cyclandelate, which may be prepared as disclosed in U.S. Pat. No. 3,663,597; ciclonicate, which may be prepared as disclosed in German Patent No. 1,910,481; diisopropylamine dichloroacetate, which may be prepared as disclosed in British Patent No. 862,248; eburnamonine, which may be prepared as disclosed in Hermann et al., Journal of the American Chemical Society, 1979, 101, 1540; fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No. 3,773,939; ibudilast, which may be prepared as disclosed in U.S. Pat. No. 3,850,941; ifenprodil, which may be prepared as disclosed in U.S. Pat. No. 3,509,164; lomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., Journal of the American Chemical Society, 1942, 64, 1722; nicergoline, which may be prepared as disclosed above; nimodipine, which may be prepared as disclosed in U.S. Pat. No. 3,799,934; papaverine, which may be prepared as reviewed in Goldberg, Chem. Prod. Chem. News, 1954, 17, 371; pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444. The disclosures of all such U.S. patents are incorporated herein by reference.

Coronary vasodilators within the scope of this invention include, but are not limited to: amotriphene, which may be prepared as disclosed in U.S. Pat. No. 3,010,965; bendazol, which may be prepared as disclosed in J. Chem. Soc. 1958, 2426; benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No. 3,282,938; clobenfural, which may be prepared as disclosed in British Patent No. 1,160,925; clonitrate, which may be prepared from propanediol according to methods well known to those skilled in the art, e.g., see Annalen, 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113, efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Patent No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., Journal of the Chemical Society, 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638,422-3; perhexilline, which may be prepared as disclosed above; pimefylline, which may be prepared as disclosed in U.S. Pat. No. 3,350,400; prenylamine, which may be prepared as disclosed in U.S. Pat. No. 3,152,173; propatyl nitrate, which may be prepared as disclosed in French Patent No. 1,103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699. The disclosures of all such U.S. patents are incorporated herein by reference.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., Journal of the American Chemical Society, 1945, 67, 1894; bencyclane, which may be prepared as disclosed above; betahistine, which may be prepared as disclosed in Walter et al.; Journal of the American Chemical Society, 1941, 63, 2771; bradykinin, which may be prepared as disclosed in Hamburg et al., Arch. Biochem. Biophys., 1958, 76, 252; brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent Nos. 1,460,571; ciclonicate, which may be prepared as disclosed in German Patent No. 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810; fenoxedil, which may be prepared as disclosed above; flunarizine, which may be prepared as disclosed above; heproni- cate, which may be prepared as disclosed in U.S. Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgett et al., Journal of the American Chemical Society, 1947, 69, 2907; isoxsuprine, which may be prepared as disclosed in U.S. Pat. No. 3,056,836; kallidin, which may be prepared as disclosed in *Biochem. Biophys. Res. Commun.*, 1961, 6, 210; kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No. 3,422,107; piribedil, which may be prepared as disclosed in U.S. Pat. No. 3,299,067; prostaglandin $E_1$, which may be prepared by any of the methods referenced in the Merck Index, Twelfth Edition, Budaveri, Ed., New Jersey, 1996, p. 1353; suloctidil, which may be prepared as disclosed in German Patent No. 2,334,404; tolazoline, which may be prepared as disclosed in U.S. Pat. No. 2,161,938; and xanthinol niacinate, which may be prepared as disclosed in German Patent No. 1,102,750 or Korbonits et al., Acta. Pharm. Hung., 1968, 38, 98. The disclosures of all such U.S. patents are incorporated herein by reference.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255,241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., Ber., 1957, 90, 957; muzolimine, which may be prepared as disclosed in U.S. Pat. No. 4,018,890; perhexiline, which may be prepared as disclosed above; ticrynafen, which may be prepared as disclosed in U.S. Pat. No. 3,758,506; triamterene which may be prepared as disclosed in U.S. Pat. No. 3,081,230; and urea. The disclosures of all such U.S. patents are incorporated herein by reference.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136th Am. Soc. Meeting (Atlantic City, September 1959), Abstract of papers, pp 13-O; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which may be prepared as disclosed in Belgian Patent No. 587,225; cyclothiazide, which may be prepared as disclosed in Whitehead et al., Journal of Organic Chemistry, 1961, 26, 2814; epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164,588; hydroflumethiazide, which may be prepared as disclosed in U.S. Pat. No. 3,254,076; methyclothiazide, which may be prepared as disclosed in Close et al., Journal of the American Chemical Society, 1960, 82, 1132; meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., Journal of the American Chemical Society, 1960, 82, 1132; and trichlormethiazide, which may be prepared as disclosed in deStevens et al., Experientia, 1960, 16, 113. The disclosures of all such U.S. patents are incorporated herein by reference.

Diuretic sulfonamide derivatives within the scope of this invention include, but are not limited to: acetazolamide, which may be prepared as disclosed in U.S. Pat. No. 2,980,679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, Rec. Trav. Chim., 1918, 37, 307; clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777. The disclosures of all such U.S. patents are incorporated herein by reference.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase threefold over the next 60 years, and one study has estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, the disclosure of which is incorporated herein by reference. Preferred polyphosphonates are geminal diphosphonates (also referred to as bis-phosphonates). Tiludronate disodium is an especially preferred polyphosphonate. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used in the combination aspect of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods, and Eriksen E. F. et al., Bone Histomorphometry, Raven Press, New York, 1994, pages 1-74; Grier S. J. et. al., The Use of Dual-Energy X-Ray Absorptiometry In Animals, Inv. Radiol., 1996, 31(1): 50-62; Wahner H. W. and Fogelman I., The Evaluation of Osteoporosis: Dual Energy X-Ray Absorptiometry in Clinical Practice., Martin Dunitz Ltd., London 1994, pages 1-296). A variety of these compounds are described and referenced below.

Another preferred estrogen agonist/antagonist is 3-(4-(1,2-diphenyl-but-1-enyl)-phenyl)-acrylic acid, which is disclosed in Willson et al., Endocrinology, 1997, 138, 3901-3911.

Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516, the disclosure of which is incorporated herein by reference.

Another related compound is 4-hydroxy tamoxifen, which is disclosed in U.S. Pat. No. 4,623,660, the disclosure of which is incorporated herein by reference.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)-hydrochloride) which is disclosed in U.S. Pat. No. 4,418,068, the disclosure of which is incorporated herein by reference.

Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225, the disclosure of which is incorporated herein by reference.

Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287, the disclosure of which is incorporated herein by reference. Also preferred is levormeloxifene.

Another preferred estrogen agonist/antagonist is idoxifene: (E)-1-(2-(4-(1-(4-iodo-phenyl)-2-phenylbut-1-enyl)-phenoxy)-ethyl)-pyrrolidinone, which is disclosed in U.S. Pat. No. 4,839,155, the disclosure of which is incorporated herein by reference.

Another preferred estrogen agonist/antagonist is 2-(4-methoxy-phenyl)-3-[4-(2-piperidin-1-ylethoxy)-phenoxy]- benzo[b]thiophen-6-ol which is disclosed in U.S. Pat. No. 5,488,058, the disclosure of which is incorporated herein by reference.

Another preferred estrogen agonist/antagonist is 6-(4-hydroxy-phenyl)-5-(4-(2-piperidin-1-ylethoxy)-benzyl)-naphthalen-2-ol, which is disclosed in U.S. Pat. No. 5,484,795, the disclosure of which is incorporated herein by reference.

Another preferred estrogen agonist/antagonist is (4-(2-(2-aza-bicyclo[2.2.1]hept-2-yl)-ethoxy)phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc.

Other preferred estrogen agonist/antagonists include the compounds, TSE-424 (Wyeth-Ayerst Laboratories) and arazoxifene.

Other preferred estrogen agonist/antagonists include compounds as described in commonly assigned U.S. Pat. No. 5,552,412, the disclosure of which is incorporated herein by reference. Especially preferred compounds described therein are:
cis-6-(4-fluoro-phenyl)-5-(4-(2-piperidin-1-yl-ethoxy)-phenyl)-5,6,7,8-tetrahydro-naphthalen-2-ol;
(−)-cis-6-phenyl-5-(4-(2-pyrrolidin-1-yl-ethoxy)-phenyl)-5,6,7,8-tetrahydro-naphthalen-2-ol (also known as lasofoxifene);
cis-6-phenyl-5-(4-(2-pyrrolidin-1-yl-ethoxy)-phenyl)-5,6,7,8-tetrahydro-naphthalen-2-ol;
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4''-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalen-2-ol; and
1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is incorporated herein by reference). U.S. Pat. No. 4,133,814 discloses derivatives of 2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; and vitamin D and vitamin D analogs.

Any selective androgen receptor modulator (SARM) can be used in combination with a compound of the present invention. A selective androgen receptor modulator (SARM) is a compound that possesses androgenic activity and which exerts tissue-selective effects. SARM compounds can function as androgen receptor agonists, partial agonists, partial antagonists or antagonists. Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino[3,2-g]quinoline derivatives, 1,2-dihydropyridino [5,6-g]quinoline derivatives and piperidino[3,2-g]quinolinone derivatives.

Cypterone, also known as (1b,2b) 6-chloro-1,2-dihydro-17-hydroxy-3'H-cyclopropa[1,2]pregna-1,4,6-triene-3,20-dione is disclosed in U.S. Pat. No. 3,234,093. Chlormadinone, also known as 17-(acetyloxy)-6-chloropregna-4,6-diene-3,20-dione, in its acetate form, acts as an anti-androgen and is disclosed in U.S. Pat. No. 3,485,852. Nilutamide, also known as 5,5-dimethyl-3-[4-nito-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a', a',a'-trifluoro-3-(4-fluorophenylsulfonyl)-2-hydroxy-2-methylpropiono-m-toluidide and the trade name Casodex® is disclosed in EP-100172. The enantiomers of biclutamide are discussed by Tucker and Chesterton, *J. Med. Chem.* 1988, 31, 885-887. Hydroxyflutamide, a known androgen receptor antagonist in most tissues, has been suggested to function as a SARM for effects on IL-6 production by osteoblasts as disclosed in Hofbauer et al. *J. Bone Miner. Res.* 1999, 14, 1330-1337. Additional SARMs have been disclosed in U.S. Pat. No. 6,017,924; WO 01/16108, WO 01/16133, WO 01/16139, WO 02/00617, WO 02/16310, U.S. Patent Application Publication No. US 2002/0099096, U.S. Patent Application Publication No. US 2003/0022868, WO 03/1011302 and WO 03/011824. All of the above references are hereby incorporated by reference herein.

The starting materials and reagents for the above described compounds, are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Some of the compounds of this invention or intermediates in their synthesis have asymmetric carbon atoms and therefore are enantiomers or diastereomers. Diasteromeric mixtures can be separated into their individual diastereomers on the basis of their physical chemical differences by methods known per se, for example, by chromatography and/or fractional crystallization. Enantiomers can be separated by, for example, chiral HPLC methods or converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the compounds or an intermediate in their synthesis which contain an acidic or basic moiety may be separated into their corresponding pure enantiomers by forming a diastereomic salt with an optically pure chiral base or acid (e.g., 1-phenyl-ethyl amine, dibenzyl tartrate or tartaric acid) and separating the diasteromers by fractional crystallization followed by neutralization to break the salt, thus providing the corresponding pure enantiomers. All such isomers, including diastereomers, enantiomers and mixtures thereof are considered as part of this invention for all of the compounds of the present invention, including the compounds of the present invention. Also, some of the compounds of this invention are atropisomers (e.g., substituted biaryls) and are considered as part of this invention.

More specifically, the compounds of this invention may be obtained in enantiomerically enriched form by resolving the racemate of the final compound or an intermediate in its synthesis, employing chromatography (preferably high pressure liquid chromatography [HPLC]) on an asymmetric resin (preferably Chiralcel™ AD or OD (obtained from Chiral Technologies, Exton, Pa.)) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine), Concentration of the product containing fractions affords the desired materials.

Some of the compounds of this invention are acidic and they form a salt with a pharmaceutically acceptable cation. Some of the compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

In addition, when the compounds of this invention form hydrates or solvates they are also within the scope of the invention.

The compounds of this invention, their prodrugs and the salts of such compounds and prodrugs are all adapted to therapeutic use as agents that inhibit cholesterol ester transfer protein activity in mammals, particularly humans. Thus, the compounds of this invention elevate plasma HDL cholesterol, its associated components, and the functions performed by them in mammals, particularly humans. By virtue of their activity, these agents also reduce plasma levels of triglycerides, VLDL cholesterol, Apo-B, LDL cholesterol and their associated components in mammals, particularly humans. Moreover, these compounds are useful in equalizing LDL cholesterol and HDL cholesterol. Hence, these compounds are useful for the treatment and correction of the various dyslipidemias observed to be associated with the development and incidence of atherosclerosis and cardiovascular disease, including coronary artery disease, coronary heart disease, coronary vascular disease, peripheral vascular disease, hypoalphalipoproteinemia, hyperbetalipoproteinemia, hypertriglyceridemia, hypercholesterolemia, familial-hypercholesterolemia, low HDL and associated components, elevated LDL and associated components, elevated Lp(a), elevated small-dense LDL, elevated VLDL and associated components and post-prandial lipemia.

Further, introduction of a functional CETP gene into an animal lacking CETP (mouse) results in reduced HDL levels (Agellon, L. B., et al: *J. Biol. Chem.* (1991) 266: 10796-10801.) and increased susceptibility to atherosclerosis. (Marotti, K. R., et al: *Nature* (1993) 364: 73-75.). Also, inhibition of CETP activity with an inhibitory antibody raises HDL-cholesterol in hamster (Evans, G. F., et al: *J. of Lipid Research* (1994) 35: 1634-1645.) and rabbit (Whitlock, M. E., et al: *J. Clin. Invest.* (1989) 84: 129-137). Suppression of increased plasma CETP by intravenous injection with antisense oligodeoxynucleotides against CETP mRNA reduced atherosclerosis in cholesterol-fed rabbits (Sugano, M., et al: *J. of Biol. Chem.* (1998) 273: 5033-5036.) Importantly, human subjects deficient in plasma CETP, due to a genetic mutation possess markedly elevated plasma HDL-cholesterol levels and apolipoprotein A-l, the major apoprotein component of HDL. In addition, most demonstrate markedly decreased plasma LDL cholesterol and apolipoprotein B (the major apolipoprotein component of LDL. (Inazu, A., Brown, M. L., Hester, C. B., et al.: *N. Engl. J. Med.* (1990) 323: 1234-1238.)

Given the negative correlation between the levels of HDL cholesterol and HDL associated lipoproteins, and the positive correlation between triglycerides, LDL cholesterol, and their associated apolipoproteins in blood with the development of cardiovascular, cerebral vascular and peripheral vascular diseases, the compounds of this invention, their prodrugs and the salts of such compounds and prodrugs, by virtue of their pharmacologic action, are useful for the prevention, arrestment and/or regression of atherosclerosis and its associated disease states. These include cardiovascular disorders (e.g., angina, ischemia, cardiac ischemia and myocardial infarction), complications due to cardiovascular disease therapies (e.g., reperfusion injury and angioplastic restenosis), hypertension, elevated cardiovascular risk associated with hypertension, stroke, atherosclerosis associated with organ transplantation, cerebrovascular disease, cognitive dysfunction (including, but not limited to, dementia secondary to atherosclerosis, transient cerebral ischemic attacks, neurodegeneration, neuronal deficient, and delayed onset or procession of Alzheimer's disease), elevated levels of oxidative stress, elevated levels of CReactive Protein, Metabolic Syndrome and elevated levels of HbA1C.

Because of the beneficial effects widely associated with elevated HDL levels, an agent which inhibits CETP activity in humans, by virtue of its HDL increasing ability, also provides valuable avenues for therapy in a number of other disease areas as well.

Thus, given the ability of the compounds of this invention, their prodrugs and the salts of such compounds and prodrugs to alter lipoprotein composition via inhibition of cholesterol ester transfer, they are of use in the treatment of vascular complications associated with diabetes, lipoprotein abnormalities associated with diabetes and sexual dysfunction associated with diabetes and vascular disease. Hyperlipidemia is present in most subjects with diabetes mellitus (Howard, B. V. 1987. J. Lipid Res. 28, 613). Even in the presence of normal lipid levels, diabetic subjects experience a greater risk of cardiovascular disease (Kannel, W. B. and McGee, D. L. 1979. Diabetes Care 2, 120). CETP-mediated cholesteryl ester transfer is known to be abnormally increased in both insulin-dependent (Bagdade, J. D., Subbaiah, P. V. and Ritter, M. C. 1991. Eur. J. Clin. Invest. 21, 161) and non-insulin dependent diabetes (Bagdade. J. D., Ritter, M. C., Lane, J. and Subbaiah. 1993. Atherosclerosis 104, 69). It has been suggested that the abnormal increase in cholesterol transfer results in changes in lipoprotein composition, particularly for VLDL and LDL, that are more atherogenic (Bagdade, J. D., Wagner, J. D., Rudel, L. L., and Clarkson, T. B. 1995 J. Lipid Res. 36, 759). These changes would not necessarily be observed during routine lipid screening. Thus the present invention will be useful in reducing the risk of vascular complications as a result of the diabetic condition.

The described agents are useful in the treatment of obesity and elevated cardiovascular risk associated with obesity. In both humans (Radeau, T., Lau, P., Robb, M., McDonnell, M., Ailhaud, G. and McPherson, R., 1995. *Journal of Lipid Research*. 36 (12):2552-61) and nonhuman primates (Quinet, E., Tall, A., Ramakrishnan, R. and Rudel, L., 1991. *Journal of Clinical Investigation*. 87 (5):1559-66) mRNA for CETP is expressed at high levels in adipose tissue. The adipose message increases with fat feeding (Martin, L. J., Connelly, P. W., Nancoo, D., Wood, N., Zhang, Z. J., Maguire, G., Quinet, E., Tall, A. R., Marcel, Y. L. and McPherson, R., 1993. *Journal of Lipid Research*. 34 (3):437-46), and is translated into functional transfer protein and through secretion contributes significantly to plasma CETP levels. In human adipocytes the bulk of cholesterol is provided by plasma LDL and HDL (Fong, B. S., and Angel, A., 1989. *Biochimica et Biophysica Acta*. 1004 (1):53-60). The uptake of HDL cholesteryl ester is dependent in large part on CETP (Benoist, F., Lau, P., McDonnell, M., Doelle, H., Milne, R. and McPherson, R., 1997. *Journal of Biological Chemistry.* 272 (38):23572-7). This ability of CETP to stimulate HDL cholesteryl uptake, coupled with the enhanced binding of HDL to adipocytes in obese subjects (Jimenez, J. G., Fong, B., Julien, P., Despres, J. P., Rotstein, L., and Angel, A., 1989. *International Journal of Obesity.* 13 (5):699-709), suggests a role for CETP, not only in generating the low HDL phenotype for these subjects, but in the development of obesity itself by promoting cholesterol accumulation. Inhibitors of CETP activity that block this process therefore serve as useful adjuvants to dietary therapy in causing weight reduction.

CETP inhibitors are useful in the treatment of inflammation due to Gram-negative sepsis and septic shock. For example, the systemic toxicity of Gram-negative sepsis is in large part due to endotoxin, a lipopolysaccharide (LPS) released from the outer surface of the bacteria, which causes an extensive inflammatory response. Lipopolysaccharide can form complexes with lipoproteins (Ulevitch, R. J., Johnston, A. R., and Weinstein, D. B., 1981. J. Clin. Invest. 67, 827-37). In vitro studies have demonstrated that binding of LPS to HDL substantially reduces the production and release of mediators of inflammation (Ulevitch, R. J., Johhston, A. R., 1978. J. Clin. Invest. 62, 1313-24). In vivo studies show that transgenic mice expressing human apo-AI and elevated HDL levels are protected from septic shock (Levine, D. M., Parker, T. S., Donnelly, T. M., Walsh, A. M., and Rubin, A. L. 1993. Proc. Natl. Acad. Sci. 90, 12040-44). Importantly, administration of reconstituted HDL to humans challenged with endotoxin resulted in a decreased inflammatory response (Pajkrt, D., Doran, J. E., Koster, F., Lerch, P. G., Arnet, B., van der Poll, T., ten Cate, J. W., and van Deventer, S. J. H. 1996. J. Exp. Med. 184, 1601-08). The CETP inhibitors, by virtue of the fact that they raise HDL levels, attenuate the development of inflammation and septic shock. These compounds would also be useful in the treatment of endotoxemia, autoimmune diseases and other systemic disease indications, organ or tissue transplant rejection and cancer.

The utility of the compounds of the invention, their prodrugs and the salts of such compounds and prodrugs as medical agents in the treatment of the above described disease/ conditions in mammals (e.g. humans, male or female) is demonstrated by the activity of the compounds of this invention in conventional assays and the in vitro assay described below. The in vivo assay (with appropriate modifications within the skill in the art) may be used to determine the activity of other lipid or triglyceride controlling agents as well as the compounds of this invention. Such assays also provide a means whereby the activities of the compounds of this invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases.

The following protocols can of course be varied by those skilled in the art.

The hyperalphacholesterolemic activity of the compounds can be determined by assessing the effect of these compounds on the action of cholesteryl ester transfer protein by measuring the relative transfer ratio of radiolabeled lipids between lipoprotein fractions, essentially as previously described by Morton in J. Biol. Chem. 256, 11992, 1981 and by Dias in Clin. Chem. 34, 2322, 1988.

CETP in Vitro Assay

The following is a brief description of assays of cholesteryl ester transfer in 97% (whole) or diluted human plasma (in vitro) and animal plasma (ex vivo): CETP activity in the presence or absence of drug is assayed by determining the transfer of $^3$H-labeled cholesteryl oleate (CO) from exogenous tracer HDL or LDL to the nonHDL or HDL lipoprotein fraction in human plasma, respectively, or from $^3$H-labeled LDL to the HDL fraction in animal plasma. Labeled human lipoprotein substrates are prepared similarly to the method described by Morton in which the endogenous CETP activity in plasma is employed to transfer $^3$H—CO from phospholipid liposomes to all the lipoprotein fractions in plasma. $^3$H-labeled LDL and HDL are subsequently isolated by sequential ultracentrifugation at the density cuts of 1.019-1.063 and 1.10-1.21 g/ml, respectively.

For the 97% or whole plasma activity assay, $^3$H-labeled HDL is added to plasma at 10-25 nmoles CO/ml and the samples incubated at 37° C. for 2.5-3 hrs. Non-HDL lipoproteins are then precipitated by the addition of an equal volume of 20% (wt/vol) polyethylene glycol 8000 (Dias). The samples are centrifuged 750 g×20 minutes and the radioactivity contained in the HDL-containing supernatant determined by liquid scintillation counting. Introducing varying quantities of the compounds of this invention as a solution in dimethylsulfoxide into human plasma, before addition of the radiolabeled cholesteryl oleate, and comparing the amounts of radiolabel transferred compared to incubations containing no inhibitor compounds allows the cholesteryl ester transfer inhibitory activities to be determined.

When a more sensitive assay is desirable, an in vitro assay using diluted human plasma is utilized. For this assay, $^3$H-labeled LDL is added to plasma at 50 nmoles CO/ml and the samples incubated at 37° C. for 7 hrs. Non-HDL lipoproteins are then precipitated by the addition of potassium phosphate to 100 mM final concentration followed by manganese chloride to 20 mM final concentration. After vortexing, the samples are centrifuged 750 g×20 minutes and the radioactivity contained in the HDL-containing supernatant determined by liquid scintillation counting. Introducing varying quantities of the compounds of this invention as a solution in dimethylsulfoxide into diluted human plasma, before addition of the radiolabeled cholesteryl oleate, and comparing the amounts of radiolabel transferred compared to incubations containing no inhibitor compounds allows the cholesteryl ester transfer inhibitory activities to be determined. This assay has been adapted to run in microtiter plate format with liquid scintillation counting accomplished using a Wallac plate reader.

Alternatively, the CETP inhibitory activity of compounds can be determined using microtiter plate-based fluorescent transfer assays where the CETP-dependent transfer of a self-quenching cholesteryl ester analog (Bodipy-CE) from human ApoAl-containing emulsion particles to the endogenous lipoproteins in plasma is monitored.

Fluorescent Bodipy-CE donors are prepared by drying down 14 mg of PC, 1.6 mg triolein and 3.5 mg of BODIPY-CE at 60° C. in a vacuum oven and then hydrating the lipids at 80° C. in 12 ml of PBS by probe sonication (at 25% of full power setting) for 2 min under a stream of $N_2$. The lipid mixture is then cooled to 45° C. and 5 mg (0.125 ?M) of human apolipoprotein Al (from Biodesign, Saco Me.) is added, and again sonicated (at 25% of full power) for 20 min at 45° C., pausing after each minute to allow the probe to cool. The resulting emulsion is spun for 30 min at 3000×g to remove metal probe fragments and then adjusted to 1.12 gm/ml with sodium bromide and layered below a solution of NaBr 1.10 g/ml (16 ml) and subjected to density gradient ultracentrifugation for 24 hours at 50,000-×g to remove unincorporated apolipoprotein Al and small dense particles that remain at the bottom of the gradient. The more buoyant emulsion particles are collected from the top of the gradient and dialyzed in 6 liters (2 changes) of PBS/0.02% azide, and diluted to the appropriate concentrations prior to use.

The CETP-dependent transfer of fluorescent CE analog is monitored in incubations containing the fluorescent human-apolipoprotein Al-containing donor particles, and a source of CETP and acceptor lipoproteins which in these cases are present in diluted human plasma. Bodipy CE fluorescence in the donor particles in the unincubated donor particles is quenched, and the CETP-dependent transfer of Bodipy CE to acceptor particles results in an increase in fluorescence.

When a high sensitivity assay is desired, compounds in 100% dimethyl sulfoxide are tested in a 2.5% plasma 384-well microtiter plate assay. One microliter of compound in 100% dimethyl sulfoxide is added to wells containing 20 ul of 3.75% human plasma (diluted with PBS) using a clonemaster solution transfer device. Transfer is initiated via the addition of 10 ul of 7.5% donors (also diluted with PBS). Following mixing, each plate is taped or placed in a Matripress plate stacker to avoid evaporation and incubated overnight at room temp. (16-20 hrs). Fluorescence is determined on a fluorescent plate reader, 485/530 nm filters, 505 nm dichroic filter. Note that depending upon liquid handling capabilities the intermediate dilutions of plasma and fluorescent donors and the aliquot size of those dilutions can be adjusted as necessary.

When a lower sensitivity assay is desired compounds are tested in a 20% plasma assay that is conceptually similar to the 2.5% assay. Two microliters of compound are added to dry, 96-well, half-area microtiter plates followed by 48 ul of 40% human plasma (diluted in PBS) and 50 ul of 40% donor solution. The fluorescent intensity is monitored after 3 hr incubation at room temperature. In the case of either the 2.5% or the 20% assay, the percent inhibition of CE transfer by compound is calculated by comparing to wells containing fluorescent donors and plasma but no compound.

CETP in Vivo Assay

Activity of these compounds in vivo can be determined by the amount of agent required to be administered, relative to control, to inhibit cholesteryl ester transfer activity by 50% at various time points ex vivo or to elevate HDL cholesterol by a given percentage in a CETP-containing animal species. Transgenic mice expressing both human CETP and human apolipoprotein Al (Charles River, Boston, Mass.) may be used to assess compounds in vivo. The compounds to be examined are administered by oral gavage in an emulsion vehicle containing 20% (v:v) olive oil and 80% sodium taurocholate (0.5%). Blood is taken from mice retroorbitally before dosing, if a predose blood sample is desirable. At various times after dosing, ranging from 4 h to 24 h, the animals are sacrificed, blood obtained by heart puncture, and lipid parameters measured, including total cholesterol, HDL and LDL cholesterol, and triglycerides. CETP activity is determined by a method similar to that described above except that $^3$H-cholesteryl oleate-containing LDL is used as the donor source as opposed to HDL. The values obtained for lipids and transfer activity are compared to those obtained prior to dosing and/or to those from mice receiving vehicle alone.

Plasma Lipids Assay

The activity of these compounds may also be demonstrated by determining the amount of agent required to alter plasma lipid levels, for example HDL cholesterol levels, LDL cholesterol levels, VLDL cholesterol levels or triglycerides, in the plasma of certain mammals, for example marmosets that possess CETP activity and a plasma lipoprotein profile similar to that of humans (Crook et al. Arteriosclerosis 10, 625, 1990). Adult marmosets are assigned to treatment groups so that each group has a similar mean±SD for total, HDL, and/or LDL plasma cholesterol concentrations. After group assignment, marmosets are dosed daily with compound as a dietary admix or by intragastric intubation for from one to eight days. Control marmosets receive only the dosing vehicle. Plasma total, LDL VLDL and HDL cholesterol values can be determined at any point during the study by obtaining blood from an antecubital vein and separating plasma lipoproteins into their individual subclasses by density gradient centrifugation, and by measuring cholesterol concentration as previously described (Crook et al. Arteriosclerosis 10, 625, 1990).

In Vivo Atherosclerosis Assay

Anti-atherosclerotic effects of the compounds can be determined by the amount of compound required to reduce the lipid deposition in rabbit aorta. Male New Zealand White rabbits are fed a diet containing 0.2% cholesterol and 10% coconut oil for 4 days (meal-fed once per day). Rabbits are bled from the marginal ear vein and total plasma cholesterol values are determined from these samples. The rabbits are then assigned to treatment groups so that each group has a similar mean±SD for total plasma cholesterol concentration, HDL cholesterol concentration, triglyceride concentration and/or cholesteryl ester transfer protein activity. After group assignment, rabbits are dosed daily with compound given as a dietary admix or on a small piece of gelatin based confection. Control rabbits receive only the dosing vehicle, be it the food or the gelatin confection. The cholesterol/coconut oil diet is continued along with the compound administration throughout the study. Plasma cholesterol values and cholesteryl ester transfer protein activity can be determined at any point during the study by obtaining blood from the marginal ear vein. After 3-5 months, the rabbits are sacrificed and the aortae are removed from the thoracic arch to the branch of the iliac arteries. The aortae are cleaned of adventitia, opened longitudinally and then analyzed unstained or stained with Sudan IV as described by Holman et. al. (Lab, Invest. 1958, 7, 42-47). The percent of the lesioned surface area is quantitated by densitometry using an Optimas Image Analyzing System (Image Processing Systems). Reduced lipid deposition is indicated by a reduction in the percent of lesioned surface area in the compound-receiving group in comparison with the control rabbits.

Antiobesity Protocol

The ability of CETP inhibitors to cause weight loss can be assessed in obese human subjects with body mass index (BMI)≧30 kg/m². Doses of inhibitor are administered sufficient to result in an increase of ≧25% in HDL cholesterol levels. BMI and body fat distribution, defined as waist (W) to hip (H) ratio (WHR), are monitored during the course of the 3-6 month studies, and the results for treatment groups compared to those receiving placebo.

In Vivo Sepsis Assay

In vivo studies show that transgenic mice expressing human apo-AI and elevated HDL levels are protected from septic shock. Thus the ability of CETP inhibitors to protect from septic shock can be demonstrated in transgenic mice expressing both human apo-AI and human CETP transgenes (Levine, D. M., Parker, T. S., Donnelly, T. M., Walsh, A. M. and Rubin, A. L., 1993. Proc. Natl. Acad. Sci. 90, 12040-44). LPS derived from *E. coli* is administered at 30 mg/kg by i.p. injection to animals which have been administered a CETP inhibitor at an appropriate dose to result in elevation of HDL. The number of surviving mice is determined at times up to 48 h after LPS injection and compared to those mice administered vehicle (minus CETP inhibitor) only.

In Vivo Blood Pressure Assay

In Vivo Rabbit Model
Methods: New Zealand White male rabbits (3-4 kg) are anesthetized with sodium pentobarbital (30 mg/kg, i.v.) and a surgical plane of anesthesia is maintained by a continuous infusion of sodium pentobarbital (16 mg/kg/hr) via an ear vein catheter. A tracheotomy is performed through a ventral midline cervical incision and the rabbits are ventilated with 100% oxygen using a positive pressure ventilator. Body temperature is maintained at 38.5° C. using a heating pad connected to a YSI temperature controller model 72 (Yellow Springs instruments, Yellow Springs, Md.). Fluid-filled catheters are placed in the right jugular vein (for intravenous drug administration) and in the right carotid artery for arterial pressure monitoring and for blood gas analysis using a model 248 blood gas analyzer (Bayer Diagnostics, Norwood, Mass.). The ventilator is adjusted as needed to maintain blood pH and $pCO_2$ within normal physiological ranges for rabbits. Arterial pressure is measured using a strain gauge transducer (Spectromed, Oxnard, Calif.), previously calibrated using a mercury manometer, positioned at the level of the heart and connected to the arterial catheter. Arterial pressure signals are digitized at 500 Hz and analyzed using a Po—Ne-Mah Data Acquisition System (Gould Instrument Systems, Valley View, Ohio) to obtain mean arterial pressure and heart rate values. Baseline values are collected when mean arterial pressure and heart rate have stabilized. The test compound is then administered either as a subcutaneous (SC) bolus or as an intravenous (IV) infusion. For subcutaneous (SC) dosing the test compound can be dissolved in an appropriate vehicle such as 5% ethanol in water (5% EtOH: 95% $H_2O$), while for intravenous dosing the test compound can be dissolved in an appropriate vehicle such as 0.9% normal saline. Arterial pressure and heart rate are monitored continuously for 4 hours following dosing of the test compound or for the duration of a continuous 4 hour infusion of the test compound. Blood is sampled after dosing or during the infusion of the test compound to determine plasma concentrations of the test compounds.
In vivo Primate Model
Methods: Adult *M. fascicularis* primates (6-8 kg) that have been previously instrumented with subcutaneous vascular access ports in the descending thoracic aorta and conditioned to sit quietly in specially designed primate-restraining chairs are used. All primates are fasted for 12-18 hours prior to the experiment. On the day of the experiment, with the primates restrained in the chairs, a strain gauge pressure transducer (Spectromed, Oxnard, Calif.), previously calibrated using a mercury manometer, is positioned at the level of the heart and connected to the vascular access port to measure arterial pressure. The primates are allowed to acclimate to the chair for at least one hour. Arterial pressure signals are digitized at 500 Hz and continuously recorded throughout the experiment and analyzed using a Po—Ne-Mah Data Acquisition System (Gould Instrument Systems, Valley View, Ohio) to obtain the measurements of mean arterial pressure and heart rate. Baseline values are collected when the primates are sitting calmly and when mean arterial pressure and heart rate have stabilized. The test compound is then administered as a subcutaneous (SC) bolus of a solution of the test compound in an appropriate vehicle such as 5% ethanol in water (5% EtOH: 95% $H_2O$). The solution of test compound or vehicle is filtered through a 0.22 micron filter prior to injection and a typical dosing volume is 0.2 ml/kg. Arterial pressure and heart rate are monitored continuously for 4 hours following dosing of the test compound and are recorded at selected time intervals for data comparison (vehicle vs test compound). Blood samples (1.5 ml) are withdrawn to determine plasma concentrations of the test compound and withdrawn blood is immediately replaced with 0.9% sterile saline to maintain blood volume.

Administration of the compounds of this invention can be via any method which delivers a compound of this invention systemically and/or locally. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate for the target or where the patient is unable to ingest the drug.

In general an amount of a compound of this invention is used that is sufficient to achieve the therapeutic effect desired (e.g., HDL elevation).

In general an effective dosage for the compounds of this invention is about 0.001 to 100 mg/kg/day of the compound, a prodrug thereof, or a pharmaceutically acceptable salt of said compound or of said prodrug. An especially preferred dosage is about 0.01 to 10 mg/kg/day of the compound, a prodrug thereof, or a pharmaceutically acceptable salt of said compound or of said prodrug.

A dosage of the combination pharmaceutical agents to be used in conjunction with the CETP inhibitors is used that is effective for the indication being treated.

For example, typically an effective dosage for HMG-CoA reductase inhibitors is in the range of 0.01 to 100 mg/kg/day. In general an effect dosage for a PPAR modulator is in the range of 0.01 to 100 mg/kg/day.

The compounds of the present invention are generally administered in the form of a pharmaceutical composition comprising at least one of the compounds of this invention together with a pharmaceutically acceptable vehicle, diluent or carrier as described below. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example, a vegetable oil, such as olive oil; triglycerides such as those marketed under the name, Miglyol™; or mono- or diglycerides such as those marketed under the name, Capmul™, for example, in a soft gelatin capsule. Antioxidants may be added to prevent long-term degradation as appropriate. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

Pharmaceutical compositions comprising a solid amorphous dispersion of a cholesteryl ester transfer protein (CETP) inhibitor and a concentration-enhancing polymer are described in International Publication Nos. WO 02/11710 and WO 03/000238, which are hereby incorporated by reference herein. Self-emulsifying formulations of cholesteryl ester transfer protein (CETP) inhibitors are described in International Publication No. WO 03/000295, which is hereby incorporated by reference herein. Methods for depositing small drug crystals on excipients are set forth in the literature, such as in J. Pharm. Pharmacol. 1987, 39.769-773, which is hereby incorporated by reference herein.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain 0.1%-95% of the compound(s) of this invention, preferably 1%-70%. In any event, the composition or formulation to be administered will contain a quantity of a compound(s) according to the invention in an amount effective to treat the disease/condition of the subject being treated, e.g., atherosclerosis.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of the present invention, a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of compounds of the present invention can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other or other compounds generally will be administered in a convenient formulation. The following formulation examples only are illustrative and are not intended to limit the scope of the present invention.

In the formulations which follow, "active ingredient" means a compound of this invention.

Formulation 1: Gelatin Capsules

Hard gelatin capsules are prepared using the following:

| Ingredient | Quantity (mg/capsule) |
|---|---|
| Active ingredient | 0.25-100 |
| Starch, NF | 0-650 |
| Starch flowable powder | 0-50 |
| Silicone fluid 350 centistokes | 0-15 |

A tablet formulation is prepared using the ingredients below:

| Formulation 2: Tablets | |
|---|---|
| Ingredient | Quantity (mg/tablet) |
| Active ingredient | 0.25-100 |
| Cellulose, microcrystalline | 200-650 |
| Silicon dioxide, fumed | 10-650 |
| Stearate acid | 5-15 |

The components are blended and compressed to form tablets.

Alternatively, tablets each containing 0.25-100 mg of active ingredients are made up as follows:

| Formulation 3: Tablets | |
|---|---|
| Ingredient | Quantity (mg/tablet) |
| Active ingredient | 0.25-100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25-100 mg of active ingredient per 5 ml dose are made as follows:

| Formulation 4: Suspensions | |
|---|---|
| Ingredient | Quantity (mg/5 ml) |
| Active ingredient | 0.25-100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

An aerosol solution is prepared containing the following ingredients:

| Formulation 5: Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6: Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
|---|---|
| Ingredient | Quantity |
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

| Formulation 8: Soft Gelatin Capsule with Oil Formulation | |
|---|---|
| Ingredient | Quantity (mg/capsule) |
| Active ingredient | 10-500 |
| Olive Oil or Miglyol ™ Oil | 500-1000 |

The active ingredient above may also be a combination of agents.

General Experimental Procedures

The following examples are put forth so as to provide those of ordinary skill in the art with a disclosure and description of how the compounds, compositions, and methods claimed herein are made and evaluated, and are intended to be purely exemplary of the invention and are not intended to limit the scope of what the inventors regard as their invention. Unless indicated otherwise, percent is percent by weight given the component and the total weight of the composition, temperature is in °C. or is at ambient temperature, and pressure is at or near atmospheric. Commercial reagents were utilized without further purification. Room or ambient temperature refers to 20-25° C. All non-aqueous reactions were run under a nitrogen atmosphere for convenience and to maximize yields. Concentration in vacuo means that a rotary evaporator was used. The names for the compounds of the invention were created by the Autonom 2.0 PCbatch version from Beilstein Informationssysteme GmbH (ISBN 3-89536-976-4) or by Chemdraw® Ultra, CambridgeSoft Corporation, Cambridge Mass. The chemical structures depicted may be only exemplary of the general structure or of limited isomers, and not include specific stereochemistry as recited in the chemical name. Some of the examples are prepared in a racemic form and a procedure for resolving the racemate into individual enantiomers is described. In certain cases the absolute stereochemistry of these enantiomers is not determined however both are within the scope of this invention. In these cases the order of presentation of the enantiomeric structures does not imply any relationship to their chromatographic order of separation.

NMR spectra were recorded on a Varian Unity 400 (Varian Co., Palo Alto, Calif.) NMR spectrometer at ambient temperature. Chemical shifts are expressed in parts per million (δ) relative to an external standard (tetramethylsilane). The peak shapes are denoted as follows: s, singlet; d, doublet, t, triplet, q, quartet, m, multiplet with the prefix br indicating a broadened signal. The coupling constant (J) data given have a maximum error of ±0.41 Hz due to the digitization of the spectra that are acquired. Mass spectra were obtained by (1) atmospheric pressure chemical ionization (APCI) in alternating positive and negative ion mode using a Fisons Platform II Spectrometer or a Micromass MZD Spectrometer (Micromass, Manchester, UK) or (2) electrospray ionization in alternating positive and negative ion mode using a Micromass MZD Spectrometer (Micromass, Manchester, UK) with a Gilson LC-MS interface (Gilson Instruments, Middleton, Wis.), (3) a QP-8000 mass spectrometer (Shimadzu Corporation, Kyoto, Japan) operating in positive or negative single ion monitoring mode, utilizing electrospray ionization or atmospheric pressure chemical ionization or (4) a Hewlett Packard HP6890 gas chromatograph (Agilent Technologies Inc., Santa Clara, Calif.) coupled to a Hewlett Packard HP5973 electron impact quadrupole mass spectrometer. Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the position of only the lower mass ion is given unless stated otherwise.

Column chromatography was performed with either Baker Silica Gel (40 μm) (J. T. Baker, Phillipsburg, N.J.) or Silica Gel 60 (40-63 μm)(EM Sciences, Gibbstown, N.J.). Flash chromatography was performed using a Flash 12 or Flash 40 column (Biotage, Dyar Corp., Charlottesville, Va.) or a CombiFlash Companion system using RediSep silica columns (Teledyne Isco, Teledyne Technologies Company, Lincoln, Nebr.). Radial chromatography was performed using a chromatotron Model 7924T (Harrison Research, Palo Alto, Calif.). Preparative HPLC purification was performed on a Shimadzu 10A preparative HPLC system (Shimadzu Corporation, Kyoto, Japan) using a model SIL-10A autosampler and model 8A HPLC pumps.

Preparative HPLC purification was performed on a Waters Fractionlynx LC/MS/UV system (Waters Corporation; Milford, Mass., USA) equipped with model 2767 injector/collector, model 2525 high flow binary pump modified by a model 515 low flow pump, a model 515 low flow pump for makeup flow, model GS splitter, model ZQ single quad mass spectrometer on the low flow side, model 996 photodiode array UV detector on the high flow side in pre-collector configuration, and a model 2487 dual UV detector on the high flow side in post-collector configuration. Fraction trigger is performed by the ZQ detector in electrospray positive (ESI+) ionization mode operating on single mass triggering. Chromatography methods are either 0.05% trifluoroacetic acid or 0.10% ammonia modified acetonitrile-water gradients. In the case of acid modified gradients Waters Symmetry C8 or C18 (19×50 nm; 5 um) are typically used and in basic conditions Waters Xterra MS C8 or MS C18 (19×50 mm; 5 um).

Microwave-assisted reactions were conducted in an Emrys Optimizer from Personal Chemistry (Uppsala, Sweden) or a Biotage Initiator from Biotage (Uppsala, Sweden).

Optical rotations were determined using a Jasco P-1020 Polarimeter (Jasco Inc., Easton, Md.)

Dimethylformamide ("DMF"), tetrahydrofuran ("THF"), toluene and dichloromethane ("DCM") were the anhydrous grade supplied by Aldrich Chemical Company (Milwaukee, Wis.). Unless otherwise specified, reagents were used as obtained from commercial sources. The terms "concentrated" and "evaporated" refer to removal of solvent at 1-200 mm of mercury pressure on a rotary evaporator with a bath temperature of less than 45° C. The abbreviation "min" stands for "minutes" and "h" or "hr" stands for "hours." The abbreviation "gm" or "g" stands for grams. The abbreviation "μl" or "μL" stands for microliters.

Preparation 1: 2-Bromo-5-trifluoromethyl)benzoic acid

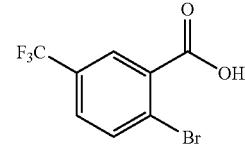

To a solution of n-BuLi (26.7 mL of 2.5M solution in tetrahydrofuran (THF), 66.7 mmol) in THF (130 mL) at −78° C. was added 2,2,6,6-tetramethylpiperidine (22.5 mL, 133.4 mmol). The mixture was stirred at −78° C. for 30 minutes and then carefully lowered to −100° C. using liquid nitrogen. Neat 1-bromo-4-(trifluoromethyl)benzene (15 g, 66.7 mmol) was added. The mixture was kept at −100° C. for 6 hours and poured onto freshly crushed dry ice. The resulting mixture was stirred at room temperature for 16 hours. The residue solvent was removed by evaporation. Water (150 mL) was added and the mixture was extracted with diethyl ether (3×50 mL). The aqueous layer was acidified using concentrated hydrochloric acid (HCl), extracted with methylene chloride (3×50 mL). The combined organic layers were washed with saturated sodium chloride (NaCl) (75 ml), dried with magnesium sulfate (MgSO$_4$), filtered and concentrated to yield the title compound as a white solid (5.41 g). $^1$H NMR (400 MHz, CDCl$_3$) δ 7.7 (dd, J=8.4, 2.3 Hz, 1H) 7.9 (d, J=8.4 Hz, 1H) 8.3 (d, J=2.0 Hz, 1H). MS (ES+) Calc: 267.93, Found: 266.7 (M−1).

Preparation 2: (2-Bromo-5-(trifluoromethyl)phenyl)methanol

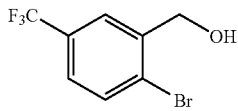

To an ice-cooled solution of 2-bromo-5-(trifluoromethyl) benzoic acid (5.16 g, 19 mmol) in THF (50 mL) was added borane-tetrahydrofuran complex (70 mL of 1M solution in THF, 70 mmol). The resulting mixture was stirred at room temperature for 16 hours. The reaction mixture was quenched with methanol. Solvent was removed. The residue was partitioned between ethyl acetate (3×40 mL) and 1M sodium bicarbonate (50 mL). The combined organic layers were washed with saturated NaCl (50 mL), dried (MgSO$_4$) and concentrated to yield the title compound as an oil (4.85 g). $^1$H NMR (400 MHz, CDCl$_3$) δ 4.8 (s, 2H) 7.5 (m, 1H) 7.7 (d, J=8.2 Hz, 1H) 7.8 (d, J=1.6 Hz, 1H).

Preparation 3: 1-Bromo-2-(bromomethyl)-4-(trifluoromethyl)benzene

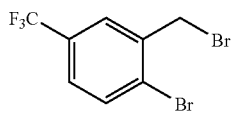

To a solution of (2-bromo-5-(trifluoromethyl)phenyl) methanol (4.7 g, 18 mmol) in methylene chloride (50 mL) at −10° C. was added carbon tetrabromide (CBr$_4$) (7.17 g, 21.6 mmol). The resulting mixture was stirred at −10° C. for 15 minutes. Triphenylphosphine (5.61 g, 21.4 mmol) was then slowly added portionwise. This mixture was stirred at room temperature for 16 hours. The mixture was partitioned between saturated ammonium chloride (NH$_4$Cl) (50 ml) and methylene chloride (2×50 mL). The combined organic layers were washed with saturated NaCl (50 mL), dried (MgSO$_4$) and concentrated. The residue was purified by flash chromatography (silica gel) (eluted with 3:1 hexanes-ethyl acetate) to yield the title compound as a white solid (4.01 g). $^1$H NMR (400 MHz, CDCl$_3$) δ 4.6 (s, 2H) 7.5 (dd, J=8.3, 1.6 Hz, 1H) 7.8 (m, 2H).

Preparation 4: 2-Methyl-2H-tetrazol-5-amine

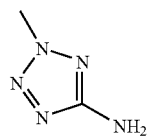

The title compound was prepared according to procedures described in *J. Am. Chem. Soc.* 1954, 76, 923.

Preparation 5: N-(3,5-Bis(trifluoromethyl)benzyl)-2-methyl-2H-tetrazol-5-amine

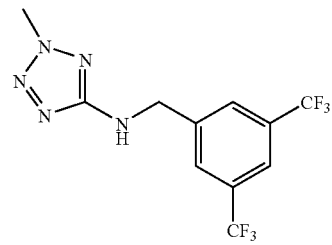

A mixture of 3,5-bis(trifluoromethyl)benzaldehyde (4 g, 16.5 mmol), 2-methyl-2H-tetrazol-5-amine (1.96 g, 19.8 mmol) and molecular sieves (5-10 Å beads) in toluene (50 mL) was heated at reflux for 4 hours, after which time the solvent was removed. Ethanol (50 mL) and sodium borohydride (1.25 g, 33 mmol) were added. The resulting mixture was stirred at room temperature for 30 minutes and then partitioned between saturated NH$_4$Cl (50 mL) and ethyl acetate (2×50 mL). The combined organic layers were washed with saturated NaCl (50 mL), dried (MgSO$_4$), filtered and concentrated to yield the title compound as a white solid (4.7 g). $^1$H NMR (400 MHz, CDCl$_3$) δ 4.2 (s, 3H) 4.7 (s, 1H) 4.7 (s, 1H) 5.0 (t, J=6.0 Hz, 1H) 7.8 (s, 1H) 7.9 (s, 2H). MS (ES+) Calc: 325.08, Found: 325.8 (M+1).

Preparation 6: (3,5-Bis-trifluoromethyl-benzyl)-(2-bromo-5-trifluoromethyl-benzyl)-(2-methyl-2H-tetrazol-5-yl)-amine

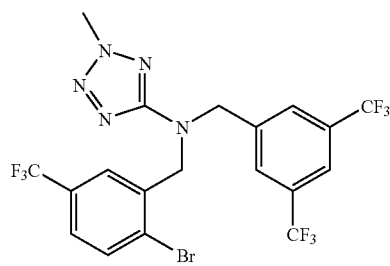

To a solution of N-(3,5-bis(trifluoromethyl)benzyl)-2-methyl-2H-tetrazol-5-amine (3.9 g, 12 mmol) in THF (50 mL) at room temperature was added potassium tert-butoxide (KOtBu) (13.2 ml of 1M solution, 13.2 mmol) followed by 1-bromo-2-(bromomethyl)-4-(trifluoromethyl)benzene (4 g, 12.6 mmol). The mixture was stirred at room temperature for 16 hours. Additional KOtBu in THF (13.2 mL of 1M solution, 13.2 mmol) was added and the mixture was stirred at room temperature for 2 hours. The reaction mixture was partitioned between water (50 mL) and ethyl acetate (3×50 mL). The combined organic layers were washed with saturated NaCl (50 mL), dried (MgSO$_4$) and concentrated. The residue was purified by flash chromatography (silica gel) (eluted with 3:1 hexane-ethyl acetate) to yield the title compound (4.72 g). $^1$H NMR (400 MHz, CDCl$_3$) δ 4.2 (s, 3H) 4.8 (s, 2H) 4.9 (s, 2H)

7.4 (dd, J=8.2, 1.7 Hz, 1H) 7.5 (d, J=1.7 Hz, 1H) 7.7 (m, 3H) 7.8 (s, 1H). MS (ES+) Calc: 561.02, Found: 561.7 (M+1).

Preparation 7: 2-{[(3,5-Bis-trifluoromethyl-benzyl)-(2-methyl-2H-tetrazol-5-yl)-amino]-methyl}-4-trifluoromethyl-benzonitrile

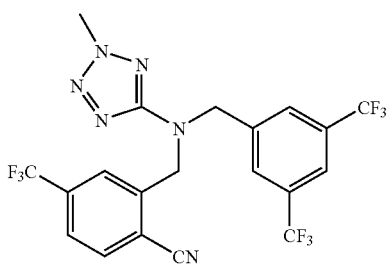

A solution of (3,5-bis-trifluoromethyl-benzyl)-(2-bromo-5-trifluoromethyl-benzyl)-(2-methyl-2H-tetrazol-5-yl)-amine (6 g, 10.6 mmol) in DMF (20 mL) at room temperature was deoxygenated by bubbling nitrogen gas through the solution for 10 minutes. Copper cyanide (CuCN) (1.14 g, 12.8 mmol) was added to the reaction mixture and it was heated to 170° C. for 16 hours. The reaction was cooled to room temperature and diluted with ethyl acetate. The organic layer was washed twice with saturated aqueous ammonium chloride solution and then washed with brine. It was dried over sodium sulfate and concentrated. The residue was purified by flash chromatography (silica gel, 320 g) (eluted over a gradient 5-25% ethyl acetate and hexane) to give 2.59 g (95%) of the title compound as yellow oil. $^1$H NMR (400 MHz, CDCl$_3$) δ 4.2 (s, 3H) 4.82 (s, 2H) 4.9 (s, 2H) 7.6 (dd, 1H) 7.7 (s, 2H) 7.8(s, 2H) 7.8 (dd, 1H). MS (ES+) Calc: 508.1, Found: 509.2 (M+1).

Preparation 8: 2-{[(3,5-Bis-trifluoromethyl-benzyl)-(2-methyl-2H-tetrazol-5-yl)-amino]-methyl}-4-trifluoromethyl-benzaldehyde

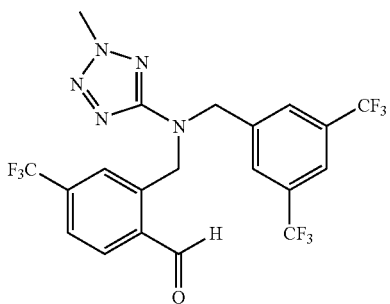

A solution of 2-{[(3,5-bis-trifluoromethyl-benzyl)-(2-methyl-2H-tetrazol-5-yl)-amino]-methyl}-4-trifluoromethyl-benzonitrile (5.45 g, 10.7 mmol) in dichloromethane was cooled to −20° C. with an acetone/dry ice bath. To this solution 7.5 mL of a 1.5 M solution of diisobutylaluminium hydride (DIBAL-H) (11.25 mmol) in toluene was added dropwise. The reaction mixture was stirred for 4 hours while the ice bath warmed to room temperature. The reaction was cooled to 0° C. in ice bath and solid ice (approx. 8 g) was carefully added to the reaction mixture, which was then stirred vigorously for 12 hours while warming to room temperature. Dichloromethane was added to the mixture. The organic layer was dried over sodium sulfate and then concentrated to give a yellow oil. The crude product was absorbed onto silica gel (120 g) and purified by normal phase flash chromatography (ISCO gradient 5-25% ethyl acetate/hexane) to give 4.4 g (80%) of the title compound as a yellow oil. $^1$H NMR (400 MHz, CDCl$_3$) δ 4.2 (s, 3H) 4.8 (s, 2H) 5.2 (s, 2H) 7.5 (s, 1H) 7.7 (s, 2H) 7.78 (m, 1H) 7.9 (dd, 1H). MS (ES+) Calc: 511.1, Found: 512.2 (M+1).

EXAMPLE 1

(3,5-Bis-trifluoromethyl-benzyl)-[2-(cyclohexyl-methoxy-methyl)-5-trifluoromethyl-benzyl]-(2-methyl-2H-tetrazol-5-yl)-amine

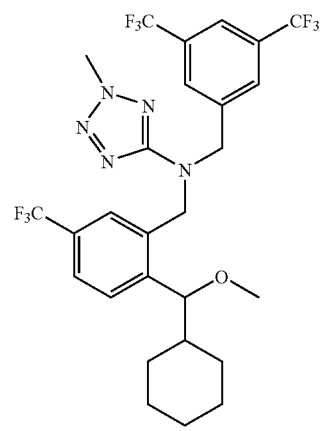

Step A: Preparation of (2-{[(3,5-Bis-trifluoromethyl-benzyl)-(2-methyl-2H-tetrazol-5-yl)-amino]-methyl}-4-trifluoromethyl-phenyl)-cyclohexyl-methanol

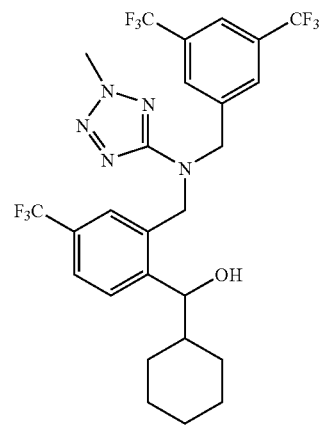

To a solution of 2-{[(3,5-bis-trifluoromethyl-benzyl)-(2-methyl-2H-tetrazol-5-yl)-amino]-methyl}-4-trifluoromethyl-benzaldehyde (244 mg, 0.48 mmoles) in THF (3 mL) at 0° C. was added cyclohexylmagnesium bromide (18% solution in THF, 0.6 mL, 0.57 mmoles) and the reaction was allow to warm to room temperature and stirred overnight. The reaction mixture was quenched with aqueous NH$_4$Cl and extracted with ethyl acetate. The organic layer was washed with brine, dried over sodium sulfate and concentrated in vacuo. The residue was purified over 25+S Biotage silica column (eluted with 0-30% ethyl acetate in hexane) to yield 110 mg (39%) of the title compound. $^1$H NMR (400 MHz, CDCl$_3$) δ ppm 1.0 (m, 6H) 1.6 (m, 3H) 1.8 (m, 1H) 1.9 (d, J=12.4 Hz, 1H) 2.2 (s, 1H) 4.2 (s, 3H) 4.6 (d, J=7.5 Hz, 1H) 4.8 (m, 4H) 7.3 (s, 1H) 7.5 (m, 2H) 7.6 (s, 2H) 7.8 (s, 1H)). MS (ES$^+$) Calc: 595.2, Found: 596.4 (M+1).

Step B: Preparation of (3,5-Bis-trifluoromethyl-benzyl)-[2-(cyclohexyl-methoxy-methyl)-5-trifluoromethyl-benzyl]-(2-methyl-2H-tetrazol-5-yl)-amine

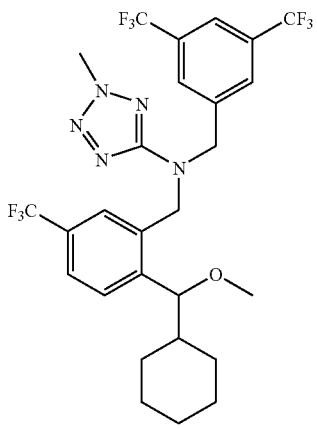

To a solution of (2-{[(3,5-bis-trifluoromethyl-benzyl)-(2-methyl-2H-tetrazol-5-yl)-amino]-methyl}-4-trifluoromethyl-phenyl)-cyclohexyl-methanol (35.5 mg, 0.059 mmoles) in THF (0.3 mL) at 0° C. under nitrogen was added sodium hydride (4.8 mg, 0.12 mmoles, 60% dispersion in mineral oil). The reaction was stirred for 30 min., allowing it to warm to room temperature. The reaction mixture was then treated in a dropwise manner with methyl iodide (11 μL, 0.179 mmoles) at 0° C. The ice bath was removed after the addition and the reaction was stirred at room temperature overnight. Solvent was removed in vacuo. The residue was purified using silica gel chromatography over 12+S Biotage silica column (eluted with 0-30% ethyl acetate in hexanes) to yield the title compound (30.1 mg, 83%) as colorless oil. $^1$H NMR (400 MHz, CDCl$_3$) δ ppm 1.1 (m, 6H) 1.5 (m, 1H) 1.6 (m, 2H) 1.7 (m, 1H) 1.9 (d, J=12.9 Hz, 1H) 3.1 (s, 3H) 4.1 (d, J=7.1 Hz, 1H) 4.2 (s, 3H) 4.7 (d, J=15.8 Hz, 1H) 4.7 (s, 2H) 4.9 (d, J=16.2 Hz, 1H) 7.3 (s, 1H) 7.5 (d, J=7.9 Hz, 1H) 7.6 (d, J=8.3 Hz, 1H) 7.7 (s, 2H) 7.8 (s, 1H). MS (ES$^+$) Calc: 609.2, Found: 610.4 (M+1).

EXAMPLE 2 AND 3

(R)— and (S)-(3,5-Bis-trifluoromethyl-benzyl)-[2-(cyclohexyl-methoxy-methyl)-5-trifluoromethyl-benzyl]-(2-methyl-2H-tetrazol-5-yl)-amine

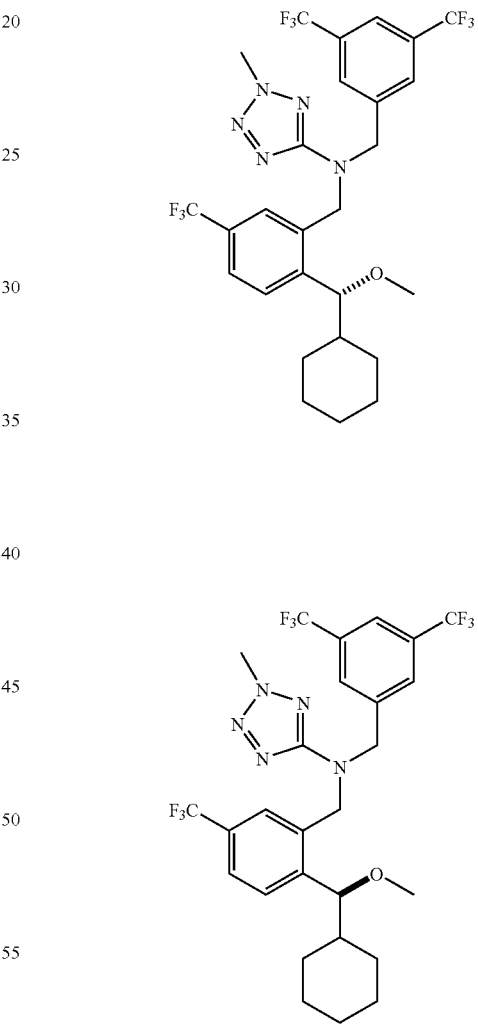

The enantiomers of Example 1 were prepared as follows. The racemic mixture of the alcohol from Step A of Example 1 (110 mg) was dissolved in methanol, injected onto a Chiralpak AD column (2.1 cm×25 cm) (Chiral Tech Inc. Westchester, Pa., USA) and eluted using heptane/2-propanol (90:10, 20 mL/min). Enantiomer 1 (37 mg, 97.5% ee) eluted at 7.364 min, and enantiomer 2 (18.8 mg, 85% ee) eluted at 8.948 min on a Chiralpak AD-H column. Each enantiomer was converted to the title compound according to the procedure described in Step B of Example 1. MS found for each enantiomer: 610.4 (M+1).

EXAMPLE 4

(S)-(3,5-Bis-trifluoromethyl-benzyl)-[2-(cyclohexyl-methoxy-methyl)-5-trifluoromethyl-benzyl]-(2-methyl-2H-tetrazol-5-yl)-amine

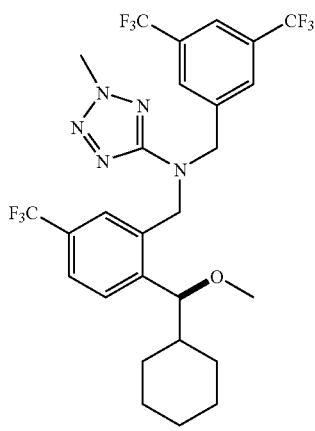

Step A: Preparation of (2-{[(3,5-bis-trifluoromethyl-benzyl)-(2-methyl-2H-tetrazol-5-yl)-amino]-methyl}-4-trifluoromethyl-phenyl)-cyclohexyl-methanol

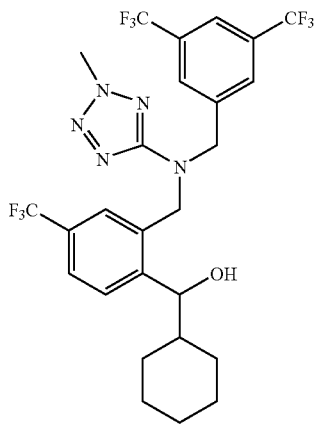

To a solution of (3,5-bis-trifluoromethyl-benzyl)-(2-bromo-5-trifluoromethyl-benzyl)-(2-methyl-2H-tetrazol-5-yl)-amine (from Preparation 6, 6.08 g, 10.8 mmol) in THF at 0° C. was added isopropylmagnesium chloride/lithium chloride (21 mL, 27 mmol) in THF. The isopropylmagnesium chloride/lithium chloride reagent was prepared according to the procedure described in *Angew. Chem. Int. Ed.* 2004, 43, 3333. The mixture was stirred at 0° C. for 3.5 hours. Cyclohexanecarboxaldehyde (3.3 g, 29 mmol) was added. The mixture was stirred at 0° C. for 3.5 hours, quenched with saturated aqueous ammonium chloride and extracted with ethyl acetate. Combined organic layers (200 mL) were washed with aqueous sodium bicarbonate, brine, dried with sodium sulfate and concentrated in vacuo. The residue was purified by chromatography over 65i Biotage silica column (eluted with 0-30% ethyl acetate in heptane) to afford the title compound as a yellow oil (2.98 g, 46%). $^1$H NMR (400 MHz, CDCl$_3$) δ ppm 0.92-1.17 (m, 5H) 1.24 (d, J=15.77 Hz, 1H) 1.54-1.60 (m, 1H) 1.61-1.67 (m, J=2.07 Hz, 2H) 1.73-1.79 (m, 1H) 1.93 (d, J=12.86 Hz, 1H) 2.25 (s, 1H) 4.20 (s, 3H) 4.65 (d, J=7.05 Hz, 1H) 4.70 (d, J=15.77 Hz, 1H) 4.76 (t, J=15.35 Hz, 2H) 4.86 (d, J=15.77 Hz, 1H) 7.34 (s, 1H) 7.50-7.59 (m, 2H) 7.65 (s, 2H) 7.77 (s, 1H). MS (ES$^+$) Calc: 595.2, Found: 596.5 (M+1)

Step B: Preparation of (2-{[(3,5-bis-trifluoromethyl-benzyl)-(2-methyl-2H-tetrazol-5-yl)-amino]-methyl}-4-trifluoromethyl-phenyl)-cyclohexyl-methanone

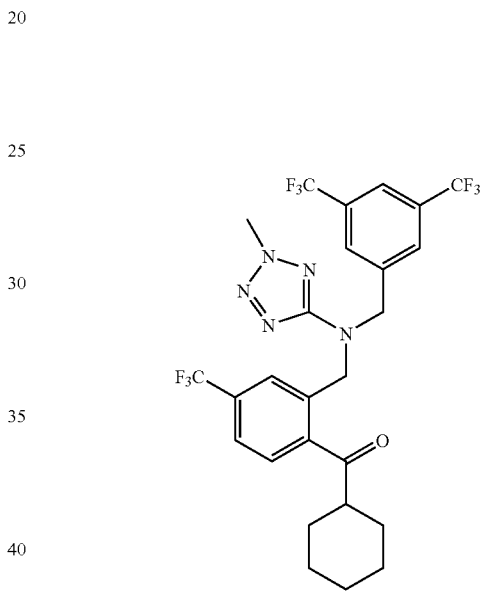

To a solution of (2-{[(3,5-bis-trifluoromethyl-benzyl)-(2-methyl-2H-tetrazol-5-yl)-amino]-methyl}-4-trifluoromethyl-phenyl)-cyclohexyl-methanol (5.46 g, 9.17 mmol) in methylene chloride (150 mL) at room temperature was added Dess-Martin periodinane (4.36 g, 10.3 mmol). The mixture was stirred at room temperature for 2 hours, diluted with ether (50 mL) and 1N sodium hydroxide (40 mL) was added. The mixture was extracted with ethyl acetate (2×100 mL). Combined organic layers were washed with 1N sodium hydroxide (2×40 mL), brine (50 mL), dried with sodium sulfate and concentrated in vacuo. The crude was purified by chromatography over 40+M Biotage silica column (eluted with 0-30% ethyl acetate in heptane) to afford the title compound as a pale yellow oil (5.2 g, 96%). $^1$H NMR (400 MHz, CDCl$_3$) δ ppm 1.16-1.42 (m, 5H) 1.70 (d, J=12.03 Hz, 1H) 1.80 (d, J=9.54 Hz, 4H) 2.96-3.05 (m, 1H) 4.18 (s, 3H) 4.79 (s, 2H) 4.82 (s, 2H) 7.53 (s, 1H) 7.57 (d, J=8.30 Hz, 1H) 7.64 (d, J=7.88 Hz, 1H) 7.66 (s, 2H) 7.72 (s, 1H). MS (ES$^+$) Calc: 593.2, Found: 594.5 (M+1)

Step C: Preparation of (S)-(2-{[(3,5-bis-trifluoromethyl-benzyl)-2-methyl-2H-tetrazol-5-yl)-amino]-methyl}-4-trifluoromethyl-phenyl)-cyclohexyl-methanol

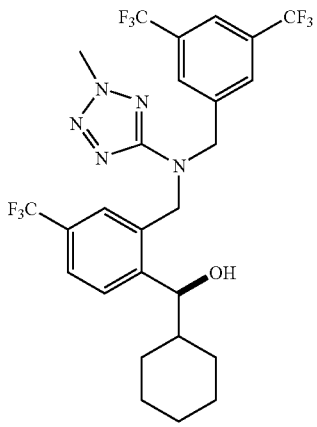

A mixture of [IrHCl₂(COD)]₂ (54.4 mg, 0.073 mmol) and (1R,2R)—N,N'-bis[2-(diphenylphosphino)benzyl]cyclohexane-1,2-diamine (44.8 mg, 0.067 mmol) in isopropanol was stirred at room temperature for 30 minutes. A solution of (2-{[(3,5-bis-trifluoromethyl-benzyl)-(2-methyl-2H-tetrazol-5-yl)-amino]-methyl}-4-trifluoromethyl-phenyl)-cyclohexyl-methanone in isopropanol was added to mixture followed by potassium hydroxide (44.8 mg, 0.799 mmol) and stirred at room temperature for 18 hours. Isopropanol was removed in vacuo and the crude product was purified on Biotage 40+M silica column, eluted with 0-30% ethyl acetate in heptane, to afford 3.7 g (92%) of the title compound. $^1$H NMR (400 MHz, CDCl₃) δ ppm 0.92-1.17 (m, 5H) 1.24 (d, J=15.77 Hz, 1H) 1.54-1.60 (m, 1H) 1.61-1.67 (m, J=2.07 Hz, 2H) 1.73-1.79 (m, 1H) 1.93 (d, J=12.86 Hz, 1H) 2.25 (s, 1H) 4.20 (s, 3H) 4.65 (d, J=7.05 Hz, 1H) 4.70 (d, J=15.77 Hz, 1H) 4.76 (t, J=15.35 Hz, 2H) 4.86 (d, J=15.77 Hz, 1H) 7.34 (s, 1H) 7.50-7.59 (m, 2H) 7.65 (s, 2H) 7.77 (s, 1H). MS (ES⁺) Calc: 595.2, Found: 596.5 (M+1). 95.9% ee determined by chiral HPLC on Chiralpak AD-H (4.6 mm×25 cm) eluted at 6.912 min using 90/10 heptane/IPO (1 mL/min).

Step D: Preparation of (S)-(3,5-bis-trifluoromethyl-benzyl)-[2-(cyclohexyl-methoxy-methyl)-5-trifluoromethyl-benzyl]-(2-methyl-2H-tetrazol-5-yl)-amine

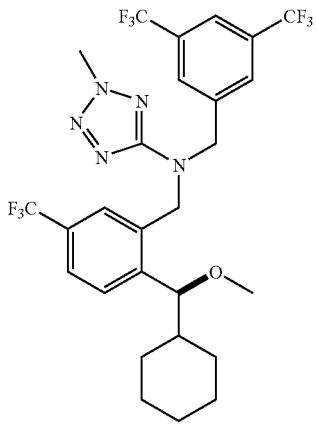

To a solution of (S)-(2-{[(3,5-bis-trifluoromethyl-benzyl)-(2-methyl-2H-tetrazol-5-yl)-amino]-methyl}-4-trifluoromethyl-phenyl)-cyclohexyl-methanol (1.81 g, 3.04 mmol) in THF (20 mL) at 0° C. was added sodium hydride (60% dispersion in mineral oil, 254.4 mg, 6.4 mmol). The mixture was stirred at room temperature for 30 minutes, cooled to 0° C. and methyl iodide (1.31 g, 9.2 mmol) was added. The mixture was stirred at room temperature for 5 hours. Water (10 mL) was added and the mixture was extracted with ethyl acetate. Combined organic layers were washed with brine, dried with sodium sulfate and concentrated in vacuo. The residue was purified by chromatography over 25+M Biotage silica column (eluted with 0-30% ethyl acetate in heptane) to afford the title compound as a colorless oil (1.77 g, 96%). $^1$H NMR (400 MHz, CDCl₃) δ ppm 0.93-1.14(m, 5H) 1.18 (d, J=10.79 Hz, 1H) 1.43-1.54(m, 1H) 1.59-1.65(m, J=4.56 Hz, 2H) 1.68-1.74 (m, J=2.49 Hz, 1H) 1.90 (d, J=12.03 Hz, 1H) 3.06 (s, 3H) 4.08 (d, J=7.05 Hz, 1H) 4.21 (s, 3H) 4.71 (d, J=15.77 Hz, 1H) 4.71 (s, 2H) 4.88 (d, J=16.18 Hz, 1H) 7.35 (s, 1H) 7.49 (d, J=8.30 Hz, 1H) 7.55 (d, J=8.30 Hz, 1H) 7.66 (s, 2H) 7.78 (s, 1H). MS (ES⁺) Calc: 609.2, Found: 610.5 (M+1). [α]$_D^{20}$=36.49 deg (c=10.05 mg/mL, acetone)

Determination of absolute configuration of (S)-(3,5-bis-trifluoromethyl-benzyl)-[2-(cyclohexyl-methoxymethyl)-5-trifluoromethyl-benzyl]-(2-methyl-2H-tetrazol-5-yl)-amine Step A: Preparation of (2-bromo-5-trifluoromethyl-benzyloxy)-tert-butyl-dimethyl-silane

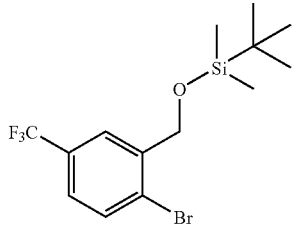

To a solution of (2-bromo-5-(trifluoromethyl)phenyl)methanol (from Preparation 2, 10 g, 39 mmol) in DMF (20 mL) was added imidazole (5.87 g, 86.3 mmol) followed by t-butyldimethylsilyl chloride (7.11 g, 47.2 mmol) and the reaction was stirred at room temperature for 16 hours. The mixture was partitioned between ethyl acetate and water. The organic layer was washed with brine, dried over sodium sulfate and concentrated in vacuo. The residue was purified by chromatography over 25+M Biotage silica column (eluted with 0-20% ethyl acetate in heptane) (5CV), 20% (1 CV) to afford a colorless oil (14 g, 97%) of the title compound. $^1$H NMR (400 MHz, CDCl₃) δ ppm 0.15 (s, 6H) 0.98 (s, 9H) 4.75 (s, 2H) 7.36 (m, 1H) 7.60 (d, J=8.3 Hz, 1H) 7.84 (s, 1H)). GCMS: 311 (M-57, t-bu).

Step B: Preparation of [2-(tert-butyl-dimethyl-silanyloxymethyl)-4-trifluoromethyl-phenyl]-cyclohexyl-methanone

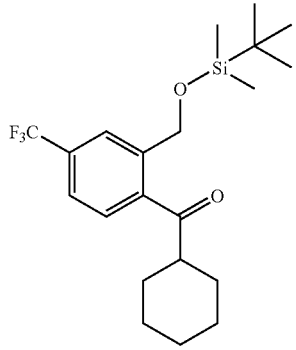

To a solution of (2-bromo-5-trifluoromethyl-benzyloxy)-tert-butyl-dimethyl-silane (3.69 g, 10 mmol) in THF (35 mL) at room temperature was added isopropyl magnesium chloride/lithium chloride (21 mL, 1.5M, 30.5 mmol) in THF. The mixture was stirred at room temperature for 3 hours. Transmetallation was followed by GC-MS. The reaction mixture was cooled to −78° C. and CuCN.2LiCl (10 ml, 1M, 10.0 mmol) was added and stirred for 30 minutes. Cyclohexanecarbonyl chloride (2.93 g, 20.0 mmol) in 3 ml THF was added to reaction mixture. The reaction mixture was allowed to warm to room temperature and stirred at room temperature for 30 minutes. Reaction was quenched by pouring onto saturated aqueous ammonium chloride in ammonium hydroxide solution and extracted with ethyl acetate. Combined organic layers (200 mL) were washed with brine, dried over sodium sulfate and concentrated in vacuo The crude product was purified on Biotage column (40+M), eluting with ethyl acetate in heptane, starting with 0-20% (10CV), 20% (2CV) to yield the title compound (4.5 g, 41.5%) as colorless oil. $^1$H NMR (400 MHz, CDCl$_3$) δ ppm 0.09 (s, 6H) 0.9 (s, 9H) 1.2 (m, 4H) 1.7 (m, 4H) 2.4 (m, 2H) 3.1 (m, 1H) 4.8 (s, 2H) 7.5 (d, J=7.9 Hz, 1H) 7.7 (d, J=8.3 Hz, 1H) 8.0 (s, 1H). GCMS: Calc: 400, Found: 343 (M-57, t-bu).

Step C: Preparation of (S)-[2-(tert-butyl-dimethyl-silanyloxymethyl)-4-trifluoromethyl-phenyl]-cyclohexyl-methanol

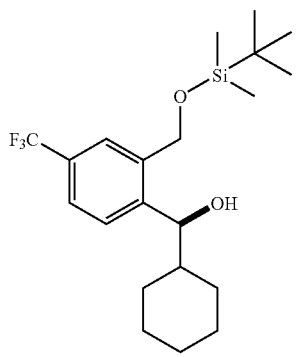

A mixture of [IrHCl$_2$(COD)]$_2$ (33 mg, 0.044 mmol) and (1R, 2R)—N,N'-bis[2-(diphenylphosphino)benzyl]cyclohexane-1,2-diamine (29 mg, 0.044 mmol) in isopropanol (37 ml) was stirred at room temperature for 30 minutes. A solution of [2-(tert-butyl-dimethyl-silanyloxymethyl)-4-trifluoromethyl-phenyl]-cyclohexyl-methanone (1.6 g, 4 mmol) in isopropanol (5 ml) was added to mixture followed by potassium hydroxide (28 mg, 0.5 mmol) and stirred for 16 hours. Isopropanol was removed in vacuo and the residue was purified by chromatography over 25+M Biotage silica column eluted with ethyl acetate in heptanes 0% (1 CV), 2-20% (10CV), 20% (2CV) to yield the title compound (1.4 g, 87%) as colorless oil. $^1$H NMR (400 MHz, CDCl$_3$) δ ppm 0.09 (s, 6H) 0.9 (s, 9H) 1.2 (m, 3H) 1.6 (d, J=7.4 Hz, 1H) 1.7 (m, 4H) 2.0 (m, 1H) 2.2 (m, 1H) 2.4 (m, 1H) 4.5 (m, 1H) 4.7 (d, J=13.7 Hz, 1H) 4.8 (d, J=13.7 Hz, 1H) 7.5 (d, J=1.2 Hz, 2H) 7.6 (s, 1H). Chiral SFC, Retention timet=1.93 min. indicates product is 95.0% ee. [α]$_D^{20}$=−12.99 deg (c=9.5 mg/mL, acetone)

Step D: Preparation of (S)-tert-butyl-[2-(cyclohexyl-methoxyl-methyl)-5-trifluoromethyl-benzyloxy]-dimethyl-silane

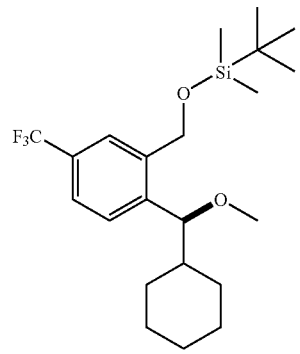

To a solution of (S)-[2-(tert-butyl-dimethyl-silanyloxymethyl)-4-trifluoromethyl-phenyl]-cyclohexyl-methanol (1.4 g, 3.5 mmol) in THF (3 mL) at 0° C. under nitrogen was added sodium hydride (278 mg, 7.0 mmol, 60% dispersion in mineral oil). The reaction was stirred for 30 minutes, allowing it to warm to room temperature. The reaction mixture was then treated in a dropwise manner with methyl iodide (1.5 g, 650 µL, 10.4 mmol) at 0° C. The ice bath was removed after the addition and the reaction was stirred at room temperature overnight. Ethyl ether was added and the reaction was washed with brine, dried over magnesium sulfate and concentrated in vacuo. The residue was purified by chromatography on Biotage column 25+S, eluting with ethyl acetate in heptane 2-30% (10CV) and 30% (3CV) to yield the title compound (1.0 g, 88%) as colorless oil. $^1$H NMR (400 MHz, CDCl$_3$) δ ppm 0.08 (s, 6H) 0.9 (s, 9H) 1.2 (m, 3H) 1.6 (m, 2H) 1.7 (m, 4H) 2.0 (d, J=12.8, 1H) 2.2 (m, 1H) 3.1 (s, 3H) 4.0 (d, J=7.5, 1H) 4.0 (d J=13.7, 1H) 4.7 (d, J=13.7 Hz, 1H) 7.4 (d, J=7.9 Hz, 1H) 7.5 (d, J=7.9 Hz, 1H) 7.7 (s, 1H).

Step E: Preparation of (S)-[2-(cyclohexyl-methoxy-methyl)-5-trifluoromethyl-phenyl]-methanol

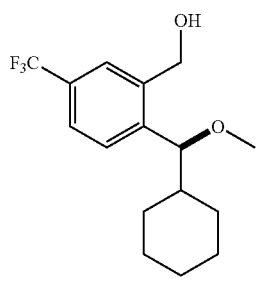

To a solution of (S)-tert-butyl-[2-(cyclohexyl-methoxy-methyl)-5-trifluoromethyl-benzyloxy]-dimethyl-silane (1.13 g, 2.4 mmol) in THF (5 ml) was added a solution of tetrabutylammonium fluoride (4.8 ml, 1 M, 4.8 mmol) at room temperature and stirred for overnight. The reaction mixture was concentrated in vacuo and purified on Biotage column 25+M, eluting with 0-30% ethyl acetate in heptane (10 CV), 30% (2 CV) to yield the title compound (0.6 g, 73%) as colorless oil. $^1$H NMR (400 MHz, CDCl$_3$) δ ppm 0.8 m (m, 2H) 1.1 (m, 4H) 1.3 (m, 1H) 1.5 (m, 2H) 1.6 (m, 1H) 2.0 (d, J=12.9, 1H) 2.3 (m, 1H) 3.1 (s, 3H) 4.0 (d, J=7.9, 1H) 4.7 (dd, J=13.7 & 7.5 Hz, 2H) 7.3 (d, J=8.3 Hz, 1H) 7.4 (d, J=7.8 Hz, 1H) 7.7 (s, 1H).

Step F: Preparation of (S)-2-bromomethyl-1-(cyclohexyl-methoxy-methyl)-4-trifluoromethyl-benzene

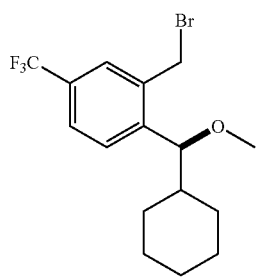

To a solution of (S)-[2-(cyclohexyl-methoxy-methyl)-5-trifluoromethyl-phenyl]-methanol (340 mg, 1.2 mmol) in methylene chloride (10 mL) at 0° C. was added carbon tetrabromide (485 mg, 1.46 mmol) and stirred for 10 minutes followed by addition of triphenylphosphine (383 mg, 1.46 mmol). Reaction was stirred at 0° C. for 1 hour and allowed to warm to room temperature and stirred for 16 hours. Reaction was concentrated in vacuo and purified on 25+S Biotage column eluting with 0-20% ethyl acetate in heptane (10 CV), 20% (2CV), to yield the title compound (270 mg, 66%) as a colorless oil. This oil solidified upon standing and was recrystalized from hexane to yield crystals (mp=43-45° C.), which were submitted to X-ray crystallography to establish absolute configuration. $^1$H NMR (400 MHz, CDCl$_3$) δ ppm 1.1 (m, 4H) 1.3 (m, 2H) 1.6 (m, 3H) 1.7 (m, 1H) 2.0 (d, J=12.6, 1H) 3.2 (s, 3H) 4.2 (d, J=7.9, 1H) 4.5 (d, J=10.3 Hz, 1H) 4.6 (d, J=10.3 Hz, 1H) 7.4 (d, J=8.3 Hz, 1H) 7.5 (d, J=8.3 Hz, 1H) 7.6 (s, 1H). $[\alpha]_D^{20}$=−50 deg (c=11.5 mg/mL, acetone)

Step G: Preparation of (S)-(3,5-bis-trifluoromethyl-benzyl)-[2-(cyclohexyl-methoxy-methyl)-5-trifluoromethyl-benzyl]-(2-methyl-2H-tetrazol-5-yl)-amine

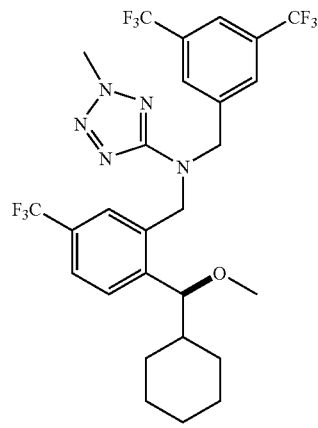

To a solution of N-(3,5-bis(trifluoromethyl)benzyl)-2-methyl-2H-tetrazol-5-amine (26.7 mg, 0.082 mmol) in DMF (1 ml) at 0° C. under nitrogen was added sodium hydride (6 mg, 0.1 mmol, 60% dispersion in mineral oil). The reaction was stirred for 30 minutes while allowing it to warm to room temperature. The reaction mixture was then treated with (S)-2-bromomethyl-1-(cyclohexyl-methoxy-methyl)-4-trifluoromethyl-benzene (25 mg, 0.068 mmol) at 0° C. The ice bath was removed after the addition and the reaction was stirred at room temperature overnight. Water was added and the mixture was extracted with ethyl acetate. Combined organic layers were washed with water, brine, dried over sodium sulfate and concentrated in vacuo. The residue was purified by chromatography on 12+S Biotage silica column, eluting with ethyl acetate in heptane 0-30% (10CV) and 30% (3CV) to yield the title compound (20 mg, 48%) as colorless oil. $^1$H NMR (400 MHz, CDCl$_3$) δ ppm 1.07 (m, 4H) 1.2 (m, 2H) 1.46 (m, 1H) 1.57 (m, 2H) 1.61(m, 1H) 1.90 (d, J=12.4, 1H) 3.06 (s, 3H) 4.08 (d, J=7.1, 1H) 4.2 (s, 3H) 4.70 (d, J=15.7, 1H) 4.89 (d, J=15.7, 1H) 7.35 (s, 1H) 7.50 (d, J=7.9, 1H) 7.55 (d, J=7.9, 1H) 7.65 (s, 2H) 7.77 (s, 1H). $[\alpha]_D^{20}$=−26.6 deg (c=13 mg/mL, acetone).

EXAMPLE 5

(3,5-Bis-trifluoromethyl-benzyl)-{2-[methoxy-(1-methyl-piperidin-4-yl)-methyl]-5-trifluoromethyl-benzyl}-(2-methyl-2H-tetrazol-5-yl)-amine

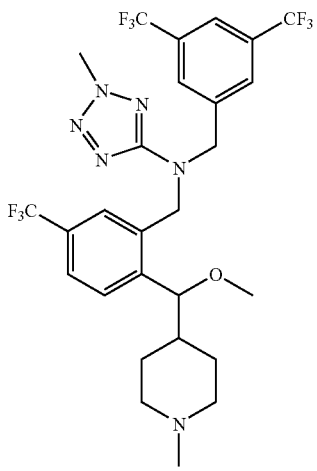

To a solution of the aldehyde from Preparation 8 (0.230 g, 0.45 mmol) in THF (3 mL) at −78° C. was added a THF solution 1-methylpiperidine-4-magnesium chloride (0.21 g, 1.35 mmol) (Collection of Czechoslovak Chemical Communications, 47(11), 3077-93, 1982), and the solution was stirred for 3 hours as it warmed to room temperature. The reaction mixture was quenched with saturated $NH_4Cl$ and extracted with $CHCl_3$. The extract was dried, concentrated and purified over silica gel to afford the desired alcohol. MS ($ES^+$) Calc: 610.53, Found: 611.5 (M+1).

To a THF solution (1 mL) of the above alcohol (0.024 g, 0.038 mmol) was added NaH (0.0017 g, 0.042 mmol, 60% dispersion in mineral oil) and the resulting suspension was stirred for 30 min. A THF (1 mL) solution of methyl 4-toluenesulfonate (0.008 g, 0.042 mmol) was added and the mixture was refluxed for 12 h. The solution was cooled to room temperature and was quenched with saturated $NH_4Cl$ and extracted with $CH_2Cl_2$. The extract was dried, concentrated and purified to yield the title compound. MS ($ES^+$) Calc: 624.55, Found: 625.3 (M+1). $^1$H NMR (400 MHz, $CDCl_3$) δ ppm 7.8 (s, 1H), 7.63 (s, J=38.3 Hz, 2H), 7.57 (d, J=8.3 Hz, 2H), 7.50 (d, 2H), 7.38 (s, 1H), 4.90 (d, J=16.2 Hz, 1H), 4.70 (q, J=14 Hz, 4H), 4.20 (s, 3H), 4.12 (d, J=7 Hz, 1H) 3.05 (s, 3H), 2.80 (d of d, J=16 Hz, 2H), 2.2 (s, 3H), 1.92 (d, J=12 Hz. 1H), 1.77 (d of t, J=21, 12 Hz, 4H), 1.5 (m, 1H), 1.38 (m, 2H), 1.05 (m, 1H).

According to the procedure described in Example 1, and using corresponding Grignard and alkylating reagents, Examples 6 to 15 were made:

| Example # | Chemical Name | Structure | MS Calc | MS Found M + 1 |
|---|---|---|---|---|
| 6 | (3,5-Bis-trifluoromethyl-benzyl)-[2-(1-methoxy-propyl)-5-trifluoromethyl-benzyl]-(2-methyl-2H-tetrazol-5-yl)-amine | 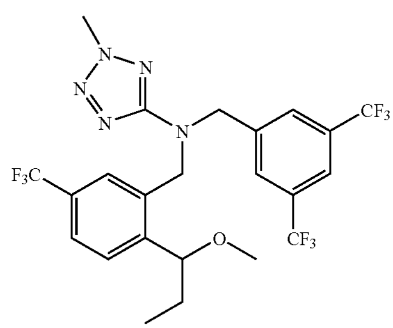 | 555.2 | 556.1 |
| 7 | [2-(1-Benzyloxy-propyl)-5-trifluoromethyl-benzyl]-(3,5-bis-trifluoromethyl-benzyl)-(2-methyl-2H-tetrazol-5-yl)-amine | 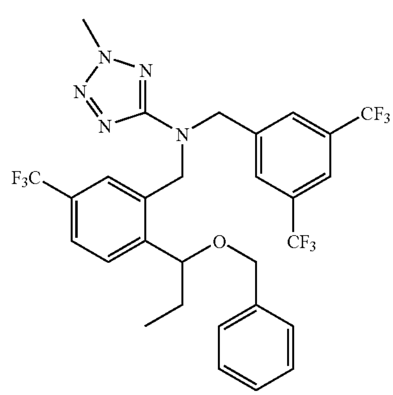 | 631.2 | 632.1 |

-continued

| Example # | Chemical Name | Structure | MS Calc | MS Found M + 1 |
|---|---|---|---|---|
| 8 | (3,5-Bis-trifluoromethyl-benzyl)-[2-(cyclopropyl-methoxy-methyl)-5-trifluoromethyl-benzyl]-(2-methyl-2H-tetrazol-5-yl)-amine | 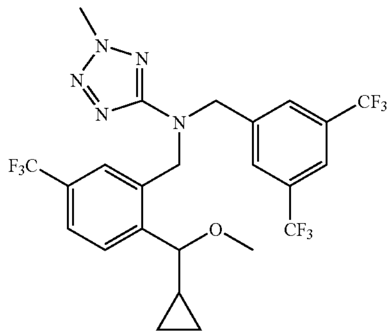 | 567.2 | 568.3 |
| 9 | (3,5-Bis-trifluoromethyl-benzyl)-[2-(methoxy-phenyl-methyl)-5-trifluoromethyl-benzyl]-(2-methyl-2H-tetrazol-5-yl)-amine | 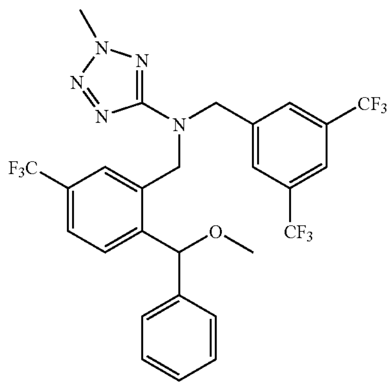 | 603.2 | 604.3 |
| 10 | (3,5-Bis-trifluoromethyl-benzyl)-[2-(1-methoxy-2-phenyl-ethyl)-5-trifluoromethyl-benzyl]-(2-methyl-2H-tetrazol-5-yl)-amine | 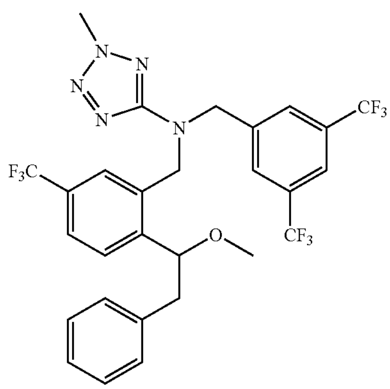 | 617.2 | 618.1 |
| 11 | (3,5-Bis-trifluoromethyl-benzyl)-[2-(cyclohexyl-ethoxy-methyl)-5-trifluoromethyl-benzyl]-(2-methyl-2H-tetrazol-5-yl)-amine | 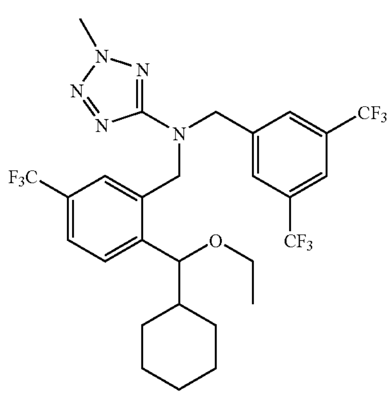 | 623.2 | 624.4 |

-continued

| Example # | Chemical Name | Structure | MS Calc | MS Found M + 1 |
|---|---|---|---|---|
| 12* | (R)-(3,5-Bis-trifluoromethyl-benzyl)-[2-(cyclohexyl-ethoxy-methyl)-5-trifluoromethyl-benzyl]-(2-methyl-2H-tetrazol-5-yl)-amine | 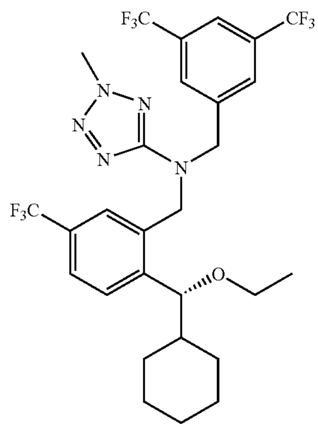 | 623.2 | 624.1 |
| 13** | (S)-(3,5-Bis-trifluoromethyl-benzyl)-[2-(cyclohexyl-ethoxy-methyl)-5-trifluoromethyl-benzyl]-(2-methyl-2H-tetrazol-5-yl)-amine | 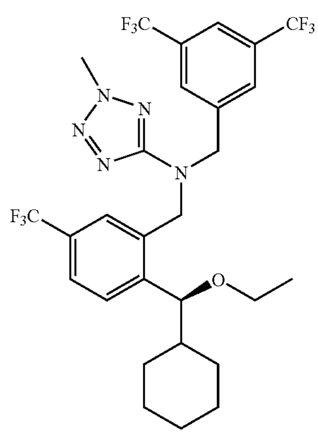 | 623.2 | 624.1 |
| 14 | (3,5-Bis-trifluoromethyl-benzyl)-[2-(cyclopropyl-ethoxy-methyl)-5-trifluoromethyl-benzyl]-(2-methyl-2H-tetrazol-5-yl)-amine | 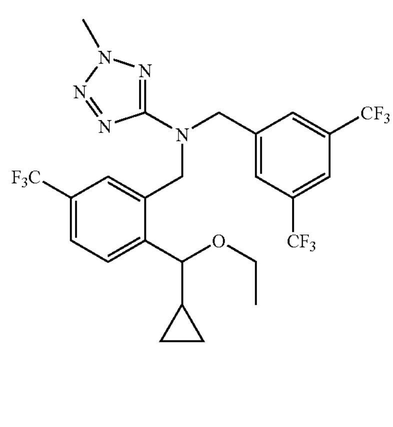 | 581.2 | 582.3 |

-continued

| Example # | Chemical Name | Structure | MS Calc | MS Found M + 1 |
|---|---|---|---|---|
| 15 | (3,5-Bis-trifluoromethyl-benzyl)-{2-[methoxy-(tetrahydro-pyran-4-yl)-methyl]-5-trifluoromethyl-benzyl}-(2-methyl-2H-tetrazol-5-yl)-amine | 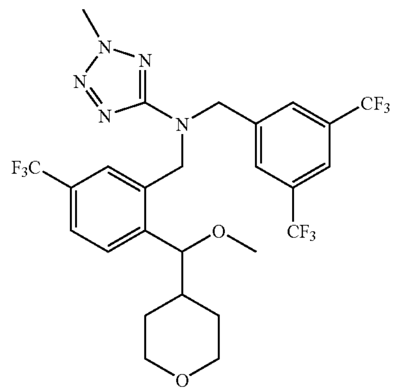 | 611.2 | 612.3 |

*For example 12: $^1$H NMR (400 MHz, CDCl$_3$) δ ppm 0.94-1.19 (m, 6H) 1.07 (t, J=7.05 Hz, 3H) 1.43-1.53 (m, 1H) 1.57-1.64 (m, 2H) 1.66-1.75 (m, 1H) 1.94 (d, J=12.86 Hz, 1H) 3.04-3.22 (m, 2H) 4.16 (d, J=7.47 Hz, 1H) 4.21 (s, 3H) 4.71 (s, 2H) 4.72 (d, J=16.18 Hz, 1H) 4.88 (d, J=16.18 Hz, 1H) 7.33 (s, 1H) 7.49-7.57 (m, 2H) 7.65 (s, 2H) 7.77 (s, 1H)

**For example 13: $^1$H NMR (400 MHz, CDCl$_3$) δ ppm 0.94-1.19 (m, 6H) 1.07 (t, J=7.05 Hz, 3H) 1.42-1.53 (m, 1H) 1.59-1.65 (m, 2H) 1.67-1.75 (m, 1H) 1.94 (d, J=12.86 Hz, 1H) 3.03-3.21 (m, 2H) 4.16 (d, J=7.05 Hz, 1H) 4.21 (s, 3H) 4.71 (s, 2H) 4.72 (d, J=16.18 Hz, 1H) 4.88 (d, J=16.18 Hz, 1H) 7.33 (s, 1H) 7.50-7.58 (m, 2H) 7.65 (s, 2H) 7.77 (s, 1H)

EXAMPLES 16 AND 17

(R) and (S) (3,5-Bis-trifluoromethyl-benzyl)-{2-[methoxy-(tetrahydro-pyran-4-Yl)methyl]-5-trifluoromethyl-benzyl}-(2-methyl-2H-tetrazol-5-yl)-amine

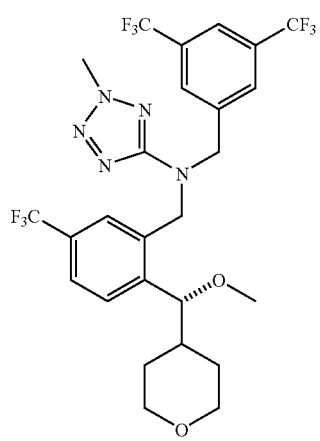

-continued

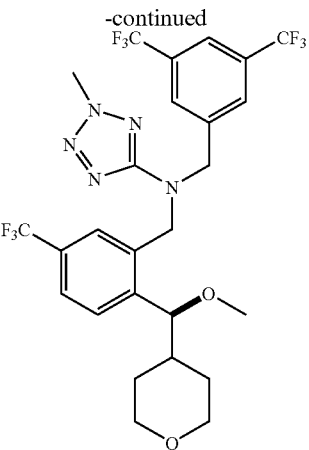

Step A: Preparation of (2-{[(3,5-bis-trifluoromethyl-benzyl)-(2-methyl-2H-tetrazol-5-yl)-amino]-methyl}-4-trifluoromethyl-phenyl)-(tetrahydro-pyran-4-yl)-methanol

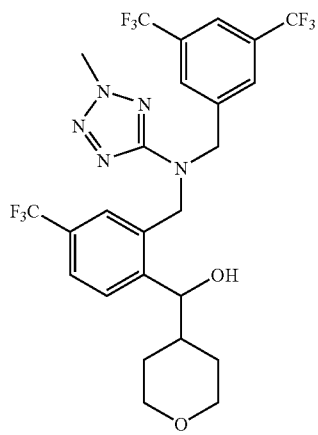

To a suspension of magnesium in THF was added iodine followed by 4-chlorotetrahydropyran in THF at 65° C. Small amount of methylmagnesium bromide (3 drops) was added to initiate the reaction. The mixture was stirred at 65° C. for 1.5 hours, cooled to room temperature. 2-{[(3,5-Bis-trifluoromethyl-benzyl)-(2-methyl-2H-tetrazol-5-yl)-amino]-methyl}-4-trifluoromethyl-benzaldehyde in THF was treated with trimethylsilyl chloride and stirred at room temperature for 1 hour. The Grignard was then added to the aldehyde in THF at 0° C. via syringe. The mixture was stirred at 0° C. for 1.5 hours, quenched with saturated aqueous ammonium chloride and extracted with ethyl acetate. Combined organic layers were washed with brine, dried over sodium sulfate, and concentrated in vacuo. The residue was purified by chromatography over 25+S Biotage silica column (eluted with 0-50% ethyl acetate in hexanes) to afford the title compound as a pale yellow foam (91.6 mg, 52%). $^1$H NMR (400 MHz, CDCl$_3$) δ ppm 1.07 (d, J=13.28 Hz, 1H) 1.27-1.37 (m, 1H) 1.40-1.52 (m, 1H) 1.77-1.89 (m, 2H) 2.51 (s, 1H) 3.19-3.34 (m, 2H) 3.86 (dd, J=11.14, 3.53 Hz, 1H) 3.99 (dd, J=11.62, 3.73 Hz, 1H) 4.18 (s, 3H) 4.68-4.83 (m, 4H) 4.88 (d, J=15.35 Hz, 1H) 7.34 (s, 1H) 7.55 (s, 2H) 7.64 (s, 2H) 7.77 (s, 1H). MS (ES$^+$) Calc: 597.2, Found: 598.4 (M+1).

The racemic alcohol mixture was separated by chiral chromatography using preparative HPLC (Column: Chiralcel OJ; Dimension: 5 cm×50 cm; Mobile phase: 95/5 heptane/ethanol with 0.1% DEA, Flow rate: 120 mL/minutes). The expected preparative retention times for the two enantiomers are 26 minutes (Enantiomer 1) and 36 minutes (Enantiomer 2). Enantiomer 1: MS Calc: 597.2, Found: 598.4; 100% ee. Enantiomer 2: MS Calc: 597.2, Found: 598.4; 100% ee Step B: (R) and (S) (3,5-Bis-trifluoromethyl-benzyl)-{2-[methoxy-(tetrahydro-pyran-4-yl)-methyl]-5-trifluoromethyl-benzyl}-(2-methyl-2H-tetrazol-5-yl)-amine

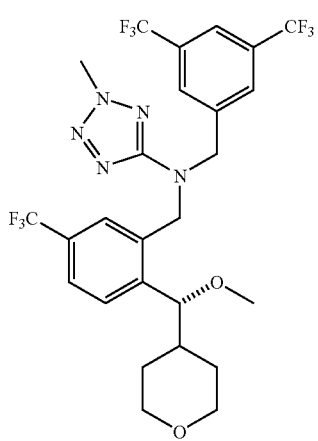

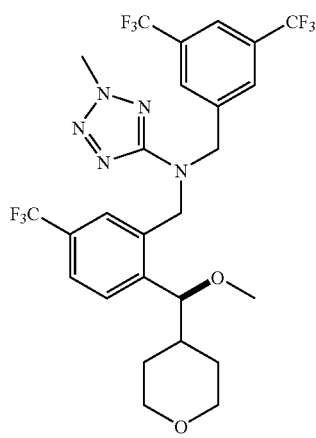

To a solution of (2-{[(3,5-bis-trifluoromethyl-benzyl)-(2-methyl-2H-tetrazol-5-yl)-amino]-methyl}-4-trifluoromethyl-phenyl)-(tetrahydro-pyran-4-yl)-methanol (enantiomer 1 from chiral separation of the racemic alcohol (STEP A) using preparative HPLC, 29.5 mg, 0.049 mmol) in THF (0.2 mL) at 0° C. was added sodium hydride (60% dispersion in mineral oil, 12 mg, 0.3 mmol). The mixture was stirred at room temperature for 30 minutes, cooled to 0° C. and methyl iodide (70 mg, 30 µL, 0.5 mmol) was added. The mixture was stirred at room temperature overnight and then purified by chromatography over 12+S Biotage column (eluted with 0-30% ethyl acetate in hexanes) to afford the title compound as a colorless oil (22 mg, 73%). $^1$H NMR (400 MHz, CDCl$_3$) δ ppm 1.02 (d, J=12.45 Hz, 1H) 1.32-1.51 (m, 2H) 1.69-1.83 (m, 2H) 3.06 (s, 3H) 3.15-3.31 (m, 2H) 3.86 (dd, J=11.41, 3.53 Hz, 1H) 3.97 (dd, J=11.62, 4.15 Hz, 1H) 4.15 (d, J=7.05 Hz, 1H) 4.21 (s, 3H) 4.70 (d, J=15.77 Hz, 1H) 4.71 (d, J=5.39 Hz, 2H) 4.91 (d, J=15.77 Hz, 1H) 7.36 (s, 1H) 7.51 (d, J=8.30 Hz, 1H) 7.58 (d, J=9.13 Hz, 1H) 7.65 (s, 2H) 7.78 (s, 1H). MS (ES$^+$) Calc: 611.2, Found: 612.5 (M+1).

To a solution of (2-{[(3,5-bis-trifluoromethyl-benzyl)-(2-methyl-2H-tetrazol-5-yl)-amino]-methyl}-4-trifluoromethyl-phenyl)-(tetrahydro-pyran-4-yl)-methanol (enantiomer 2 from chiral separation of the racemic alcohol (STEP A) using preparative HPLC, 26.4 mg, 0.044 mmol) in THF (0.2 mL) at 0° C. was added sodium hydride (60% dispersion in mineral oil, 12 mg, 0.3 mmol). The mixture was stirred at room temperature for 30 minutes, cooled to 0° C. and methyl iodide (70 mg, 30 µL, 0.5 mmol) was added. The mixture was stirred at room temperature overnight and then purified by chromatography over 12+S Biotage column (eluted with 0-30% ethyl acetate in hexanes) to afford the title compound as a colorless oil (20.2 mg, 75%). $^1$H NMR (400 MHz, CDCl$_3$) δ ppm 1.02 (d, J=12.86 Hz, 1H) 1.33-1.49 (m, 2H) 1.70-1.83 (m, 2H) 3.06 (s, 3H) 3.16-3.30 (m, 2H) 3.86 (dd, J=11.41, 3.53 Hz, 1H) 3.97 (dd, J=11.62, 3.73 Hz, 1H) 4.15 (d, J=7.05 Hz, 1H) 4.21 (s, 3H) 4.66-4.77 (m, 3H) 4.91 (d, J=15.77 Hz, 1H) 7.36 (s, 1H) 7.51 (d, J=8.30 Hz, 1H) 7.58 (d, J=7.88 Hz, 1H) 7.65 (s, 2H) 7.78 (s, 1H). MS (ES⁺) Calc: 611.2, Found: 612.5 (M+1).

EXAMPLE 18

(3,5-Bis-trifluoromethyl-benzyl)-[2-(1-cyclopentyl-1-methoxy-ethyl)-5-trifluoromethyl-benzyl]-(2-methyl-2H-tetrazol-5-yl)-amine

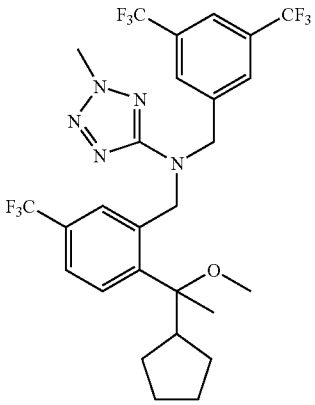

Step A: Preparation of (2-{[(3,5-bis-trifluoromethyl-benzyl)-(2-methyl-2H-tetrazol-5-yl)-amino]-methyl}-4-trifluoromethyl-phenyl)-cyclopentyl-methanol

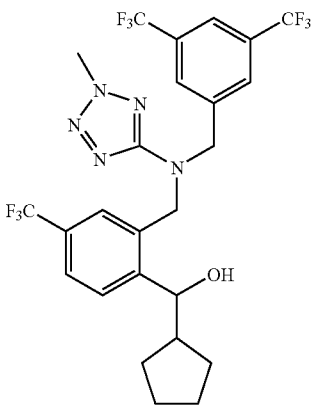

To a solution of (3,5-bis-trifluoromethyl-benzyl)-(2-bromo-5-trifluoromethyl-benzyl)-(2-methyl-2H-tetrazol-5-yl)-amine (117.4 mg, 0.21 mmol) in THF (0.5 mL) at 0° C. was added iPrMgCl/LiCl in THF (0.35 mL, 0.7 mmol). The mixture was stirred at 0° C. for 3 hours. Cyclopentanecarboxaldehyde (41 mg, 0.42 mmol) was added. The mixture was stirred at 0° C. for 3 hours, quenched with saturated aqueous ammonium chloride and extracted with ethyl acetate. Combined organic layers were washed with brine, dried over sodium sulfate and concentrated in vacuo. The residue was purified by chromatography over 25+S Biotage silica column (eluted with 0-30% ethyl acetate in hexanes) to afford the title compound as a colorless oil (55.5 mg, 46%). ¹H NMR (400 MHz, CDCl₃) δ ppm 0.97-1.10 (m, 1H) 1.33-1.42 (m, 1H) 1.43-1.70 (m, 5H) 1.76-1.86 (m, 1H) 2.17-2.32 (m, 1H) 2.56 (s, 1H) 4.17-4.20 (m, 3H) 4.69-4.79 (m, 3H) 4.81 (s, 1H) 4.90 (d, J=15.77 Hz, 1H) 7.34 (s, 1H) 7.52 (d, J=8.71 Hz, 1H) 7.58 (d, J=8.30 Hz, 1H) 7.66 (s, 2H) 7.77 (s, 1H). MS (ES⁺) Calc: 581.2, Found: 582.4 (M+1).

Step B: Preparation of (2-{[(3,5-bis-trifluoromethyl-benzyl)-(2-methyl-2H-tetrazol-5-yl)-amino]-methyl}-4-trifluoromethyl-phenyl)-cyclopentyl-methanone

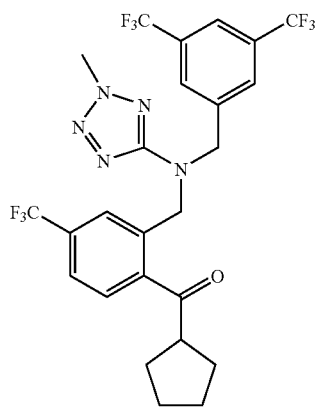

To a solution of (2-{[(3,5-bis-trifluoromethyl-benzyl)-(2-methyl-2H-tetrazol-5-yl)-amino]-methyl}-4-trifluoromethyl-phenyl)-cyclopentyl-methanol (44,5 mg, 0.077 mmol) in methylene chloride (1.0 mL) at room temperature was added Dess-Martin periodinane reagent (35.7 mg, 0.084 mmol). The mixture was stirred at room temperature for 1.5 hours. Ether and 1N sodium hydroxide was added. The mixture was extracted with ethyl acetate. Combined organic layers were washed with brine, dried over sodium sulfate and concentrated in vacuo to yield a pale yellow oil (41.6 mg, 94%). ¹H NMR (400 MHz, CDCl₃) δ ppm 1.58-1.72 (m, 4H) 1.75-1.88 (m, 4H) 3.48-3.58 (m, 1H) 4.18 (s, 3H) 4.81 (s, 2H) 4.88 (s, 2H) 7.53 (s, 1H) 7.57 (d, J=8.30 Hz, 1H) 7.66 (s, 2H) 7.71 (d, 1H) 7.73 (s, 1H). MS (ES⁺) Calc: 579.2, Found: 580.4 (M+1).

Step C: Preparation of 1-(2-{[3,5-bis-trifluoromethyl-benzyl)-(2-methyl-2H-tetrazol-5-yl)-amino]-methyl}-4-trifluoromethyl-phenyl)-1-cyclopentyl-ethanol

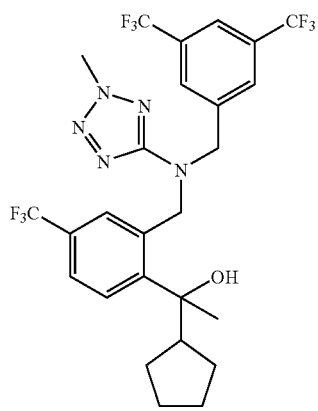

To a solution of (2-{[(3,5-bis-trifluoromethyl-benzyl)-(2-methyl-2H-tetrazol-5-yl)-amino]-methyl}-4-trifluoromethyl-phenyl)-cyclopentyl-methanone (112.5 mg, 0.194 mmol) in THF (2 mL) at room temperature was added cerium (III) chloride (71.8 mg, 0.29 mmol). The mixture was sonicated for 30 minutes and stirred at room temperature for 1 hour. The mixture was cooled to 0° C. and methylmagnesium bromide (0.2 mL of 3M solution in THF, 0.6 mmol) was added. The mixture was stirred at 0° C. for 1.5 hours, quenched with saturated aqueous ammonium chloride and extracted with ethyl acetate. Combined organic layers were washed with brine, dried over sodium sulfate and concentrated to afford a pale yellow oil (115.2 mg, 100%). $^1$H NMR (400 MHz, CDCl$_3$) δ ppm 1.30-1.44 (m, 2H) 1.45-1.69 (m, 6H) 1.54 (s, 3H) 2.37-2.48 (m, J=7.88, 7.88 Hz, 1H) 2.90 (s, 1H) 4.16 (s, 3H) 4.83 (s, 2H) 5.08 (d, J=16.18 Hz, 1H) 5.32 (d, J=16.18 Hz, 1H) 7.39 (s, 1H) 7.41 (s, 2H) 7.71 (s, 2H) 7.76 (s, 1H). MS (ES$^+$) Calc: 595.2, Found: 596.5 (M+1).

Step D: Preparation of (3,5-bis-trifluoromethyl-benzyl)-[2-(1-cyclopentyl-1-methoxy-ethyl)-5-trifluoromethyl-benzyl]-(2-methyl-2H-tetrazol-5-yl)-amine

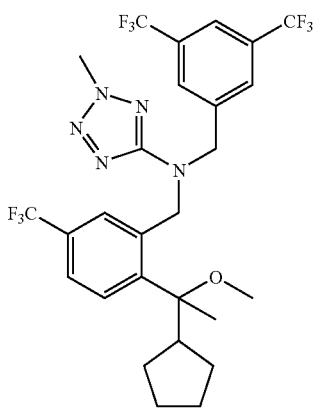

To a solution of 1-(2-{[(3,5-bis-trifluoromethyl-benzyl)-(2-methyl-2H-tetrazol-5-yl)-amino]-methyl}-4-trifluoromethyl-phenyl)-1-cyclopentyl-ethanol (24.8 mg, 0.041 mmol) in THF (0.2 mL) at 0° C. was added sodium hydride (60% dispersion in mineral oil, 8 mg, 0.2 mmol). The mixture was stirred at room temperature for 30 minutes, cooled to 0° C. and methyl iodide (30 µL, 0.5 mmol) was added. The mixture was stirred at room temperature overnight. The reaction mixture was purified by chromatography over 12+S Biotage silica column (eluted with 0-20% ethyl acetate in hexanes) to afford the title compound (17 mg, 67%). $^1$H NMR (400 MHz, CDCl$_3$) δ ppm 1.07 (t, J=8.09 Hz, 2H) 1.31-1.65 (m, 6H) 1.55 (s, 3H) 2.26-2.38 (m, 1H) 3.03 (s, 3H) 4.18 (s, 3H) 4.68-4.75 (m, J=16.18 Hz, 1H) 4.84 (d, J=16.18 Hz, 1H) 5.08 (d, J=17.84 Hz, 1H) 5.22 (d, J=17.43 Hz, 1H) 7.31 (d, J=8.71 Hz, 1H) 7.42-7.47 (m, 2H) 7.71 (s, 2H) 7.76 (s, 1H). MS (ES$^+$) Calc: 609.2, Found: 610.5 (M+1).

EXAMPLES 19 AND 20

(R) and (S) (3,5-Bis-trifluoromethyl-benzyl)-[2-(1-cyclopentyl-1-methoxy-ethyl)-5-trifluoromethyl-benzyl]-(2-methyl-2H-tetrazol-5-yl)-amine

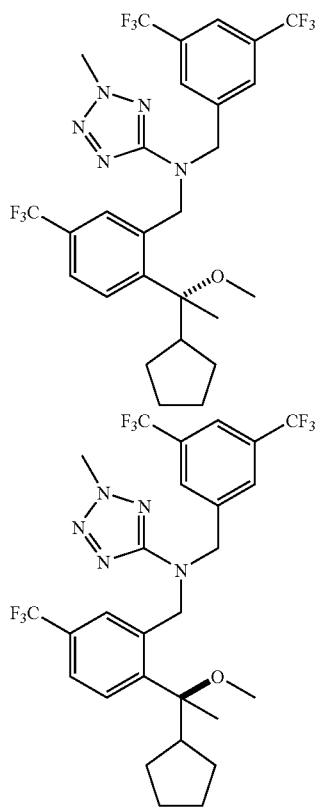

The enantiomers of example 18 were prepared as follows. The racemic mixture of the alcohol from STEP C of example 18 was separated by chiral chromatography using preparative HPLC (Column: ChiralPak AD; Dimension: 5 cm×50 cm; Mobile phase 98/2 heptane/IPA:, Flow rate: 120 mL/minutes). The expected preparative retention times for the two enantiomers are 19 minutes (Enantiomer 1) and 25 minutes (Enantiomer 2). Enantiomer 1: MS Calc: 595.2, Found: 100% ee. Enantiomer 2: MS Calc: 595.2, Found: 93.7% ee Each enantiomer was converted to the title compound according to the procedure described in STEP D of example 18.

Enantiomer 1: $^1$H NMR (400 MHz, CDCl$_3$) δ ppm 1.07 (t, J=8.09 Hz, 2H) 1.31-1.65 (m, 6H) 1.55 (s, 3H) 2.26-2.38 (m, 1H) 3.03 (s, 3H) 4.18 (s, 3H) 4.68-4.75 (m, J=16.18 Hz, 1H) 4.84 (d, J=16.18 Hz, 1H) 5.08 (d, J=17.84 Hz, 1H) 5.22 (d, J=17.43 Hz, 1H) 7.31 (d, J=8.71 Hz, 1H) 7.42-7.47 (m, 2H) 7.71 (s, 2H) 7.76 (s, 1H). MS (ES$^+$) Calc: 609.2, Found: 610.5 (M+1).

Enantiomer 2: $^1$H NMR (400 MHz, CDCl$_3$) δ ppm 1.07 (t, J=8.09 Hz, 2H) 1.31-1.65 (m, 6H) 1.55 (s, 3H) 2.26-2.38 (m, 1H) 3.03 (s, 3H) 4.18 (s, 3H) 4.68-4.75 (m, J=16.18 Hz, 1H) 4.84 (d, J=16.18 Hz, 1H) 5.08 (d, J=17.84 Hz, 1H) 5.22 (d, J=17.43 Hz, 1H) 7.31 (d, J=8.71 Hz, 1H) 7.42-7.47 (m, 2H) 7.71 (s, 2H) 7.76 (s, 1H). MS (ES+) Calc: 609.2, Found: 610.5 (M+1).

EXAMPLE 21 AND 22

(R) and (S)-(3,5-Bis-trifluoromethyl-benzyl)-[2-(cyclopentyl-methoxy-methyl)-5-trifluoromethyl-benzyl]-(2-methyl-2H-tetrazol-5-yl)-amine

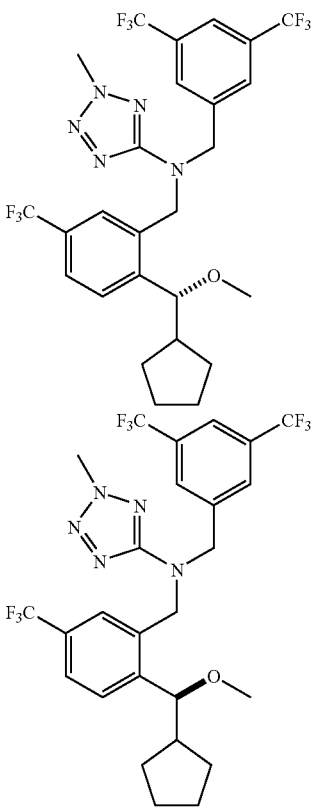

Step A: Preparation of (2-((tert-butyldimethylsilyloxy)methyl)-4-(trifluoromethyl)-phenyl)-(cyclopentyl)methanol

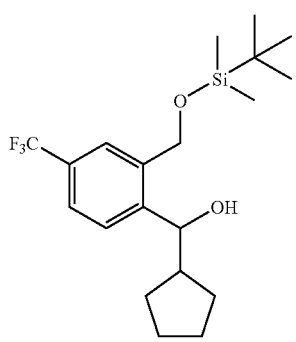

To a solution of (2-((tert-butyldimethylsilyloxy)methyl)-4-(trifluoromethyl)-phenyl)-(cyclopentyl)-methanone (138 mg, 0.35 mmol) in methanol (0.5 mL) at room temperature was added sodium borohydride (40.5 mg, 1.07 mmol). The mixture was stirred at room temperature overnight. Methanol was removed in vacuo. The residue was partitioned between ethyl acetate and water. The organic layer was washed with brine, dried over sodium sulfate and concentrated in vacuo to yield the title compound (126.8 mg, 91%). $^1$H NMR (400 MHz, CDCl$_3$) δ ppm 0.13 (s, 3H) 0.14 (s, 3H) 0.94 (s, 9H) 1.04-1.12 (m, 1H) 1.43-1.74 (m, 6H) 1.87-1.97 (m, 1H) 2.30-2.44 (m, 1H) 2.62-2.75 (m, J=1.66 Hz, 1H) 4.64 (d, J=8.71 Hz, 1H) 4.77 (d, J=12.86 Hz, 1H) 4.92 (d, J=12.86 Hz, 1H) 7.55 (s, 2H) 7.66 (s, 1H).

Step B: Preparation of (2-(cyclopentyl(methoxy)methyl)-5-(trifluoromethyl)benzyloxy)(tert-butyl)dimethylsilane

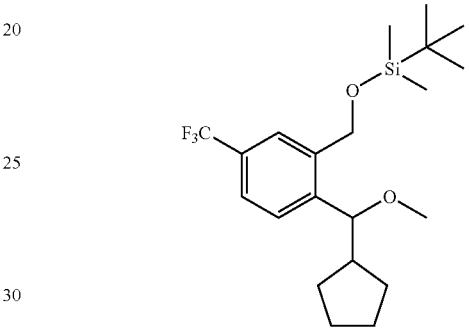

To a solution of (2-((tert-butyldimethylsilyloxy)methyl)-4-(trifluoromethyl)-phenyl)-(cyclopentyl)-methanol (126.8 mg, 0.33 mmol) in THF at 0° C. was added sodium hydride (39.2 mg, 0.98 mmol). The mixture was stirred at room temperature for 30 minutes, cooled to 0° C. and methyl iodide (100 μL, 1.6 mmol) was added. The mixture was stirred at room temperature overnight. Solvent was removed and the residue was purified by chromatography over 12+S Biotage silica column (eluted with 0-20% ethyl acetate in hexanes) to afford the title compound as a colorless oil (120 mg, 91%). $^1$H NMR (400 MHz, CDCl$_3$) δ ppm 0.13 (s, 6H) 0.96 (s, 9H) 1.11-1.21 (m, 1H) 1.30-1.40 (m, 1H) 1.44-1.70 (m, 5H) 1.77-1.86 (m, 1H) 2.13-2.23 (m, 1H) 3.15 (s, 3H) 4.20 (d, J=7.88 Hz, 1H) 4.77 (d, J=13.69 Hz, 1H) 4.89 (d, J=13.28 Hz, 1H) 7.46-7.55 (m, 2H) 7.77 (s, 1H).

Step C: Preparation of (2-(cyclopentyl(methoxy)methyl)-5-(trifluoromethyl)phenyl)methanol

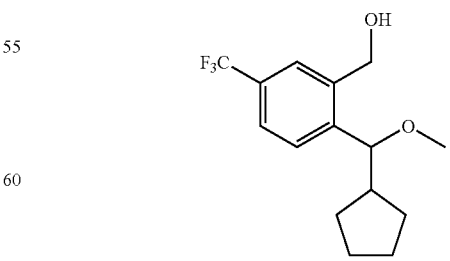

To a solution of (2-(cyclopentyl(methoxy)methyl)-5-(trifluoromethyl)benzyloxy)(tert-butyl)-dimethylsilane (120 mg, 0.298 mmol) in THF at room temperature was added TBAF in THF (1.0M, 0.45 mL, 0.45 mmol). The mixture was stirred at room temperature overnight. Solvent was removed and the residue was purified by chromatography over 12+S Biotage silica column (eluted with 0-20% ethyl acetate in hexane) to afford the title compound as a colorless oil (70 mg, 81%). $^1$H NMR (400 MHz, CDCl$_3$) δ ppm 1.05-1.16 (m, 1H) 1.23-1.35 (m, 1H) 1.38-1.69 (m, 5H) 1.81-1.91 (m, 1H) 2.19-2.33 (m, 1H) 2.92-2.99 (m, 1H) 3.17 (s, 3H) 4.21 (d, J=8.71 Hz, 1H) 4.80 (s, 2H) 7.47 (d, J=7.88 Hz, 1H) 7.54 (d, J=7.88 Hz, 1H) 7.69 (s, 1H).

The racemic mixture was separated by chiral chromatography using preparative HPLC (Column: ChiralPak AD; Dimension: 5 cm×50 cm; Mobile phase: 98/2 heptane/ethanol, Flow rate: 120 mL/minutes). The expected preparative retention times for the two enantiomers were 15 minutes (Enantiomer 1) and 20 minutes (Enantiomer 2). Enantiomer 1: $^1$H NMR (400 MHz, CDCl$_3$) δ ppm 1.05-1.17 (m, 1H) 1.26-1.37 (m, 1H) 1.42-1.72 (m, 5H) 1.83-1.92 (m, 1H) 2.23-2.33 (m, 1H) 2.38-2.47 (m, 1H) 3.18 (s, 3H) 4.20 (d, J=8.30 Hz, 1H) 4.82 (d, J=3.73 Hz, 2H) 7.47 (d, J=8.30 Hz, 1H) 7.55 (d, J=7.88 Hz, 1H) 7.69 (s, 1H). Enantiomer 2: $^1$H NMR (400 MHz, CDCl$_3$) δ ppm 1.05-1.17 (m, 1H) 1.28-1.36 (m, 1H) 1.42-1.71 (m, 5H) 1.81-1.93 (m, 1H) 2.22-2.35 (m, 1H) 2.36-2.48 (m, 1H) 3.18 (s, 3H) 4.20 (d, J=8.71 Hz, 1H) 4.82 (d, J=3.73 Hz, 2H) 7.47 (d, J=8.30 Hz, 1H) 7.55 (d, J=8.30 Hz, 1H) 7.69 (s, 1H).

Step D: Preparation of (R) and (S)-2-(bromomethyl)-1-(cyclopentyl(methoxy)methyl)-4-(trifluoro-methyl)benzene

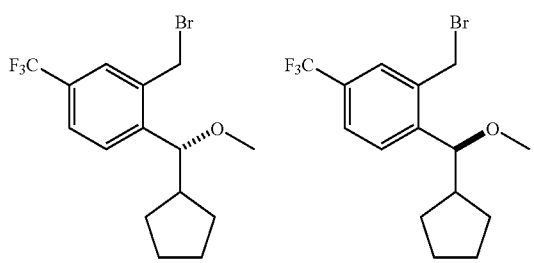

To a solution of (2-(cyclopentyl(methoxy)methyl)-5-(trifluoromethyl)phenyl)methanol (enatiomer 2 from the chiral separation of the racemate in STEP C, 23.1 mg, 0.080 mmol) and carbon tetrabromide (34.5 mg, 0.10 mmol) in methylene chloride (0.5 mL) at room temperature was added triphenyl phosphine (27.3 mg, 0.10 mmol). The mixture was stirred at room temperature overnight. Solvent was removed and the residue was purified by chromatography over 12+S Biotage silica column (eluted with 0-20-30% ethyl acetate in heptane) to afford the title compound (23.1 mg, 82%). $^1$H NMR (400 MHz, CDCl$_3$) δ ppm 1.15-1.27 (m, 1H) 1.34-1.44 (m, 1H) 1.44-1.72 (m, 5H) 1.78-1.87 (m, 1H) 2.16-2.26 (m, 1H) 3.21 (s, 3H) 4.32 (d, J=7.88 Hz, 1H) 4.57 (d, J=10.37 Hz, 1H) 4.67 (d, J=10.37 Hz, 1H) 7.49-7.59 (m, 2H) 7.61 (s, 1H).

The other enantiomer of the title compound was prepared in the same manner using enantiomer 1 from the chiral separation of the racemate in STEP C.

Step E: Preparation of (R) and (S)-(3,5-bis-trifluoromethyl-benzyl)-[2-(cyclopentyl-methoxy-methyl)-5-trifluoromethyl-benzyl]-(2-methyl-2H-tetrazol-5-yl)-amine

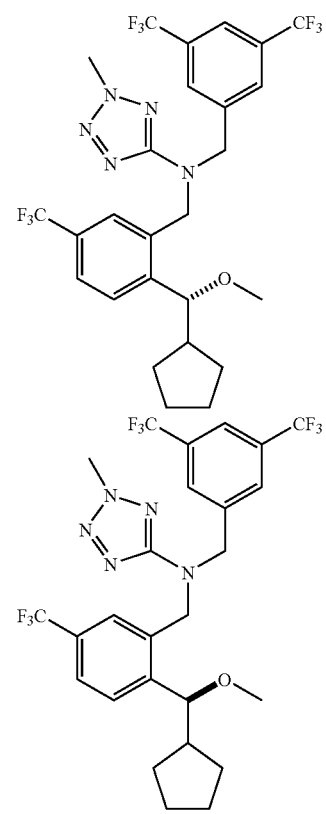

To a solution of N-(3,5-bis(trifluoromethyl)benzyl)-2-methyl-2H-tetrazol-5-amine (25.7 mg, 0.078 mmol) in DMF (0.1 mL) at room temperature was added sodium hydride (6 mg, 0.2 mmol). The mixture was stirred at room temperature for 1 hour. 2-(Bromomethyl)-1-(cyclopentyl(methoxy)methyl)-4-(trifluoromethyl)benzene (Enantiomer 1 from STEP D, 23.1 mg, 0.066 mmol) in DMF (0.2 mL) was added. The mixture was stirred at room temperature for 2 days. Solvent was removed in vacuo. The residue was purified by chromatography over 12+S Biotage silica column (eluted with 0-25% ethyl acetate in heptane) to afford the title compound (7.5 mg, 19%). $^1$H NMR (400 MHz, CDCl$_3$) δ ppm 1.04-1.16 (m, 1H) 1.22-1.33 (m, 1H) 1.38-1.50 (m, 3H) 1.51-1.63 (m, 2H) 1.65-1.76 (m, 1H) 2.02-2.14 (m, 1H) 3.07 (s, 3H) 4.19 (d, J=7.88 Hz, 1H) 4.20-4.23 (m, 3H) 4.72 (d, J=2.49 Hz, 2H) 4.76 (d, J=16.18 Hz, 1H) 4.90 (d, J=16.18 Hz, 1H) 7.35 (s, 1H) 7.51-7.58 (m, 2H) 7.66 (s, 2H) 7.78 (s, 1H). MS (ES$^+$) Calc: 595.2, Found: 596.5 (M+1)

To a solution of N-(3,5-bis(trifluoromethyl)benzyl)-2-methyl-2H-tetrazol-5-amine (27.2 mg, 0.084 mmol) in DMF (0.1 mL) at room temperature was added sodium hydride (6 mg, 0.2 mmol). The mixture was stirred at room temperature for 1 hour. 2-(Bromomethyl)-1-(cyclopentyl(methoxy)methyl)-4-(trifluoromethyl)benzene (Enantiomer 2 from STEP D, 24.5 mg, 0.070 mmol) in DMF (0.2 mL) was added. The mixture was stirred at room temperature overnight. Solvent was removed in vacuo. The residue was purified by chromatography over 12+S Biotage silica column (eluted with 0-30% ethyl acetate in heptane) to afford the title compound (18.6 mg, 45%). The residue was purified by chromatography over 12+S Biotage silica column (eluted with 0-30% ethyl acetate in hexanes) to afford a colorless oil (18.6 mg, 45%). $^1$H NMR (400 MHz, CDCl$_3$) δ ppm 1.04-1.15 (m, 1H) 1.23-1.33 (m, 1H) 1.38-1.63 (m, 5H) 1.66-1.75 (m, 1H) 2.03-2.11 (m, 1H) 3.07 (s, 3H) 4.19 (d, J=7.88 Hz 1H) 4.21 (s, 3H) 4.72 (d, J=2.90 Hz, 2H) 4.76 (d, J=16.18 Hz, 1H) 4.90 (d, J=16.18 Hz, 1H) 7.35 (s, 1H) 7.51-7.58 (m, 2H) 7.66 (s, 2H) 7.77 (s, 1H). MS (ES$^+$) Calc: 595.2, Found: 596.5 (M+1).

Preparation 9: 2-(2-Bromo-5-iodo-4-methylbenzyl) isoindoline-1,3-dione

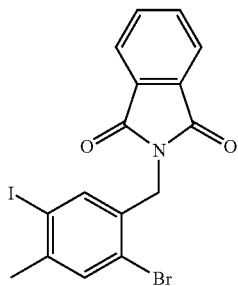

To a solution of 5-bromo-2-iodo toluene (512 mg, 1.72 mmol) in trifluoroacetic acid (5 mL) was added N-(hydroxymethy) phthalimide (305 mg, 1.72 mmol). The mixture developed a pink color. The solution was stirred at room temperature for 22 hours then concentrated sulfuric acid (1 mL) was added. The homogeneous solution was stirred for 18 hours at room temperature. Water was added and the precipitated solid collected by filtration and dried in a current of air (0.776 gm). This material, which by proton NMR analysis contained approximately 15% of an isomeric product, was carried forward to the following procedure without further purification. $^1$H NMR (400 MHz, CDCl$_3$) δ7.85 (m, 2H) 7.76(m, 2H) 7.5 (s, 1H) 7.38(s, 1H) 4.84(s, 2H) 2.31(s, 3H).

GC-MS calc. 455, found 455.

Preparation 10: 2-(2-Bromo-4-methyl-5-(trifluoromethyl) benzyl) isoindoline-1,3-dione

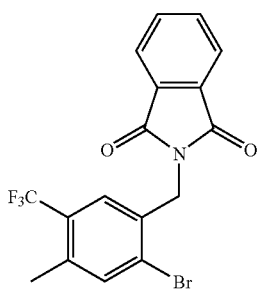

To a solution of 2-(2-bromo-5-iodo-4-methylbenzyl) isoindoline-1,3-dione (560 mg, 1.22 mmol) in N,N-dimethylformamide (10 mL) was added copper iodide (467.6 mg, 2.45 mmol) and potassium fluoride (291.1 mg, 4.91 mmol). The solution was heated to 120° C. After 20 minutes methyl-2-chloro-2,2-difluoroacetate (709.71 mg, 4.91 mmol) was added to the orange suspension and the heating was continued for 8 hours. After about 30 minutes gas evolution was observed and the solution became yellow. After cooling the mixture was poured into water (50 mL), forming an emulsion, to which was added dichloromethane (300 mL). The mixture was stirred for 20 minutes then filtered through a pad of Celite®, rinsing through with dichloromethane. The organic layer was washed with 25 mL of 2 N HCl, dried with anhydrous sodium sulfate and concentrated under reduced pressure to a yellow solid (510 mg). This material was recrystallized from hot ethanol (30 mL) then allowed to stand at room temperature for 72 hours. The crystals were collected by filtration and rinsed with ethanol to give a white crystalline solid (314 mg). Final purification was achieved by recrystallization from hot acetonitrile to give the title compound (200 mg, 40%). $^1$H NMR (400 MHz, CDCl$_3$) δ 7.86 (m, 2H) 7.74(m, 2H) 7.50 (s, 1H) 7.39(s, 1H) 4.84(s, 2H) 2.32(s, 3H). GC-MS calc. 398, found 376 (M-F)

Preparation 11:
(2-Bromo-4-methyl-5-(trifluoromethyl) phenyl) methanamine

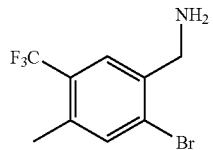

A mixture of 2-(2-bromo-5-iodo-4-methylbenzyl) isoindoline-1,3-dione (460 mg, 1.15 mmol) and hydrazine hydrate (148.1 mg, 4.62 mmol) was heated under reflux for 1 hour and the volatiles removed under reduced pressure. To the residue was added 1 M sodium hydroxide (50 mL) and dichloromethane (40 mL). The mixture was stirred for 20 minutes then filtered through a sintered glass funnel, rinsing with dichloromethane. The organic layer was separated, the aqueous layer extracted with dichloromethane (2×75 mL) and the combined organics dried with anhydrous magnesium sulfate and concentrated to dryness under reduced pressure. This material was purified by flash chromatography on a 4 gm RediSep column (Teledyne Isco Inc., Lincoln Nebr.) (eluted with ethyl acetate) to yield the title compound (0.189 gm, 84.6%). $^1$H NMR (400 MHz, CDCl$_3$) δ 7.62 (s, 1H) 7.48(s, 1H) 3.93 (s, 2H) 2.51(s, 3H)

Preparation 12: N-(2-Bromo-4-methyl-5-(trifluoromethyl) benzyl) (3,5-bis(trifluoromethyl) phenyl) methanamine

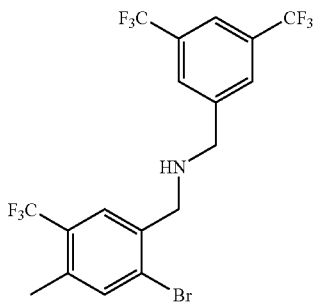

A mixture of (2-bromo-4-methyl-5-(trifluoromethyl) phenyl) methanamine (189 mg, 0.705 mmol) and 3,5 bistrifluoromethyl benzaldehyde (170 mg, 0.705 mmol) in anhydrous toluene (10 mL) was heated under reflux for 3 hours. The solvent was removed under reduced pressure and the residue was dissolved in dichloromethane (25 mL). Sodium triacetoxyborohyride (373.5 mg, 1.76 mmol) was added and the mixture was stirred for 18 hours at room temperature. The mixture was poured into a mixture of saturated NaHCO$_3$ (50 mL) and ethyl acetate (50 mL) and stirred for 30 minutes. The layers were separated and the aqueous layer was extracted with ethyl acetate (2×50 mL). The combined organic layer was dried with anhydrous sodium sulfate, filtered and concentrated to give the title compound (98.4%). $^1$H NMR (400 MHz, CDCl$_3$) δ 7.83 (s, 2H) 7.76(s, 1H) 7.58(s, 1H) 7.41 (s, 1H) 3.92(s, 2H) 3.89(s, 2H) 2.44(s, 3H)

Preparation 13: (2-Bromo-4-methyl-5-(trifluoromethyl) benzyl) (3,5-bis(trifluoromethyl) benzyl) cyanamide

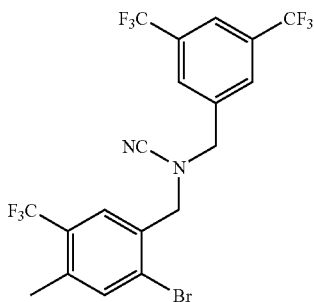

N-(2-Bromo-4-methyl-5-(trifluoromethyl)benzyl)(3,5-bis (trifluoromethyl)phenyl)methanamine (89 mg, 0.180 mmol) was dissolved in methanol (10 mL). To this solution was added sodium carbonate (53.9 mg, 0.396 mmol) followed by cyanogen bromide (5.0M solution in acetonitrile, 21.9 mg, 0.041 mL, 0.207 mmol). The solution stirred at room temperature for 20 hours then concentrated under reduced pressure to dryness. The residue was partitioned between water (10 mL) and ethyl acetate (50 mL). The aqueous layer was extracted with ethyl acetate (2×20 mL), the organics were combined and dried with anhydrous sodium sulfate, filtered, and concentrated under reduced pressure to give the title compound (97.5%). $^1$H NMR (400 MHz, CDCl$_3$) δ 7.85 (s, 1H) 7.72 (s, 2H) 7.54 (s, 1H) 7.51 (s, 1H) 4.34(s, 4H) 2.45(s, 3H). LC-MS calc. 519, found 520 (M+H)

Preparation 14: N-(2-Bromo-4-methyl-5-trifluoromethyl)benzyl)-N-(3,5-bis(trifluoromethyl)benzyl)-2H-tetrazol-5-amine

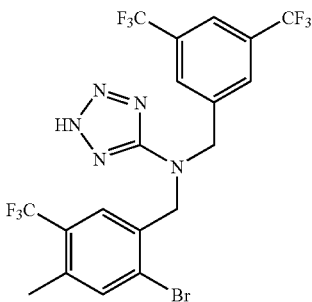

To a solution of (2-bromo-4-methyl-5-(trifluoromethyl) benzyl)(3,5-bis(trifluoromethyl) benzyl) cyanamide (80 mg, 0.154 mmol) in toluene (10 mL) was added triethylamine hydrochloride (63.62 mg, 0.462 mmol) and sodium azide (30.05 mg, 0.462 mmol). The mixture was heated to 115° C. for 18 hours, cooled, then 0.1 N hydrogen chloride (30 mL) was added to the mixture and stirred for 30 minutes. The aqueous layer was extracted with ethyl acetate (2×30 mL) and the combined organic layers were dried with anhydrous sodium sulfate, filtered, and concentrated to dryness under reduced pressure. The residue was purified by flash chromatography on a 12 g RediSep column (Teledyne Isco Inc., Lincoln Nebr.) (eluted with 25-100% ethyl acetate in heptane) to yield the title compound (66%). $^1$H NMR (400 MHz, CDCl$_3$) δ 7.71(s, 1H) 7.59 (s, 2H) 7.43(s, 1H) 7.34(s, 1H) 4.80(s, 2H) 4.77(s, 2H) 2.37(s, 3H). LC-MS calc. 562, found 563 (M+H)

Preparation 15: N-(2-Bromo-4-methyl-5-(trifluoromethyl) benzyl)-N-(3,5-bis(trifluoromethyl) benzyl)-2-methyl-2H-tetrazol-5-amine

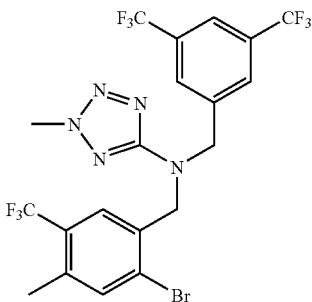

To a solution of N-(2-bromo-4-methyl-5-(trifluoromethyl) benzyl)-N-(3,5-bis(trifluoromethyl)benzyl)-2H-tetrazol-5-amine (76 mg, 0.135 mmol) in anhydrous THF (5 mL) was added sodium carbonate (28 mg, 0.270 mmol) and N,N-dimethylformamide (1 mL) followed by dimethyl sulfate (34 mg. 0.270 mmol). The solution was heated to 70° C. for 18 hours then the solvent was removed under reduced pressure. The residue was partitioned between ethyl acetate (20 mL) and water (10 mL). The aqueous layer was extracted with ethyl acetate (3×20 mL) and the combined organics were washed with water (3×20 mL). The combined organics were dried with anhydrous sodium sulfate, filtered and concentrated under reduced pressure to give the title compound (76 mg, 97.5%). $^1$H NMR (400 MHz, CDCl$_3$) δ 7.71 (s, 1H) 7.62 (s, 2H) 7.44(s, 1H) 7.40(s, 1H) 4.79(s, 2H) 4.76(s, 2H) 4.20(s, 3H) 2.39(s, 3H). LC-MS calc. 576 found 577 (M+H)

EXAMPLE 23

(3,5-Bis-trifluoromethyl-benzyl)-[2-(cyclohexyl-methoxy-methyl)-4-methyl-5-trifluoromethyl-benzyl]-(2-methyl-2H-tetrazol-5-yl)-amine

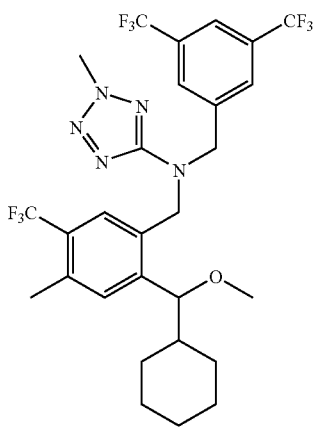

Step 1: Preparation of (2-{[(3,5-bis-trifluoromethyl-benzyl)-(2-methyl-2H-tetrazol-5-yl)amino]-methyl}-5-methyl-4-trifluoromethyl-phenyl)-cyclohexyl-methanol

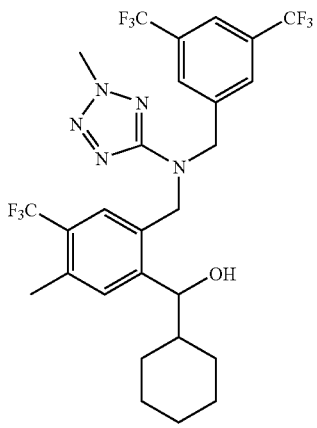

To a solution of N-(2-bromo-4-methyl-5-(trifluoromethyl) benzyl)-N-(3,5-bis(trifluoromethyl)benzyl)-2-methyl-2H-tetrazol-5-amine (20 mg, 0.035 mmol) in THF (0.2 mL) at 0° C. was added iPrMgCl/LiCl (0.075 mL, 0.11 mmol). The mixture was stirred at 0° C. for 3 hours and cyclohexanecarboxaldehyde (9.3 mg, 0.083 mmol) was added. The mixture was stirred at 0° C.-room temperature for 2 hours, quenched with aqueous ammonium chloride and diluted with ethyl acetate. The organic layer was filtered through a short pad of sodium sulfate and concentrated in vacuo. The residue was purified by chromatography over 12+S Biotage silica column (eluted with 0-30% ethyl acetate in heptane) to afford the title compound (8.6 mg, 41%). $^1$H NMR (400 MHz, CDCl$_3$) δ ppm 0.91-1.32 (m, 6H) 1.52-1.60 (m, 1H) 1.61-1.67 (m, 2H) 1.77 (d, 1H) 1.95 (d, J=12.86 Hz, 1H) 2.19 (d, J=3.32 Hz, 1H) 2.45 (s, 3H) 4.19 (s, 3H) 4.61 (dd, J=7.47, 2.90 Hz, 1H) 4.67 (d, J=15.77 Hz, 1H) 4.64-4.79 (m, 2H) 4.82 (d, J=15.35 Hz, 1H) 7.30 (s, 1H) 7.34 (s, 1H) 7.63 (s, 2H) 7.76 (s, 1H). MS (ES$^+$) Calc: 609.2, Found: 610.56 (M+1)

Step 2: Preparation of (3,5-bis-trifluoromethyl-benzyl)-[2-(cyclohexyl-methoxy-methyl)-4-methyl-5-trifluoromethyl-benzyl]-(2-methyl-2H-tetrazol-5-yl)-amine

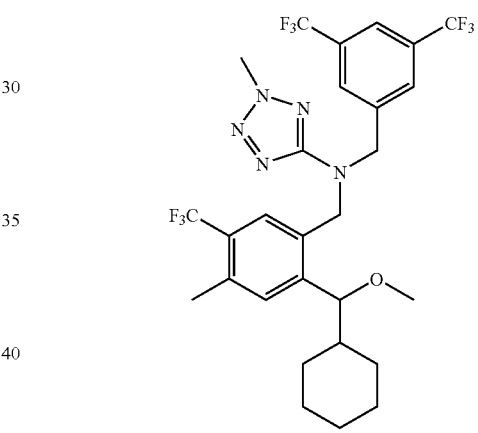

To a solution of (2-{[(3,5-Bis-trifluoromethyl-benzyl)-(2-methyl-2H-tetrazol-5-yl)-amino]-methyl}-5-methyl-4-trifluoromethyl-phenyl)-cyclohexyl-methanol (8 mg, 0.01 mmol) in THF (0.15 mL) at 0° C. was added sodium hydride (4.2 mg, 0.11 mmol). The mixture was stirred at room temperature for 30 minutes. Methyl iodide (10 µL, 0.2 mmol) was added at 0° C. The mixture was stirred at room temperature overnight. The mixture was quenched with methanol and purified by chromatography over 12+S Biotage silica column (eluted with 0-30% ethyl acetate in heptane) to afford the title compound (3.6 mg, 40%). $^1$H NMR (400 MHz, CDCl$_3$) δ ppm 0.92-1.20 (m, 6H) 1.41-1.51 (m, 1H) 1.61 (d, J=8.71 Hz, 2H) 1.67-1.74 (m, 1H) 1.93 (d, J=11.62 Hz, 1H) 2.46 (s, 3H) 3.04 (s, 3H) 4.04 (d, J=7.05 Hz, 1H) 4.21 (s, 3H) 4.63-4.72 (m, 3H) 4.84 (d, J=16.18 Hz, 1H) 7.27 (s, 1H) 7.30 (s, 1H) 7.63 (s, 2H) 7.77 (s, 1H). MS (ES$^{30}$) Calc: 623.2, Found: 624.6 (M+1)

According to the procedure described in example 23 and using the corresponding aryl bromide and aldehyde reagent, example 24 was prepared.

| Example # | Chemical Name | Structure | MS Calc | MS Found M + 1 |
|---|---|---|---|---|
| 24 | (3,5-Bis-trifluoromethyl-benzyl)-[2-(1-methoxy-3-pyridin-3-yl-propyl)-5-trifluoromethyl-benzyl]-(2-methyl-2H-tetrazol-5-yl)-amine | 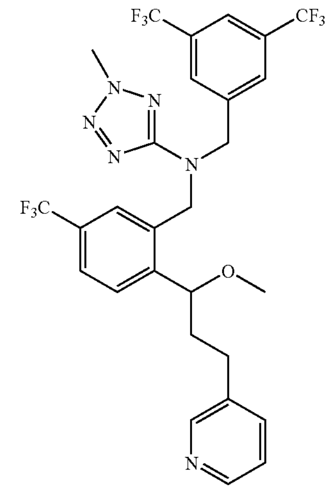 | 532.2 | 533.6 |

Preparation 16: (2-(((3,5-Bis(trifluoromethyl)benzyl)-2-methyl-2H-tetrazol-5-yl)amino)methyl)-5-methyl-4-(trifluoromethyl)phenyl)(cyclohexl)methanone

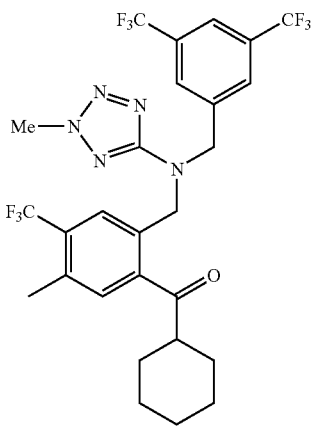

To a solution of (2-(((3,5-bis(trifluoromethyl)benzyl)(2-methyl-2H-tetrazol-5-yl)amino)methyl)-5-methyl-4-(trifluoromethyl)phenyl)(cyclohexyl)methanol (53 mg, 0.086 mmol) in dichloromethane (3 mL) was added the Dess-Martin periodinane (47.9 mg, 0.113 mmol) and the mixture was stirred at room temperature for 1.5 hours. Diethyl ether (20 mL) was added to the solution followed by 2 M NaOH (5 mL). The layers were separated, the organic layer was dried with anhydrous sodium sulfate and concentrated under reduced pressure to give the title compound as a yellow gum (52.2 mg). $^1$H NMR (400 MHz, CDCl$_3$) δ7.70 (s, 1H) 7.62 (s, 2H) 7.48 (s, 1H) 7.36 (s, 1H) 4.76 (s, 4H) 4.18 (s, 3H) 2.47 (s, 3H) 1.80 (d, J=10.0 Hz, 4H) 1.22 (m, 7H). LC-MS calc. 607.5, found 608.6 (M+H).

Preparation 17: 1-(2-(((3,5-Bis(trifluoromethyl)benzyl)(2-methyl-2H-tetrazol-5-yl)amino)methyl)-5-methyl-4-(trifluoromethyl)phenyl)-1-cyclohexylethanol

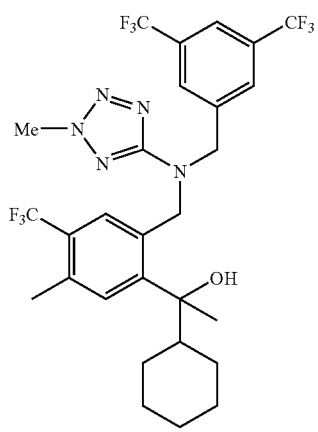

To a solution of (2-(((3,5-bis(trifluoromethyl)benzyl)(2-methyl-2H-tetrazol-5-yl)amino)methyl)-5-methyl-4-(trifluoromethyl)phenyl)(cyclohexyl)methanone (52 mg, 0.085 mmol) in anhydrous THF (10 mL) under nitrogen at 0° C. was added methylmagnesium bromide (3.0 M solution in THF, 25.6 mg, 0.114 mL, 0.342 mmol). The solution was stirred at 0° C. for 30 minutes, then warmed to room temperature and stirred for 1.5 hours. The solution was then poured into a mixture of 2 N hydrochloric acid (10 mL) and ethyl acetate (20 mL). The solution was stirred at room temperature for 10 minutes then the layers were separated and the aqueous layer was extracted with ethyl acetate (3×15 mL). The combined organics layer was dried with anhydrous sodium sulfate, filtered, and concentrated under reduced pressure. The crude product was purified by flash chromatography on a 4 g RediSep column (Teledyne Isco Inc., Lincoln Nebr.) (eluted with 1-50% ethyl acetate in heptane) to yield the title compound (97.2%). $^1$H NMR (400 MHz, CDCl$_3$) δ 7.73 (s, 1H) 7.68 (s, 2H) 7.33 (s, 1H) 7.17 (s, 1H) 5.39 (d, J=16.17 Hz, 1H) 4.82 (d, J=15.76 Hz, 1H) 4.77(s, 2H) 4.15(s, 3H) 2.39 (s, 3H) 1.62 (m, 6H) 1.24 (s, 3H) 1.04 (m, 5H). LC-MS calc. 623.5, found 624.6 (M+H)

EXAMPLE 25

N-(2-(1-cyclohexyl-1-methoxyethyl)-4-methyl-5-(trifluoromethyl)benzyl)-N-(3,5-bis (trifluoromethyl) benzyl)-2-methyl-2H-tetrazol-5-amine

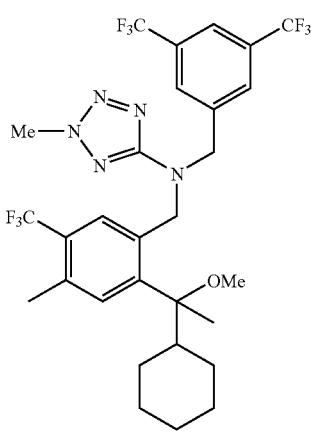

To a solution of 1-(2-(((3,5-bis(trifluoromethyl)benzyl)(2-methyl-2H-tetrazol-5-yl)amino)methyl)-5-methyl-4-(trifluoromethyl)phenyl)-1-cyclohexylethanol (18 mg, 0.028 mmol) in THF (3 mL) was added sodium hydride (60% dispersion in mineral oil, 8 mg, 0.202 mmol) at room temperature. After stirring for 5 minutes methyl iodide (12.2 mg, 0.086 mmol) was added and the solution was stirred at room temperature for 18 hours. Water (5 mL) was added and the mixture was extracted with ethyl acetate (3×20 mL). The organics were combined, dried with anhydrous sodium sulfate, filtered and concentrated to give an oil (17 mg). This material was purified by flash chromatography on a 4 g RediSep column (Teledyne Isco Inc., Lincoln Nebr.) (eluted with 10% ethyl acetate in heptane) to yield the title compound (11 mg, 59%). $^1$H NMR (400 MHz, CDCl$_3$) δ7.75 (s, 1H) 7.70 (s, 2H) 7.39 (s, 1H) 7.01 (s, 1H) 5.19 (d, J=17.42 Hz, 1H) 5.0 (d, J=17.42 Hz, 1H) 4.74 (q, J=16.72 Hz, J=16.18 Hz, 2H) 4.17 (s, 3H) 3.0 (s, 3H) 2.42 (s, 3H) 1.99 (d, J=12.40 Hz, 1H) 1.72 (m, 2H) 1.58 (s, 3H) 0.99 (m, 8H). MS calc. 637.5, found 638.5 (M+H)

EXAMPLE 26

4-[(2-{[(3,5-Bis-trifluoromethyl-benzyl)-(2-methyl-2H-tetrazol-5-yl)-amino]-methyl}-4-trifluoromethyl-phenyl)-methoxy-methyl]-piperidine-1-carboxylic acid methyl ester

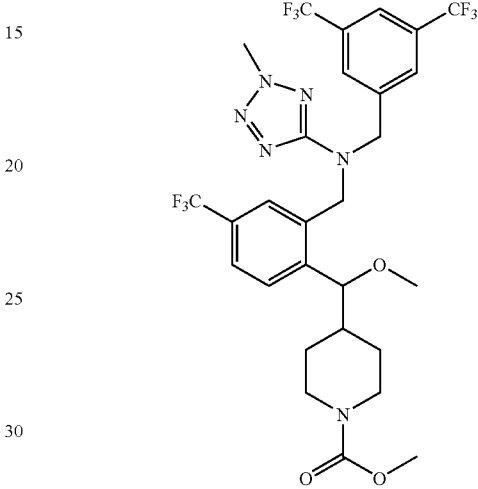

Step A: Preparation of tert-butyl 4-[((2-(((3,5-bis (trifluoromethyl)benzyl)(2-methyl-2H-tetrazol-5-yl) amino)methyl)-4-(trifluoromethyl)phenyl])(hydroxy) methyl)piperidine-1-carboxylate

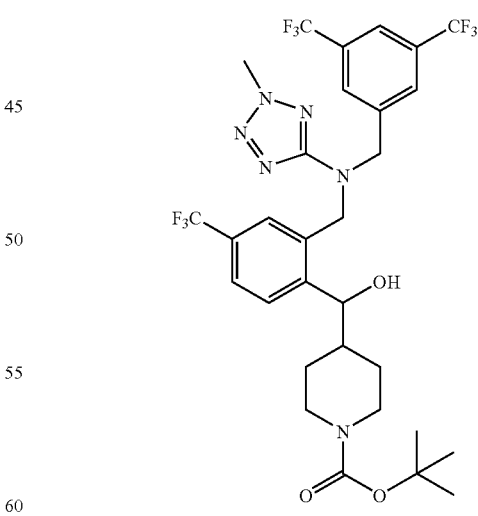

To a solution of (3,5-bis-trifluoromethyl-benzyl)-(2-bromo-5-trifluoromethyl-benzyl)-(2-methyl-2H-tetrazol-5-yl)-amine (115 mg, 0.21 mmol) in THF (0.5 mL) at 0° C. was added i-PrMgCl/LiCl (0.3 mL, 0.39 mmol). The mixture was stirred 0° C. for 3 hours and tert-butyl 4-formylpiperidine-1-carboxylate (70.7 mg, 0.33 mmol) in THF (0.1 mL) was added. The mixture was stirred at 0° C. to room temperature for 3 hours and quenched with saturated aqueous ammonium chloride. The mixture was extracted with ethyl acetate. Combined organic layers were washed with brine, dried over sodium sulfate and concentrated in vacuo. The residue was purified by chromatography over 25+S Biotage silica column (eluted with 0-50% ethyl acetate in hexanes) to afford the title compound (62.2 mg, 44%). $^1$H NMR (400 MHz, CDCl$_3$) δ ppm 1.12-1.19 (m, 1H) 1.20-1.32 (m, 1H) 1.43 (s, 9H) 1.69-1.78 (m, 1H) 1.89 (dd, J=13.07, 1.87 Hz, 1H) 2.46-2.67 (m, 2H) 3.99-4.15 (m, 2H) 4.18 (s, 3H) 4.66-4.73 (m, 2H) 4.68-4.83 (m, 4H) 4.87 (d, J=15.77 Hz, 1H) 7.33 (s, 1H) 7.55 (s, 2H) 7.64 (s, 2H) 7.77 (s, 1H). MS (ES$^+$) Calc: 696.2, Found: 697.6 (M+1)

Step B: Preparation of tert-butyl 4-((2-(((3,5-bis(trifluoromethyl)benzyl)(2-methyl-2H-tetrazol-5-yl)amino)methyl)-4-(trifluoromethyl)phenyl)(methoxy)methyl)piperidine-1-carboxylate

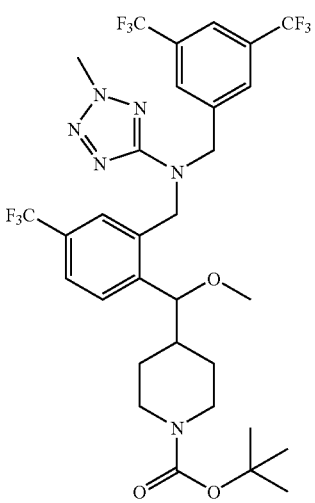

To a solution of tert-butyl 4-((2-(((3,5-bis(trifluoromethyl)benzyl)(2-methyl-2H-tetrazol-5-yl)amino)methyl)-4-(trifluoromethyl)phenyl)(hydroxy)methyl)piperidine-1-carboxylate (62.2 mg, 0.089 mmol) in THF at 0° C. was added sodium hydride (10.7 mg, 0.27 mmol). The mixture was stirred at room temperature for 30 minutes, cooled to 0° C. and methyl iodide (30 μL, 0.5 mmol) was added. The mixture was stirred at room temperature overnight. The reaction was quenched with methanol. Solvent was removed and the residue was purified by chromatography over 12+S Biotage silica column (eluted with 0-30% ethyl acetate in hexanes) to afford the title compound (45.9 mg, 72%). $^1$H NMR (400 MHz, CDCl$_3$) δ ppm 1.09-1.16 (m, 1H) 1.17-1.29 (m, 2H) 1.43 (s, 9H) 1.58-1.69 (m, 1H) 1.84 (d, J=13.28 Hz, 1H) 2.44-2.58 (m, 2H) 3.04 (s, 3H) 4.04 (d, J=12.45 Hz, 1H) 4.11 (d, J=7.47 Hz, 1H) 4.15 (d, J=7.05 Hz, 1H) 4.20 (s, 3H) 4.68 (d, J=15.77 Hz, 1H) 4.71 (s, 2H) 4.88 (d, J=16.18 Hz, 1H) 7.36 (s, 1H) 7.50 (d, J=8.30 Hz, 1H) 7.57 (d, J=7.88 Hz, 1H) 7.65 (s, 2H) 7.78 (s, 1H). MS (ES$^+$) Calc: 710.3, Found: 711.6 (M+1)

Step C: Preparation of N-(2-(methoxy(piperidin-4-yl)methyl)-5-(trifluoromethyl)benzyl)-N-(3,5-bis(trifluoromethyl)benzyl)-2-methyl-2H-tetrazol-5-amine

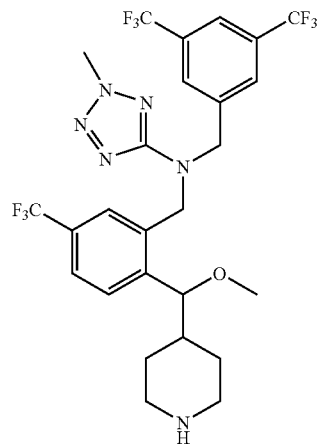

To a solution of tert-butyl 4-((2-(((3,5-bis(trifluoromethyl)benzyl)(2-methyl-2H-tetrazol-5-yl)amino)methyl)-4-(trifluoromethyl)phenyl)(methoxy)methyl)piperidine-1-carboxylate (36.3 mg, 0.051 mmol) in dioxane (0.3 mL) at room temperature was added 4N HCl in dioxane (0.15 mL, 0.6 mmol). The mixture was stirred at room temperature for 2 hours and additional HCl (0.05 mL) was added. The mixture was stirred for 2 hours. Solvent was removed in vacuo. Ethyl acetate was added and removed. Isopropyl ether was added and removed to yield a thick oil The HCl salt was dissolved in methanol and filtered through SCX cartridge (released with ammonia in methanol) to yield the title compound (23.5 mg, 75%). $^1$H NMR (400 MHz, CDCl$_3$) δ ppm 1.07-1.15 (m, 1H) 1.16-1.31 (m, 2H) 1.56-1.69 (m, 1H) 1.83-1.92 (m, J=7.05 Hz, 2H) 2.37-2.52 (m, 2H) 2.98 (d, J=12.45 Hz, 1H) 3.05 (s, 3H) 3.09 (s, 1H) 4.13 (d, J=7.05 Hz, 1H) 4.21 (s, 3H) 4.69 (d, J=15.77 Hz, 1H) 4.71 (d, J=3.73 Hz, 2H) 4.90 (d, J=16.18 Hz, 1H) 7.35 (s, 1H) 7.50 (d, J=8.30 Hz, 1H) 7.56 (d, J=9.13 Hz, 1H) 7.65 (s, 2H) 7.77 (s, 1H). MS (ES$^+$) Calc: 610.2, Found: 611.4 (M+1)

Step D: Preparation of 4-[(2-{[(3,5-Bis-trifluoromethyl-benzyl)-(2-methyl-2H-tetrazol-5-yl)-amino]-methyl}-4-trifluoromethyl-phenyl)-methoxy-methyl]-piperidine-1-carboxylic acid methyl ester

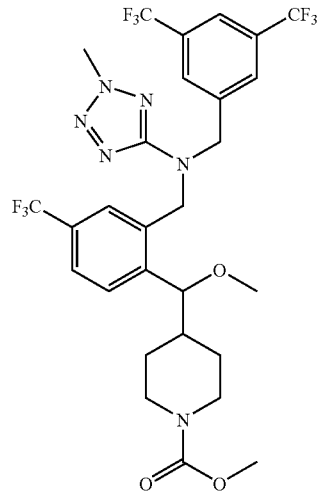

To a solution of N-(2-(methoxy(piperidin-4-ylmethyl)-5-(trifluoromethyl)benzyl)-N-(3,5-bis(trifluoromethyl)benzyl)-2-methyl-2H-tetrazol-5-amine (21.5 mg, 0.035 mmol) in methylene choride at room temperature was added Hunig's base (11 mg, 15 μL, 0.084 mmol) followed by methyl chloroformate (10 μL). The mixture was stirred at room temperature overnight. Solvent was removed in vacuo and the residue was purified by chromatography over 12+S Biotage silica column (eluted with 0-30% ethyl acetate in hexanes) to afford the title compound (18.6 mg, 79%). $^1$H NMR (400 MHz, CDCl$_3$) δ ppm 1.11-1.18(m, 1H) 1.18-1.31 (m, 2H) 1.62-1.71 (m, 1H) 1.85(d, J=13.28 Hz, 1H) 2.50-2.64 (m, 2H) 3.04(s, 3H) 3.66 (s, 3H) 3.99-4.20 (m, 2H) 4.16 (d, J=7.05 Hz, 1H) 4.21 (s, 3H) 4.68 (d, J=15.77 Hz, 1H) 4.71 (s, 2H) 4.88 (d, J=15.77 Hz, 1H) 7.36 (s, 1H) 7.50 (d, J=8.30 Hz, 1H) 7.58 (d, J=9.13 Hz, 1H) 7.64 (s, 2H) 7.78 (s, 1H). MS (ES$^+$) Calc: 668.2, Found: 669.6 (M+1)

EXAMPLE 27

4-[(2-{[(3,5-Bis-trifluoromethyl-benzyl)-(2-methyl-2H-tetrazol-5-yl)-amino]-methyl}-4-trifluoromethyl-phenyl)-methoxy-methyl]-piperidine-1-carboxylic acid amide

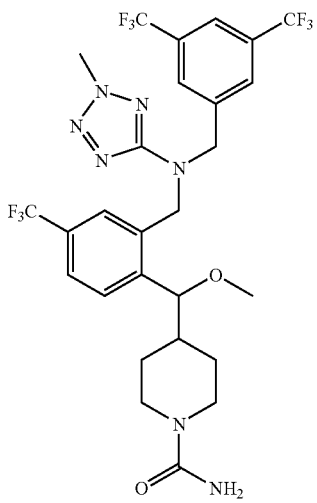

To a solution of N-(2-(methoxy(piperidin-4-yl)methyl)-5-(trifluoromethyl)benzyl)-N-(3,5-bis(trifluoromethyl)benzyl)-2-methyl-2H-tetrazol-5-amine (19.5 mg, 0.030 mmol) in methylene chloride (0.2 mL) at room temperature was added Hunig's base (7 mg, 10 μL, 0.06 mmol) followed by phosgene in toluene (20%, 25 μL, 0.048 mmol). The mixture was stirred at room temperature for 1 hour. Aqueous ammonia (0.2 mL) was added. The mixture was stirred at room temperature overnight. Solvent was removed in vacuo. The residue was purified by chromatography over 12+S Biotage silica column (eluted with 1-7% methanol in methylene chloride) to afford the title compound (13 mg, 62%). $^1$H NMR (400 MHz, CDCl$_3$) δ ppm 1.15-1.21 (m, 1H) 1.23-1.37(m, 2H) 1.61-1.76 (m, 3H) 1.88(d, J=12.45 Hz, 1H) 2.57-2.73 (m, 2H) 3.04 (s, 3H) 3.86-3.97 (m, 2H) 4.18 (d, J=7.05 Hz, 1H) 4.21 (s, 3H) 4.66-4.73 (m, 3H) 4.87 (d, J=16.18 Hz, 1H) 7.36 (s, 1H) 7.50 (d, J=7.88 Hz, 1H) 7.58 (d, J=8.30 Hz, 1H) 7.64 (s, 2H) 7.78 (s, 1H). MS (ES$^+$) Calc: 653.2, Found: 654.6 (M+1)

EXAMPLE 28

2-{4-[(2-{[3,5-Bis-trifluoromethyl-benzyl)-(2-methyl-2-tetrazol-5-yl)-amino]-methyl}-4-trifluoromethyl-phenyl)-methoxy-methyl]-piperidin-1-yl}-acetamide

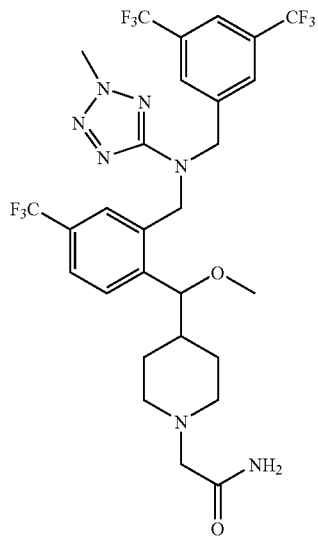

To a solution of N-(2-(methoxy)piperidin-4-yl)methyl)-5-(trifluoromethyl)benzyl)-N-(3,5-bis(trifluoromethyl)benzyl)-2-methyl-2H-tetrazol-5-amine (19.1 mg, 0.030 mmol) and 2-bromoacetamide (5.0 mg, 0.036 mmol) in acetonitrile (0.2 mL) at room temperature was added sodium carbonate (6.5 mg, 0.061 mmol). The slurry was stirred at 50° C. overnight. Solvent was removed in vacuo. The residue was partitioned between ethyl acetate and water. The organic layer was washed with brine, dried over sodium sulfate and concentrated in vacuo. The residue was purified by chromatography over 12+S Biotage silica column (eluted with 1-7% methanol in methylene chloride) to afford a colorless oil (9.2 mg, 47%). $^1$H NMR (400 MHz, CDCl$_3$) δ ppm 1.14-1.30 (m, 1H) 1.34-1.56 (m, 4H) 1.85 (d, J=14.52 Hz, 1H) 1.97-2.10 (m, 2H) 2.81-3.01 (m, 4H) 3.05-3.07 (m, 3H) 4.19 (d, J=6.22 Hz, 1H) 4.20-4.23 (m, 3H) 4.69 (d, J=15.77 Hz, 1H) 4.71 (s, 2H) 4.89 (d, J=15.77 Hz, 1H) 5.44 (s, 1H) 7.37 (s, 1H) 7.50 (d, J=7.88 Hz, 1H) 7.58 (d, J=9.13 Hz, 1H) 7.64 (s, 2H) 7.78 (s, 1H). MS (ES$^+$) Calc: 667.2, Found: 668.6 (M+1)

EXAMPLE 29

1-{4-[(2-{[(3,5-Bis-trifluoromethyl-benzyl)-(2-methyl-2H-tetrazol-5-yl)-amino]-methyl}-4-trifluoromethyl-phenyl)-methoxy-methyl]-piperidin-1-yl}-ethanone

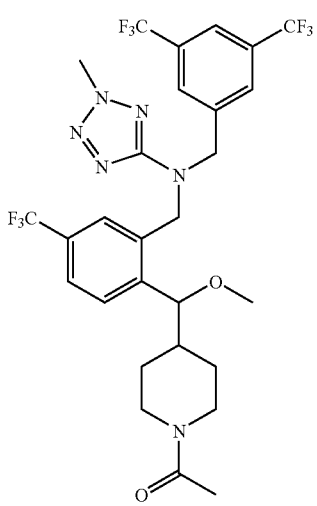

To a solution of N-(2-(methoxy piperidin-4-ylmethyl)-5-(trifluoromethyl)benzyl)-N-(3,5-bis(trifluoromethyl)benzyl)-2-methyl-2H-tetrazol-5-amine (20.5 mg, 0.034 mmol) in methylene chloride (0.5 mL) at room temperature was added pyridine (10 μL, 0.1 mmol) followed by acetyl chloride (5 μL, 0.07 mmol). The mixture was stirred at room temperature overnight. Solvent was removed in vacuo. The residue was purified by chromatography over 12+S Biotage silica column (eluted with 10-100% ethyl acetate in hexanes) to afford the title compound (14 mg, 64%). $^1$H NMR (400 MHz, CDCl$_3$) δ ppm 1.17-1.34 (m, 3H) 1.69-1.78 (m, 1H) 1.87 (t, J=12.65 Hz, 1H) 2.04 (s, 1.5H) 2.06 (s, 1.5H) 2.27-2.41 (m, 1H) 2.82-2.93 (m, 1H) 3.04 (s, 3H) 3.72 (d, J=15.77 Hz, 0.5H) 3.81 (d, J=12.45 Hz, 0.5H) 4.18 (d, J=6.64 Hz, 1H) 4.21 (s, 3H) 4.54-4.65 (m, 1H) 4.65-4.73 (m, 3H) 4.87 (d, J=16.60 Hz, 1H) 7.37 (s, 1H) 7.50 (d, J=7.88 Hz, 1H) 7.59 (d, J=7.88 Hz, 1H) 7.64 (s, 2H) 7.78 (s, 1H). MS (ES$^+$) Calc: 652.2, Found: 653.5 (M+1)

EXAMPLE 30

4-[(2-{[(3,5-Bis-trifluoromethyl-benzyl)-(2-methyl-2H-tetrazol-5-yl)-amino]-methyl}-4-trifluoromethyl-phenyl)-methoxy-methyl]-piperidine-1-carboxylic acid ethyl ester

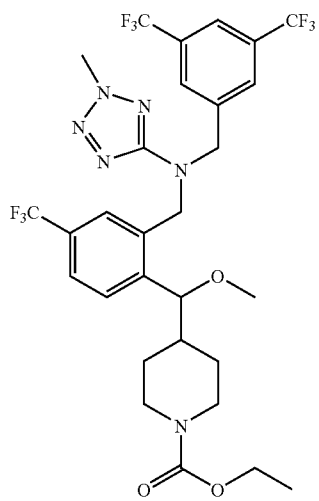

To a solution of N-(2-(methoxy(piperidin-4-yl)methyl)-5-(trifluoromethyl)benzyl)-N-(3,5-bis(trifluoromethyl)benzyl)-2-methyl-2H-tetrazol-5-amine (19.4 mg, 0.032 mmol) in methylene chloride (0.5 mL) at room temperature was added Hunig's base (8.9 mg, 12 μL, 0.069 mmol) followed by phosgene in toluene (20%, 25 μL, 0.048 mmol). The mixture was stirred at room temperature for 3 hours. Ammonia in ethanol (1 mL) was added and the mixture was stirred at room temperature overnight. Solvent was removed in vacuo The residue was purified by chromatography over 12+S Biotage silica column (eluted with 0-50% ethyl acetate in hexane) to afford the title compound (7.4 mg, 34%). $^1$H NMR (400 MHz, CDCl$_3$) δ ppm 1.11-1.18(m, 1H) 1.20-1.31 (m, 2H) 1.24(t, J=7.05 Hz, 3H) 1.61-1.71 (m, 1H) 1.85(d, J=12.86 Hz, 1H) 2.56 (q, J=14.94 Hz, 2H) 3.04 (s, 3H) 4.05-4.19 (m, 2H) 4.10 (q, J=7.05 Hz, 2H) 4.16 (d, J=7.05 Hz, 1H) 4.21 (s, 3H) 4.68 (d, J=15.77 Hz, 1H) 4.71 (s, 2H) 4.88 (d, J=15.77 Hz, 1H) 7.36 (s, 1H) 7.50 (d, J=7.88 Hz, 1H) 7.58 (d, J=8.71 Hz, 1H) 7.64 (s, 2H) 7.78 (s, 1H). MS (ES$^+$) Calc: 682.6, Found: 683.6 (M+1)

EXAMPLE 31

(3,5-Bis-trifluoromethyl-benzyl)-[2-(1-methoxy-cyclobutyl)-5-trifluoromethyl-benzyl]-2-methyl-2H tetrazol-5-yl)-amine

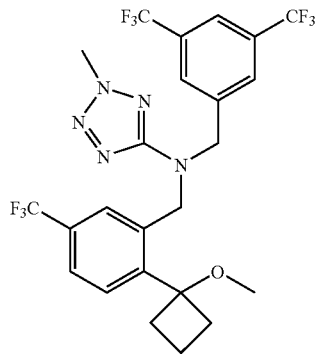

Step A: Preparation of 1-(2-{[(3,5-bis-trifluoromethyl-benzyl)-2-methyl-2H-tetrazol-5-yl)-amino]-methyl}-4-trifluoromethyl-phenyl)-cyclobutanol

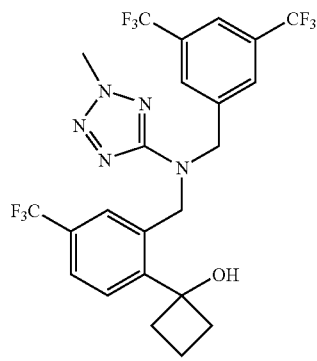

To a solution of 3,5-bis-trifluoromethyl-benzyl)-(2-bromo-5-trifluoromethyl-benzyl)-2-methyl-2H-tetrazol-5-yl)-amine (114.3 mg, 0.20 mmol) in THF at 0° C. was added iPrMgCl/LiCl (0.25 mL, 0.32 mmol). The mixture was stirred at 0° C. for 3 hours. Cyclobutanone (21.4 mg, 0.31 mmol) was stirred with CeCl$_3$ (50.1 mg, 0.20 mmol) at room temperature for 1 hour, cooled to 0° C. and the Grignard was added. The mixture was stirred at 0° C. for 2 hours and quenched with ammonium chloride. The mixture was extracted with ethyl acetate. Combined organic layers were washed with brine, dried over sodium sulfate and concentrated in vacuo. The residue was purified by chromatography over 25+S Biotage silica column (eluted with 0-30% ethyl acetate in hexane) to afford the title compound (34.6 mg, 31%). $^1$H NMR (400 MHz, CDCl$_3$) δ ppm 1.62-1.75 (m, 1H) 2.08-2.21 (m, 1H) 2.34-2.45 (m, 2H) 2.56-2.68 (m, 2H) 3.59 (d, J=7.05 Hz, 1H) 4.16 (s, 3H) 4.84 (s, 2H) 4.86 (s, 2H) 7.38 (s, 1H) 7.42-7.51 (m, 2H) 7.76 (s, 2H) 7.78 (s, 1H). MS (ES$^+$) Calc: 553.2, Found: 554.4 (M+1)

Step B: Preparation of (3,5-bis-trifluoromethyl-benzyl)-[2-(1-methoxy-cyclobutyl)-5-trifluoromethyl-benzyl]-(2-methyl-2H-tetrazol-5-yl)-amine

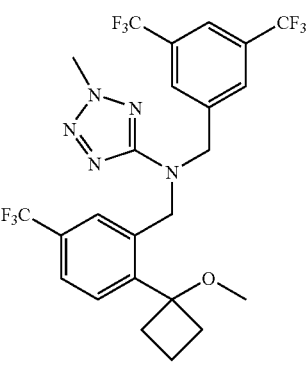

To a solution of 1-(2-{[(3,5-bis-trifluoromethyl-benzyl)-(2-methyl-2H-tetrazol-5-yl)-amino]-methyl}-4-trifluoromethyl-phenyl)-cyclobutanol (17.3 mg, 0.031 mmol) in THF (0.2 mL) at 0° C. was added sodium hydride (5 mg, 0.1 mmol). The mixture was stirred at room temperature for 30 minutes and methyl iodide (20 μL, 0.3 mmol) was added at 0° C. The mixture was stirred at room temperature overnight. Solvent was removed in vacuo. The residue was purified by chromatography over 12+S Biotage silica column (eluted with 0-20% ethyl acetate in hexane) to afford the title compound (11.1 mg, 63%). $^1$H NMR (400 MHz, CDCl$_3$) δ ppm 1.64-1.76 (m, 1H) 1.98-2.10 (m, 1H) 2.33-2.43 (m, 2H) 2.43-2.53 (m, 2H) 2.85 (s, 3H) 4.17-4.21 (m, 3H) 4.75 (s 2H) 4.86 (s, 2H) 7.41-7.46 (m, 2H) 7.50 (d, J=8.30 Hz, 1H) 7.73 (s, 2H) 7.76 (s, 1H). MS (ES$^+$) Calc 567.2, Found: 568.4 (M+1)

According to the procedure described in example 31 and using the corresponding ketone reagent, example 32 was prepared.

| Example # | Chemical Name | Structure | MS Calc | MS Found M + 1 |
|---|---|---|---|---|
| 32 | (3,5-Bis-trifluoromethyl-benzyl)-[2-(dicyclopropyl-methoxy-methyl)-5-trifluoromethyl-benzyl]-(2-methyl-2H-tetrazol-5-yl)-amine | 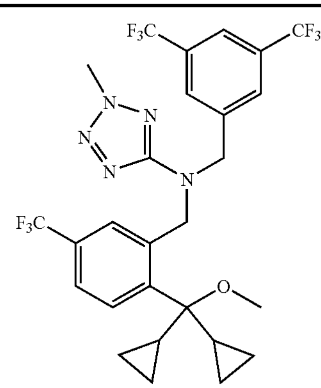 | 607.2 | 576.5 (M − OMe) |

EXAMPLE 33

(3,5-Bis-trifluoromethyl-benzyl)-{2-[ethoxy-(tetrahydro-pyran-4-yl)-methyl]-5-trifluoromethyl-benzyl}-(2-methyl-2H-tetrazol-5-yl)-amine

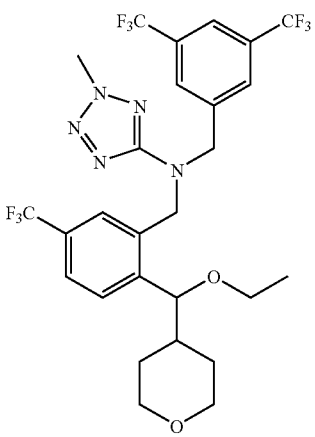

To a solution of (2-(((3,5-bis(trifluoromethyl)benzyl)(2-methyl-2H-tetrazol-5-yl)amino)methyl)-4-(trifluoromethyl)phenyl)(tetrahydro-2H-pyran-4-yl)methanol (20.4 mg, 0.034 mmo) in THF (0.15 mL) at 0° C. was added sodium hydride (60% dispersion in mineral oil, 4.1 mg, 0.10 mmol). The mixture was stirred at room temperature for 30 minutes, recooled to 0° C. and DMF (5 drops) was added followed by iodoethane (8 μL, 0.10 mmol). The mixture was stirred at room temperature overnight. Solvent was removed in vacuo. The residue was purified by chromatography over 12+S Biotage silica column (eluted with 0-30% ethyl acetate in hexanes) to afford the title compound (11.5 mg, 54%). $^1$H NMR (400 MHz, CDCl$_3$) δ ppm 1.0 (m, 1H) 1.1 (t, J=7.1 Hz, 3H) 1.4(m, 2H) 1.7(m, 1H) 1.8(d, J=13.3 Hz, 1H) 3.2 (m, 4H) 3.9 (dd, J=11.6, 3.3 Hz, 1H) 4.0 (dd, J=11.4, 3.9 Hz, 1H) 4.2 (s, 3H) 4.2 (d, J=7.1 Hz, 1H) 4.7 (d, J=13.3 Hz, 1H) 4.7 (s, 2H) 4.9 (d, J=15.8 Hz, 1H) 7.3 (s, 1H) 7.6 (m, 2H) 7.6 (s, 2H) 7.8 (s, 1H). MS (ES$^+$) Calc: 625.2, Found: 626.4 (M+1)

According to the procedure described in example 33 and using the appropriate secondary alcohol and alkylating reagent, examples 34-40 were prepared.

| Example # | Chemical Name | Structure | MS Calc | MS Found M + 1 |
|---|---|---|---|---|
| 34 | (3,5-Bis-trifluoromethyl-benzyl)-[2-(cyclohexyl-propoxy-methyl)-5-trifluoromethyl-benzyl]-(2-methyl-2H-tetrazol-5-yl)-amine | 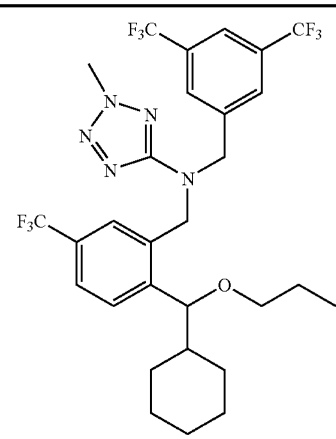 | 637.2 | 638.6 |
| 35 | 3-[(2-{[(3,5-Bis-trifluoromethyl-benzyl)-(2-methyl-2H-tetrazol-5-yl)-amino]-methyl}-4-trifluoromethyl-phenyl)-cyclohexyl-methoxy]-propionitrile | 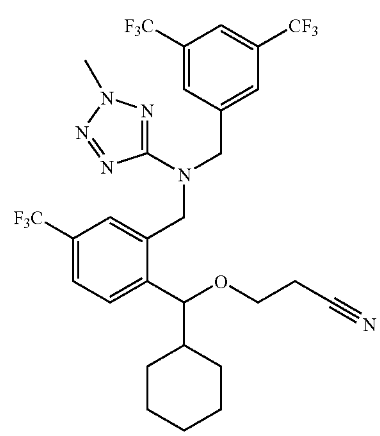 | 648.2 | 649.6 |

| Example # | Chemical Name | Structure | MS Calc | MS Found M + 1 |
|---|---|---|---|---|
| 36 | (3,5-Bis-trifluoromethyl-benzyl)-{2-[cyclohexyl-(2-methoxy-ethoxy)-methyl]-5-trifluoromethyl-benzyl}-(2-methyl-2H-tetrazol-5-yl)-amine | 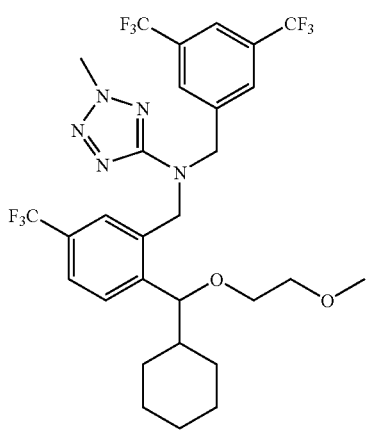 | 653.2 | 654.6 |
| 37 | [2-(Allyloxy-cyclohexyl-methyl)-5-trifluoromethyl-benzyl]-(3,5-bis-trifluoromethyl-benzyl)-(2-methyl-2H-tetrazol-5-yl)-amine | 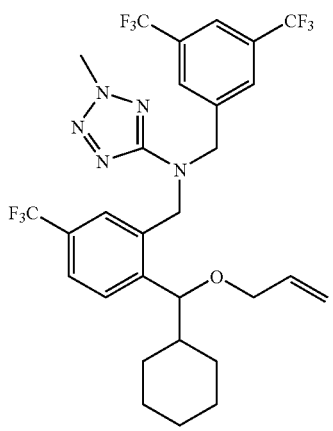 | 635.2 | 636.5 |

| Example # | Chemical Name | Structure | MS Calc | MS Found M + 1 |
|---|---|---|---|---|
| 38 | (3,5-Bis-trifluoromethyl-benzyl)-{2-[(4,4-dimethyl-cyclohexyl)-ethoxy-methyl]-5-trifluoromethyl-benzyl}-(2-methyl-2H-tetrazol-5-yl)-amine | 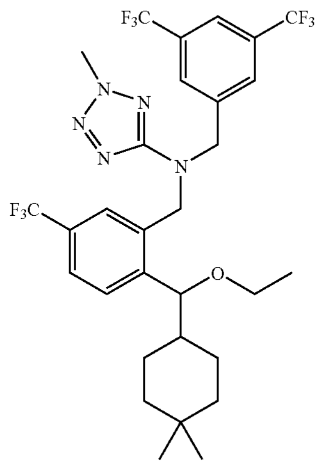 | 651.3 | 652.4 |
| 39 | (3,5-Bis-trifluoromethyl-benzyl)-{2-[ethoxy-(4-methyl-cyclohexyl)-methyl]-5-trifluoromethyl-benzyl}-(2-methyl-2H-tetrazol-5-yl)-amine | 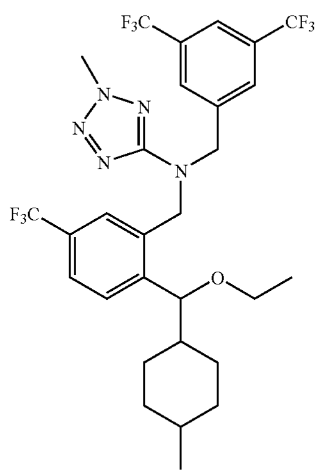 | 637.2 | 638.4 |
| 40 | (3,5-Bis-trifluoromethyl-benzyl)-[2-(ethoxy-o-tolyl-methyl)-5-trifluoromethyl-benzyl]-(2-methyl-2H-tetrazol-5-yl)-amine | 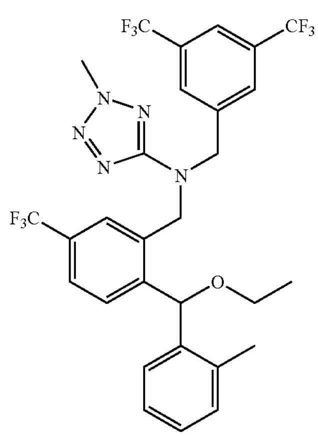 | 632.3 | |

EXAMPLE 41

2-(5-{(3,5-Bis-trifluoromethyl-benzyl)-[2-(cyclo-hexyl-methoxy-methyl)-5-trifluoromethyl-benzyl]-amino}-tetrazol-2-yl)-ethanol

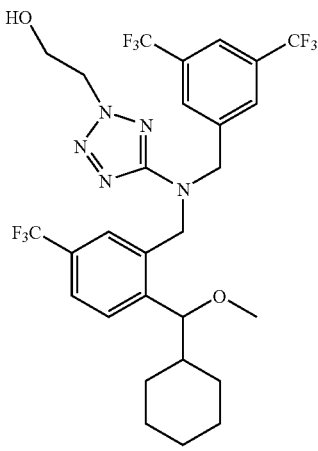

Step A: Preparation of (2-((tert-butyldimetylsilyloxy)methyl)-4-(trifluoro-methyl)phenyl)(cyclohexyl)methanol

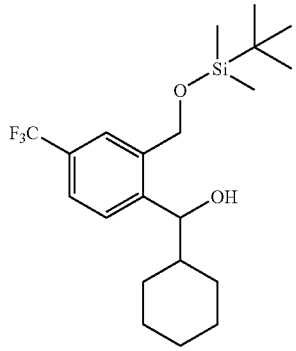

To a solution of (2-bromo-5-(trifluoromethyl)benzyloxy)(tert-butyl)dimethylsilane (1.3 g, 3.5 mmol) in THF at 0° C. was added i-PrMgCl/LiCl in THF (3.5 mL, 4.5 mmol). The mixture was stirred at 0° C. for 4 hours and cyclohexanecarboxaldehyde (0.61 g, 0.65 mL, 5.4 mmol) was added. The mixture was stirred at 0° C.-room temperature for 1 hour, quenched with saturated aqueous ammonium chloride and extracted with ethyl acetate. Combined organic layers were washed with brine, dried over sodium sulfate and concentrated in vacuo. The residue was purified by chromatography over 25+M Biotage silica column (eluted with 0-20% ethyl acetate in heptane) to afford the title compound (1.27 g, 90%). $^1$H NMR (400 MHz, CDCl$_{13}$) δ ppm 0.13 (s, 6H) 0.94 (s, 9H) 0.96-1.38 (m, 7H) 1.63-1.73 (m, 2H) 1.77-1.83 (m, 1H) 2.06 (d, J=13.28 Hz, 1H) 2.28 (d, J=3.73 Hz, 1H) 4.58 (dd, J=7.68, 3.94 Hz, 1H) 4.75 (d, J=13.28 Hz, 1H) 4.85 (d, J=13.28 Hz, 1H) 7.53 (s, 2H) 7.68 (s, 1H).

Step B: Preparation of (2-(cyclohexyl(methoxy)methyl)-5-(trifluoromethyl)benzyloxy)(tert-butyl)dimethylsilane

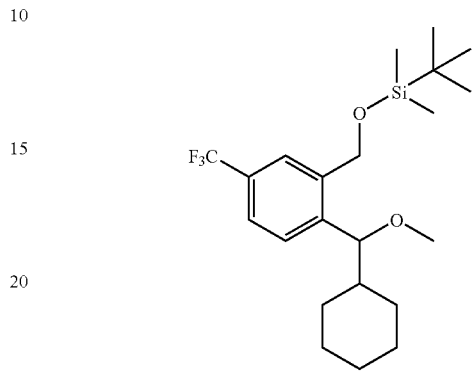

To a solution of (2-((tert-butyldimethylsilyloxy)methyl)-4-(trifluoromethyl)-phenyl)-(cyclohexyl)-methanol (1.25 g, 3.11 mmol) in THF (5 mL) at 0° C. was added sodium hydride (385 mg, 9.6 mmol). The mixture was stirred at room temperature for 1 hour, cooled to 0° C. and methyl iodide (1.0 mL, 16 mmol) was added. The mixture was stirred at room temperature overnight. Water was added and the mixture was extracted with ethyl acetate. The organic layer was washed with brine, dried over sodium sulfate and concentrated in vacuo. The residue was purified by chromatography over 25+S Biotage silica column (eluted with 0-5% ethyl acetate in heptane) to afford the title compound as a colorless oil (1.14 g, 88%). $^1$H NMR (400 MHz, CDCl$_3$) δ ppm 0.12 (s, 6H) 0.94-0.96 (m, 9H) 0.98-1.29 (m, 6H) 1.54-1.59 (m, 1H) 1.61-1.67 (m, 2H) 1.71-1.79 (m, 1H) 2.00 (d, J=12.03 Hz, 1H) 3.13 (s, 3H) 4.08 (d, J=7.47 Hz, 1H) 4.71 (d, J=13.69 Hz, 1H) 4.85 (d, J=13.69 Hz, 1H) 7.44 (d, J=8.30 Hz, 1H) 7.52 (d, J=7.88 Hz, 1H) 7.76 (s, 1H).

Step C: Preparation of (2-(cyclohexyl(methoxy)methyl)-5-(trifluoromethyl)phenyl)methanol

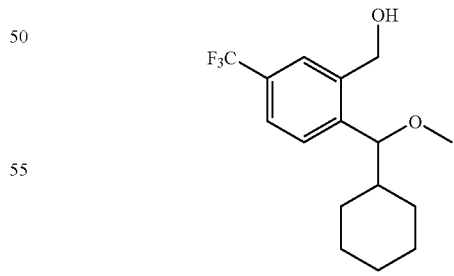

To a solution of (2-(cyclohexyl(methoxy)methyl)-5-(trifluoromethyl)benzyloxy)(tert-butyl)dimethylsilane (1.13 g, 2.4 mmol) in THF (5 mL) at room temperature was added TBAF in THF (1.0 M, 4.8 mL, 4.8 mmol). The mixture was stirred at room temperature overnight. Water was added and the mixture was extracted with ethyl acetate. Combined organic layers were washed with brine, dried over sodium sulfate and concentrated in vacuo. The residue was purified by chromatography over 25+M Biotage silica column (eluted with 0-30% ethyl acetate in heptane) to afford the title compound (633.9 mg, 88%). $^1$H NMR (400 MHz, CDCl$_3$) δ ppm 0.91-1.27 (m, 6H) 1.63-1.70 (m, 3H) 1.72-1.81 (m, 1H) 2.07 (d, J=12.86 Hz, 1H) 2.33-2.42 (m, 1H) 3.18 (s, 3H) 4.10 (d, J=7.88 Hz, 1H) 4.78 (dd, J=5.81, 3.32 Hz, 2H) 7.43 (d, J=7.88 Hz, 1H) 7.55 (d, J=8.30 Hz, 1H) 7.69 (s, 1H).

Step D: Preparation of 2-(cyclohexyl(methoxy)methyl)-5-(trifluoromethyl)benzaldehyde

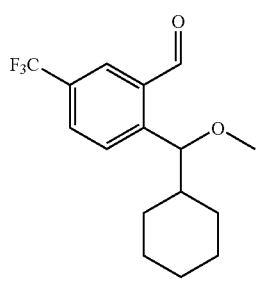

To a solution of (2-(cyclohexyl(methoxy)methyl)-5-(trifluoromethyl)phenyl)methanol (113.1 mg, 0.37 mmol) in methylene chloride (2 mL) at room temperature was added Dess-Martin periodinane reagent (175 mg, 0.41 mmol). The mixture was stirred at room temperature for 1 hour. 1N NaOH was added and the mixture was extracted with ethyl acetate. Combined organic layers were washed with 1N NaOH, brine, dried over sodium sulfate and concentrated in vacuo to yield the title compound (107.2 mg, 95%). $^1$H NMR (400 MHz, CDCl$_3$) δ ppm 1.07-1.18 (m, 4H) 1.36 (d, J=5.81 Hz, 1H) 1.53-1.69 (m, 4H) 1.71-1.76 (m, J=2.49 Hz, 1H) 1.83-1.90 (m, 1H) 3.22 (s, 3H) 4.73 (d, J=6.22 Hz, 1H) 7.66 (d, J=8.30 Hz, 1H) 7.81 (dd, J=8.30, 1.66 Hz, 1H) 8.14 (s, 1H) 10.41 (s, 1H).

Step E: Preparation of N-(2-(cyclohexyl(methoxy)methyl)-5-(trifluoromethyl)benzyl)(3,5-bis(trifluoromethyl)phenyl)methanamine

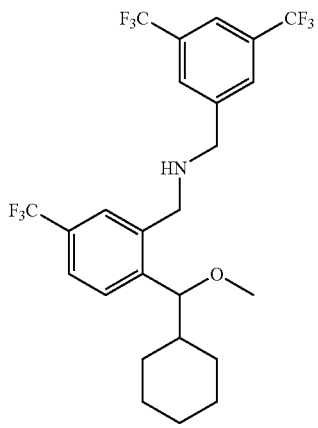

A mixture of 2-(cyclohexyl(methoxy)methyl)-5-(trifluoromethyl)benzaldehyde (107 my, 0.36 mmol) and 3,5-bistrifluoromethylbenzylamine (113.8 mg, 0.37 mmol) in ethanol was stirred at room temperature overnight. Sodium borohydride (16.5 mg, 0.44 mmol) was added and the mixture was stirred at room temperature overnight. Solvent was removed and the residue was partitioned between ethyl acetate and water. The organic layer was washed with brine, dried over sodium sulfate and concentrated in vacuo. The residue was purified by chromatography over 25+S Biotage silica column (eluted with 0-15% ethyl acetate in heptane) to afford the title compound (150 mg, 80%). $^1$H NMR (400 MHz, CDCl$_3$) δ ppm 0.94-1.23 (m, 6H) 1.51-1.59 (m, 1H) 1.62 (d, J=7.05 Hz, 2H) 1.69-1.78 (m, 1H) 1.99 (d, J=12.45 Hz, 1H) 3.17 (s, 3H) 3.83 (d, J=12.86 Hz, 1H) 3.92 (d, J=12.86 Hz, 1H) 4.00 (d, J=6.64 Hz, 2H) 4.22 (d, J=7.05 Hz, 1H) 7.50 (d, J=8.30 Hz, 1H) 7.55 (d, J=7.88 Hz, 1H) 7.63 (s, 1H) 7.80 (s, 1H) 7.86 (s, 2H). MS (ES$^{30}$) Calc: 527.2, Found: 528.5 (M+1).

Step F: Preparation of (2-(cyclohexyl(methoxy)methyl)-5-(trifluoromethyl)benzyl)(3,5-bis(trifluoromethyl)benzyl)cyanamide

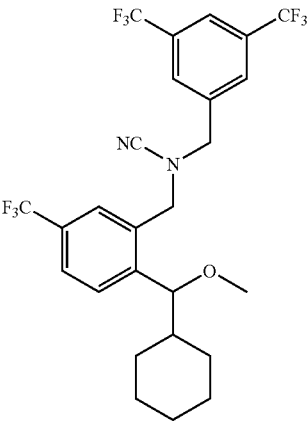

To a solution of N-(2-(cyclohexyl(methoxy)methyl)-5-(trifluoromethyl)benzyl)(3,5-bis(trifluoromethyl)phenyl)methanamine (150 mg, 0.28 mmol) and NaOAc.3H$_2$O (77.6 mg, 0.57 mmol) in methanol was added cyanogen bromide in acetonitrile (5.0 M, 0.1 mL, 0.5 mmol). The slurry was stirred at room temperature overnight. The mixture was loaded onto a samplet and purified by chromatography over 25+S Biotage silica column (eluted with 0-30% ethyl acetate in heptane) to afford the title compound (144.1 mg, 92%). ¹H NMR (400 MHz, CDCl₃) δ ppm 0.91-1.19 (m, 6H) 1.41-1.53 (m, 1H) 1.62 (d, J=7.88 Hz, 2H) 1.71-1.79 (m, 1H) 1.96 (d, J=12.45 Hz, 1H) 3.16 (s, 3H) 4.00 (d, J=7.47 Hz, 1H) 4.32 (d, J=14.11 Hz, 1H) 4.32 (s, 2H) 4.40 (d, J=14.11 Hz, 1H) 7.50 (d, J=8.30 Hz, 1H) 7.54 (s, 1H) 7.63 (d, J=8.30 Hz, 1H) 7.78 (s, 2H) 7.91 (s, 1H). MS (ES⁻) Calc: 552.2, Found: 551.5 (M−1).

Step G: Preparation of N-(2-(cyclohexyl(methoxy) methyl)-5-(trifluoromethyl)benzyl)-N-(3,5-bis(trifluoromethyl)benzyl)-2H-tetrazol-5-amine

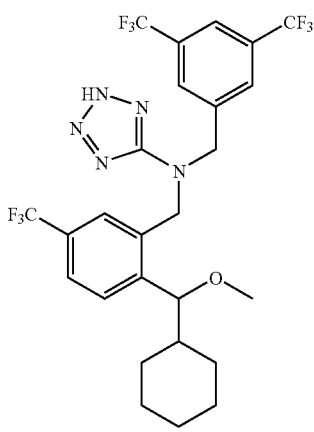

To solution of (2-(cyclohexyl(methoxy)methyl)-5-(trifluoromethyl)benzyl)(3,5-bis(trifluoromethyl)benzyl)cyanamide (144 mg, 0.26 mmol) in toluene was added sodium azide (84.9 mg, 1.31 mmol) followed by TEA-HCl (178.8 mg, 1.3 mmol). The mixture was stirred at 115° C. overnight. Water was added and the mixture was extracted with ethyl acetate. Combined organic layers were washed with brine, dried over sodium sulfate and concentrated in vacuo. The residue was purified by chromatography over 25+S Biotage silica column (eluted with 5-50% ethyl acetate in heptane) to afford the title compound (90.9 mg, 59%). ¹H NMR (400 MHz, CDCl₃) δ ppm 0.90-1.16 (m, 5H) 1.23-1.32 (m, 1H) 1.49-1.61 (m, 3H) 1.69 (s, 1H) 1.97 (d, J=12.45 Hz, 1H) 3.21 (s, 3H) 4.05 (d, J=7.88 Hz, 1H) 4.74-4.93 (m, 4H) 7.31 (s, 1H) 7.41 (d, J=7.88 Hz, 1H) 7.52 (d, J=7.88 Hz, 1H) 7.69 (s, 2H) 7.78 (s, 1H). MS (ES⁺) Calc: 595.2, Found: 596.5 (M+1).

Step H: Preparation of N-(2-(cyclohexyl(methoxy) methyl)-5-(trifluoromethyl)benzyl)-N-(3,5-bis(trifluoromethyl)benzyl)-2-(2-(tert-butyldimethylsilyloxy)ethyl)-2H-tetrazol-5-amine

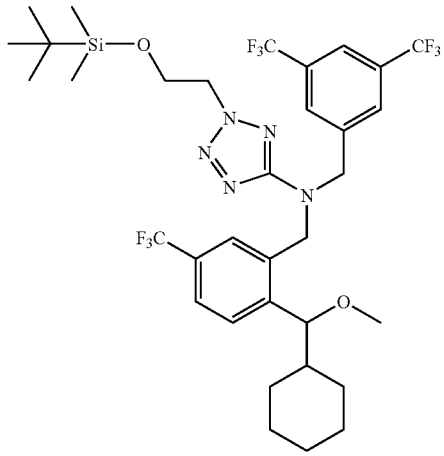

To a mixture of N-(2-(cyclohexyl(methoxy)methyl)-5-(trifluoromethyl)benzyl)-N-(3,5-bis(trifluoromethyl)benzyl)-2H-tetrazol-5-amine (40.4 mg, 0.068 mmol) and (2-bromoethoxy)(tert-butyl)dimethylsilane (25 mg, 22 μL, 0.10 mmol) in 2-MeTHF/DMF was added sodium carbonate (29.1 mg, 0.275 mmol). The slurry was stirred at 60° C. overnight. The reaction was diluted and filtered. The filtrate was concentrated and the residue was purified by chromatography over 12+S Biotage silica column (eluted with 0-20% ethyl acetate in heptane) to afford the title compound (39.3 mg, 77%). ¹H NMR (400 MHz, CDCl₃) δ ppm 0.08 (s, 6H) 0.80 (s, 9H) 0.92-1.12 (m, 5H) 1.15-1.21 (m, 1H) 1.42-1.52 (m, 1H) 1.57-1.62 (m, 2H) 1.68-1.72 (m, J=2.90 Hz, 1H) 1.89 (d, J=12.44 Hz, 1H) 3.03 (s, 3H) 4.05-4.09 (m, 3H) 4.54 (t, J=5.60 Hz, 2H) 4.64-4.76 (m, 3H) 4.89 (d, J=16.17 Hz, 1H) 7.35 (s, 1H) 7.47 (d, J=7.88 Hz, 1H) 7.54 (d, J=9.12 Hz, 1H) 7.65 (s, 2H) 7.75 (s, 1H). MS (ES⁺) Calc: 753.3, Found: 754.6 (M+1).

Step I: Preparation of 2-(5-{(3,5-Bis-trifluoromethyl-benzyl)-[2-(cyclohexyl-methoxy-methyl)-5-trifluoromethyl-benzyl]-amino}-tetrazol-2-yl-ethanol

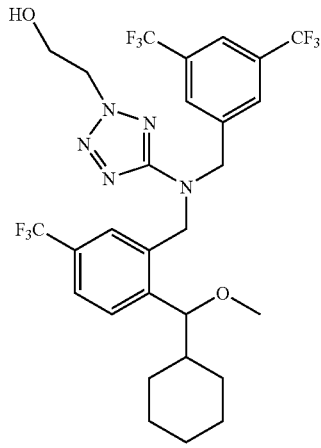

To N-(2-(cyclohexyl(methoxy)methyl)-5-(trifluoromethyl)benzyl)-N-(3,5-bis(trifluoromethyl)benzyl)-2-(2-(tert-butyldimethylsilyloxy)ethyl)-2H-tetrazol-5-amine (39.3 mg, 0.052 mmol) in THF (0.3 mL) at room temperature was added TBAF in THF (1.0 M, 0.1 mL, 0.1 mmol). The mixture was stirred at room temperature overnight. Solvent was removed and the residue was purified by chromatography over 12+S Biotage silica column (eluted with 0-50% ethyl acetate in heptane) to afford a colorless oil (29.5 mg, 89%). $^1$H NMR (400 MHz, CDCl$_3$) δ ppm 0.94-1.13 (m, 5H) 1.17 (d, J=11.20 Hz, 1H) 1.43-1.53 (m, 1H) 1.60 (s, 2H) 1.67-1.74 (m, J=2.90 Hz, 1H) 1.91 (d, J=12.86 Hz, 1H) 2.35-2.42 (m, 1H) 3.06 (s, 3H) 4.08 (d, J=7.05 Hz, 1H) 4.12-4.16 (m, J=5.39 Hz, 2H) 4.62 (t, J=4.98 Hz, 2H) 4.72 (s, 2H) 4.75 (d, J=16.18 Hz, 1H) 4.88 (d, J=16.18 Hz, 1H) 7.36 (s, 1H) 7.49 (d, J=7.88 Hz, 1H) 7.56 (d, J=8.30 Hz, 1H) 7.67 (s, 2H) 7.78 (s, 1H). MS (ES$^+$) Calc: 639.2, Found: 640.5 (M+1).

EXAMPLE 42

(3,5-Bis-trifluoromethyl-benzyl)-[2-(cyclohexyl-methoxy-methyl)-5-trifluoromethyl-benzyl]-carbamic acid methyl ester

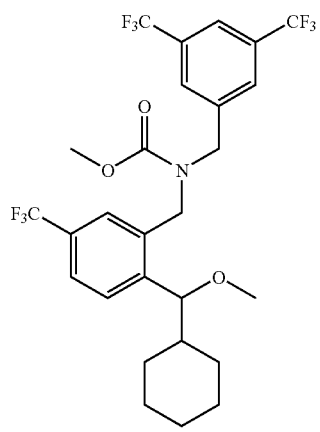

To a solution of (3,5-bis-trifluoromethyl-benzyl)-[2-(cyclohexyl-methoxy-methyl)-5-trifluoromethyl-benzyl]-amine (Example 41, STEP E, 22 mg, 0.042 mmol) in dichloromethane (1 ml) was added diisopropylethyl amine (8.09 mg, 0.063 mmol) followed by methyl chloroformate (3.94 mg, 0.042 mmol) at room temperature and stirred for overnight. Reaction mixture was then concentrated in vacuo and the product was purified on Biotage column (12+S), eluting with 2% ethyl acetate in heptane (1 CV), 2-20% (10CV), 20% (2CV) to yield the title compound (7 mg, 30%) as colorless oil. $^1$H NMR (400 MHz, CDCl$_3$) δ ppm 1.0 (m, 6H) 1.4(m, 1H) 1.5(m, 2H) 1.7(s, 1H) 1.9 (d, J=11.2 Hz, 1H) 3.0 (s, 3H) 3.8(s, 3H) 4.0 (d, J=17.9 Hz, 1H) 4.6 (m, 4H) 7.25 (d, J=10.4 Hz, 1H) 7.45 (d, J=7.5 Hz, 1H) 7.53 (m, 3H) 7.7 (s, 1H) 7.8 (s, 1H). MS (ES$^+$) Calc: 585.2, Found: 630.3 (M+45).

EXAMPLE 43

N-(3,5-Bis-trifluoromethyl-benzyl)-N-[2-(cyclohexyl-methoxy-methyl)-5-trifluoromethyl-benzyl]-acetamide

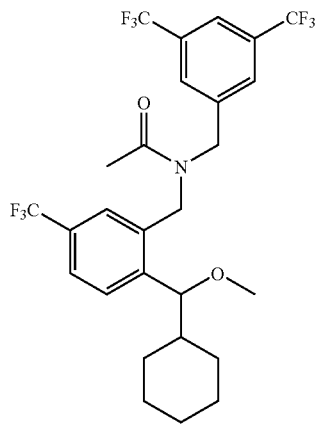

To a solution (3,5-bis-trifluoromethyl-benzyl)-[2-(cyclohexyl-methoxy-methyl)-5-trifluoromethyl-benzyl]-amine (Example 41, STEP E, 20 mg, 0.038 mmol) in dichloromethane (1 ml) was added pyridine (9.0 mg, 0.114 mmol) followed by acetyl chloride (2.98 mg, 0.038 mmol) at room temperature and stirred for overnight. Reaction mixture was diluted with dichloromethane and washed with water. The organic layer was dried over anhydrous magnesium sulphate and concentrated in vacuo. The product was purified on Biotage column (12+S), eluting with 2% ethyl acetate in heptane (1 CV), 2-20% (10CV), 20% (2CV) to yield the title compound (8 mg, 37%) as colorless oil. $^1$H NMR (400 MHz, CDCl$_3$) δ ppm 0.9 (m, 6H) 1.2 (m, 3H) 1.7 (m, 1H) 1.9 (m, 1H) 2.2 (s, 3H) 3.1 (s, 3H) 3.9 (m, 1H) 4.6 (m, 4H) 7.4 (m, 1H) 7.5 (m, 2H) 7.6 (m, 2H) 7.8 (s, 1H). MS (ES$^+$) Calc: 569.2, Found: 614.2 (M+45).

EXAMPLE 44

1-(3,5-Bis-trifluoromethyl-benzyl)-1-[2-(cyclohexyl-methoxy-methyl)-5-trifluoromethyl-benzyl]-urea

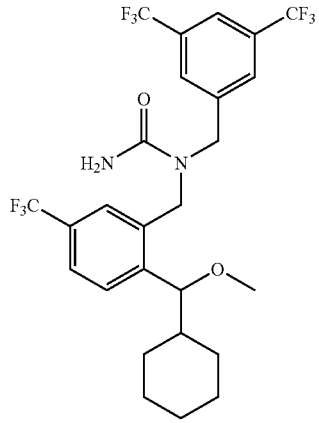

To a solution of (3,5-bis-trifluoromethyl-benzyl)-[2-(cyclohexyl-methoxy-methyl)-5-trifluoromethyl-benzyl]-amine (Example 41, STEP E, 20 mg, 0.038 mmol) in dichloromethane (1 ml) was added diisopropylethyl amine (6 mg, 0.045 mmol) followed by phosgene (18.8 mg, 0.038 mmol) at room temperature and stirred for 1 hour. Reaction mixture was then treated with concentrated ammonium hydroxide (0.5 ml) and stirred at room temperature for overnight. The reaction mixture was diluted with dichloromethane, washed with water, dried over anhydrous magnesium sulphate and concentrated in vacuo. The product was purified on Biotage column (12+S), eluting with 2% ethyl acetate in heptane (1CV), 2-20% (10CV), 20% (2CV) to yield the title compound (7 mg, 30%) as colorless oil. $^1$H NMR (400 MHz, CDCl$_3$) δ ppm 1.0 (m, 6H) 1.4 (m, 1H) 1.59 (m, 4H) 1.67 (s, 1H) 1.94 (d, J=12.4 Hz, 1H) 3.1 (s, 3H) 3.92 (d, J=7.8 Hz, 1H) 4.6 (m, 4H) 7.36 (s, 1H) 7.45 (d, J=7.9 Hz, 1H) 7.53 (d, J=8.3 Hz, 1H) 7.68 (s, 2H) 7.78 (s, 1H). MS (ES$^+$) Calc: 570.2, Found: 615.6 (M+45).

Preparation 18:
(3-Bromo-5-(trifluoromethyl)phenyl)methanol

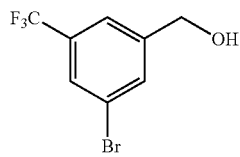

Step A: 3-Amino-5-(trifluoromethyl)benzoic acid

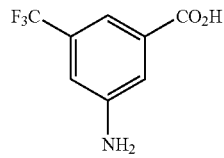

To a solution of 3-nitro-5-(trifluoromethyl)benzoic acid (9.8 gm, 41.7 mmol) in methanol (100 mL) was added 10% palladium on carbon (50% water content, 1.5 gm) and the suspension was shaken in a Parr® hydrogenation apparatus (Parr Instrument Company, Moline, Ill.) under a hydrogen atmosphere (40 psi). After 2 hours the catalyst was removed by filtration through a pad of celite, the pad rinsed through with methanol and the solvent evaporated under reduced pressure to give the title compound as a yellow solid (7.90 gm, 92%).

LC-MS (ES−) Calc: 205, Found: 204 (M−H). $^1$H NMR (CD$_3$OD) δ ppm 7.51 (brs, 1H), 7.47 (brs, 1H), 7.10 (brs, 1H).

Step B: 3-Bromo-5-(trifluoromethyl)benzoic acid

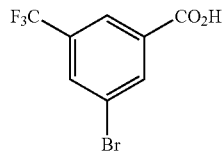

To a stirred suspension of 3-amino-5-(trifluoromethyl)benzoic acid (7.90 gm, 38.5 mmol) in a mixture of hydrobromic acid (43% w/v, 100 mL) and water (100 mL) at 0° C. was slowly added a solution of sodium nitrite (7.97 gm, 0.116 mol) in water (50 mL). After 1 hour the inhomogeneous yellow liquid was added to a solution of copper (II) bromide (16.44 gm, 0.115 mol) in water (100 mL) and the mixture was stirred at room temperature for 16 hours. The mixture was extracted with diethyl ether (250 mL), the aqueous layer was separated and extracted with diethyl ether (3×75 mL). The combined organic layers were dried with anhydrous sodium sulfate and the solvent removed under vacuum to give the title compound as a yellow solid (9.0 gm, 87%) which was used in the following reaction without further purification.

LC-MS (ES−) Calc: 269, Found: 268 (M−H). $^1$H NMR (CD$_3$OD) δ ppm 8.38 (brs, 1H), 8.23 (brs, 1H), 8.09 (brs, 1H).

Step C:
(3-Bromo-5-(trifluoromethyl)phenyl)methanol

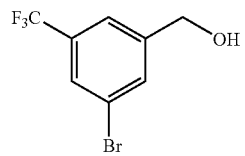

To a solution of 3-bromo-5-(trifluoromethyl)benzoic acid (2.13 gm, 7.92 mmol) in anhydrous THF under nitrogen was added borane dimethylsulfide complex (15.83 mmol, 7.91 mL) and the mixture was stirred at room temperature for 16 hours. A further aliquot of borane dimethylsulfide complex (15.83 mmol, 7.91 mL) was then added and stirring was continued at room temperature for a further 4 hours. LC-MS indicated complete consumption of starting material. Methanol was added cautiously until effervescence ceased then 2N hydrochloric acid (20 mL) was added. The mixture was stirred at room temperature for 20 hours then concentrated to dryness under reduced pressure. The residue was extracted with diethyl ether and the solution washed with water. The organic layer was dried with anhydrous sodium sulfate and the solvent removed under vacuum. The residue was dissolved in a mixture of dichloromethane and methanol, silica gel was added and the solvent removed under vacuum. The solid was placed on a column of silica gel (50 gm) and eluted with hexane-ethyl acetate (85:15) to give the title compound as a yellow oil which crystallized on standing (1.16 gm, 57%).

LC-MS (ES−) Calc: 255, Found: 254 (M−H). ¹H NMR (CDCl₃) δ ppm 7.72 (brs, 1H), 7.69 (brs, 1H), 7.57 (brs, 1H), 4.77 (s, 2H), 1.86 (brs, 1H).

EXAMPLE 45

3-{[[2-(Cyclohexyl-methoxy-methyl)-5-trifluoromethyl-benzyl]-(2 methyl-2H-tetrazol-5-yl)amino]-methyl}-5-trifluoromethyl-benzonitrile

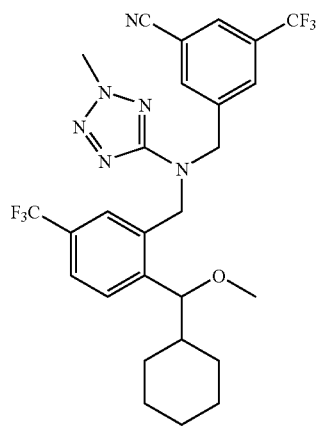

Step A: Preparation of 3-hydroxymethyl-5-trifluoromethyl-benzonitrile

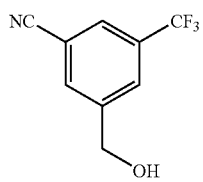

A mixture of (3-bromo-5-trifluoromethyl-phenyl)-methanol (500 mg, 1.96 mmol), zinc cyanide (230 mg, 1.96 mmol) and tetrakis(triphenylphosphine) palladium (68 mg, 0.059 mmol) in DMF (2 ml) was heated by microwave at 160° C. for 20 minutes. The mixture was partitioned between ethyl ether (20 ml) and water (10 ml). The aqueous layer was extracted with ether and combined organic layers were washed with brine, dried (MgSO₄) and concentrated in vacuo. The product was purified on Biotage column (12+M), eluting with 2% ethyl acetate in heptane (1 CV), 2-20% (10 CV), 20% (2CV) to yield the title compound (240 mg, 61%) as a colorless oil. ¹H NMR (400 MHz, CDCl₃) δ ppm 2.05 (s, 1H) 4.8 (s, 2H) 7.82 (s, 1H) 7.86 (s, 2H).

Step B: Preparation of 3-bromomethyl-5-trifluoromethyl-benzonitrile

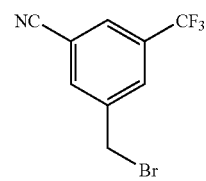

A solution of 3-hydroxymethyl-5-trifluoromethyl-benzonitrile (100 mg, 0.497 mmol) in dichloromethane (1 ml) at 0° C. was treated in a dropwise manner with a solution of phosphorus tribromide (0.3 ml, 1M, 0.3 mmol) in dichloromethane at 0° C. for 1 hour. The ice bath was removed and the reaction was stirred at room temperature for 2 hours. Reaction was quenched with sat'd NaHCO₃ solution until reaction was no longer yellow-orange in color. Reaction was extracted with dichloromethane and organic layer was dried over anhydrous magnesium sulphate and concentrated in vacuo. The crude residue was purified by chromatography on Biotage column (12+M), eluting with ethyl acetate in heptane 0-30% (10CV), 30% (2CV) to yield the title compound (56 mg, 43%) as a colorless oil. ¹H NMR (400 MHz, CDCl₃) δ ppm 4.46 (s, 2H) 7.80 (s, 1H) 7.84 (s, 2H).

Step C: Preparation of 3-azidomethyl-5-trifluoromethyl-benzonitrile

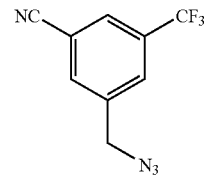

A solution of 3-hydroxymethyl-5-trifluoromethyl-benzonitrile (200 mg, 0.994 mmol) in toluene (1 ml) at 0° C. was treated with diphenyl phosphoryl azide (328 mg, 1.19 mmol), followed by DBU (182 mg, 1.19 mmol) and stirred at 0° C. for 2 hours. The ice bath was removed and the reaction was stirred at room temperature for overnight. Reaction was diluted with ethyl acetate and washed with 10% HCl solution, dried over anhydrous magnesium sulphate and concentrated in vacuo. The residue was purified by silica gel chromatography over 12+S Biotage silica column (eluted with 0-30% ethyl acetate in hexanes) to yield the title compound (150 mg, 67%) as a colorless oil. ¹H NMR (400 MHz, CDCl₃) δ ppm 4.54 (s, 2H) 7.82 (s, 2H) 7.88 (s, 1H).

Step D: Preparation of 3-aminomethyl-5-trifluoromethyl-benzonitrile

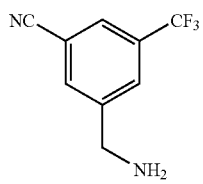

A solution of 3-azidomethyl-5-trifluoromethyl-benzonitrile (140 mg, 0.619 mmol) in THF (1 ml) was treated with trimethyl phosphine (94.2 mg, 1.24 mmol) at room temperature and stirred for 2 hours. Reaction was quenched with water and stirred for 30 minutes. Reaction was extracted with ethyl ether and organic layer was dried over anhydrous magnesium sulphate and concentrated in vacuo. The crude product (70 mg, 56%) was used without further purification. ¹H NMR (400 MHz, CDCl₃) δ ppm 1.64 (s, 2H) 3.98 (s, 2H) 7.74 (s, 1H) 7.83 (s, 2H).

Step E: Preparation of [2-(cyclohexyl-methoxy-methyl)-5-trifluoromethyl-benzyl]-(2-methyl-2H-tetrazol-5-yl)-amine

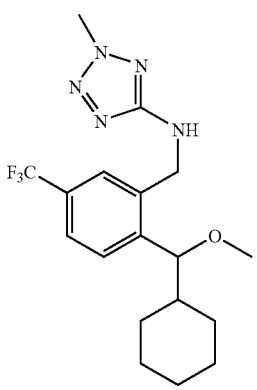

A solution of 2-(cyclohexyl-methoxy-methyl)-5-trifluoromethyl-benzaldehyde (90 mg, 0.30 mmol) and 2-methyl-2H-tetrazol-5-amine (35.6 mg, 0.36 mol) in toluene (1.5 ml) was heated at 50° C. for overnight. Solvent was removed in vacuo and reaction mixture was diluted with ethanol (2 ml) and treated with sodium borohydride (21.8 mg, 0.577 mmol) and stirred at room temperature for overnight. Reaction mixture was concentrated in vacuo and diluted with ethyl acetate (100 ml) and washed with water (30 ml). Organic layer was dried over anhydrous magnesium sulphate and concentrated in vacuo. The crude product was purified on Biotage column (12+M), eluting with 7% ethyl acetate in heptane (1 CV), 7-60% (10CV), 60% (2CV) to yield the title compound (65 mg, 58%) as a colorless oil. ¹H NMR (400 MHz, CDCl₃) δ ppm 1.1 (m, 4H) 1.25 (s, 2H) 1.62 (m, 3H) 1.76 (m, 1H) 1.99 (d, J=14.1 Hz, 1H) 3.16 (s, 3H) 4.13 (s, 3H) 4.2 (d, J=7.5 Hz, 1H) 4.48 (dd, J=5.4 Hz, 1H) 4.65 (dd, J=6.6 Hz, 1H) 4.93 (m, 1H) 7.47 (d, J=7.8 Hz, 1H) 7.54 (d, J=8.3 Hz, 1H) 7.67 (s, 1H). MS (ES⁺) Calc: 383.4, Found: 349.3 (M−34).

Step F: Preparation of 3-{[[(2-Cyclohexyl-methoxy-methyl)-5-trifluoromethyl-benzyl]-(2-methyl-2H-tetrazol-5-yl)-amino]-methyl}-5-trifluoromethyl-benzonitrile

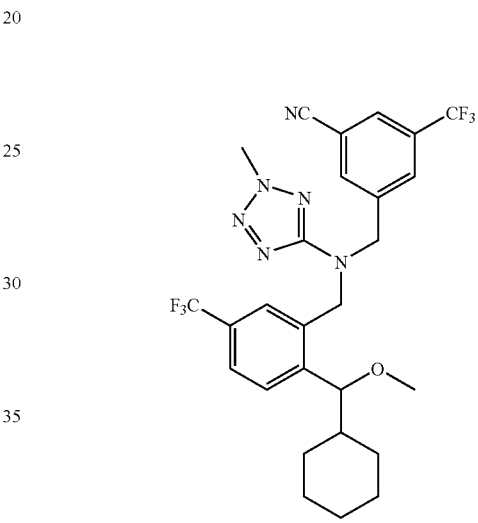

To a solution of [2-(cyclohexyl-methoxy-methyl)-5-trifluoromethyl-benzyl]-(2-methyl-2H-tetrazol-5-yl)-amine (28 mg, 0.073 mmol) in DMF (2 mL) at 0° C. under nitrogen was added sodium hydride (4.4 mg, 0.11 mmol, 60% dispersion in mineral oil). The reaction was stirred for 30 minutes, allowing it to warm to room temperature. The reaction mixture was then treated with 3-(bromomethyl)-5-(trifluoromethyl)benzonitrile (19.3 mg, 0.073 mmol) at room temperature and stirred for overnight. Solvent was removed in vacuo. The residue was diluted with ethyl acetate and washed with satd. sodium bicarbonate solution, water and brine, dried over anhydrous magnesium sulphate and concentrated in vacuo. The product was purified on Biotage column (12+S), eluting with 2% ethyl acetate in heptane (1CV), 2-20% (10CV), 20% (2CV) to yield the title compound (21 mg, 49%) as a colorless oil, ¹H NMR (400 MHz, CDCl₃) δ ppm 1.07 (m, 4H) 1.2 (m, 3H) 1.65(m, 3H) 1.73 (m, 1H) 3.18 (s, 3H) 4.06 (s, 3H) 4.2 (m, 1H) 4.67-5.04 (m, 2H) 5.4 (m, 1H) 7.39 (s, 1H) 7.50 (m, 3H) 7.5 (m, 2H). MS (ES⁺) Calc: 566.2, Found: 567.5 (M+1).

According to the procedures described in Examples 42-45 and using the appropriate amine, Examples 46-50 were prepared.

| Example # | Chemical Name | Structure | MS Calc | MS Found M + 1 |
|---|---|---|---|---|
| 46 | N-(3-Cyano-5-trifluoromethyl-benzyl)-N-[2-(cyclohexyl-methoxy-methyl)-5-trifluoromethyl-benzyl]-acetamide | 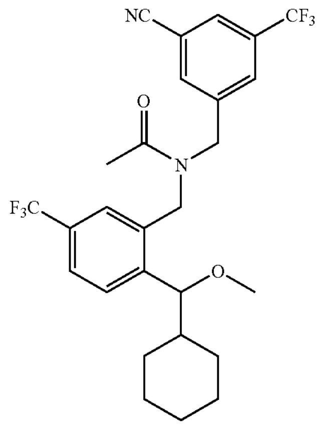 | 526.2 | 571.6 (M + 45) |
| 47 | N-[2-(Cyclohexyl-methoxy-methyl)-5-trifluoromethyl-benzyl]-N-(3,5-dichloro-benzyl)-acetamide | 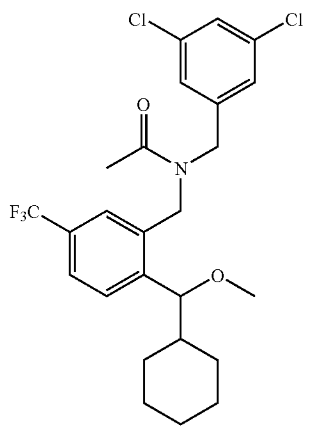 | 501.1 | 470.3 (M − 31) |
| 48 | [2-(Cyclohexyl-methoxy-methyl)-5-trifluoromethyl-benzyl]-(3,5-dichloro-benzyl)-(2-methyl-2H-tetrazol-5-yl)-amine | 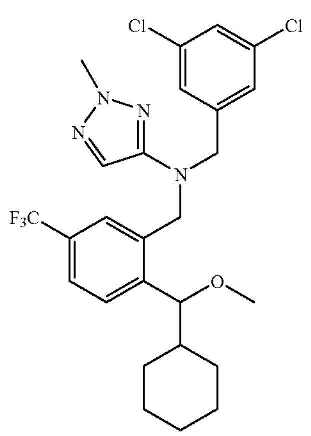 | 541.2 | 542.5 |

-continued

| Example # | Chemical Name | Structure | MS Calc | MS Found M + 1 |
|---|---|---|---|---|
| 49 | [2-(Cyclohexyl-methoxy-methyl)-5-trifluormethyl-benzyl]-(3,5-dichloro-benzyl)-carbamic acid methyl ester | 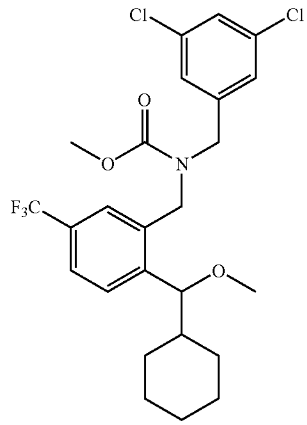 | 517.2 | 486.4 (M − 31) |
| 50 | (3-Cyano-5-trifluoromethyl-benzyl)-[2-(cyclohexyl-methoxy-methyl)-5-trifluoromethyl-benzyl]-carbamic acid methyl ester | 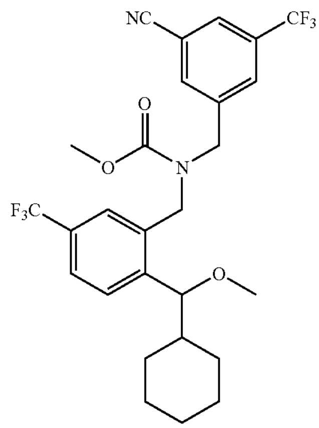 | 542.2 | 587.6 (M + 45) |

Preparation 19: (2-bromo-5-(trifluoromethyl)benzyloxy)triisopropylsilane

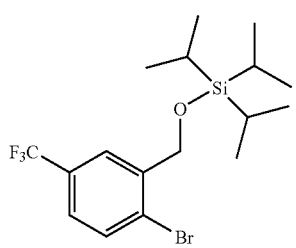

To a solution of (2-bromo-5-(trifluoromethyl)phenyl)methanol (10 g; 39 mmol) in N,N-dimethylformamide (100 mL) was added imidazole (6.82 g; 100.1 mmol) and triisopropylsilyl chloride (9.6 mL; 55.2 mmol) under $N_2$. The reaction was stirred at room temperature for 48 hours. The reaction was diluted with ethyl acetate and washed with water (4×) and brine. The organic layer was dried over sodium sulfate and concentrated under reduced pressure. The residue was purified by 80 g RediSep column (Teledyne Isco Inc., Lincoln Nebr.) (eluted with 5-10% ethyl acetate in heptane) to yield the title compound (16.47 g, 100%) as a colorless oil. MS (GC) Calc: 410.0, Found: 391 (M−F). $^1$H NMR (400 MHz, CDCl$_3$) δ ppm 7.94 (s, 1H), 7.62 (d, J=8.30 Hz, 1H), 7.39 (d, J=8.30 Hz, 1H), 4.84 (s, 2H), 1.25 (m, 3H), 1.12(d, 18H).

Preparation 20: 1-(4-(trifluoromethyl)-2-(triisopropylsilyloxy)methyl)phenyl)cycloheptanol

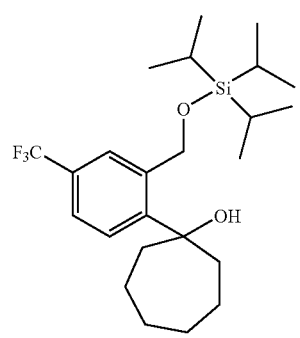

To a solution of (2-bromo-5-(trifluoromethyl)benzyloxy)triisopropylsilane (604 mg; 1.47 mmol) in tetrahydrofuran (4 mL) under $N_2$ at −78° C. was added n-butyllithium (0.9 mL; 2.25 mmol; 2.5M in hexanes) dropwise over 10 minutes. Reaction was stirred for 5 minutes. A solution of cycloheptanone (0.21 mL; 1.78 mmol) in hexanes (1.0 mL) was added dropwise over 6 minutes. After stirring for 1 hour at −78° C., the bath was removed and stirred for 1 hour. The reaction mixture was quenched with aqueous saturated ammonium chloride and extracted with ethyl acetate. The organic layer was washed twice with water and then with brine. The organic layer was dried over sodium sulfate and concentrated under reduced pressure. The residue was purified over a 12 g RediSep column (Teledyne Isco Inc., Lincoln Nebr.) (eluted with 5-10% ethyl acetate in heptane) to yield 387 mg (59.3%) of the title compound as a colorless oil. MS GC (El): Calc: 444.6, Found: 426 (M−H$_2$O). $^1$H NMR (400 MHz, CDCl$_3$) δ ppm 7.62 (s, 1H), 7.49 (dd, J=8.30, 7.88 Hz, 1H), 7.44 (d, J=8.30 Hz, 1H), 5.11 (s, 2H), 4.03 (s, 1H), 2.07-1.98 (m, 4H), 1.94-1.82 (m, 2H), 1.79-1.69 (m, 2H), 1.67-1.5 (m, 4H), 1.19 (m, 3H), 1.08 (s, 18H).

Preparation 21: (2-(1-methoxycycloheptyl)-5-(trifluoromethyl)benzyloxy)triisopropylsilane

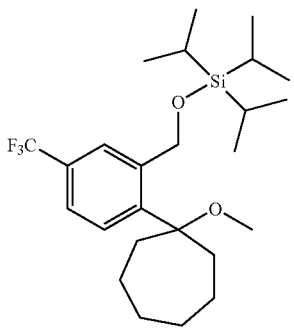

To a solution of 1-(4-(trifluoromethyl)-2-((triisopropylsilyloxy)methyl)phenyl)cycloheptanol (284 mg; 0.639 mmol) in tetrahydrofuran (3.5 mL) at room temperature was added sodium hydride (40 mg; 1 mmol; 60% dispersion in mineral oil). After stirring at room temperature for 15 minutes methyl iodide (80 uL; 1.28 mmol) was added. Reaction stirred for 16 hours. More sodium hydride (20 mg; 0.5 mmol; 60% dispersion in mineral oil) was added. After 5 minutes methyl iodide (0.1 mL; 1.6 mmol) was added. The reaction was stirred for 16 hours. The reaction was quenched with water and extracted with ethyl acetate. The organic layer was washed with water (2×) and brine. The organic layer was dried over sodium sulfate and concentrated under reduced pressure. The residue was purified over a 12 g RediSep column (Teledyne Isco Inc., Lincoln Nebr.) (eluted with 5-15% ethyl acetate in heptanes) to yield 279 mg (95.2%) of the title compound as a colorless oil. MS-GC (El): Calc: 458.6 Found: 439 (M−F). $^1$H NMR (400 MHz, CDCl$_3$) δ ppm 8.22 (d, J=1.24 Hz, 1H), 7.44 (dd, J=8.30, 1.24 Hz, 1H), 7.34 (d, J=8.30 Hz, 1H), 5.11 (s, 2H), 2.95 (s, 3H), 2.16 (m, 2H), 2.01 (m, 2H), 2.0 (dd, J=14.94, 14.52 Hz, 1H), 1.97 (dd, J=14.94, 14.52 Hz, 1H), 1.83-1.58 (m, 6H), 1.3-1.16 (m, 2H), 1.13 (s, 12H), 1.11 (s, 6H).

Preparation 22: (2-(1-methoxycycloheptyl)-5-(trifluoromethyl)phenyl)methanol

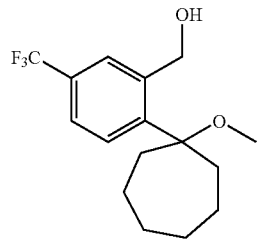

To a solution of (2-(1-methoxycycloheptyl)-5-(trifluoromethyl)benzyloxy)triisopropylsilane (276 mg; 0.602 mmol) in tetrahydrofuran (3.5 mL) was added tetrabutylammonium fluoride (0.62 mL; 0.62 mmol; 1.0 M solution in tetrahydrofuran). Reaction was stirred at room temperature for 1.5 hours. Solvent was evaporated under reduced pressure. The residue was purified by 12 g RediSep column (Teledyne Isco Inc., Lincoln Nebr.) (eluted with 10-30% ethyl acetate in heptane) to yield 169 mg (92.9%) of the title compound as a colorless gum. MS-GC (El): Calc: 302.3, Found: 302 (M). $^1$H NMR (400 MHz, CDCl$_3$) δ ppm 7.89 (s, 1H), 7.49 (dd, J=8.30 Hz, 1H), 7.40 (d, J=8.30 Hz, 1H), 5.03 (s, 2H), 3.00 (s, 3H), 2.54 (bs, 1H), 2.23 (m, 2H), 2.04 (m, 2H), 1.88-1.55 (m, 8H).

Preparation 23

2-(1-methoxycycloheptyl)-5-(trifluoromethyl)benzaldehyde

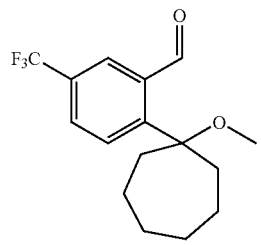

To a solution of (2-(1-methoxycycloheptyl)-5-(trifluoromethyl)phenyl)methanol (167 mg; 0.552 mmol) in methylene chloride (3.0 mL) was added Dess-Martin reagent (290 mg; 0.683 mmol). Reaction was stirred at room temperature for 5 hours. The reaction was diluted with ethyl acetate and quenched with aqueous 1N sodium hydroxide. After partitioning off the aqueous layer, the organic layer was washed with water and brine. It was dried over sodium sulfate and concentrated under reduced pressure. The residue was purified over a Bakerbond 1 g silica cartridge (Mallinkrodt Baker Inc. Phillipsburg, N.J.) (eluted with 0-5% heptane) to yield 167 mg of a cloudy oil. $^1$H NMR (400 MHz, CDCl$_3$) δ ppm 10.91 (s, 1H), 811 (d, J=2.07 Hz, 1H), 7.73 (dd, J=8.71, 8.30

Hz, 1H), 7.48 (d, J=7.88 Hz, 1H), 2.96 (s, 3H), 2.25 (m, 2H), 2.09 (m, 2H), 1.94-1.57 (m, 8H).

Preparation 24: N-(2-(1-methoxycycloheptyl)-5-(trifluoromethyl)benzyl)(3.5 bis(trifluoromethyl)phenyl)methanamine

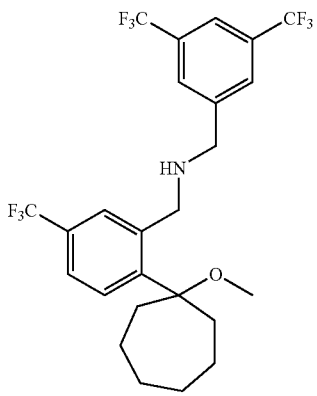

A mixture of 2-(1-methoxycycloheptyl)-5-(trifluoromethyl) benzaldehyde (167 mg; 0.556 mmol) and 3,5-bistrifluoromethyl benzylamine (150 mg; 0.616 mmol) in toluene (4 mL) was heated at reflux for 16 hours, after which solvent was removed. Ethanol (4 mL) and sodium borohydride (31 mg; 0.819 mmol) were added to the residue. The resulting mixture was stirred at room temperature for 16 hours. Solvent was evaporated under reduced pressure. The residue was taken up in ethyl acetate and washed twice with water and dried over sodium sulfate and concentrated under reduced pressure. The residue was purified over a 12 g RediSep column (Teledyne Isco Inc., Lincoln Nebr.) (eluted with 5-25% ethyl acetate in heptane) to yield 194 mg (66.1% for 2 steps) of the title compound as a gum. MS (ES+): Calc: 527.4 Found: 528.4 (M+H).

EXAMPLE 51

N-(2-(1-methoxycycloheptyl)-5-(trifluoromethyl)benzyl)-N-(3,5-bis(trifluoromethyl)benzyl)-2H-tetrazol-5-amine

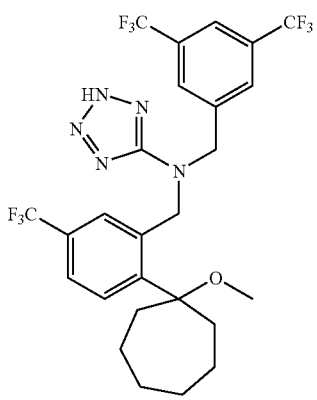

To a solution of N-(2-(1-methoxycycloheptyl)-5-(trifluoromethyl)benzyl) (3,5-bis(trifluoromethyl)phenyl)methanamine (181 mg; 0.343 mmol) and sodium acetate trihydrate (100 mg; 0.734 mmoll) in methanol (2 mL) was added cyanogen bromide (0.9 mL; 4.5 mmol; 5.0M solution in acetonitrile). Reaction was stirred at room temperature for 16 hours. Solvent evaporated under reduced pressure. The residue was dissolved in ethyl acetate and washed twice with water and then with brine. It was dried over sodium sulfate and concentrated under reduced pressure to give 199 mg (68%) of crude gum. MS (ES–): Calc: 552.4, Found: 551.5 (M–H).

A mixture of amino-nitrile (197 mg; 0.357 mmol), sodium azide (120 mg; 1.84 mmol) and triethylamine hydrochloride (247 mg; 1.79 mmol) in toluene (3 mL) was heated at reflux for 16 hours. The reaction was diluted with ethyl acetate and washed twice with water and then brine. The organic was dried over sodium sulfate and concentrated under reduced pressure. The residue was purified by 12 g RediSep column (Teledyne Isco Inc., Lincoln Nebr.) (eluted with 20-75% ethyl acetate) to give 145 mg (70% yield for 2 steps) of colorless gum. MS (ES+): Calc: 595.5 Found: 596.5 (M+H). $^1$H NMR (400 MHz, CDCl$_3$) δ ppm 7.79 (s, 1H), 7.72 (s, 2H), 7.52 (m, 2H), 7.35 (s, 1H), 4.92 (s, 4H), 3.15 (bm, 3H), 2.17 (m, 2H), 1.98 (m, 2H), 1.86-1047 (m, 8H).

EXAMPLE 52

N-(2-(1-methoxycycloheptyl)-5-(trifluoromethyl)benzyl)-N-(3,5-bis(trifluoromethyl)benzyl)-2-methyl-2H-tetrazol-5-amine

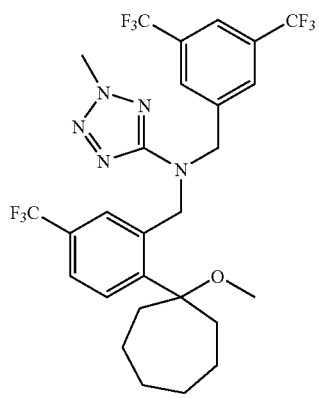

To a solution of N-(2-(1-methoxycycloheptyl)-5-(trifluoromethyl)benzyl)-N-(3,5-bis(trifluoromethyl)benzyl)-2H-tetrazol-5-amine (145 mg; 0.243 mmol) in 2-methyltetrahydrofuran (2.5 mL) was added sodium carbonate (110 mg; 1.03 mmol), N,N-dimethylformamide (1.0 mL) and dimethyl sulfate (70 uL; 0.739 mmol). Reaction was stirred for 16 hours at 60° C. The reaction was diluted with ethyl acetate, washed twice with water and then brine. The organic was dried sodium sulfate and concentrated under reduced pressure. The residue was purified by 12 g RediSep column (Teledyne Isco Inc., Lincoln Nebr.) (eluted with 10-30% ethyl acetate in heptane) to give 120 mg (80.9% yield) of a colorless gum which crystallized into a white solid upon sitting. Melting point: 103-104° C. MS (ES+): Calc: 609.5, Found: 610.5 (M+H). $^1$H NMR (400 MHz, CDCl$_3$) δ ppm 7.77 (s, 1H), 7.72 (s, 2H), 7.47 (d, J=7.47 Hz, 1H), 7.46 (s, 1H), 7.41 (d, J=8.30 Hz, 1H), 5.10 (s, 2H), 4.79 (s, 2H), 4.20 (s, 3H), 2.94 (s, 3H), 2.12 (m, 2H), 1.97 (m, 2H), 1.8-1.46 (m, 8H).

Preparation 25: N-(2-(1-methoxycycloheptyl)-5-(trifluoromethyl)benzyl)-2-methyl-2H-tetrazol-5-amine

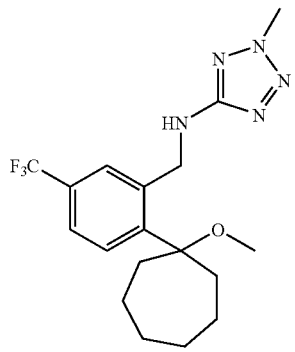

A mixture of 2-(1-methoxycycloheptyl)-5-(trifluoromethyl) benzaldehyde (118 mg, 0.393 mmol) and 2-methyl-2H-tetrazol-5-amine (148 mg, 1.49 mmol) in toluene (3 mL) was heated at reflux for 16 hours, after which solvent was removed to give a gummy solid. Ethanol (3 mL) and sodium borohydride (25 mg; 0.660 mmol) were added to the residue. The resulting mixture was stirred at room temperature for 16 hours. Solvent was evaporated under reduced pressure. The residue was taken up in ethyl acetate and washed twice with water and dried over sodium sulfate and concentrated under reduced pressure. The crude was purified over 4 g RediSep (eluted with 20-60% ethyl acetate in heptane) to give 83 mg (55% yield) of title compound. MS (ES+): Calc: 383.4, Found: 352.3 (M-OMe). $^1$H NMR (400 MHz, CDCl$_3$) δ ppm 7.84 (s, 1H), 7.48 (dd, J=8.77 Hz, 1H), 7.42 (d, J=8.30 Hz, 1H), 4.92 (d, J=6.22 Hz, 2H), 4.75 (t, J=6.22 Hz, 1H), 4.16 (s, 3H), 3.03 (s, 3H), 2.26 (m, 2H), 2.07 (m, 2H), 1.88-1.77 (m, 2H), 1.75-1.65 (m, 2H), 1.64-1.52 (m, 4H).

EXAMPLE 53

3-(((2-(1-methoxycycloheptyl)-5-(trifluoromethyl)benzyl)(2-methyl-2H-tetrazol-5-yl)amino)methyl)-5-trifluoromethyl)benzonitrile

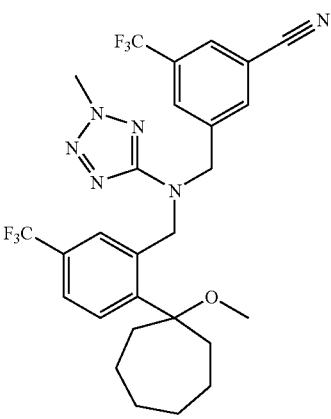

A mixture of N-(2-(1-methoxycycloheptyl)-5-(trifluoromethyl)benzyl)-2-methyl-2H-tetrazol-5-amine (75 mg; 0.2 mmol) was stirred in N,N-dimethylformamide (1 mL). To this was added sodium hydride (16 mg; 0.4 mmol; 60% dispersion in mineral oil). After stirring at room temperature for 20 minutes, a solution of 3-(bromomethyl)-5-(trifluoromethyl) benzonitrile (60 mg; 0.227 mmol) in N,N-dimethylformamide (0.1 mL) was added. The reaction was stirred at room temperature for 5 hours. More sodium hydride (5 mg; 0.125 mmol; 60% dispersion in mineral oil) was added. Reaction was stirred for 15 minutes. The reaction was quenched with water, diluted with ethyl acetate and washed with water (2×) and brine. The organic layer was dried over sodium sulfate and concentrated under reduced pressure. The crude was purified over a 4 g RediSep column (Teledyne Isco Inc., Lincoln Nebr.) (eluted with 10-30% ethyl acetate in heptane) to give 86 mg (78% yield) of the title compound as a gum. MS (ES+): Calc: 566.5, Found: 567.3 (M+H). $^1$H NMR (400 MHz, CDCl$_3$) δ ppm 7.81 (s, 1H), 7.77 (s, 1H), 7.72 (s, 1H), 7.48 (d, J=8.30 Hz, 1H), 7.45 (s, 1H), 7.42 (d, J=8.30 Hz, 1H), 5.12 (s, 2H), 4.75 (s, 2H), 4.21 (s, 3H), 2.95 (s, 3H), 2.13 (m, 2H), 2.00 (m, 2H), 1.82-1.62 (m, 4H), 1.62-1.47 (m, 4H).

Preparation 26: (2-{[(3,5-Bis-trifluoromethyl-benzyl)-(2-methyl-2H-tetrazol-5-yl)-amino]-methyl}-4-trifluoromethyl-phenyl)-cyclohexyl-methanone

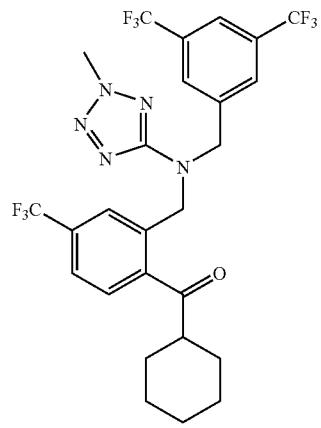

A mixture of 2-{[(3,5-bis-trifluoromethyl-benzyl)-(2-methyl-2H-tetrazol-5-yl)-amino]-methyl}-4-trifluoromethyl-benzonitrile (445 mg; 0.875 mmol) and cyclohexylmagnesium chloride (1.8 mL; 3.6 mmol; 2.0M in diethyl ether) in toluene (7 mL) was heated in a microwave reactor at 66° C. for 50 minutes. The reaction was added to aqueous 2N hydrochloric acid (30 mL) and stirred at room temperature for 42 hours. Reaction was extracted with ethyl acetate. The organic layer was washed with water and brine. It was dried over sodium sulfate and concentrated under reduced pressure. The residue was purified over a 12 g RediSep column (Teledyne Isco Inc., Lincoln Nebr.) (eluted with 10-35% ethyl acetate in heptane) to give 235 mg (45.2%) of a light yellow orange gum. MS (ES+): Calc: 593.4, Found: 594.4 (M+H). $^1$H NMR (400 MHz, CDCl$_3$) δ ppm 7.74 (s, 1H), 7.67 (s, 2H), 7.64 (d, J=8.30 Hz, 1), 7.58 (d, J=7.88 Hz, 1H), 7.54 (s, 1H), 4.83 (s, 2H), 4.80 (s, 2H), 4.19 (s, 3H), 3.02 (m, 1H), 1.81 (d, J=9.96 Hz, 3H), 1.71 (d J=12.86 Hz, 1H), 1.42-1.18 (m, 6H).

149

Preparation 27: (2-{[(3,5-Bis-trifluoromethyl-benzyl)-(2-methyl-2H-tetrazol-5-yl)-amino]-methyl}-4-trifluoromethyl-phenyl)-cyclohexyl-methanol

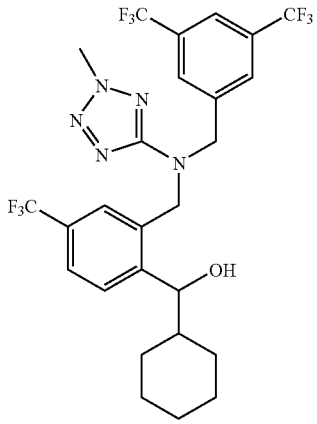

A solution of (2-{[(3,5-bis-trifluoromethyl-benzyl)-(2-methyl-2H-tetrazol-5-yl)-amino]-methyl}-4-trifluoromethyl-phenyl)-cyclohexyl-methanone (152 mg; 0.256 mmol) and sodium borohydride (22 mg; 0.582 mmol) in methanol (1.5 mL) was stirred at room temperature for 16 hours. The solvent was evaporated under reduced pressure. The residue was taken up in ethyl acetate, washed twice with water and then brine. The organic layer was dried sodium sulfate and concentrated under reduced pressure. The residue was purified over 12 g RediSep column (Teledyne Isco Inc., Lincoln Nebr.) (eluted with 20-50% ethyl acetate in heptane) to give 152 mg (99.7% yield) of the title compound as a colorless gum. MS (ES+): Calc: 595.5, Found: 596.1 (M+H). $^1$H NMR (400 MHz, CDCl$_3$) δ ppm 7.78 (s, 1H), 7.66 (s, 2H), 7.57 (d, J=8.30 Hz, 1H), 7.55 (d, J=8.30 Hz, 1H), 7.36 (s, 1H), 4.88 (d, J=15.77 Hz, 1H), 4.79 (d, J=15.77 Hz, 1H), 4.76 (d, J=15.77 Hz, 1H), 4.70 (d, J=16.18 Hz, 1H), 4.66 (d, J=7.05 Hz, 1H), 4.21 (s, 3H), 2.20 (bs, 1H), 1.94 (d, J=12.45 Hz, 1H), 1.78 (m, 1H), 1.69-1.51 (m, 4H), 1.2-0.88 (m, 4H).

Preparation 28: (3,5-Bis-trifluoromethyl-benzyl)-[2-(bromo-cyclohexyl-methyl)-5-trifluoromethyl-benzyl]-(2-methyl-2H-tetrazol-5-yl)-amine

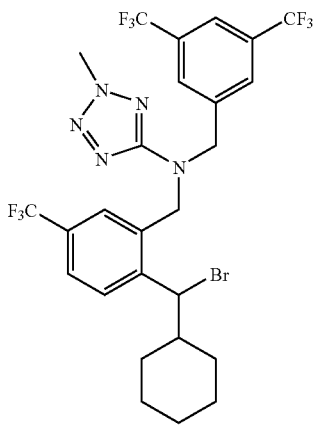

150

To a solution of (2-{[(3,5-bis-trifluoromethyl-benzyl)-(2-methyl-2H-tetrazol-5-yl)-amino]-methyl}-4-trifluoromethyl-phenyl)-cyclohexyl-methanol (51 mg; 0.086 mmol) in methylene chloride (1.2 mL) was added N-bromosuccinimide (63 mg; 0.354 mmol) and triphenylphosphine (97 mg; 0.369 mmol). The reaction was stirred at room temperature for 16 hours. Reaction was directly purified over 4 g RediSep column (Teledyne Isco Inc., Lincoln Nebr.) (eluted with 10-45% ethyl acetate in heptane) to give 27 mg (48% yield) of the title compound as a colorless gum. MS (ES+): Calc: 657.1, Found: 658.3 (M+H). $^1$H NMR (400 MHz, CDCl$_3$) δ ppm 7.78 (s, 1H), 7.71 (d, J=8.30 Hz, 1H), 7.65 (s, 2H), 7.59 (d, J=8.30 Hz, 1H), 7.28 (s, 1H), 4.99 (d, J=9.96 Hz, 1H), 4.91 (d, J=15.35 Hz, 1H), 4.68 (q, J=15.77 Hz, 2H), 4.68 (d, J=16.26 Hz, 1H), 4.24 (s, 3H), 2.34 (d, J=12.86, 1H), 2.00 (m, 1H), 1.80 (d, 13.28 Hz, 1H), 1.63 (t, J=10.35 Hz, 2H), 1.39-1.22 (m, 2H), 1.14 (m, 2H), 0.98 (m, 1H), 0.76 (m, 1H).

EXAMPLE 54

(3,5-Bis-trifluoromethyl-benzyl)-[2-(cyclohexyl-methylsulfanyl-methyl)-5-trifluoromethyl-benzyl]-(2-methyl-2H-tetrazol-5-yl)-amine

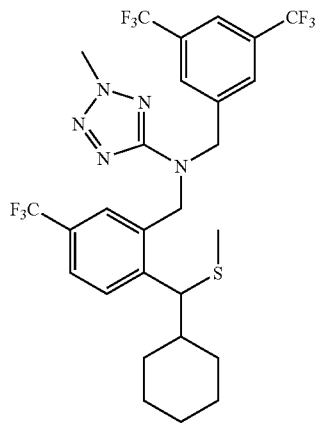

To a solution of (3,5-bis-trifluoromethyl-benzyl)-[2-(bromo-cyclohexyl-methyl)-5-trifluoromethyl-benzyl]-(2-methyl-2H-tetrazol-5-yl)-amine (26 mg; 0.039 mmol) in THF (1 mL) was added sodium thiomethoxide (8 mg; 0.114 mmol). Reaction stirred at room temperature for 16 hours. Reaction was diluted with ethyl acetate and washed twice with water. The organic layer was dried sodium sulfate and concentrated to give 23 mg (93% yield) of the title compound as a gum. MS (ES+): Calc: 625.6, Found: 626.0 (M+H). $^1$H NMR (400 MHz, CDCl$_3$) δ ppm 7.79 (s, 1H), 7.67 (s, 2H), 7.57 (d, J=7.88 Hz, 1H), 7.75-7.56 (bs, 1H), 7.27 (s, 1H), 4.79 (t, J=15.35 Hz, 2H), 4.69 (t, J=15.77 Hz, 2H), 4.23 (s, 3H), 3.81

(bs, 1H), 2.21 (d, J=12.86 Hz, 1H), 1.76 (s, 3H), 1.76-1.57 (m, 4H), 1.36 (d, J=12.45 Hz, 1H), 1.25-1.03 (m, 3H), 1.0-0.76 (m, 2H).

EXAMPLE 55

(3,5-Bis-trifluoromethyl-benzyl)-[2-(cyclohexyl-methanesulfonyl-methyl)-5-trifluoromethyl-benzyl]-(2-methyl-2H-tetrazol-5-yl)-amine

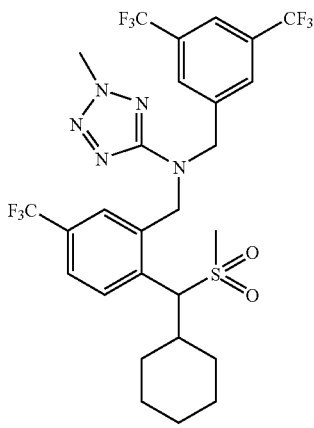

To a solution of (3,5-bis-trifluoromethyl-benzyl)-[2-(cyclohexyl-methylsulfanyl-methyl)-5-trifluoromethyl-benzyl]-(2-methyl-2H-tetrazol-5-yl)-amine (27 mg; 0.043 mmol) in methylene chloride (1.0 mL) was added meta-chloroperbenzoic acid (17 mg; 0.098 mmol). The reaction was stirred at room temperature for 16 hours. After adding saturated aqueous sodium bicarbonate (2 drops), the reaction was stirred for 15 minutes. The resulting mixture was filtered over sodium sulfate and concentrated under reduced pressure The residue was purified over 4 g RediSep column (Teledyne Isco Inc., Lincoln Nebr.) (eluted with 5-40% ethyl acetate in heptane) to give 16.5 mg (58% yield) of the title compound as a gum. MS (ES+): Calc: 657.6, Found: 658.5 (M+H). 1H NMR (400 MHz, CDCl$_3$) δ ppm 7.89 (d, J=8.3 Hz, 1H), 7.84 (s, 1H), 7.70 (s, 2H), 7.67 (d, J=8.3 Hz, 1H, 7.34 (s, 1H), 4.91 (d, J=15.77 Hz, 1H), 4.83 (d, J=16.18 Hz, 1H), 4.62 (d, J=14.11 Hz, 1H), 4.58 (d, J=15.77 Hz, 1H), 4.52 (d, J=8.3 Hz, 1H), 4.24 (s, 3H), 2.58 (s, 3H), 2.39 (m, 2H), 1.78 (d, J=14.11 Hz, 1H), 1.63 (t, J=12.86, 12.03 Hz. 2H), 1.4-1.05 (m, 5H), 0.79 (m, 1H).

Preparation 29: Cyclobutylmagnesium bromide

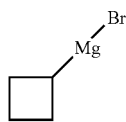

To a suspension of magnesium granules (210 mg; 8.64 mmol) and iodine (54 mg, 0.212 mmol) in dimethoxyethane (3.5 mL) was added cyclobutyl bromide (0.2 mL; 2.12 mmol) with stirring in an oil bath at 50° C. Iodomethane (0.05 mL; 0.8 mmol) was added followed by cyclobutyl bromide (0.2 mL; 2.12 mmol). An additional aliquot of iodomethane (0.1 ml; 1.6 mmol) was added then the reaction was stirred at 50° C. for 1.5 hours before allowing to cool to room temperature. The concentration of cyclobutylmagnesium bromide was determined using the method described by Love, B. E. and Jones, E. G., Journal of Organic Chemistry, 1999, 64, 3755 as follows.

To a solution of salicylaldehyde phenylhydrazone (80 mg; 0.376 mmol) in tetrahydrofuran (10 mL) at room temperature was added the cyclobutylmagnesium bromide solution dropwise. The endpoint, indicated by a color change from yellow to orange, was reached after the addition of 0.62 mL of the cyclobutylmagnesium bromide solution, indicating a molarity of 0.6M.

Preparation 30: (2-(((3,5-bis(trifluoromethyl)benzyl)(2-methyl-2H-tetrazol-5-yl)amino)methyl)-4-trifluoromethyl)phenyl)(cyclobutyl)methanone

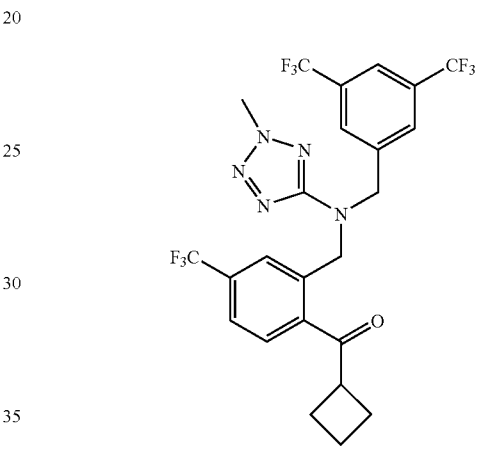

To a solution of (3,5-bis-trifluoromethyl-benzyl)-(2-bromo-5-trifluoromethyl-benzyl)-2-methyl-2H-tetrazol-5-yl)-amine (Preparation 6, 0.5 mmol, 281 mg) in anhydrous THF was added isopropylmagnesium chloride/lithium chloride in THF (0.72M, 1.5 mmol, 2.1 mL, prepared according to the procedure described in Angew. Chem. Int. Ed. 2004, 43, 3333). The mixture was cooled to 0° C. and stirred for 3 hours before cooling to −78° C. To this was added a solution of CuCN.2LiCl in THF (1M, 0.5 mmol, 0.5 mL, solution prepared by stirring 1 equivalent of CuCN with 2 equivalents of freshly dried LiCl in anhydrous THF (1 mL per equivalent) until all of the solid was dissolved). After 30 minutes at −78° C., a solution of cyclobutylcarbonyl chloride (1.5 mmol, 178 mg) in anhydrous THF (2 mL) was added and the mixture was allowed to warm to room temperature before pouring into an aqueous solution of ammonium chloride to which some ammonium hydroxide had been added. This mixture was filtered through Celite® and extracted with dichloromethane (2×). The organic layer was dried with anhydrous sodium sulfate and evaporated to dryness under reduced pressure. The residue was purified by silica chromatography using a 12 g RediSep column (Teledyne Isco Inc., Lincoln Nebr.) (eluted with 0-65% ethyl acetate in heptane) to give the title compound (81.7 mg, 29%) MS (ES+): Calc: 565.4, Found: 566.4 (M+H). 1H NMR (400 MHz, CDCl$_3$) δ ppm 7.75 (s, 1H), 7.68 (s, 2H), 7.66 (d, J=8.71 Hz, 1H), 7.56 (d, J=9.54 Hz, 2H), 5.00 (s, 2H), 4.84 (s, 2H), 4.19 (s, 3H), 3.88 (m, 1H), 2.4-1.2.1 (m, 4H), 2.1-1.2.0 (m, 1H), 1.96-1.8 (m, 1H).

Preparation 31: (2-{[(3,5-Bis-trifluoromethyl-benzyl)-(2-methyl-2H-tetrazol-5-yl)-amino]-methyl}-4-trifluoromethyl-phenyl-cyclobutyl-methanol

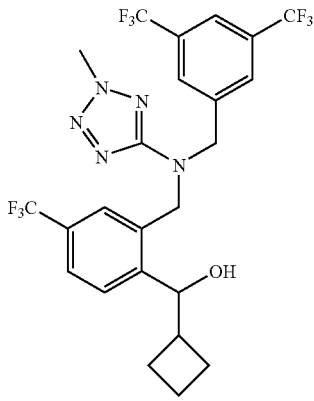

To a solution of 2-{[(3,5-bis-trifluoromethyl-benzyl)(2-methyl-2H-tetrazol-5-yl)amino]-methyl}-4-trifluoromethyl-benzaldehyde (1.5 g; 2.9 mmol) in tetrahydrofuran (14 mL) at −10° C. was added dropwise cyclobutylmagnesium bromide (9 mL; 5.4 mmol; 0.6M solution in tetrahydrofuran). The reaction was stirred at −10° C. for 1.5 hours. To quench the reaction, at 0° C. was added aqueous 2N hydrochloric acid. Reaction extracted with ethyl acetate. The organic was washed with aqueous 2N hydrochloric acid, water and brine. It was dried sodium sulfate and concentrated under reduced pressure. The residue was purified by 40 g RediSep column (Teledyne Isco Inc., Lincoln Nebr.) (eluted with 15-70% ethyl acetate in heptane) to give 420 mg (25% yield) as a gum. MS (ES−): Calc; 567.4, Found: 612.6 (M+HCO$_2$). $^1$H NMR (400 MHz, CDCl$_3$) δ ppm 7.78 (s, 1H), 7.66 (s, 2H), 7.52 (d, J=8.30 Hz, 1H), 7.49 (d, J=8.30 Hz, 1H), 7.35 (s, 1H), 4.86 (q, J=15.77 Hz, 2H), 4.86 (s, 1H), 4.77 (q, J=15.77, 16.18 Hz, 2H), 4.20 (s, 3H), 2.68 (m, 1H), 2.05-1.96 (m, 2H), 1.93-1.76 (m, 3H), 1.70 (m, 1H).

EXAMPLE 56

(3,5-Bis-trifluoromethyl-benzyl)-[2-(cyclobutyl-ethoxy-methyl)-5-trifluoromethyl-benzyl]-(2-methyl-2H-tetrazol-5-yl)-amine

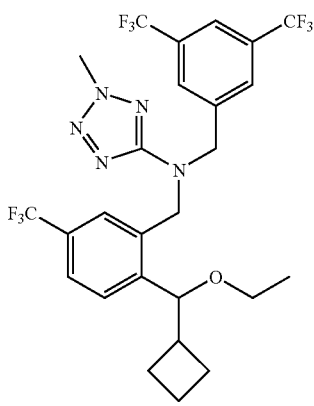

To a solution of (2-{[(3,5-bis-trifluoromethyl-benzyl)-(2-methyl-2H-tetrazol-5-yl)-amino]-methyl}-4-trifluoromethyl-phenyl)-cyclobutyl-methanol (23 mg; 0.041 mmol) in THF (1.5 mL) at 0° C. was added sodium hydride (15 mg; 0.375 mmol; 60% dispersion in mineral oil). After stirring at room temperature for 30 minutes ethyl iodide (0.05 mL; 0.625 mmol) was added. Reaction was stirred for 2 hours. More sodium hydride (15 mg; 0.375 mmol; 60% dispersion in mineral oil) and iodoethane (0.05 mL; 0.625 mmol) were added. Reaction stirred for 72 hours. Reaction was quenched with 2 drops of water. The reaction was filtered over a 1 g Bakerbond silica cartridge (Mallinkrodt Baker Inc. Phillipsburg, N.J.) (eluted with ethyl acetate). The crude was purified by RediSep column (Teledyne Isco Inc., Lincoln Nebr.) (eluted with 5-30% ethyl acetate in heptane) to give 21 mg (87% yield) of a gum. MS (ES+): Calc: 595.5, Found: 596.4 (M+H). $^1$H NMR (400 MHz, CDCl$_3$) δ ppm 7.78 (s, 1H), 7.65 (s, 2H), 7.53 (s, 2H), 7.33 (s, 1H), 4.83 (q, J=16.18 Hz, 2H), 4.73 (q, J=16.18, 14.11 Hz, 2H), 4.42 (d, J=6.64 Hz, 1H), 4.22 (s, 3H), 3.20 (m, J=7.05, 6.64 Hz, 2H), 2.49 (m, J=7.88, 7.05 Hz, 1H), 2.07-1.57 (m, 6H), 1.11 (t, J=7.05 Hz, 3H).

EXAMPLE 57

N-(2-(1-methoxy-2,2-dimethylpropyl)-5-(trifluoromethyl)benzyl)-N-(3,5-bis(trifluoromethyl)benzyl)-2-methyl-2H-tetrazol-5-amine

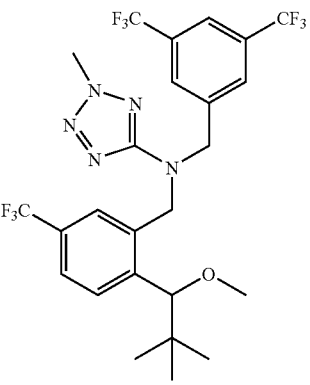

The title compound was prepared in an analogous manner to that described for the preparation of (3,5-bis-trifluoromethyl-benzyl)-[2-(cyclobutyl-ethoxy-methyl)-5-trifluoromethyl-benzyl]-(2-methyl-2H-tetrazol-5-yl)amine from 2-{[(3,5-bis-trifluoromethyl-benzyl)-(2-methyl-2H-tetrazol-5-yl)-amino]-methyl}-4-trifluoromethyl-benzaldehyde by the addition of tert-butylmagnesium chloride followed by O-methylation with methyl iodide LC-MS (ES−): Calc: 583.4, Found: 628 (M+HCO$_2^-$).

EXAMPLES 58 AND 59

(R)—N-(2-(cyclobutyl(methoxy)methyl)-5-(trifluoromethyl)benzyl)-N-(3,5-bis(trifluoromethyl)benzyl)-2-methyl-2H-tetrazol-5-amine and (S)—N-(2-cyclobutyl(methoxy)methyl)-5-(trifluoromethyl)benzyl)-N-(3,5-bis(trifluoromethyl)benzyl)-2-methyl-2H-tetrazol-5-amine

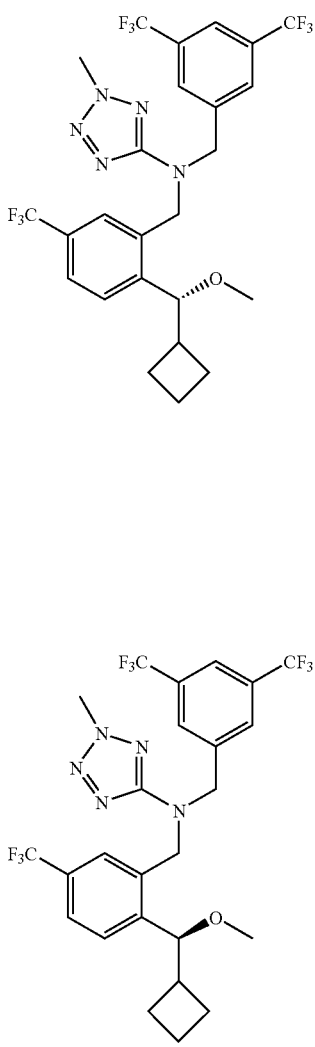

The enantiomers of (2-{[(3,5-bis-trifluoromethyl-benzyl)-(2-methyl-2H-tetrazol-5-yl)-amino]-methyl}-4-trifluoromethyl-phenyl)-cyclobutyl-methanol were separated as follows. The racemic mixture of the alcohol (431 mg) was dissolved in methanol, injected onto a Chiralpak AD column (10 cm×50 cm) (Chiral Tech Inc. Westchester, Pa., USA) and eluted using heptane/2-propanol (96:4, 475 mL/minute). Enantiomer 1 (170 mg, 100% ee) eluted at 9.880 minutes, and enantiomer 2 (163 mg, 95.8% ee) eluted at 11.200 minutes on a Chiralpak AD-H column. Each enantiomer was converted to the title compound using an O-methylation procedure analogous to that used for the preparation of (3,5-bis-trifluoromethyl-benzyl)-[2-(cyclohexyl-methoxy-methyl)-4-methyl-5-trifluoromethyl-benzyl]-(2-methyl-2H-tetrazol-5-yl)-amine.

Enantiomer 1 (from the 9.88 minute peak): $[\alpha]_D^{20}=+38.02°$ (c 0.0142 g/ml, methanol). Enantiomer 2 (from the 11.2 minute peak): $[\alpha]_D^{20}=-35.88°$ (c 0.0119 g/ml, methanol). MS (ES+): Calc: 581.4, Found: 582.5 (M+H). $^1$H NMR (400 MHz, CDCl$_3$) δ ppm 7.79 (s, 1H), 7.66 (s, 2H), 7.55 (d, J=8.30 Hz, 1H), 7.50 (d, J=8.30 Hz, 1H), 7.35 (s, 1H), 4.82 (q, J16.18 Hz, 2H), 4.73 (s, 2H), 4.34 (d, J=7.05 Hz, 1H), 4.23 (s, 3H), 3.12 (s, 3H), 2.50 (m, 1H), 2.04-1.85 (m, 2H), 1.83-1.61 (m, 4H).

Preparation 32: 1-(2-(((3,5-bis(trifluoromethyl)benzyl)(2-methyl-2H-tetrazol-5-yl)amino)methyl)-4-(trifluoromethyl)phenyl)-1-cyclobutylethanol

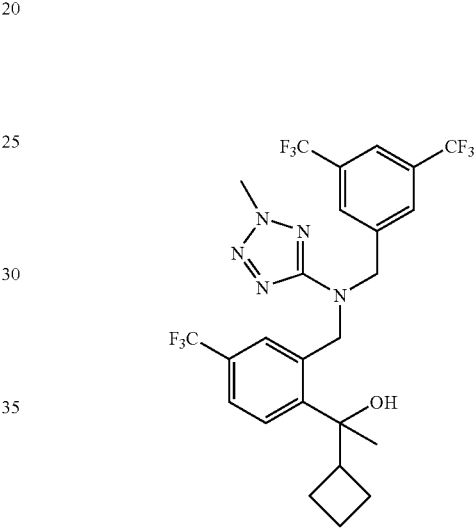

To a solution of (2-(((3,5-bis(trifluoromethyl)benzyl)(2-methyl-2H-tetrazol-5-yl)amino)methyl)-4-(trifluoromethyl)phenyl)(cyclobutyl)methanone (Preparation 29, 28 mg; 0.050 mmol) in tetrahydrofuran (0.5 mL) was added methylmagnesium bromide (50 uL; 0.15 mmol; 3.0M in diethyl ether). The reaction was stirred at room temperature for 2 hours. The reaction was quenched with 2 drops water and 1 drop aqueous 2N hydrochloric acid. The mixture was diluted with ethyl acetate and filtered over a column containing silica gel and sodium sulfate. The crude was purified over 4 g RediSep column (Teledyne Isco Inc., Lincoln Nebr.) (eluted with 10-50% ethyl acetate in heptane) to give 22 mg (76% yield) of the title compound as a colorless gum. MS (ES-): Calc: 581.4, Found: 580.6 (M-H). $^1$H NMR (400 MHz, CDCl$_3$) δ ppm 7.78 (s, 1H), 7.74 (s, 2H), 7.42 (d, 1H), 7.41 (s, 1H), 7.33 (d, J=9.13 Hz, 1H), 5.27 (d, J=16.60 Hz, 1H), 5.15 (d, J=16.18 Hz, 1H), 4.85 (s, 2H), 4.18 (s, 3H), 2.97 (m, 1H), 2.12-1.69 (m, 6H), 1.43 (s, 3H).

EXAMPLE 60

N-(2-(1-cyclobutyl-1-methoxyethyl)-5-(trifluoromethyl)benzyl)-N-(3,5-bis(trifluoromethyl)benzyl)-2-methyl-2H-tetrazol-5-amine

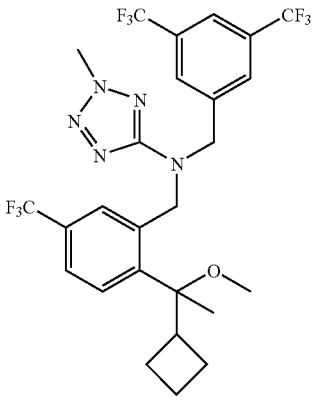

To a solution of 1-(2-(((3,5-bis(trifluoromethyl)benzyl)(2-methyl-2H-tetrazol-5-yl)amino)methyl)-4-(trifluoromethyl)phenyl)-1-cyclobutylethanol (22 mg; 0.038 mmol) in tetrahydrofuran (1.5 mL) was added sodium hydride (10 mg; 0.25 mmol; 60% dispersion in mineral oil). The reaction was stirred for 10 minutes. Iodomethane (0.05 mL; 0.80 mmol) was added. The reaction was stirred at room temperature for 16 hours. The reaction was quenched with water. The mixture was diluted with ethyl acetate and filtered over sodium sulfate and silica get column. After being concentrated under reduced pressure, the residue was taken up in ethyl acetate and washed with water (2×) and brine. The organic layer was dried over sodium sulfate and concentrated under reduced pressure. The residue was purified over a 4 g RediSep column (Teledyne Isco Inc., Lincoln Nebr.) (eluted with 10-50% ethyl acetate in hexanes) to give 18 mg (80% yield) of the title compound as a colorless gum. MS (ES+): Calc: 595.5, Found: 596.5 (M+H). $^1$H NMR (400 MHz, CDCl$_3$) δ ppm 7.78 (s, 1H), 7.73 (s, 2H), 7.45 (d, J=8.3 Hz, 1H), 7.43 (s, 1H), 7.3 (d, J=8.3 Hz, 1H), 5.09 (s, 2H), 4.8 (q, J=16.18 Hz, 2H), 4.2 (s, 3H), 3.04 (s, 3H), 2.83 (m, 1H) 1.99 (m, 1H), 1.89-1.6 (m, 6H), 1.59 (s, 3H).

Preparation 33: 1-(2-{[(3,5-Bis-trifluoromethyl-benzyl)-(2-methyl-2H-tetrazol-5-yl)-amino]-methyl}-4-trifluoromethyl-phenyl)-1-cyclohexyl-ethanol

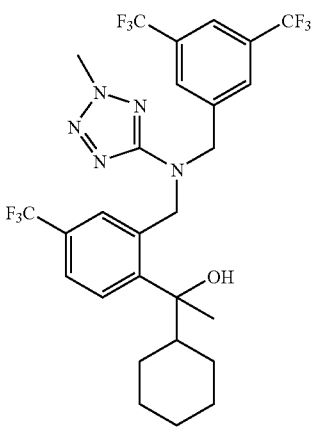

To a solution of (2-{[(3,5-bis-trifluoromethyl-benzyl)-(2-methyl-2H-tetrazol-5-yl)-amino]-methyl}-4-trifluoromethyl-phenyl)-cyclohexyl-methanone (143 mg; 0.241 mmol) in tetrahydrofuran (2.5 mL) at 0° C. was added 3.0M methylmagnesium bromide in tetrahydrofuran (0.25 mL; 0.75 mmol). After 15 minutes, the bath was removed and reaction was stirred at room temperature for 3 hours. The reaction was quenched with 2 drops of water. The reaction was diluted with ethyl acetate and dried over sodium sulfate and concentrated under reduced pressure. The residue was purified over 12 g RediSep column (Teledyne Isco Inc., Lincoln Nebr.) (eluted with 10-50% ethyl acetate in heptane) to give 158 mg (108% yield) of a colorless oil. MS (ES+): Calc: 609.5, Found: 610.4 (M+H). $^1$H NMR (400 MHz, CDCl$_3$) δ ppm 7.77 (s, 1H), 7.74 (s, 1H) 7.42 (m, 2H), 7.34 (d, J=8.30 Hz, 1H), 5.46 (d, J=16.18 Hz, 1H), 4.93 (d, J=16.60 Hz, 1H), 4.82 (q, J=16.18 Hz, 2H), 4.18 (s, 3H), 1.78-1.6 (m, 6H), 1.58 (s, 3H), 1.40 (m, 1H), 1.13-0.94 (m, 4H).

EXAMPLE 61

(3,5-Bis-trifluoromethyl-benzyl)-[2-(1-cyclohexyl-1-methoxy-ethyl)-5-trifluoromethyl-benzyl]-(2-methyl-2H-tetrazol-5-yl)-amine

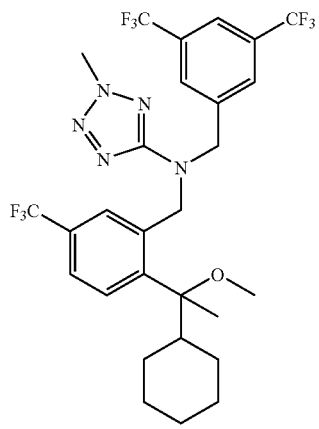

To a solution of 1-(2-(((3,5-bis(trifluoromethyl)benzyl)(2-methyl-2H-tetrazol-5-yl)amino)methyl)-4-(trifluoromethyl)phenyl)-1-cyclohexylethanol (26 mg; 0.043 mmol) in tetrahydrofuran (0.7 mL) was added sodium hydride (11 mg; 0.275 mmol; 60% dispersion in mineral oil). After stirring for 30 minutes at room temperature, iodomethane (30 uL; 0.485 mmol) was added. The reaction was stirred for 16 hours. More sodium hydride (12 mg; 0.3 mmol; 60% dispersion in mineral oil) and iodomethane (30 uL; 0.485 mmol) were added. After 1 hour more sodium hydride (12 mg; 0.3 mmol; 60% dispersion in mineral oil) was added. After 30 minutes, iodomethane (30 uL; 0.485 mmol) was added. The reaction was stirred for 2 hours. The reaction was quenched with aqueous 2N hydrochloric acid (6 drops). The mixture was diluted with ethyl acetate and filtered over sodium sulfate/silica plug. Then the solution was concentrated. The residue was purified by 4 g RediSep column (Teledyne Isco Inc., Lincoln Nebr.) (eluted with 5-25% ethyl acetate in heptane) to give 19 mg (71% yield) of a colorless gum. MS (ES+): Calc: 623.5, Found: 592.5 (M-OCH$_3$). $^1$H NMR (400 MHz, CDCl$_3$) δ ppm 7.78 (s, 1H), 7.73 (s, 2H), 7.46 (s, 1H), 7.45 (d, J=7.47 Hz, 1H), 7.27 (d, J=8.30 Hz, 1H), 5.25 (d, J=17.43 Hz, 1H), 5.07 (d, J=17.43 Hz, 1H), 4.79 (q, J=16.60, 16.18 Hz, 2H), 4.19 (s, 3H), 3.02 (s, 3H), 2.01 (d, J=11.2 Hz, 1H), 1.78-1.67 (m, 2H), 1.66-1.55 (m, 2H), 1.53 (s, 3H), 1.11-0.83 (m, 6H).

EXAMPLES 62 AND 63

Separation of Isomers-(S)—N-(2-(1-cyclohexyl-1-methoxyethyl)-5-(trifluoromethyl)benzyl)-N-(3,5-bis(trifluoromethyl)benzyl)-2-methyl-2H-tetrazol-5-amine AND (R)—N-(2-(1-cyclohexyl-1-methoxyethyl)-5-trifluoromethyl)benzyl)-N-3,5-bis(trifluoromethyl)benzyl)-2-methyl-2H-tetrazol-5-amine

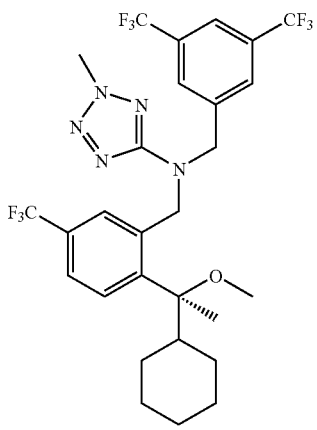

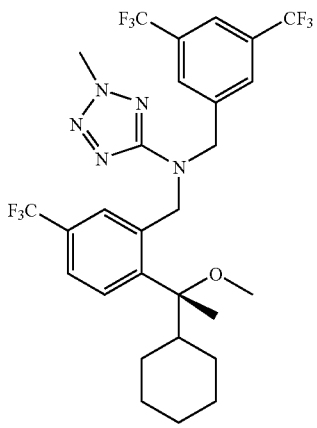

The enantiomers of Example 61 were prepared as follows. The racemic mixture of the alcohol (Preparation 33, 154 mg) was dissolved in methanol, injected onto a Chiralpak AD column (10 cm×50 cm) (Chiral Tech Inc. Westchester, Pa., USA) and eluted using heptane/2-propanol (96:4, 475 mL/minute). Enantiomer 1 (91 mg, 100% ee) eluted at 4.429 minutes, and enantiomer 2 (85 mg, 100% ee) eluted at 5.513 minutes on a Chiralpak AD-H column. Each enantiomer was converted to the title compound according to the procedure analogous to that used for the preparation of Example 61. Enantiomer 1 (from earlier eluting alcohol): $[\alpha]_D^{20}$=+17.56° (c=0.00705 g/mL, methanol). Enantiomer 2 (from later eluting alcohol): $[\alpha]_D^{20}$=−17.41° (c=0.0065 g/mL, methanol). MS (ES+): Calc: 623.5, Found: 592.5 (M-OCH$^3$). $^1$H NMR (400 MHz, CDCl$_3$) δ ppm 7.78 (s, 1H), 7.73 (s, 2H), 7.46 (s, 1H), 7.45 (d, J=7.47 Hz, 1H), 7.27 (d, J=7.88 Hz, 1H), 5.25 (d, J=17.43 Hz, 1H), 5.07 (d, J=17.84 Hz, 1H), 4.84 (d, J=16.18 Hz, 1H), 4.73 (d, J=16.6 Hz, 1H), 4.19 (s, 3H), 3.02 (s, 3H), 2.01 (d, J=11.62 Hz, 1H), 1.78-1.67 (m, 2H), 1.66-1.55 (m, 2H), 1.53 (s, 3H), 1.11-0.89 (m, 3H).

Preparation 34: tert-Butyl 4-(2-((tert-butyldimethylsilyloxy)methyl)-4-(trifluoromethyl)phenyl)-4-hydroxypiperidine-1-carboxylate

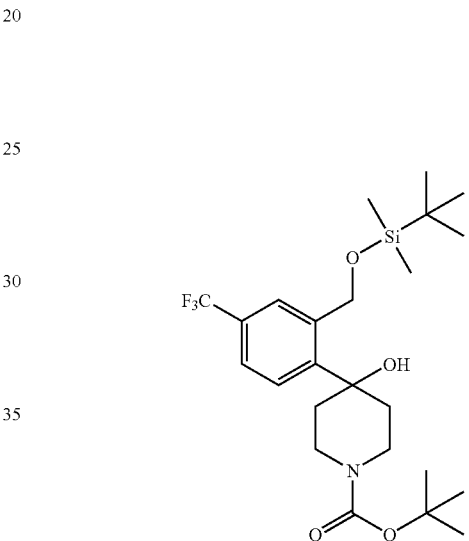

To a solution of (2-bromo-5-(trifluoromethyl)benzyloxy)(tert-butyl)dimethylsilane (904 mg; 2.45 mmol) in tetrahydrofuran (6.0 mL) at −78° C. was added dropwise n-butyllithium (1.5 mL; 3.75 mmol: 2.5M in hexanes). The reaction was stirred at −78° C. for 5 minutes. Then a solution of Boc-piperidone (831 mg; 4.17 mmol) in tetrahydrofuran (3 mL) was added dropwise into reaction. During addition reaction turned yellow in color. The reaction was stirred at −78° C. allowing it to warm to −40° C. within 1 hour. The reaction was quenched with water and extracted with ethyl acetate. The organic layer was washed with saturated aqueous ammonium chloride, water and brine. The organic layer was dried sodium sulfate and concentrated under reduced pressure. The residue was purified over 40 g RediSep column (Teledyne Isco Inc., Lincoln Nebr.) (eluted with 5-15% ethyl acetate in heptane) to give 526 mg (43.9% yield) of a white solid. MS (ES+): Calc. 489.6, Found: 534.6 (M−HCO$_3$). $^1$H NMR (400 MHz, CDCl$_3$) δ ppm 7.54 (dd, J=8.30, 8.71 Hz, 1H), 7.49 (d, J=1.66 Hz, 1H), 7.40 (d, J=8.30 Hz, 1H), 5.02 (s, 2H), 4.78 (s, 1H), 4.04 (d, J=16.18 Hz, 2H), 3.28 (dt, J=12.86, 2.90, 13.28, 2H), 2.00 (dt, J=12.86, 13.28, 4.98, 4.56, 2H), 1.84 (d, J=12.45 Hz, 2H), 1.50 (s, 9H), 0.92 (s, 9H), 0.13 (s, 6H).

Preparation 35: tert-Butyl 4-(2-((tert-butyldimethylsilyloxy)methyl)-4-(trifluoromethyl)phenyl)-4-methoxypiperidine-1-carboxylate

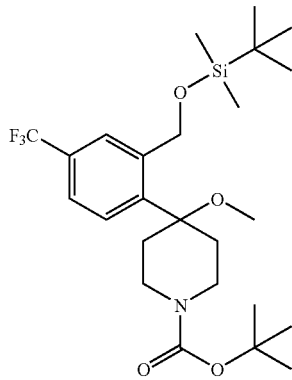

To a solution of tert-butyl 4-(2-((tert-butyldimethylsilyloxy)methyl)-4-(trifluoromethyl)phenyl)-4-hydroxypiperidine-1-carboxylate (526 mg; 1.07 mmol) in tetrahydrofuran (6 mL) at 0° C. was added sodium hydride (75 mg; 60% dispersion in mineral oil). The reaction was stirred for 10 minutes. Then iodomethane (0.10 mL; 1.61 mmol) was added. The reaction was stirred for 72 hours at room temperature. The reaction was quenched with water and 2N hydrochloric acid. The reaction was extracted with ethyl acetate. The organic layer was washed with water and brine. It was dried sodium sulfate and concentrated under reduced pressure. The residue was purified by 40 g RediSep column (Teledyne Isco Inc., Lincoln Nebr.) (eluted with 5-20% ethyl acetate in heptane) to give 540 mg (99.8% yield) of a colorless gum. MS (ES+): Calc: 503.6, Found: 445.4 (M−$^1$BuH). $^1$H NMR (400 MHz, CDCl$_3$) δ ppm 8.08 (s, 1H), 7.49, (dd, J=7.88, 8.30 Hz, 1H), 7.31 (d, J=8.30 Hz, 1H), 5.03 (s, 2H), 4.03 (bs, 2H), 3.16 (bs, 2H), 2.97 (s, 3H), 2.15 (d, J=12.86 Hz, 2H), 1.85 (bs, 2H), 1.48 (s, 9H), 0.98 (s, 9H), 0.14 (s, 6H).

Preparation 36: tert-Butyl 4-(2-hydroxymethyl)-4-(trifluoromethyl)phenyl)-4-methoxypiperidine-1-carboxylate

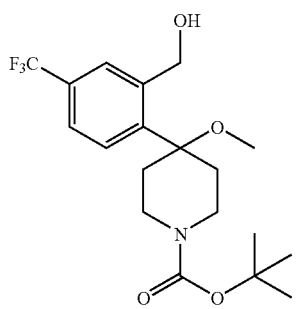

A solution of tert-butyl 4-(2-((tert-butyldimethylsilyloxy)methyl)-4-(trifluoromethyl)phenyl)-4-methoxypiperidine-1-carboxylate (540 mg; 1.07 mmol) and tetrabutylammonium fluoride (1.7 mL; 1.7 mmol; 1.0M in tetrahydrofuran) in tetrahydrofuran (6 mL) was stirred at room temperature for 2 hours. The solvent was evaporated under reduced pressure. The residue was purified by 40 g RediSep column (Teledyne Isco Inc., Lincoln Nebr.) (eluted with 10-90% ethyl acetate in heptane) to give 414 mg (99.2% yield) as a colorless gum. MS (ES+): Calc: 389.4, Found: 390.3 (M+H). $^1$H NMR (400 MHz, CDCl$_3$) δ ppm 7.92 (s, 1H), 7.53 (d, J=8.30 Hz, 1H), 7.36 (d, J=8.30 Hz, 1H), 5.04 (s, 2H), 4.02 (d, J=12.45 Hz, 2H), 3.19 (t, J=12.45 Hz, 2H), 3.00 (s, 3H), 2.39 (bs, 1H), 2.24 (d, J=14.11 Hz, 2H), 1.86 (dt, J13.28, 4.15, 4.56 Hz, 2H), 1.48 (s, 9H).

Preparation 37: tert-Butyl 4-(2-(bromomethyl)-4-(trifluoromethyl)phenyl)-4-methoxypiperidine-1-carboxylate

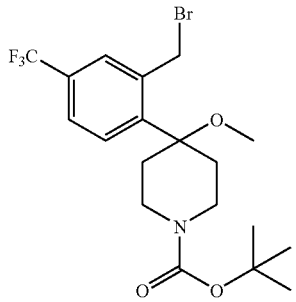

To a solution of tert-butyl 4-(2-(hydroxymethyl)-4-(trifluoromethyl)phenyl)-4-methoxypiperidine-1-carboxylate (410 mg, 1.05 mmol) in methylene chloride (7 mL) were added N-bromosuccinimide (342 mg; 1.92 mmol) and triphenylphosphine (516 mg; 1.96 mmol). The reaction was stirred at room temperature for 1 hour. The reaction was then purified over 40 g RediSep column (Teledyne Isco Inc. Lincoln Nebr.) (eluted with 5-30% ethyl acetate in heptane) to give 433 mg (90% yield) of a colorless oil. MS (ES+). Calc: 452.3 ($^{81}$Br), Found: 407.2 (M($^{81}$Br)—HCO$_2^-$). $^1$H NMR (400 MHz, CDCl$_3$) δ ppm 7.82 (d, J=1.66 Hz, 1H), 7.52 (dd, J=8.30, 1.66 Hz, 1H), 7.34, (d, J=8.30 Hz, 1H), 5.08 (s, 2H), 4.04 (d, J=12.86 Hz, 2H), 3.21 (t, J=12.86, 13.28 Hz, 2H), 3.02 (s, 3H), 2.26 (d, J=14.11 Hz, 2H), 1.86 (t, J=12.86, 14.11 Hz, 2H), 1.48 (s, 9H).

EXAMPLE 64 tert-butyl 4-(2-(((3,5-bis(trifluoromethyl benzyl)(2-methyl-2H-tetrazol-5-yl)amino)methyl)-4-(trifluoromethyl)phenyl)-4-methoxypiperidine-1-carboxylate

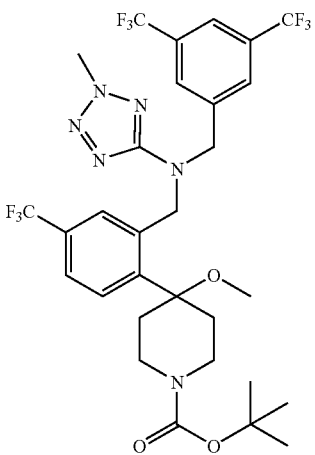

To a solution of N-(3,5-bis(trifluoromethyl)benzyl)-2-methyl-2H-tetrazol-5-amine (432 mg; 1.32 mmol)) in tetrahydrofuran (5.0 mL) was added dropwise 1.0M potassium t-butoxide in tetrahydrofuran (1.1 mL). The reaction was stirred for 5 minutes. A solution of tert-butyl 4-(2-(bromomethyl)-4-(trifluoromethyl)phenyl)-4-methoxypiperidine-1-carboxylate (432 mg; 0.955 mmol) in tetrahydrofuran (0.7 mL) was added dropwise to reaction. The reaction was stirred at room temperature. The reaction was quenched with water and extracted with ethyl acetate. The organic layer was washed with water and brine. It was then dried with sodium sulfate and concentrated under reduced pressure. The residue was purified over 40 g RediSep column (Teledyne Isco Inc., Lincoln Nebr.) (eluted with 10-50% ethyl acetate in heptane) to give 371 mg (55.8% yield) of a colorless gum. MS (ES+): Calc: 696.6, Found: 697.4 (M+H). $^1$H NMR (400 MHz, CDCl$_3$) δ ppm 7.79 (s, 1H), 7.73 (s, 2H), 7.51 (m, 2H), 7.37 (d, J=8.71 Hz, 1H), 5.10 (s, 2H), 4.81 (s, 2H), 4.20 (s, 3H), 4.0 (bs, 2H), 3.12 (bs, 2H), 2.95 (s, 3H), 2.12, (bs, 2H), 1.82 (bs, 2H), 1.47 (s, 9H).

EXAMPLE 65

N-(2-(4-methoxypiperidine-4-yl)-5-(trifluoromethyl)benzyl)-N-(3,5-bis(trifluoromethyl)benzyl)-2-methyl-2H-tetrazol-5-amine

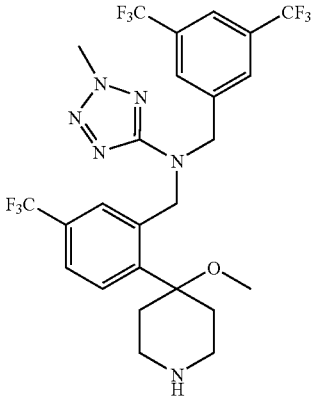

To a solution of tert-butyl 4-(2-(((3,5-bis(trifluoromethyl)benzyl)(2-methyl-2H-tetrazol-5-yl)amino)methyl)-4-(trifluoromethyl)phenyl)-4-methoxypiperidine-1-carboxylate (321 mg; 0.461 mmol) in 1,4-dioxane (2.5 mL) was added 4.0M hydrogen chloride in 1,4-dioxane (0.5 mL; 2 mmol). The reaction was stirred at room temperature for 2 hours. 4.0M hydrogen chloride in 1,4-dioxane (1.5 mL; 6 mmol) was added and stirred for 1 hour. 4.0M hydrogen chloride in 1,4-dioxane (1.5 mL; 6 mmol) was added and stirred for 1 hour. The solvent was evaporated under reduced pressure. Ethyl acetate was added to the residue and was concentrated under reduced pressure. Isopropyl ether was added and let sit for 16 hours. The solvent was evaporated under reduced pressure to give a white solid. The white solid was triturated with isopropyl ether and filtered off to give 254 mg (87.1% yield) of a white solid. MS (ES+): Calc: 596.4, Found: 597.4 (M+H). $^1$H NMR (400 MHz, CDCl$_3$) δ ppm 7.92 (s, 2H), 7.87 (s, 1H), 7.59 (d, J=8.30 Hz, 1H), 7.54 (d, J=7.88 Hz, 1H), 7.45 (s, 1H), 5.14 (s, 2H), 4.96 (s, 2H), 4.19 (s, 3H), 3.35 (m, 4H), 3.03 (s, 3H), 2.56 (d, J=12.86 Hz, 2H), 2.14 (m, 2H).

EXAMPLE 66

Methyl 4-(2-(((3,5-bis(trifluoromethyl)benzyl)(2-methyl-2H-tetrazol-5-yl)amino methyl)-4-(trifluoromethyl)phenyl)-4-methoxypiperidine-1-carboxylate

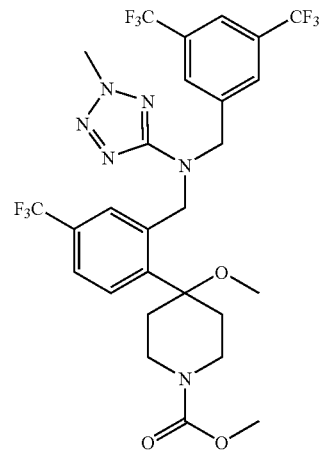

To a suspension of N-2-(4-methoxypiperidin-4-yl)-5-(trifluoromethyl)benzyl)-N-(3,5-bis(trifluoromethyl)benzyl)-2-methyl-2H-tetrazol-5-amine (31 mg; 0.049 mmol) in methylene chloride (0.5 mL) was added diisopropylethylamine (0.05 mL; 0.287 mmol). Methyl chloroformate (10 uL; 0.129 mmol) was then added. The resulting reaction was stirred at room temperature for 16 hours. The reaction was filtered over a column of silica/sodium sulfate and concentrated under reduced pressure. The residue was purified by 4 g RediSep column (Teledyne Isco Inc., Lincoln Nebr.) (5-80% ethyl acetate in heptane) to give 32 mg (100%) of a gum. MS (ES+): Calc: 654.5, Found: 655.5 (M+H). $^1$H NMR (400 MHz, CDCl$_3$) δ ppm 7.79 (s, 1H), 7.73 (s, 2H), 7.50 (d, J=7.05 Hz, 1H), 7.49 (s, 1H), 7.36 (d, J=8.71 Hz, 1H), 5.10 (s, 2H), 4.82

(s, 2H), 4.2 (s, 3H), 4.02 (bm, 2H), 3.71 (s, 3H), 3.17 (t, J=12.45, 12.03 Hz, 2H), 2.95 (s, 3H), 2.14 (m, 2H), 1.9-1.75 (m, 2H).

EXAMPLE 67

Ethyl 4-(2-(((3,5-bis(trifluoromethyl)benzyl)(2-methyl-2H-tetrazol-5-yl)amino)methyl)-4-(trifluoromethyl)phenyl)-4-methoxypiperidine-1-carboxylate

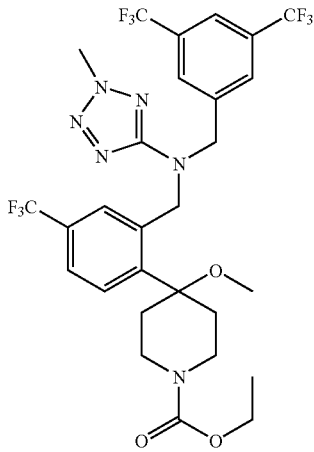

To a suspension of N-(2-(4-methoxypiperidin-4-yl)-5-(trifluoromethyl)benzyl)-N-(3,5-bis(trifluoromethyl)benzyl)-2-methyl-2H-tetrazol-5-amine (31 mg; 0.049 mmol) in methylene chloride (0.5 mL) was added diisopropylethylamine (0.05 mL; 0.287 mmol). Ethyl chloroformate (10uL; 0.104 mmol) was then added. The resulting reaction was stirred at room temperature for 16 hours. The reaction was filtered over a column of silica/sodium sulfate and concentrated under reduced pressure. The residue was purified by 4 g RediSep column (Teledyne Isco Inc., Lincoln Nebr.) (30-85% ethyl acetate in heptane) to give 32 mg (98%) of a gum. MS (ES+): Calc: 668.5, Found: 669.6 (M+H), $^1$H NMR (400 MHz, CDCl$_3$) δ ppm 7.79 (s, 1H), 7.73 (s, 2H), 7.51 (d, J=6.64 Hz, 1H), 7.50 (s, 1H), 7.36 (d, J=8.71 Hz, 1H), 5.10 (s, 2H), 4.82 (s, 2H), 4.2 (s, 3H), 4.14 (q, J=7.05, 2H), 4.02 (bm, 2H), 3.16 (t, J=12.45 Hz, 2H), 2.95 (s, 3H), 2.14 (m, 2H), 1.9-1.63 (m, 2H), 1.27 (t, J=7.05 Hz, 3H).

Preparation 38: 1-(2-((tert-butyldimethylsilyloxy)methyl)-4-(trifluoromethyl)phenyl)cyclohexanol

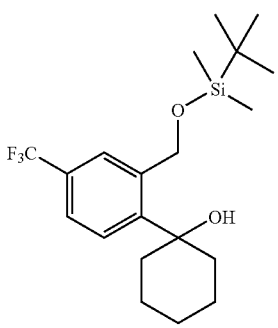

To a solution of (2-bromo-5-(trifluoromethyl)benzyloxy)(tert-butyl)dimethylsilane (140 mg; 0.379 mmol) in tetrahydrofuran (0.5 mL) at −78° C. was added dropwise n-butyllithium (0.4 mL; 0.64 mmol; 1.6M in hexanes). The reaction was stirred at −78° C. for 15 minutes. Cyclohexanone (0.8 mL; 7.7 mmol) was added stirred at −78° C. for 10 minutes. The reaction was then stirred at room temperature for 15 minutes. The reaction was quenched with 2 drops of water. It was diluted with ethyl acetate and filtered through a column containing silica gel and sodium sulfate. The crude was then purified over a 12 g RediSep column (Teledyne Isco Inc., Lincoln Nebr.) (eluted with 10-40% ethyl acetate in heptane) to give 112 mg (76%) as a liquid. MS (ES+): Calc: 388.5, Found: 433.2 (M+HCO$_2$$^−$) $^1$H NMR (400 MHz, CDCl$_3$) δ ppm 7.58 (s, 1H), 7.51 (d, J=8.30 Hz, 1H), 7.45 (d, J=8.30 Hz, 1H), 5.05 (s, 2H), 3.92 (s, 1H), 1.94-1.73 (m, 6H), 1.68-1.6 (m, 2H), 1.31 (m, 2H), 0.93 (s, 9H), 0.12 (s, 6H).

Preparation 39: (2-(1-methoxycyclohexyl)-5-(trifluoromethyl)benzyloxy)(tert-butyl)dimethylsilane

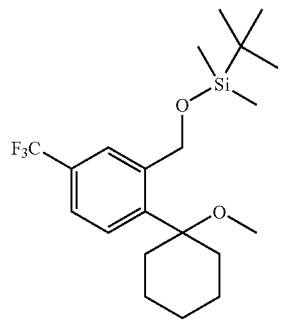

To a solution of 1-(2-((tert-butyldimethylsilyloxy)methyl)-4-(trifluoromethyl)phenyl)cyclohexanol (108 mg; 0.278 mmol) in tetrahydrofuran (2 mL) at 0° C. was added sodium hydride (22 mg; 0.55 mmol). The reaction was stirred at 0° C. for 30 minutes. Then iodomethane (50 uL; 0.80 mmol) was added. The reaction was stirred at 0° C. for 30 minutes and then at room temperature for 16 hours. More iodomethane (20 uL; 0.32 mmol) was added and stirred for 4 hours. The reaction was quenched with water and extracted with ethyl acetate. The organic layer was washed with water, dried over sodium sulfate, and concentrated under reduced pressure. The crude was purified over a 4 g RediSep column (Teledyne Isco Inc., Lincoln Nebr.) (eluted with 5-15% ethyl acetate in heptane) to give 63 mg (55%) the title compound as a colorless oil. MS-GC (EI): Calc: 402.5, Found: 383 (M−F). $^1$H NMR (400 MHz, CDCl$_3$) δ ppm 7.51 (d, J=7.88 Hz, 1H), 7.46 (d, J=7.47

Hz, 1H), 7.35 (d, J=8.30 Hz, 1H), 5.05 (s, 2H), 2.94 (s, 3H), 2.16 (d, J=12.45 Hz, 2H), 1.8-1.56 (m, 8H), 0.98 (s, 9H), 0.13 (s, 6H).

Preparation 40: (2-(1-methoxycyclohexyl)-5-(trifluoromethyl)phenyl)methanol

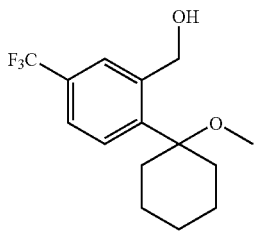

A solution of (2-(1-methoxycyclohexyl)-5-(trifluoromethyl)benzyloxy)(tert-butyl)dimethylsilane (61 mg, 0.15 mmol) and tetrabutylammonium fluoride (0.2 mL; 0.2 mmol; 1.0M in tetrahydrofuran) was stirred in tetrahydrofuran (1 mL). The reaction was stirred at room temperature for 3 hours. The solvent was evaporated under reduced pressure. The residue was purified by 4 g RediSep column (Teledyne Isco inc., Lincoln Nebr.) (eluted with 10-40% ethyl acetate in heptane) to give 30 mg (69% yield) of a colorless gum. MS-GC (EI): Calc: 288.3, Found: 288 (M). $^1$H NMR (400 MHz, CDCl$_3$) δ ppm 7.87 (s, 1H), 7.50 (d, J=8.30 Hz, 1H), 7.41 (d, J=8.30 Hz, 1H), 5.03 (s, 2H), 2.99 (s, 3H), 2.24 (d, J=13.28 Hz, 2H), 1.8-1.57 (m, 7H), 1.28 (m, 1H).

Preparation 41: 2-(bromomethyl)-1-(1-methoxycyclohexyl)-4-(trifluoromethyl)benzene

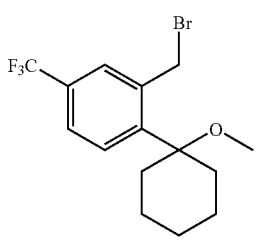

To a solution of (2-(1-methoxycyclohexyl)-5-(trifluoromethyl)phenyl)methanol (27 mg; 0.094 mmol) in methylene chloride (1 mL) was added N-bromosuccinimide (28 mg; 0.157 mmol) followed by triphenylphosphine (40 mg; 0.152 mmol). The reaction was stirred at room temperature for 4 hours. The reaction was directly loaded onto silica and purified over 4 g RediSep column (Teledyne Isco Inc., Lincoln Nebr.) (eluted with 5-40% ethyl acetate in heptane) to give 26 mg (79%) of a gum. MS-GC (EI): Calc: 351.2, Found; 352 (M+H). $^1$H NMR (400 MHz, CDCl$_3$) δ ppm 7.81 (d, J=1.66 Hz, 1H), 7.48 (td, J=8.30, 1.66 Hz, 1H), 7.39 (d, J=8.30 Hz, 1H), 5.12 (s, 2H), 3.00 (s, 3H), 2.25 (d, J=12.45 Hz, 2H), 1.84-1.71 (m, 3H), 1.65 (m, 4H), 1.27(m, 1H).

EXAMPLE 68

N-(2-(1-methoxycyclohexyl)-5-(trifluoromethyl)benzyl)-N-(3,5-bis(trifluoromethyl)benzyl)-2-methyl-2H-tetrazol-5-amine

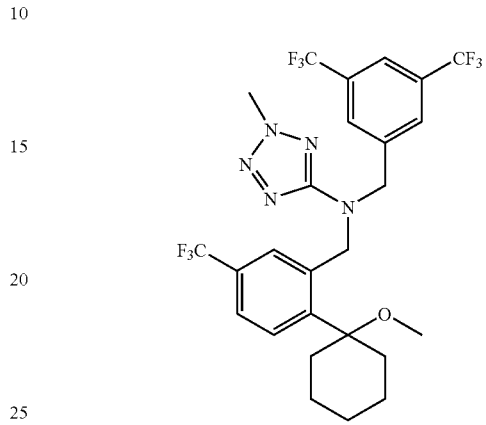

To a solution of N-(3,5-bis(trifluoromethyl)benzyl)-2-methyl-2H-tetrazol-5-amine (26 mg; 0.079 mmol) in tetrahydrofuran (0.3 mL) was added potassium t-butoxide (80 uL; 0.08 mmol; 1.0M in tetrahydrofuran). A solution of 2-(bromomethyl)-1-(1-methoxycyclohexyl)-4-(trifluoromethyl)benzene (25 mg; 0.071 mmol) in tetrahydrofuran (0.2 mL) was added. The reaction was stirred at room temperature for 3 hours. The reaction was quenched with 2 drops of water. The mixture was diluted with ethyl acetate and filtered through a column containing silica and sodium sulfate and concentrated. The residue was purified by 4 g RediSep column (Teledyne Isco Inc., Lincoln Nebr.) (eluted with 10-45% ethyl acetate in heptane) to give 25 mg (59%) of a colorless gum. MS (ES+): Calc: 595.5, Found: 596 (M+H). $^1$H NMR (400 MHz, CDCl$_3$) δ ppm 7.77 (s, 1H), 7.73 (s, 2H), 7.48 (d, J=7.47 Hz, 2H), 7.42 (d, J=8.30 Hz, 1H), 5.14 (s, 2H), 4.79 (s, 2H), 4.20 (s, 3H), 2.92 (s, 3H), 2.12 (d, J=11.62 Hz, 2H), 1.77-1.52(m, 8H).

Preparation 42: 2-(((3,5-bis(triflouromethyl)benzyl)(2-methyl-2H-tetrazol-5-yl)amino)methyl)-4-(trifluoromethyl)benzonitrile

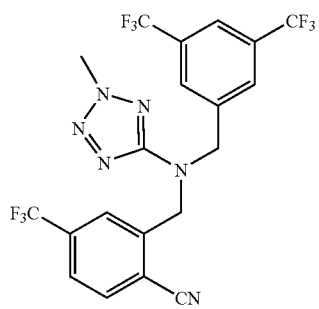

A mixture of N-(2-bromo-5-(trifluoromethyl)benzyl)-N-(3,5-bis(trifluoromethyl)benzyl)-2-methyl-2H-tetrazol-5-amine (10.4 g; 18.5 mmol), potassium hexacyanoferrate trihydrate (1.9 G; 4.49 mmol) and sodium carbonate (2.4 g; 22.6 mmol) was stirred in N,N-dimethylacetamide (32 mL). Palladium acetate was added (0.48 g; 2.13 mmol). The reaction was stirred at 120° C. for 16 hours. The reaction was diluted with diethyl ether and filtered over a pad of silica gel and celite. The mother liquor was washed with water (3×) and brine. It was dried over sodium sulfate and concentrated under reduced pressure. The crude was purified over a 330 g RediSep column (Teledyne Isco Inc., Lincoln Nebr.) (eluted with 10-30% ethyl acetate in heptane) to give 8.45 g (89.9%) of title compound as a tan solid. MS (ES+): Calc: 508.3, Found: 509.2 (M+H). $^1$H NMR (400 MHz, CDCl$_3$) δ ppm 7.76 (s, 1H), 7.75 (d, J=8.30 Hz, 1H), 7.68 (s, 3H), 7.62 (dd, J=8.30 Hz, 1H), 4.96 (s, 2H), 4.89 (s, 2H), 4.22 (s, 3H).

EXAMPLE 69

N-(2-(methoxy(1-methylcyclohexyl)methyl)-5-(trifluoromethyl)benzyl)-N-(3,5-bis(trifluoromethyl)benzyl)-2-methyl-2H-tetrazol-5-amine

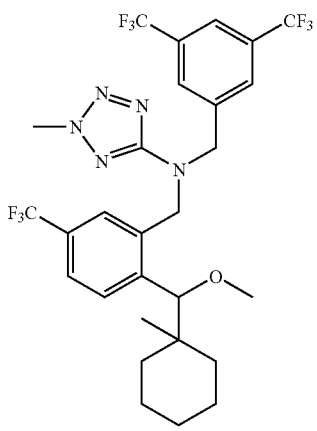

Step A: 2-bromo-5-(trifluoromethyl)benzyl-1-methylcyclohexanecarboxylate

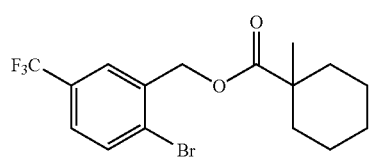

To a mixture of 1-bromo-2-(bromomethyl)-4-(trifluoromethyl)benzene (Preparation 3, 0.97 g, 3.05 mmol) and 1-methylcyclohexanecarboxylic acid (0.512 g, 3.6 mmol) in N,N-dimethylformamide (5 mL) was added cesium carbonate (1.96 g, 6 mmol) and sodium iodide (90 mg, 0.6 mmol). The mixture was heated at 60° C. for 5 hours, diluted with water and extracted with dichloromethane (3×). The combined organic layers were dried over sodium sulfate and concentrated to dryness under vacuum. The residue was purified by flash chromatography on a 40 g RediSep column (Teledyne Isco Inc., Lincoln Nebr.) (eluted with 0-30% ethyl acetate in heptane) to yield the title compound as a yellow oil (0.65 g). $^1$H NMR (400 MHz, CDCl$_3$) δ 7.71 (d, J=8.3 Hz, 1H), 7.65 (d, J=1.2 Hz, 1H), 7.45 (dd, J=8.3, 1.2 Hz, 1H), 5.23 (s, 2H), 2.10 (m, 2H), 1.64-1.48 (m, 2H), 1.46-1.21 (m, 6H), 1.24 (s, 3H). GC-MS (EI) Calc: 380 ($^{81}$Br), Found: 380 ($^{81}$Br)

Step B: 1-(1-methylcyclohexyl)-5-(trifluoromethyl)-1,3-dihydroisobenzofuran-1-ol and (2-(hydroxymethyl)-4-(trifluoromethyl)phenyl)(1-methylcyclohexyl)methanone

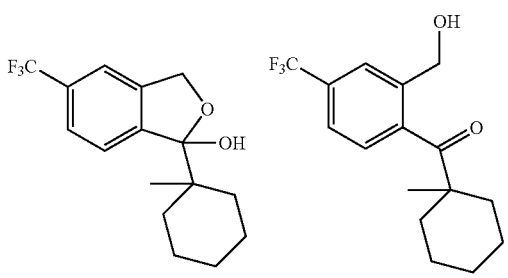

To a solution of 2-bromo-5-(trifluoromethyl)benzyl 1-methylcyclohexanecarboxylate (0.432 g, 1.14 mmol) in tetrahydrofuran (5 mL) under N$_2$ at −98° C. was slowly added s-butyllithium (1.4M in cyclohexane, 1.37 mmol, 0.98 mL). After stirring at −98° C. for 90 minutes the mixture was warmed to −78° C. for 10 minutes then allowed to warm to 0° C. The mixture was then immediately poured into an aqueous ammonium chloride solution and extracted with dichloromethane (3×). The combined organic layers were dried over sodium sulfate and concentrated to dryness under vacuum. The residue was purified by flash chromatography on a 40 g RediSep column (Teledyne Isco Inc., Lincoln Nebr.) (eluted with 0-30% ethyl acetate in heptane) to yield a white solid which in deuterochloroform solution existed as a mixture of the title compounds in a ratio of approximately 12:1 respectively. $^1$H NMR (400 MHz, CDCl$_3$)(major component) δ 7.61 (d, J=8.3 Hz, 1H), 7.58 (d, J=8.3 Hz, 1H), 7.50 (s, 1H), 5.18 (d, J=13.1 Hz, 1H), 5.03 (d, J=13.1 Hz, 1H), 2.77 (s, 1H), 1.7-1.49 (m, 6H), 1.49-1.31 (m, 4H), 1.08 (s, 3H). GC-MS (EI) Calc: 300, Found: 300

Step C: (2-((tert-butyldimethylsilyloxy)methyl)-4-(trifluoromethyl)phenyl)(1-methylcyclohexyl)methanol

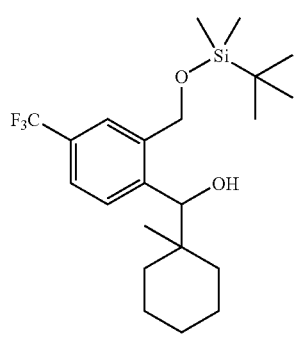

The product from Step B (0.343 g, 1.14 mmol) was dissolved in ethanol (10 mL) and sodium borohydride (50 mg, 1.32 mmol) was added in one portion. The mixture was stirred at room temperature for 2 hours then a second aliquot of sodium borohydride (50 mg, 1.32 mmol) was added. After 30 minutes acetone was added to destroy excess reducing agent, the solvent was evaporated to dryness, dilute sodium bicarbonate solution was added and the mixture extracted with dichloromethane (3×). The combined organic layers were dried over sodium sulfate and concentrated to dryness under vacuum to give a white solid. This was dissolved in anhydrous N,N-dimethylformamide (3 mL) and tert-butyldimethylchlorosilane (0.345 mg, 2.29 mmol) and imidazole (0.156 mg, 2.28 mmol) were added. The mixture was stirred at room temperature for 16 hours, diluted with water containing a little hydrochloric acid to give an acidic solution and the mixture extracted with dichloromethane (3×). The combined organic layers were dried over sodium sulfate and concentrated to dryness under vacuum. The residue was purified by flash chromatography on a 40 g RediSep column (Teledyne Isco Inc., Lincoln Nebr.) (eluted with 0-20% ethyl acetate in heptane) to yield the title compound as a colorless viscous oil (0.38 g). $^1$H NMR (400 MHz, CDCl$_3$) δ 7.78 (br s, 1H), 7.61 (d, J=8.3 Hz, 1H), 7.51 (br d, J=8.3 Hz, 1H), 4.90(d, J=13.4 Hz, 1H), 4.76(d, J=13.4 Hz, 1H), 4.63(d, J=2.9 Hz, 1H), 1.96 (d, J=2.9 Hz, 1H), 1.68-1.08 (m, 10H), 0.95 (s, 9H), 0.95 (s, 3H), 0.13 (s, 3H), 0.12 (s, 3H). MS (ES$^-$) Calc: 416.59, Found: 461.5 (M+HCO$_2^-$).

Step D: (2-(methoxy(1-methylcyclohexyl)methyl)-5-(trifluoromethyl)phenyl)methanol

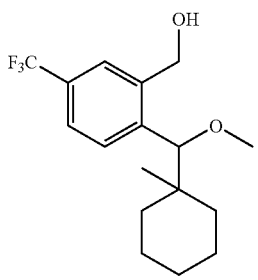

To a solution of the Step C product (0.38 g, 0.787 mmol) in anhydrous tetrahydrofuran (3 mL) was added sodium hydride (60% dispersion in mineral oil, 47 mg, 1.18 mmol). The mixture was stirred at room temperature for 10 minutes then iodomethane (1.574 mmol, 0.097 mL) was added. After 60 hours the mixture was diluted with water and extracted with heptane (3×). The combined organic layers were dried over sodium sulfate, concentrated to dryness under vacuum, the residue dissolved in toluene and concentrated to dryness under high vacuum. The residue was dissolved in anhydrous tetrahydrofuran (4 mL) under nitrogen and a solution of tetrabutylammonium fluoride in tetrahydrofuran (1M, 1.5 mL, 1.5 mmol) was added at room temperature. After 90 minutes the mixture was diluted with water and extracted with dichloromethane (3×). The combined organic layers were dried over sodium sulfate, concentrated to dryness under vacuum, the residue dissolved in xylenes and concentrated to dryness under high vacuum to give the title compound as an oil (0.218 g) $^1$H NMR (400 MHz, CDCl$_3$) δ 7.77 (s, 1H), 7.55 (s, 1H), 7.55 (s, 1H), 4.97 (dd, J=13.3, 5.4 Hz, 1H), 4.73 (dd, J=13.3, 3.5 Hz, 1H), 4.15 (s, 1H), 3.15 (s, 3H), 1.78 (m, 1H), 1.68- 1.21 (m, 8H), 1.2-1.02 (m, 2H), 0.90 (s, 3H). MS (ES$^-$) Calc: 316.17, Found: 361.3 (M+HCO$_2^-$).

Step E: N-(2-(methoxy(1-methylcyclohexyl)methyl)-5-(trifluoromethyl)benzyl)-N-3,5-bis(trifluoromethyl)benzyl)-2-methyl-2H-tetrazol-5-amine

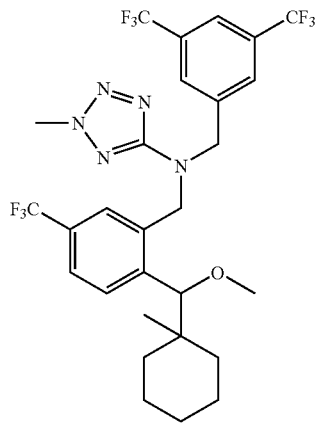

To a mixture of the Step D product (210 mg, 0.665 mmol) and tetrabromomethane (231 mg, 0.7 mmol) in anhydrous dichloromethane (5 mL) under N2 at 0° C. was added powdered triphenylphosphine (192 mg, 0.73 mmol). After 90 minutes further aliquots of tetrabromomethane (23 mg, 0.07 mmol) and powdered triphenylphosphine (19 mg, 0.073 mmol) were added and the mixture stirred for 6 hours. The solvent was then removed under vacuum and the residue was purified by flash chromatography on a 12 g RediSep column (Teledyne Isco Inc., Lincoln Nebr.) (eluted with 0-50% ethyl acetate in heptane) to give 2-(bromomethyl)-1-(methoxy(1-methylcyclohexyl)methyl)-4-(trifluoromethyl)benzene (194 mg). To N-(3,5-bis(trifluoromethyl)benzyl)-2-methyl-2H-tetrazol-5-amine (Preparation 5, 216 mg, 0.66 mmol) was added sodium hydride (60% dispersion in mineral oil, 40 mg, 1 mmol), the air in the flask was replaced by nitrogen and anhydrous N,N-dimethylformamide (4 mL) was added. Hydrogen was evolved briskly and a yellow solution formed, darkening to orange-brown over 1 hour. A solution of 2-(bromomethyl)-1-(methoxy(1-methylcyclohexyl)methyl)-4-(trifluoromethyl) benzene (194 mg, 0.51 mmol) in anhydrous N,N-dimethylformamide (2×1 mL) was added. The mixture was stirred at room temperature for 16 hours, diluted with water containing lithium chloride and a little hydrochloric acid to give an acidic solution and the mixture extracted with dichloromethane (3×). The combined organic layers were dried over sodium sulfate and concentrated to dryness under vacuum. The residue was purified by flash chromatography on a 12 g RediSep column (Teledyne Isco Inc., Lincoln Nebr.) (eluted with 0-60% ethyl acetate in heptane) to yield the title compound as a colorless viscous oil (0.24 g). $^1$H NMR (400 MHz, CDCl$_3$) δ7.79 (s, 1H), 7.65 (s, 2h), 7.65-7.51 (m, 2H), 7.37 (s, 1H), 5.06 (d, J=16 Hz, 1H), 4.79 (d, J=16.3 Hz, 1H), 4.61 (d, J=16.3 Hz, 1H), 4.61-4.51 (m, 1H), 4.22 (s, 3H), 4.10 (s, 1H), 2.98 (s, 3H), 1.65-1.56 (m, 1H), 1.56-1.18 (m, 7H), 1.17-0.98 (m, 2H), 0.88 (s, 3H)

MS (ES$^{30}$) Calc: 623.56, Found: 624.5 (M+H$^+$). .

EXAMPLE 70

(3,5-Bis-trifluoromethyl-benzyl)-[2-(2-cyclopentyl-1-methoxy-ethyl)-5-trifluoromethyl-benzyl]-(2-methyl-2H-tetrazol-5yl)-amine

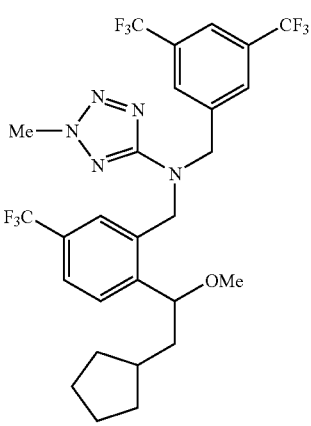

Step A: 1-(2-(((3,5-Bis(trifluoromethyl)benzyl)(2-methyl-2-H-tetrazol-5-yl)amino)methyl)-4-(trifluoromethyl)phenyl-2-cyclopentylethanone

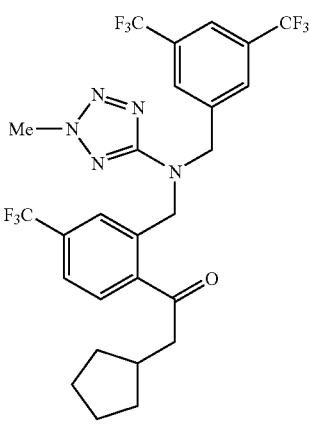

(Cyclopentylmethyl) magnesium bromide was prepared by the reaction of magnesium mesh (2.61 mol, 63.5 mg) with (bromomethyl)cyclopentane (2.61 mmol, 426 mg, added portionwise until the reaction initiated) in diethyl ether (1 mL). This solution was added by syringe to a solution of 2-((3,5-bis(trifluoromethyl)benzyl)(2-methyl-2H-tetrazole-5-yl)amino)methyl)-4-(trifluoromethyl)benzonitrile (0.653 mmol, 332 mg) in toluene (10 mL) contained in a Smith microwave vial under nitrogen. The microwave vial was heated at 65° C. in a Biotage microwave for 45 minutes. The mixture was poured into 25 mL of 2 N hydrochloric acid and 50 mL of ethyl acetate and stirred at room temperature for 16 hours. The aqueous layer was extracted with ethyl acetate (2×25 mL), the combined organic layer was dried with anhydrous sodium sulfate and concentrated under reduced pressure to give a yellow oil (160 mg). The residue was purified by flash chromatography on a 12 g RediSep column (Teledyne Isco Inc., Lincoln Nebr.) (eluted with 0-50% ethyl acetate in heptane) to yield the title compound as a yellow oil (0.185 gm, 48%). $^1$H NMR (400 MHz, CDCl$_3$) δ 7.69 (s, 1H) 7.67 (d, J=7.5 Hz, 1H) 7.62 (s, 2H) 7.54 (d, J=7.8 Hz 1H) 7.52 (s, 1H) 4.89 (s, 2H) 4.78 (s, 2H) 4.14 (s, 3H) 2.86 (d, J=7.1 Hz, 2H) 2.25-2.21 (m, 1H) 1.82-1.76 (m, 2H) 1.6-1.57 (m, 2H) 1.31-1.30 (m, 2H) 1.1-1.03 (m, 2H). LC-MS calc. 593.4, found 594.5 (M+H)

Step B: 1-(2-(((3,5-bis(trifluoromethyl)benzyl)(2-methyl-2H-tetrazol-5-yl)amino)methyl)-4-(trifluoromethyl)phenyl)-2-cyclopentylethanol

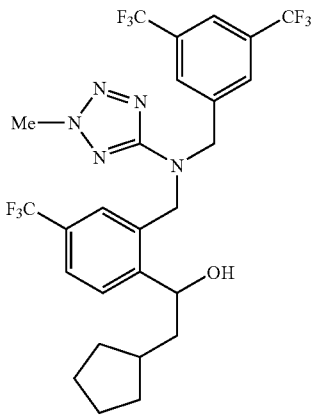

To a solution of 1-(2-(((3,5-bis(trifluoromethyl)benzyl)(2-methyl-2-H-tetrazol-5-yl)amino)methyl)-4-(trifluoromethyl)phenyl)-2-cyclopentylethanone (123 mg, 0.207 mmol) in methanol (15 mL) was added sodium borohydride (7.8 mg, 0.207 mmol) at room temperature. After 1 hour the solvent was removed under reduced pressure, the residue dissolved in 20 mL of ethyl acetate (20 mL) and washed with water (10 mL). The combined organics were dried with anhydrous sodium sulfate and concentrated to dryness under reduced pressure. The residue was dissolved in dichloromethane and purified by flash chromatography on a 4 g RediSep column (Teledyne Isco Inc., Lincoln Nebr.) (eluted with 0-60% ethyl acetate in heptane) to yield the title compound as a clear oil (0.025 gm). $^1$H NMR (400 MHz, CDCl$_3$) δ 7.76 (s, 1H) 7.62 (s, 2H) 7.56(d, J=7.8 Hz, 1H) 7.34 (s, 1H) 4.96-4.92 (m, 1H) 4.85 (s, 2H) 4.81 (q, J=15.3 Hz, J=16.1 Hz, 2H) 4.2 (s, 3H) 1.9-1.4 (m, 11H).

LC-MS calc. 595.5, found 596.5 (M+H).

Step C: (3,5-Bis-trifluoromethyl-benzyl)-[2-(2-cyclopentyl-1-methoxy-ethyl)-5-trifluoromethyl-benzyl]-(2-methyl-2H-tetrazol-5-yl)-amine

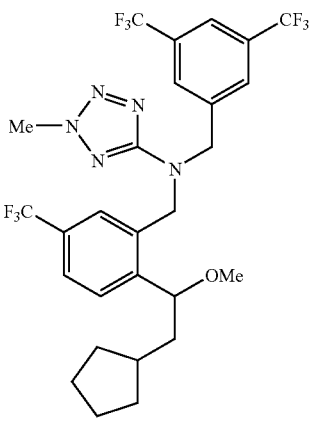

1-(2-(((3,5-bis(trifluoromethyl)benzyl)(2-methyl-2H-tetrazol-5-yl)amino)methyl)-4-(trifluoromethyl)phenyl)-2-cyclopentylethanol was converted to the methyl ether with methyl iodide using a procedure analogous to that used for the preparation of N-(2-(cyclohexyl(methoxy)methyl)-5-trifluoromethyl)benzyl)-N-(3,5-bis(trifluoromethyl)benzyl)-2-methyl-2H-tetrazol-5-amine. LC-MS Calc. 609.5, found 610.5 (M+H).

Examples 71-73 were prepared by an analogous series of reactions from 2-((3,5-bis(trifluoromethyl)benzyl)(2-methyl-2H-tetrazole-5-yl)amino)methyl)-4-(trifluoromethyl) benzonitrile using the appropriate Grignard reagent and alkylating agent

| Example # | Chemical Name | Structure | MS Calc | MS Found M + 1 |
|---|---|---|---|---|
| 71 | N-(2-(2-cyclopentyl-1-ethoxyethyl)-5-(trifluoromethyl)benzyl)-N-(3,5-bis(trifluoromethyl)benzyl)-2-methyl-2H-tetrazol-5-amine | 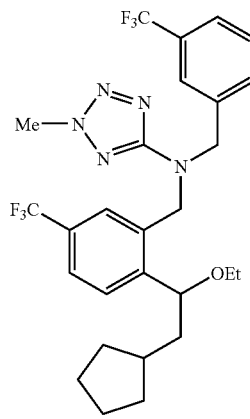 | 623.5 | 624.6 |
| 72* | N-(2-(2-ethyl-1-methoxybutyl)-5-(trifluoromethyl)benzyl)-N-(3,5-bis(trifluoromethyl)benzyl)-2-methyl-2H-tetrazol-5-amine | 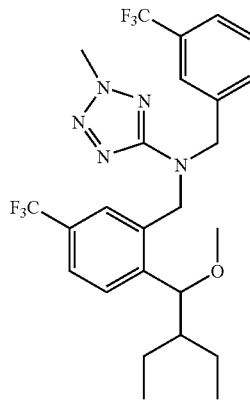 | 597.5 | 598.5 |

| Example # | Chemical Name | Structure | MS Calc | MS Found M + 1 |
|---|---|---|---|---|
| 73 | N-(2-(1-ethoxy-2-ethylbutyl)-5-(trifluoromethyl)benzyl)-N-(3,5-bis(trifluoromethyl)benzyl)-2-methyl-2H-tetrazol-5-amine | 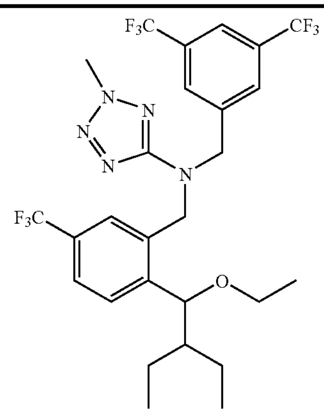 | 611.5 | 612.5 |

* For Example 72: $^1$H NMR (400 MHz, CDCl$_3$) δ ppm 7.79 (s, 1H), 7.67 (s, 2H), 7.57 (dd, J=1.24, 8.3 Hz, 1H), 7.53 (d, J=8.3, 1H), 7.38 (s, 1H), 4.85 (d, J=16.18 Hz, 1H), 4.73 (d, J=16.18 Hz, 1H), 4.74 (s, 2H), 4.28 (d, J=6.22, 1H), 4.22 (s, 3H), 3.08 (s, 3H), 1.5-1.34 (m, 3H), 1.23 (m, 1H), 1.11 (m, 1H), 0.75 (t, J=7.47, 3H), 0.74 (t, J=7.47 Hz, 3H).

EXAMPLE 74

N-(2-(1-Cyclopentyl-2-methoxypropan-2-yl)-5-(trifluoromethyl)benzyl)-N-(3,5-bis (trifluoromethyl)benzyl)-2-methyl-2H-tetrazol-5-amine

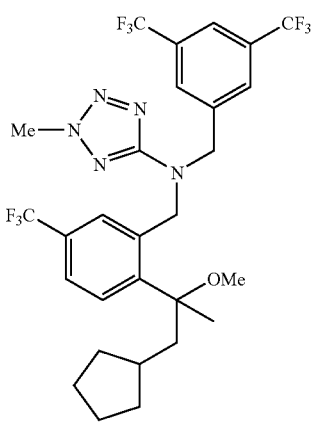

Step A: 2-(2-(((3,5-Bis(trifluoromethyl)benzyl)(2-methyl-2H-tetrazol-5-yl)amino)methyl)-4-(trifluoromethyl)phenyl)-1-cyclopentylpropan-2-ol

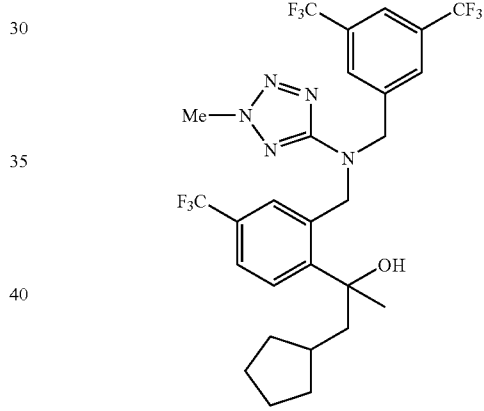

To a solution of 1,-(2-(((3,5-bis(trifluoromethyl)benzyl)(2-methyl-2-H-tetrazol-5-yl)amino)methyl)-4-(trifluoromethyl)phenyl-2-cyclopentylethanone (160 mg, 0.269 mmol) in anhydrous THF (10 mL) at 0° C. was added methylmagnesium bromide (3.0 M solution in THF, 0.359 mL, 1.07 mmol). After stirring for 30 minutes the solution was warmed to room temp and stirred for 1.5 hours. After 1.5 hours solution was portioned between 2 N HCL (10 mL) and ethyl acetate (20 mL). The mixture was stirred at room temperature for 10 minutes before the layers were separated. The aqueous layer was extracted with ethyl acetate (3×15 mL). The combined organics layers were dried with anhydrous sodium sulfate, filtered, and concentrated under reduced pressure to give a yellow oil. (160 mg, 97%). $^1$H NMR (400 MHz, CDCl$_3$) δ 7.72 (s, 1H) 7.67(s, 2H) 7.38 (m, 3H) 5.32 (d, J=16.6 Hz, 1H) 5.01 (d, J=16.6 Hz, 1H) 4.78 (s, 2H) 4.13 (s, 3H) 1.92 (dd, J=5.4 Hz, J=5.4 Hz) 1.80 (dd, J=5.81 Hz, J=6.24 Hz) 1.64 (m, 2H) 1.59 (s, 3H) 1.54 (m, 3H) 1.35 (m, 2H) 0.88 (m, 2H). LC-MS Calc. 609.5, found 610.5 (M+H).

Step B: N-(2-(1-Cyclopentyl-2-methoxypropan-2-yl)-5-(trifluoromethyl)benzyl)-N-(3,5-bis(trifluoromethyl) benzyl)-2-methyl-2H-tetrazol-5-amine

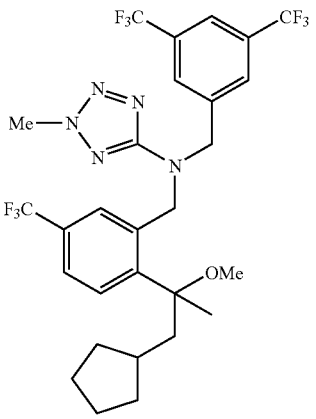

To a solution of N-(2-(1-cyclopentyl-2-methoxypropan-2-yl)-5-(trifluoromethyl)benzyl)-N-(3,5-bis(trifluoromethyl)benzyl)-2-methyl-2H-tetrazol-5-amine (20 mg, 0.032 mmol) in anhydrous THF (3 mL) at room temperature was added sodium bishexamethyldisilylamide (1.0 M solution in THF, 0082 mmol, 0.082 mL). After 10 minutes methyl iodide (0.164 mmol, 23 mg) was added and the solution was stirred at room temperature for 72 hours. The mixture was diluted with water, extracted with ethyl acetate (3×15 mL), the combined organic layers were dried with anhydrous sodium sulfate and concentrated under reduced pressure to give a yellow oil (40 mg). The residue was purified by flash chromatography on a 4 g RediSep column (Teledyne Isco Inc., Lincoln Nebr.) (eluted with 0-40% ethyl acetate in heptane) to yield the title compound as a clear oil (0.015 gm, 73%). $^1$H NMR (400 MHz, CDCl$_3$) δ 7.76 (s, 1H) 7.62 (s, 2H) 7.58 (s, 2H) 7.34 (s, 1H) 4.8 (s, 2H) 4.71 (s, 2H) 4.34 (dd, J=3.5 Hz, J=9.1 Hz, 1H) 4.21 (s, 3H) 3.1 (s, 3H) 1.91 (m, 1H) 1.75 (m, 2H) 1.52 (m, 4H) 1.21 (m, 2H) 1.0 (m, 1H) 0.84 (m, 1H). LC-MS calc 623.5, found 624.5 (M+1).

EXAMPLE 75

N-(2-(1-Cycloheptyl-1-methoxyethyl)-5-(trifluoromethyl)benzyl)-N-(3,5-bis(trifluoromethyl)benzyl)-2-methyl-2H-tetrazol-5-amine

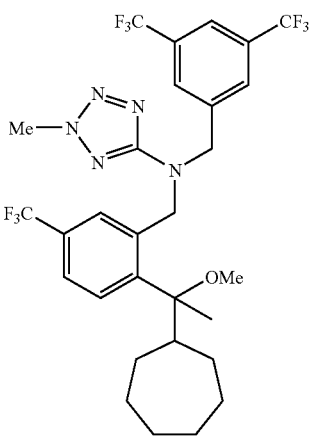

This compound was prepared by an analogous series of reactions to that used for the preparation of N-(2-(1-cyclopentyl-2-methoxypropan-2-yl)-5-(trifluoromethyl)benzyl)-N-(3,5-bis(trifluoromethyl)benzyl)-2-methyl-2H-tetrazol-5-amine from 2-((3,5-bis(trifluoromethyl)benzyl)(2-methyl-2H-tetrazole-5-yl)amino)methyl)-4-(trifluoromethyl)benzonitrile by the addition of cycloheptylmagnesium bromide followed by methylmagnesium bromide then alkylation with methyl iodide LC-MS calc 637.5, found 606 (M-OCH$_3$).

EXAMPLE 76

N-(2-(1-Cyclohexyl-1-methoxypropyl)-5-(trifluoromethyl)benzyl)-N-(3,5-bis(trifluoromethyl)benzyl)-2-methyl-2H-tetrazol-5-amine

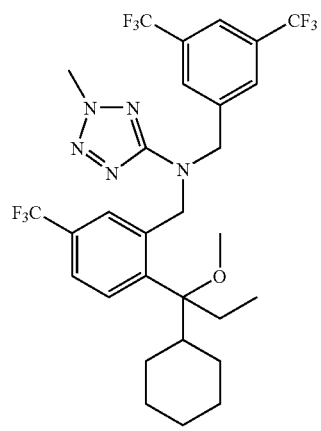

This compound was prepared by an analogous series of reactions to that used for the preparation of N-(2-(1-cyclopentyl-2-methoxypropan-2-yl)-5-(trifluoromethyl)benzyl)-N-(3,5-bis(trifluoromethyl)benzyl)-2-methyl-2H-tetrazol-5-amine from 2-((3,5-bis(trifluoromethyl)benzyl)(2-methyl-2H-tetrazole-5-yl)amino)methyl)-4-(trifluoromethyl)benzonitrile by the addition of cyclohexylmagnesium bromide followed by ethylmagnesium bromide then alkylation with methyl iodide. LC-MS calc 637.5, found 638.5 (M+H).

Preparation 43: 4,4-Dimethylcyclohexanone

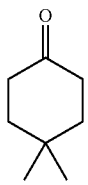

4,4-Dimethylcyclohexanone was prepared by a procedure similar to that described in patent ref: PCT Int. Appl. 2005005456 20, January 2005. 4,4-Dimethylcyclohex-2-enone (3.5 g, 28.18 mmol) was dissolved in ethyl acetate (50 mL). The solution was shaken for 45 minutes under an atmosphere of hydrogen (10 p.s.i.). The completion of the reaction was established by GC-MS then the solution was filtered through a pad of celite and rinsed through with ethyl acetate. The solvent was removed under reduced pressure to give a clear colorless oil which crystallized on standing (3.45 gm, 97%). $^1$H NMR (400 MHz, CDCl$_3$) δ 2.29 (m, 4H) 1.61 (m, 4H) 1.04 (s, 6H). MS calc 126.5, found 127.1 (M+H).

Preparation 44: 2-(Bromomethyl)-1-(1-methoxycyclopentyl)-4-(trifluoromethyl)benzene

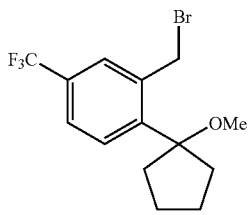

To a solution of (2-(1-methoxycyclopentyl)-5-(trifluoromethyl)phenyl)methanol (10 mg, 0.036 mmol) in anhydrous dichloromethane (5 mL) was added carbon tetrabromide (14.5 mg, 0.043 mmol) followed by triphenylphosphine (11.47 mg, 0.043 mmol). The mixture was stirred at room temperature for 72 hours then the solvent was removed under reduced pressure. The residue was diluted with dichloromethane and hexanes, placed on 1 g of silica gel (Bakerbond spe disposable extraction columns, Mallinkrodt Baker Inc. Phillipsburg, N.J.) and eluted with hexanes to give the title compound (12 mg, 97.6%). $^1$H NMR (400 MHz, CDCl$_3$) δ 7.78 (s, 1H) 7.46 (d, J=9.1 Hz, 1H) 7.40 (d, J=8.3 Hz, 1H) 4.97 (s, 2H) 2.94 (s, 3H) 2.30 (m, 2H) 2.0 (m, 2H) 1.85 (m, 2H) 1.74 (m, 2H).

GC-MS (EI) calc 337, found 337.

Preparation 45: 4-(2 (Bromomethyl)-4-(trifluoromethyl)phenyl-4-methoxycyclohexanecarbonitrile

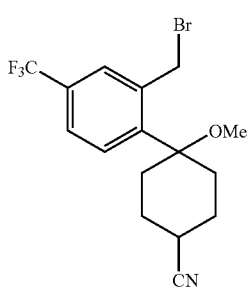

This compound was prepared from 4-cyanocyclohexanone and (2-bromo-5-(trifluoromethyl)benzyloxy) (tert-butyl) dimethylsilane in a sequence of steps analogous to the preparation of tert-butyl 4-(2-(bromomethyl)-4-trifluoromethyl)phenyl)-4-methoxypiperidine-1-carboxylate.

EXAMPLE 77

4-(2-(((3,5-Bis(trifluoromethyl)benzyl)(2-methyl-2H-tetrazol-5-yl)amino)methyl)-4-(trifluoromethyl)phenyl)-4-methoxycyclohexanecarbonitrile

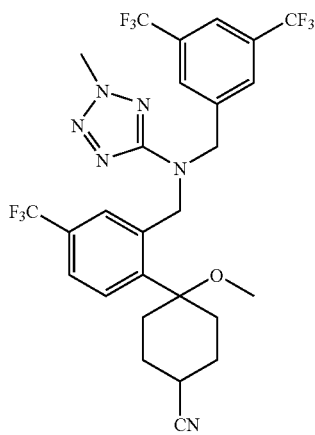

To a solution of N-(3,5-bis(trifluoromethyl)benzyl)-2-methyl-2H-tetrazole-5-amine (285 mg, 0.877 mmol) in anhydrous THF (5 mL) was added sodium hydride (60% dispersion in mineral oil, 105 mg, 2.63 mol) and the mixture was stirred for 5 minutes then a solution of 4-(2 (bromomethyl)-4-(trifluoromethyl)phenyl)-4-methoxycyclohexanecarbonitrile (330 mg, 0.877 mmol) in anhydrous THF (5 mL) was added. A further aliquot of sodium hydride (52 mg, 1.3 mmol) was added. The solution was stirred at room temperature for 72 hours. Water and 2 N HCl (5 mL) were added and the mixture was extracted with ethyl acetate (3×20 mL). The combined organics were dried with anhydrous sodium sulfate and concentrated under reduced pressure to give a yellow oil (0.65 gm). This material was initially purified by flash chromatography on a 40 g RediSep column (Teledyne Isco Inc., Lincoln Nebr.) (eluted with 5-75% ethyl acetate in heptane) and finally purified on 1 mm silica gel rotor (Chromatotron, Harrison Research) (eluted with 20-70% dichloromethane in heptane) to yield the title compound as a colorless foam (134 mg, 24.6%). $^1$H NMR (400 MHz, CDCl$_3$) δ 7.74 (s, H) 7.67(s, 2H) 7.44 (d, J=5.81 Hz, 2H) 7.29 (d, J=8.72 Hz, 1H) 5.01 (s, 2H) 4.76 (s, 2H) 4.15 (s, 3H) 2.87(s, 3H) 2.43(m, 1H) 2.20(d, J=12.45 Hz, 2H) 1.99(m, 2H) 1.55(m, 4H). LC-MS calc. 620, found 621.5 (M+H)

EXAMPLE 78

N-(2-(1-methoxycyclopentyl)-5-(trifluoromethyl)benzyl)-N-(3,5-bis(trifluoromethyl)benzyl)-2-methyl-2H-tetrazol-5-amine

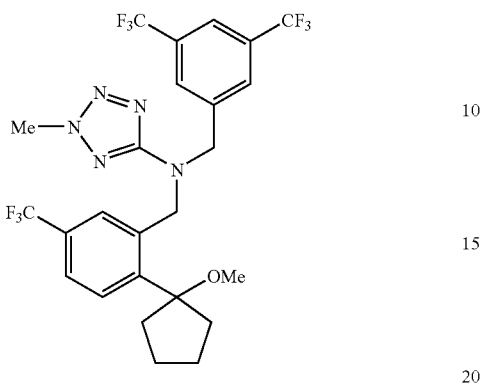

The title compound was prepared from 2-(bromomethyl)-1-(1-methoxycyclopentyl)-4-(trifluoromethyl) benzene in a analogous manner to that described above. LC-MS (ES+) calc. 581.4, found 582.4 (M+H).

Examples 79-30 were prepared by an analogous sequence of reactions starting from (2-bromo-5-(trifluoromethyl)benzyloxy)(tert-butyl)dimethylsilane and the appropriate cyclic ketone.

| Example # | Chemical Name | Structure | MS Calc | MS Found M + 1 |
|---|---|---|---|---|
| 79 | N-(2-(1-methoxy-4,4-dimethylcyclohexyl)-5-(trifluoromethyl)benzyl)-N-(3,5-bis(trifluoromethyl)benzyl)-2-methyl-2H-tetrazol-5-amine | 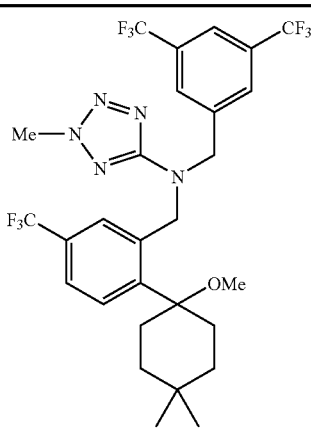 | 623.5 | 624.5 |
| 80 | methyl 4-(2-(((3,5-bis(trifluoromethyl)benzyl)(2-methyl-2H-tetrazol-5-yl)amino)methyl)-4-(trifluoromethyl)phenyl)-4-methoxycyclohexanecarboxylate | 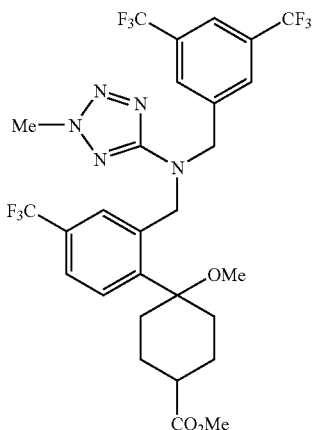 | 653.5 | 654.5 |

Preparation 46: N-(2-(1-methoxycycloheptyl)-5-(trifluoromethyl)benzyl)-N-(3,5-bis(trifluoromethyl)benzyl)-2-(2-(tert-butyldimethylsilyloxy)ethyl)-2H-tetrazol-5-amine

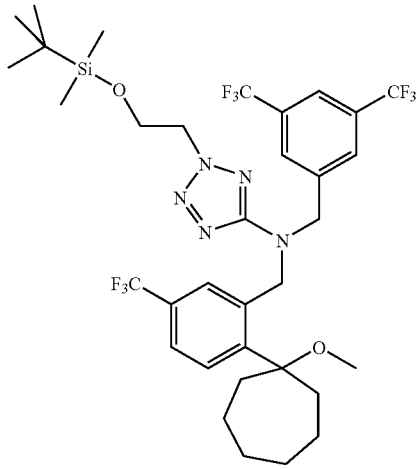

To a solution of N-(2-(1-methoxycycloheptyl)-5-(trifluoromethyl)benzyl)-N-(3,5-bis(trifluoromethyl)benzyl)-2-methyl-2H-tetrazol-5-amine (51 mg; 0.086 mmol) in 2-methyltetrahydrofuran (1.0 mL) was added sodium carbonate (38 mg; 0.358 mmol), N,N-dimethylformamide (0.4 mL) and (2-bromoethoxy)-tert-butyldimethylsilane (100 mg; 0.418 mmol). Reaction was stirred for 16 hours at 60° C. The reaction was diluted with ethyl acetate, washed twice with water and then brine. The organic was dried over sodium sulfate and concentrated in vacuo. The residue was purified by 4 g RediSep column (Teledyne Isco Inc., Lincoln Nebr.) (eluted with 5-35% ethyl acetate in heptane) to give 45 mg (70% yield) of a colorless gum. $^1$H NMR (400 MHz CDCl$_3$) δ ppm 7.77 (s, 1H), 7.73 (s, 2H), 7.47 (d, J=9.96 Hz, 2H), 7.41 (d, J=8.30 Hz, 1H), 5.11 (s, 2H), 4.80 (s, 2H), 4.55 (t, J=5.39 Hz 2H), 4.08 (t, J=5.39 Hz, 2H), 2.94 (s, 3H), 2.12 (m, 2H), 1.98 (m, 2H), 1.8-1.45 (m, 8H), 0.82 (s, 9H), −0.07 (s, 6H).

EXAMPLE 81

2-(5-((2-(1-methoxycycloheptyl)-5-(trifluoromethyl)benzyl)(3,5-bis(trifluoromethyl)benzyl)amino)-2H-tetrazol-2-yl)ethanol

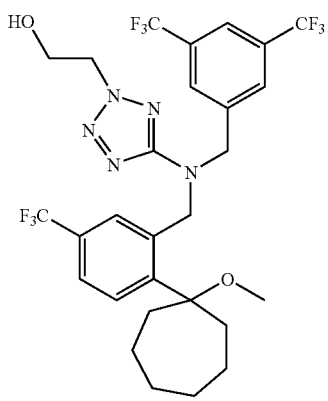

To a solution of N-(2-(1-methoxycycloheptyl)-5-(trifluoromethyl)benzyl)-N-(3,5-bis(trifluoromethyl)benzyl)-2-(2-(tert-butyldimethylsilyloxy)ethyl)-2H-tetrazol-5-amine (42 mg, 0.056 mmol) in 2-methyltetrahydrofuran (1.5 mL) was added tetrabutylammonium fluoride (0.1 mL; 0.1 mmol; 1.0M in tetrahydrofuran). Reaction was stirred at room temperature for 1.5 hours. The reaction was concentrated in vacuo. The residue was purified by 4 g RediSep column (Teledyne Isco Inc., Lincoln Nebr.) (eluted with 10-40% ethyl acetate in heptane) to give 34 mg (95% yield) of a gum. MS (ES+): Calc: 639.5, Found: 640.5 (M+H). $^1$H NMR (400 MHz, CDCl$_3$) δ ppm 7.78 (s, 1H), 7.74 (s, 2H), 7.45 (m, 3H), 5.10 (s, 2H), 4.81 (s, 2H), 4.61 (t, J=4.98 Hz, 2H), 4.11 (q, J=6.22, 5.8 Hz 1, 2H), 2.94 (s, 3H), 2.44 (t, J=6.64, 6.22 Hz, 1H), 2.11 (m, 2H), 2.19 (m, 2H), 1.82-1.45(m, 8H).

Preparation 47: (3,5-Bis-trifluoromethyl-benzyl)-(2-bromo-5-trifluoromethyl-benzyl)-(2-methyl-2H-tetrazol-5-yl)-amine

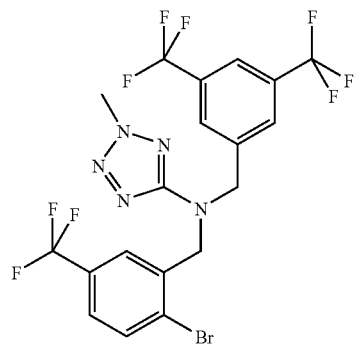

Step A: Preparation of 2:
2-Bromo-5-trifluoromethyl-benzylamine methanesulfonic acid salt

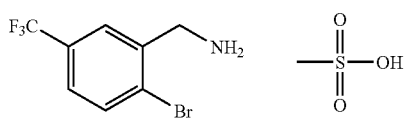

Sodium borohydride (NaBH$_4$) (225 g, 5.96 mol) was charged to a 22 L flask followed by THF (6.8 L, anhyd). The mixture was cooled in an ice-water bath. Trifluoroacetic acid (TFA) (518 ml) was added to THF (1.4 L) and this solution was also cooled in an ice-water bath. The TFA solution was added to the NaBH$_4$ suspension over 2.5 hours. The ice-water bath was removed and the resulting mixture was stirred at ambient temperature for 2 hours. 2-Bromo-5-trifluoromethyl-benzonitrile (678 g, 2.71 mol) was dissolved in THF (1.2 L). The TFA/NaBH$_4$ mixture was again cooled in an ice-water bath and the nitrile solution was added over 1.5 hours. The mixture was allowed to reach ambient temperature while stirring for 16 hours. LC analysis of an aliquot revealed complete reaction. The mixture was cooled in an ice bath and methanol (2 L) was added over 1 hour. Volatiles were removed in vacuo and ethylacetate (4 L) was added. This mixture was washed with water (3 L) containing sodium-potassium tartarate (1 Kg). The aqueous layer was washed with ethylacetate (2 L) and the combined organics were washed with brine (2 L), dried over sodium sulfate, filtered, and concentrated. The residue was dissolved in THF (3 L) and cooled in an icewater bath. Methanesulfonic acid (195 ml) was added and the mixture was stirred for 2 hours. The resulting solid was filtered and dried in vacuo (676 g, 71% yield). $^1$H-NMR (CD$_3$OD) δ 7.92 (d, 8.3 Hz, 1H), 7.87 (s, 1H), 7.65 (d, 8.3 Hz, 1H), 4.34 (s, 2H), 2.66 (s, 3H). Mass Spec (ESI): M+1=255.9

Step B: Preparation of (3,5-Bis-trifluoromethyl-benzyl)-(2-bromo-5-trifluoromethyl-benzyl)-amine

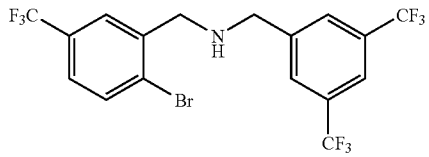

To the product from step A (640 g in methyl-tert-butyl-ether (4.3 L) was added 1N sodium hydroxide (3.4 L). The mixture was stirred until 2 clear layers formed. The organics were washed with brine, dried over sodium sulfate, filtered, and concentrated to the free amine (460 g). The free amine (460 g, 1.81 mol) was taken into 1,1-dichloroethene (4.3 L) and 3,5-bis(trifluoromethyl)benzaldehyde (438 g, 1.81 mol) was added. The mixture was cooled in an ice-water bath and NaBH(CH$_3$CO$_2$)$_3$ (767 g, 3.62 mol) was added. The mixture was stirred for 16 hours at which point LC analysis revealed complete reaction. Saturated aq potassium carbonate was added until pH 8 was reached. Added water (1 L) and filtered undissolved salts. The layers were separated and the aqueous layer was washed with 1,1-dichloroethene (2 L). The combined organics were washed with brine, dried over sodium sulfate, filtered, and concentrated (880 g product, >95% yield). $^1$H-NMR of HCl salt (CD$_3$OD) δ 8.23 (s, 2H), 8.09 (s, 1H), 7.98 (s, 1H), 7.93 (d, 8.3 Hz, 1H), 7.67 (d, 8.3 Hz, 1H) 4.61 (s, 2H), 4.56 (s, 2H). Mass Spec (ESI): M+1=480.1

Step C: Preparation of (2-bromo-5-(trifluoromethyl) benzyl)(3,5-bis(trifluoromethyl)benzyl)cyanamide

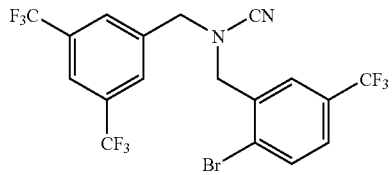

To the product of step B (873 g, 1.82 mol) in ethanol (4.6 L) was added sodium acetate (452 g, 5.46 mol). The resulting mixture was stirred for 20 minutes and then cyanogen bromide (386 g, 3.64 mol) was added. This mixture was stirred for 2 hours at which point the reaction was complete as evidenced by LC analysis. Water (4 L) was added and volatiles were removed in vacuo. Toluene (4 L) was added and the mixture was stirred until 2 clear layers formed. The layers were separated and the aqueous layer was washed with toluene (2 L). The combined organics were washed with brine (1 L), dried over sodium sulfate, filtered, and concentrated (910 g yield). $^1$H-NMR (CDCl$_3$) δ 7.83 (s, 1H), 7.71 (m, 3H), 7.54 (d, 1.7 Hz, 1H), 7.46 (dd, 2.1 Hz, 8.3 Hz, 1H), 4.38 (s, 2H), 4.34 (s, 2H). Mass Spec (ESI): M+1=505.0

Step D: Preparation of N-(2-bromo-5-(trifluoromethyl)benzyl)-N-(3,5-bis(trifluoromethyl)benzyl)-2H-tetrazol-5-amine

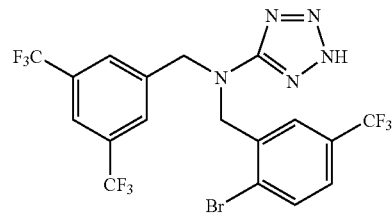

To the product of step C (909 g, 1.80 mol) in methyl tert-butyl ether (9 L) was added triethylamine (2.5 L, 18 mol) followed by trimethylsilylazide (415 g, 3.60 mol). The resulting mixture was heated to 50° C. for 8 hours. An aliquot was checked by HPLC and starting material was still present. The mixture was cooled and trimethylsilylazide (50 g) was added. The mixture was again heated to 50° C. and stirred 3 hours. After cooling, 1N sodium hydroxide (9 L) was added. The layers were separated (added 150 ml ethanol to facilitate separation). The organics were washed with aqueous 10% citric acid solution (8 L, then 2 L) until washings were acidic. The organics were dried over sodium sulfate, filtered, and concentrated. The resulting solid turned white upon standing (976 g, 99% yield). $^1$H-NMR (CD$_3$OD) δ 7.47 (m, 3H), 7.64 (d, 8.3 Hz, 1H), 7.44 (d, 2.1 Hz, 1H), 7.38 (dd, 2.1 Hz, 8.3 Hz, 1H), 4.88 (s, 2H), 4.86 (s, 2H). Mass Spec (ESI): M+1=548.0

Step E: Preparation of N-(2-bromo-5-(trifluoromethyl)benzyl)-N-(3,5-bis(trifluoromethyl)benzyl)-2-methyl-2H-tetrazol-5-amine

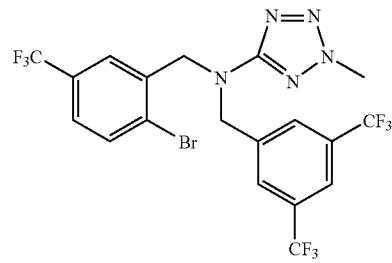

To the product of step D (500 g, 0.912 mol) in 2-methyl THF (9 L) was added sodium carbonate (386 g, 3.65 mol), dimethylformamide (4 L), and dimethyl sulfate (156 ml, 1.7 eq). The resulting mixture was heated to 50° C. for 16 hours at which point LC analysis revealed completion. After cooling, water (9 L) was added and the layers were separated. The organic layer was washed with concentrated ammonium hydroxide (6.5 L). Brine was added to facilitate layer separation. The organic layer was dried over sodium sulfate, filtered, and concentrated. The residue was heated in hexanes and filtered hot to obtain a white solid (229 g). The mother liquor was combined with the mother liquor from another batch (460 g tetrazole) and purified on a Biotage® 150M system (Uppsala, Sweden) (eluted with 5-10% ethyl acetate in hexanes). The title compound was isolated as a white solid (729 g, 74% yield). $^1$H-NMR (CDCl$_3$) δ 7.71 (s, 1H), 7.62 (m, 3H), 7.41 (d, 1.7 Hz, 1H), 7.34 (dd, 2.1 Hz, 8.3 Hz, 1H), 4.80 (s, 2H), 4.78 (s, 2H), 4.18 (s, 3H). Mass Spec (ESI): M+1=562.0

Preparation 48: (3,5-Bis-trifluoromethyl-benzyl)-(2-chloro-5-trifluoromethyl-benzyl)-(2-methyl-2H-tetrazol-5-yl)-amine

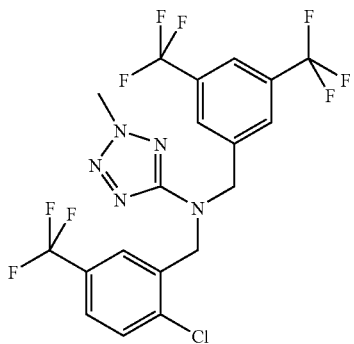

Step A: N-(3,5-bis(trifluoromethyl)benzylidene)(2-chloro-5-(trifluoromethyl)phenyl)methanamine To a 100 mL round bottom flask, equipped with a Dean Start Trap was charged 50 mL of toluene, 5.0 gm of 2-chloro-5-trifluoromethyl benzyl amine and 5.8 gm of 3,5-bis(trifluoromethyl)benzaldehyde and 50 mg of para-toluenesulfonamide. The reaction was heated until water no longer distilled off about 3 hours, then cooled to ambient temperature and the solvent removed in vacuum. The crude product was used directly in the next step without further purification. 10.0 gm.

Step B: N-(2-chloro-5-(trifluoromethyl)benzyl)(3,5-bis(trifluoromethyl)phenyl)methanamine To a solution of the compound from step A in ethanol was added 4 gm of sodium borohydride and the reaction was allowed to stir overnight at ambient temperature. The reaction was quenched with 50 mL of methanol diluted with 100 mL of water and 100 mL of methyl tert-butyl ether. The layers were separated and the organic layer dried over magnesium sulfate, filtered and concentrated to an oil. 10 gm of desired amine was collected which was used in the next step without further purification. $^1$H NMR (400 MHz, CDCl$_3$) 7.84 (s, 2H), 7.77 (s, 1H), 7.66 (s, 1H), 7.48 (s, 2H), 7.47 (s, 4H), $^{13}$C NMR (400 MHz, CDCl$_3$) δ 142.6, 183.3, 130.4, 128.4, 127.1, 127.0, 125.6, 121.4, 52.4.

Step C: (2-chloro-5-(trifluoromethyl)benzyl)(3,5-bis(trifluoromethyl)benzyl)cyanamide To the mixture of the compound from Step B (10 gm), 5.6 gm of sodium acetate 100 mL of ethanol was added over 15 minutes 15.5 mL of cyanogen bromide 3M in dichloromethane. The reaction mixture was stirred at ambient temperature until reaction completion. When the reaction was judged complete, it was diluted with 200 mL of toluene and 200 mL of sodium hydroxide. The layers were separated and the organic layer dried with magnesium sulfate, filtered and concentrated to an oil. 7.8 gm (74% yield). The product was used in the next step without further purification. $^1$H NMR (400 MHz, CDCl$_3$) 7.84 (s, 2H), 7.56 (s, 3H), 7.66 (m, 4H), 7.48 (s, 2H), 4.39 (s, 2H), 4.36 (s, 2H)

Step D: N-(2-chloro-5-(trifluoromethyl)benzyl)-N-(3,5-bis(trifluoromethyl)benzyl)-1H-tetrazol-5-amine A solution of 5 gm of the compound from Step C, 50 mL of 2-methyl THF 5 mL, triethanolamine and 2.5 mL of trimethyl silyl azide was heated at 50° C. until reaction completion. When the reaction was judged complete, the reaction mixture was cooled and 50 mL of 1 N sodium hydroxide added, The layers were separated and the organic layer washed with 50 mL of 10% citric acid. The organic layer was concentrated and triturated with hexane to yield 4.6 of the desired compound. 85% yield. $^1$H NMR (400 MHz, CDCl$_3$) 7.84 (s, 2H), 7.74 (m, 3H), 4.90 (s, 4H)C, H, N, Calculated, (found) 42.92 (42.98), 2.20 (1.97), 13.90 (13.54)

Step E: N-(2-chloro-5-(trifluoromethyl)benzyl)-N-(3,5-bis(trifluoromethyl)benzyl)-2-methyl-2H-tetrazol-5-amine To a suspension of the compound from step D 2.5 gm, 2.0 gm of sodium carbonate, 50 mL of 2-methyl THF and 2.5 mL of DMF was added 1.0 gm of dimethyl sulfate. The reaction mixture was heated at 40° C. until reaction was judged complete. When the reaction was judged complete the reaction mixture was cooled to room temperature and 12.4 mL of 5% ammonium hydroxide added. The mixture was allowed to stir for 30 minutes at ambient temperature. The organic layer was removed, dried over magnesium sulfate, filtered and concentrated to an oil to recover 2.2 gm of the desired methylated tetrazole. 88% yield. $^1$H NMR (400 MHz, CDCl$_3$) 7.70 (s, 1H), 7.64 (s, 2H), 7.25 (s, 1H), 7.24 (2, 2H), 4.21, (s, 2H), 4.20 (s, 2H). C, H, N Calculated (found) 44.07 (44.10) 2.53 (2.13), 13.53 (13.41)

Preparation 49: 5-Amino-2-methyl 2H-tetrazole

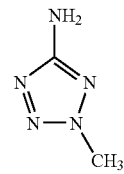

Step A: Dibenzylcyanamide

To a dry 2 L round bottom flask, equipped with an overhead stirrer, charged: sodium acetate (120 gm), 1 dibenzyl amine (100 gm) and 600 mL of ethanol. To this suspension at room temperature, was added a 3 M solution of cyanogen bromide in methylene chloride over 30 minutes (340 mL). The suspension was allowed to stir at ambient temperature until reaction completion was observed via HPLC. The reaction mixture was diluted with 1 L of toluene and 1 N sodium hydroxide was added over 15 minutes. The reaction mixture was stirred for 1 hour and the layers separated. The organic layer was dried over sodium sulfate, filtered, and concentrated to an oil that solidified upon standing. Recrystallization from a 1:1 2 L mixture of IPE/Heptanes gave 101 g (89%) of product. $^1$H NMR (400 MHz, CD$_3$OD) 7.42-7.15 (m, 10H), 1.31 (s, 4H).

$^{13}$C NMR (400 MHz, CD$_3$OD) δ 135.1, 128.8, 128.7, 128.5, 118.0, 54.6. C, H, N Calculated (found) 81.05 (80.71), 6.35 (6.52), 12.60 (12.65)

Step B: N,N-dibenzyl-1H-tetrazol-5-amine

Product from step A (50 g) was dissolved in 500 mL of toluene and 150 mL of triethyl amine and trimethyl silyl azide (60 mL) were added dropwise over 15 minutes. The reaction mixture was heated to 50° C. and held at this temperature until the reaction was complete as noted by HPLC. After cooling to room temperature, 500 mL of 1 M sodium hydroxide and 500 mL of methylene chloride were added. The biphasic solution was stirred for 1 hour and the layers separated. The lower organic layer was concentrated and redissolved in ethyl acetate. The ethyl acetate layer was then treated with 200 mL of 10% citric acid and stirred for 30-60 minutes. The layers were separated and the product layer was dried over sodium sulfate, filtered, and concentrated to an oil. The oil was crystallized from IPE to give 46 gm, (77%) of product. $^1$H NMR (400 MHz, CDCl$_3$) 7.38-7.24 (m, 10H), 4.60 (s, 4H). $^{13}$C NMR (400 MHz, CDCl$_3$) δ 159.2, 136.3, 129.1, 128.4, 55.0. C, H, N Calculated (found) 67.90 (67.73), 5.70 (5.53), 26.40 (26.01)

Step C: N,N-dibenzyl-2-methyl-2H-tetrazol-5-amine

Product from Step B (25 g) was dissolved in 250 mL of 2-methyl THF and 25 mL of DMF. To this was added sodium carbonate (40 gm) and dimethyl sulfate (18 mL) over 15 minutes. The reaction mixture was heated to 45° C. and held at this temperature until the reaction was complete as noted by HPLC. After cooling to room temperature, 250 mL of 5% ammonium chloride was added and the biphasic solution was allowed to stir for at least 30 minutes. The layers were then separated, dried over sodium sulfate, filtered, and concentrated to an oil. (26 gm) HPLC analysis of the oil showed a 9:1 mixture of 2-methyl to 1-methyl regioisomers. The two isomers were separated by flash chromatography, eluting with 9:1 Hexane/EtOAc, to provide 21.2 gm (77%) of the desired 2-methyl derivative, N,N-dibenzyl-2-methyl-2H-tetrazol-5-amine. $^1$H NMR (400 MHz, CDCl3) 7.34-7.22 (m, 10H), 4.61 (s, 4H). $^{13}$C NMR (400 MHz, CDCl$_3$) δ 159.2, 136.3, 129.1, 128.4, 55.0 $^1$H NMR (400 MHz, CDCl3) 7.34-7.22 (m, 4H), 4.15 (s, 3H) $^{13}$C NMR (400 MHz, CDCl$_3$) δ 170, 137.6, 128.7, 128.2, 127.6, 51.3, 39.6 and 1.6 g (10%) of the 1-methyl derivative N,N-Dibenzyl-1-methyl-1H-tetrazol-5-amine. Recrystallization by slow evaporation from diethyl ether provided good X-ray quality crystals. $^1$H NMR (400 MHz, CDCl$_3$) 7.34-7.22 (m, 10H), 4.47 (s, 4H), 3.74 (s 3H) $^{13}$C NMR (400 MHz, CDCl$_3$) δ 159.2, 136.3, 129.1, 128.4, 55.0

Step D: 2-methyl-2H-tetrazol-5-amine

To a clean stainless steel reactor added palladium hydroxide (1 g), 10 gm of N,N-dibenzyl-2-methyl-2H-tetrazol-5-amine from Step C (10 g) and ethanol (100 mL). The reaction was charged with hydrogen and heated to 50° C. and the pressure was maintained at 50 psi hydrogen for 16 hours. When the uptake of hydrogen had ceased, the reaction was purged with nitrogen and the catalyst removed by filtration. The pad was washed with 25 mL of ethanol and combined with the filtrate and concentrated to an off white solid to give 2.7 gm (73%) of product. An analytical sample was prepared by recrystallization from isopropanol. $^1$H NMR (400 MHz, DMSO-d$_6$) 5.94 (s 2H), 4.03 (s 3H) $^{13}$C NMR (400 MHz, DMSO-d$_6$ δ 167.8, 40.52, C, H, N Calculated (found) 68.79 (68.54), 6.13 (6.41), 25.07 (24.83)

Alternatively, employing a mixture of regioisomers: to a clean stainless steel reactor added palladium hydroxide (1.4 g), 14 g of a 9:1 mixture of N,N-dibenzyl-2-methyl-2H-tetrazol-5-amine and N,N-Dibenzyl-1-methyl-1H-tetrazol-5-amine from Step C, and ethanol (140 mL). The reaction was charged with hydrogen and heated to 50° C. and the pressure was maintained at 50 psi hydrogen for 16 hours. When the uptake of hydrogen ceased the reaction was purged with nitrogen and the catalyst removed via filtration. The pad was washed with 50 mL of ethanol and combined with the filtrate and concentrated to an off white solid to give 5.1 gm (quantitative mixture of 1-methyl-2H-tetrazol-5-amine and 2-methyl-2H-tetrazol-5-amine). The crude reaction mixture was taken up in methylene chloride and the undesired isomer filtered away. The methylene chloride layer was displaced with isopropanol to give 3.8 gm of the desired product.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound selected from the group consisting of:
    (3,5-Bis-trifluoromethyl-benzyl)-[2-(cyclohexyl-methoxy-methyl)-5-trifluoromethyl-benzyl]-(2-methyl-2H-tetrazol-5-yl)-amine;
    (R)-(3,5-Bis-trifluoromethyl-benzyl)-[2-(cyclohexyl-methoxy-methyl)-5-trifluoromethyl-benzyl]-(2-methyl-2H-tetrazol-5-yl)-amine;
    (S)-(3,5-Bis-trifluoromethyl-benzyl)-[2-(cyclohexyl-methoxy-methyl)-5-trifluoromethyl-benzyl]-(2-methyl-2H-tetrazol-5-yl)-amine;
    (3,5-Bis-trifluoromethyl-benzyl)-{2-[methoxy-(1-methyl-piperidin-4-yl)-methyl]-5-trifluoromethyl-benzyl}-(2-methyl-2H-tetrazol-5-yl)-amine;
    (R)-(3,5-Bis-trifluoromethyl-benzyl)-{2-[methoxy-(1-methyl-piperidin-4-yl)-methyl]-5-trifluoromethyl-benzyl}-(2-methyl-2H-tetrazol-5-yl)-amine;
    (S)-(3,5-Bis-trifluoromethyl-benzyl)-{2-[methoxy-(1-methyl-piperidin-4-yl)-methyl]-5-trifluoromethyl-benzyl}-(2-methyl-2H-tetrazol-5-yl)-amine;
    (3,5-Bis-trifluoromethyl-benzyl)-[2-(1-methoxy-propyl)-5-trifluoromethyl-benzyl]-(2-methyl-2H-tetrazol-5-yl)-amine;
    (R)-(3,5-Bis-trifluoromethyl-benzyl)-[2-(1-methoxy-propyl)-5-trifluoromethyl-benzyl]-(2-methyl-2H-tetrazol-5-yl)-amine;
    (S)-(3,5-Bis-trifluoromethyl-benzyl)-[2-(1-methoxy-propyl)-5-trifluoromethyl-benzyl]-(2-methyl-2H-tetrazol-5-yl)-amine;
    [2-(1-Benzyloxy-propyl)-5-trifluoromethyl-benzyl]-(3,5-bis-trifluoromethyl-benzyl)-(2-methyl-2H-tetrazol-5-yl)-amine;
    (R)-[2-(1-Benzyloxy-propyl)-5-trifluoromethyl-benzyl]-(3,5-bis-trifluoromethyl-benzyl)-(2-methyl-2H-tetrazol-5-yl)-amine;

(S)-[2-(1-Benzyloxy-propyl)-5-trifluoromethyl-benzyl]-(3,5-bis-trifluoromethyl-benzyl)-(2-methyl-2H-tetrazol-5-yl)-amine;
(3,5-Bis-trifluoromethyl-benzyl)-[2-(cyclopropyl-methoxy-methyl)-5-trifluoromethyl-benzyl]-(2-methyl-2H-tetrazol-5-yl)-amine;
(R)-(3,5-Bis-trifluoromethyl-benzyl)-[2-(cyclopropyl-methoxy-methyl)-5-trifluoromethyl-benzyl]-(2-methyl-2H-tetrazol-5-yl)-amine;
(S)-(3,5-Bis-trifluoromethyl-benzyl)-[2-(cyclopropyl-methoxy-methyl)-5-trifluoromethyl-benzyl]-(2-methyl-2H-tetrazol-5-yl)-amine;
(3,5-Bis-trifluoromethyl-benzyl)-[2-(methoxy-phenyl-methyl)-5-trifluoromethyl-benzyl]-(2-methyl-2H-tetrazol-5-yl)-amine;
(R)-(3,5-Bis-trifluoromethyl-benzyl)-[2-(methoxy-phenyl-methyl)-5-trifluoromethyl-benzyl]-(2-methyl-2H-tetrazol-5-yl)-amine;
(S)-(3,5-Bis-trifluoromethyl-benzyl)-[2-(methoxy-phenyl-methyl)-5-trifluoromethyl-benzyl]-(2-methyl-2H-tetrazol-5-yl)-amine;
(3,5-Bis-trifluoromethyl-benzyl)-[2-(1-methoxy-2-phenyl-ethyl)-5-trifluoromethyl-benzyl]-(2-methyl-2H-tetrazol-5-yl)-amine;
(R)-(3,5-Bis-trifluoromethyl-benzyl)-[2-(1-methoxy-2-phenyl-ethyl)-5-trifluoromethyl-benzyl]-(2-methyl-2H-tetrazol-5-yl)-amine;
(S)-(3,5-Bis-trifluoromethyl-benzyl)-[2-(1-methoxy-2-phenyl-ethyl)-5-trifluoromethyl-benzyl]-(2-methyl-2H-tetrazol-5-yl)-amine;
(3,5-Bis-trifluoromethyl-benzyl)-[2-(cyclohexyl-ethoxy-methyl)-5-trifluoromethyl-benzyl]-(2-methyl-2H-tetrazol-5-yl)-amine;
(R)-(3,5-Bis-trifluoromethyl-benzyl)-[2-(cyclohexyl-ethoxy-methyl)-5-trifluoromethyl-benzyl]-(2-methyl-2H-tetrazol-5-yl)-amine;
(S)-(3,5-Bis-trifluoromethyl-benzyl)-[2-(cyclohexyl-ethoxy-methyl)-5-trifluoromethyl-benzyl]-(2-methyl-2H-tetrazol-5-yl)-amine;
(3,5-Bis-trifluoromethyl-benzyl)-[2-(cyclopropyl-ethoxy-methyl)-5-trifluoromethyl-benzyl]-(2-methyl-2H-tetrazol-5-yl)-amine;
(R)-(3,5-Bis-trifluoromethyl-benzyl)-[2-(cyclopropyl-ethoxy-methyl)-5-trifluoromethyl-benzyl]-(2-methyl-2H-tetrazol-5-yl)-amine;
(S)-(3,5-Bis-trifluoromethyl-benzyl)-[2-(cyclopropyl-ethoxy-methyl)-5-trifluoromethyl-benzyl]-(2-methyl-2H-tetrazol-5-yl)-amine;
N-(2-(1-methoxycycloheptyl)-5-(trifluoromethyl)benzyl)-N-(3,5-bis(trifluoromethyl)benzyl)-2-methyl-2H-tetrazol-5-amine;
(R)—N-(2-(1-methoxycycloheptyl)-5-(trifluoromethyl)benzyl)-N-(3,5-bis(trifluoromethyl)benzyl)-2-methyl-2H-tetrazol-5-amine;
(S)—N-(2-(1-methoxycycloheptyl)-5-(trifluoromethyl)benzyl)-N-(3,5-bis(trifluoromethyl)benzyl)-2-methyl-2H-tetrazol-5-amine;
N-(2-(1-cyclohexyl-1-methoxyethyl)-5-(trifluoromethyl)benzyl)-N-(3,5-bis(trifluoromethyl)benzyl)-2-methyl-2H-tetrazol-5-amine;
(R)—N-(2-(1-cyclohexyl-1-methoxyethyl)-5-(trifluoromethyl)benzyl)-N-(3,5-bis(trifluoromethyl)benzyl)-2-methyl-2H-tetrazol-5-amine;
(S)—N-(2-(1-cyclohexyl-1-methoxyethyl)-5-(trifluoromethyl)benzyl)-N-(3,5-bis(trifluoromethyl)benzyl)-2-methyl-2H-tetrazol-5-amine;
(3,5-Bis-trifluoromethyl-benzyl)-{2-[methoxy-(tetrahydro-pyran-4-yl)-methyl]-5-trifluoromethyl-benzyl}-(2-methyl-2H-tetrazol-5-yl)-amine;
(R)-(3,5-Bis-trifluoromethyl-benzyl)-{2-[methoxy-(tetrahydro-pyran-4-yl)-methyl]-5-trifluoromethyl-benzyl}-(2-methyl-2H-tetrazol-5-yl)-amine;
(S)-(3,5-Bis-trifluoromethyl-benzyl)-{2-[methoxy-(tetrahydro-pyran-4-yl)-methyl]-5-trifluoromethyl-benzyl}-(2-methyl-2H-tetrazol-5-yl)-amine;
(3,5-Bis-trifluoromethyl-benzyl)-[2-(1-methoxy-propyl)-5-trifluoromethyl-benzyl]-(2-methyl-2H-tetrazol-5-yl)-amine;
(R)-(3,5-Bis-trifluoromethyl-benzyl)-[2-(1-methoxy-propyl)-5-trifluoromethyl-benzyl]-(2-methyl-2H-tetrazol-5-yl)-amine; and
(S)-(3,5-Bis-trifluoromethyl-benzyl)-[2-(1-methoxy-propyl)-5-trifluoromethyl-benzyl]-(2-methyl-2H-tetrazol-5-yl)-amine;
or a pharmaceutically acceptable salt of said compound.

2. A pharmaceutical composition which comprises a therapeutically effective amount of a compound of claim 1, or a pharmaceutically acceptable salt of said compound and a pharmaceutically acceptable vehicle, diluent or carrier.

3. A pharmaceutical combination composition comprising: a therapeutically effective amount of a composition comprising
   a first compound, said first compound being a compound of claim 1, or a pharmaceutically acceptable salt of said compound;
   a second compound, said second compound being an HMG CoA reductase inhibitor, an MTP/Apo B secretion inhibitor, a PPAR modulator, a bile acid reuptake inhibitor, a cholesterol absorption inhibitor, a cholesterol synthesis inhibitor, a fibrate, niacin, a combination of niacin and lovastatin, a combination of niacin and simvastatin, a combination of niacin and atorvastatin, a combination of amlodipine and atorvastatin, an ion-exchange resin, an antioxidant, an ACAT inhibitor or a bile acid sequestrant; and
   a pharmaceutical vehicle, diluent or carrier.

4. A pharmaceutical combination composition according to claim 3 wherein the second compound is an HMG-CoA reductase inhibitor, a PPAR modulator, or niacin.

5. A pharmaceutical combination composition according to claim 4 wherein the second compound is fenofibrate, gemfibrozil, lovastatin, simvastatin, pravastatin, fluvastatin, atorvastatin, rivastatin, rosuvastatin or pitavastatin.

* * * * *